(12) United States Patent
Cheng et al.

(10) Patent No.: US 11,559,648 B2
(45) Date of Patent: Jan. 24, 2023

(54) PATIENT INTERFACE WITH MOVABLE FRAME

(71) Applicant: ResMed Pty Ltd, Bella Vista (AU)

(72) Inventors: Amy Phan How Cheng, Singapore (SG); Robin Yew, Singapore (SG)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/590,843

(22) Filed: Feb. 2, 2022

(65) Prior Publication Data

US 2022/0152333 A1 May 19, 2022

Related U.S. Application Data

(63) Continuation of application No. 16/339,168, filed as application No. PCT/AU2017/050983 on Sep. 8, 2017, now Pat. No. 11,273,276.
(Continued)

(51) Int. Cl.
*A61M 16/06* (2006.01)
*A61M 16/08* (2006.01)
*A61M 16/16* (2006.01)

(52) U.S. Cl.
CPC ...... *A61M 16/0616* (2014.02); *A61M 16/065* (2014.02); *A61M 16/0683* (2013.01);
(Continued)

(58) Field of Classification Search
CPC .............. A61M 16/06; A61M 16/0605; A61M 16/0611; A61M 16/0616; A61M 16/0622;
(Continued)

(56) References Cited

U.S. PATENT DOCUMENTS

| 4,782,832 A | 11/1988 | Trimble et al. |
| 4,817,926 A | 4/1989 | Schwerdt |

(Continued)

FOREIGN PATENT DOCUMENTS

| WO | 98/004310 A1 | 2/1998 |
| WO | 98/034665 A1 | 8/1998 |

(Continued)

OTHER PUBLICATIONS

International Preliminary Report on Patentability dated Apr. 9, 2019 issued in PCT/AU2017/050983 (12 pages).
(Continued)

*Primary Examiner* — Joseph D. Boecker
(74) *Attorney, Agent, or Firm* — Nixon & Vanderhye P.C.

(57) ABSTRACT

A patient interface may include a plenum chamber pressurisable to a therapeutic pressure; a seal-forming structure constructed and arranged to form a seal with a region of the patient's face; a positioning and stabilising structure to provide an elastic force to hold the seal-forming structure on the patient's head, the positioning and stabilising structure may include a tie; a vent structure; a decoupling structure configured to provide a fluid connection between the plenum chamber and an air circuit for the flow of air at the therapeutic pressure for breathing by the patient; and a frame having at least one tie attachment structure to receive the tie, wherein the frame is configured to be resiliently movable in any direction having at least one of a component parallel to the patient's sagittal plane, a component parallel to the patient's coronal plane, a component parallel to the patient's Frankfort horizontal plane.

28 Claims, 160 Drawing Sheets

Related U.S. Application Data

(60) Provisional application No. 62/403,895, filed on Oct. 4, 2016.

(52) U.S. Cl.
CPC ......... *A61M 16/0816* (2013.01); *A61M 16/16* (2013.01); *A61M 2202/0225* (2013.01)

(58) Field of Classification Search
CPC ............ A61M 16/0633; A61M 16/065; A61M 16/0683; A62B 18/084
See application file for complete search history.

(56) References Cited

U.S. PATENT DOCUMENTS

| | | |
|---|---|---|
| 4,867,154 A | 9/1989 | Potter |
| 4,871,152 A | 10/1989 | Funahashi |
| 4,944,310 A | 7/1990 | Sullivan |
| 5,074,297 A | 12/1991 | Venegas |
| 5,121,745 A | 6/1992 | Israel |
| 5,553,834 A | 9/1996 | Je |
| 5,687,715 A | 11/1997 | Landis |
| 6,039,044 A | 3/2000 | Sullivan |
| 6,532,959 B1 | 3/2003 | Berthon-Jones |
| 6,581,594 B1 | 6/2003 | Drew et al. |
| 6,584,977 B1 | 7/2003 | Serowski |
| 6,595,214 B1 | 7/2003 | Hecker |
| 6,763,835 B1 | 7/2004 | Grove et al. |
| 7,021,311 B2 * | 4/2006 | Gunaratnam ......... A61M 16/06 128/205.25 |
| 7,219,669 B1 | 5/2007 | Lovell |
| 7,546,837 B2 | 6/2009 | Busch et al. |
| 7,562,658 B2 | 7/2009 | Madaus et al. |
| 7,861,715 B2 | 1/2011 | Jones et al. |
| 7,866,639 B2 | 1/2011 | Endo |
| 7,866,944 B2 | 1/2011 | Kenyon et al. |
| 7,900,630 B2 | 3/2011 | Geiselhart et al. |
| 8,146,595 B2 | 4/2012 | Sherman |
| 8,550,084 B2 | 10/2013 | Ng et al. |
| 8,636,479 B2 | 1/2014 | Kenyon et al. |
| 8,638,014 B2 | 1/2014 | Sears et al. |
| 8,733,349 B2 | 5/2014 | Bath et al. |
| 8,967,598 B2 | 3/2015 | Whear |
| 2002/0029780 A1 | 3/2002 | Frater |
| 2003/0196656 A1 | 10/2003 | Moore et al. |
| 2004/0025883 A1 * | 2/2004 | Eaton ................ A61M 16/0683 128/207.11 |
| 2006/0042629 A1 | 3/2006 | Geist |
| 2006/0201514 A1 | 9/2006 | Jones |
| 2006/0207599 A1 * | 9/2006 | Busch ................ A61M 16/0622 128/206.24 |
| 2006/0231101 A1 | 10/2006 | Cannon |
| 2006/0249159 A1 * | 11/2006 | Ho ........................ A61M 16/06 128/206.28 |
| 2006/0272646 A1 | 12/2006 | Ho |
| 2006/0283456 A1 * | 12/2006 | Geiselhart ............. A61M 16/06 128/205.27 |
| 2007/0044804 A1 | 3/2007 | Matula, Jr. et al. |
| 2007/0111374 A1 | 5/2007 | Islam |
| 2007/0125385 A1 | 6/2007 | Ho et al. |
| 2007/0215161 A1 | 9/2007 | Frater |
| 2008/0006270 A1 | 1/2008 | Gershman |
| 2008/0066745 A1 | 3/2008 | Janbakhsh |
| 2008/0276937 A1 | 11/2008 | Davidson et al. |
| 2009/0014008 A1 | 1/2009 | Takishita |
| 2009/0044808 A1 | 2/2009 | Guney et al. |
| 2009/0050156 A1 | 2/2009 | Ng et al. |
| 2009/0176051 A1 | 7/2009 | Eifler |
| 2009/0223521 A1 * | 9/2009 | Howard ............ A61M 16/0644 128/206.23 |
| 2009/0223523 A1 | 9/2009 | Chang |
| 2010/0000534 A1 | 1/2010 | Kooij et al. |
| 2010/0282264 A1 | 11/2010 | Chang |
| 2010/0319700 A1 | 12/2010 | Ng |
| 2011/0048425 A1 | 3/2011 | Chang |
| 2011/0226255 A1 | 9/2011 | Rothermel |
| 2011/0232647 A1 | 9/2011 | Ho |
| 2011/0277770 A1 | 11/2011 | Chang |
| 2012/0067349 A1 | 3/2012 | Barlow |
| 2012/0080035 A1 | 4/2012 | Guney |
| 2012/0138061 A1 | 6/2012 | Dravitzki |
| 2012/0152255 A1 | 6/2012 | Barlow |
| 2012/0305001 A1 | 12/2012 | Tatkov |
| 2013/0000646 A1 * | 1/2013 | Haibach ................ A61M 16/06 128/205.25 |
| 2013/0133664 A1 * | 5/2013 | Startare ............. A61M 16/0666 128/206.24 |
| 2013/0199537 A1 | 8/2013 | Formica |
| 2014/0174446 A1 | 6/2014 | Prentice |
| 2014/0290664 A1 * | 10/2014 | Grashow ........... A61M 16/0622 128/206.26 |
| 2014/0338671 A1 | 11/2014 | Chodkowski |
| 2014/0366885 A1 * | 12/2014 | Haibach ............ A61M 16/0622 128/206.24 |
| 2015/0047640 A1 | 2/2015 | McCaslin |
| 2015/0151066 A1 * | 6/2015 | Chodkowski ...... A61M 16/0611 264/161 |
| 2015/0217074 A1 | 8/2015 | Wells |
| 2015/0283349 A1 | 10/2015 | McLaren |
| 2015/0328422 A1 * | 11/2015 | Chodkowski ..... A61M 16/0683 128/206.21 |
| 2015/0328423 A1 | 11/2015 | Siew |
| 2016/0067442 A1 * | 3/2016 | Salmon ............. A61M 16/0825 128/205.25 |
| 2016/0136375 A1 * | 5/2016 | Zhan ................ A61M 16/0638 128/205.25 |
| 2017/0368286 A1 | 12/2017 | Grashow |
| 2019/0001094 A1 * | 1/2019 | Liu .................... A61M 16/0644 |
| 2019/0224436 A1 | 7/2019 | Cheng et al. |

FOREIGN PATENT DOCUMENTS

| | | | |
|---|---|---|---|
| WO | 2000/078381 A1 | 12/2000 | |
| WO | 2001/097893 A1 | 12/2001 | |
| WO | 2004/073778 A1 | 9/2004 | |
| WO | 2004/096332 A1 | 11/2004 | |
| WO | 2005/063328 A1 | 7/2005 | |
| WO | 2006/074513 A1 | 7/2006 | |
| WO | 2006/130903 A1 | 12/2006 | |
| WO | 2006/138416 A1 | 12/2006 | |
| WO | 2007/021777 A2 | 2/2007 | |
| WO | 2008/036625 A2 | 3/2008 | |
| WO | 2009/052560 A1 | 4/2009 | |
| WO | 2009/108995 A1 | 9/2009 | |
| WO | 2010/135785 A1 | 12/2010 | |
| WO | 2011/060479 A1 | 5/2011 | |
| WO | 2011/110968 A2 | 9/2011 | |
| WO | 2012/020359 A1 | 2/2012 | |
| WO | 2012/028988 A1 | 3/2012 | |
| WO | 2012/069951 A1 | 5/2012 | |
| WO | 2012/171072 A1 | 12/2012 | |
| WO | 2013/020167 A1 | 2/2013 | |
| WO | 2013/156910 A1 | 10/2013 | |
| WO | 2013/170290 A1 | 11/2013 | |
| WO | 2014/097067 A1 | 6/2014 | |
| WO | 2014/110622 A1 | 7/2014 | |
| WO | 2014/168489 A1 | 10/2014 | |
| WO | 2014/183167 A1 | 11/2014 | |
| WO | 2015/057087 A2 | 4/2015 | |

OTHER PUBLICATIONS

"*Respiratory Physiology*", by John B. West, Lippincott Williams & Wilkins, 9th edition published 2012 (8 pages).
International Search Report for PCT/AU2017/050983, dated Jun. 4, 2018, 19 pages.
Written Opinion of the ISA for PCT/AU2017/050983, dated Jun. 4, 2018, 11 pages.

* cited by examiner

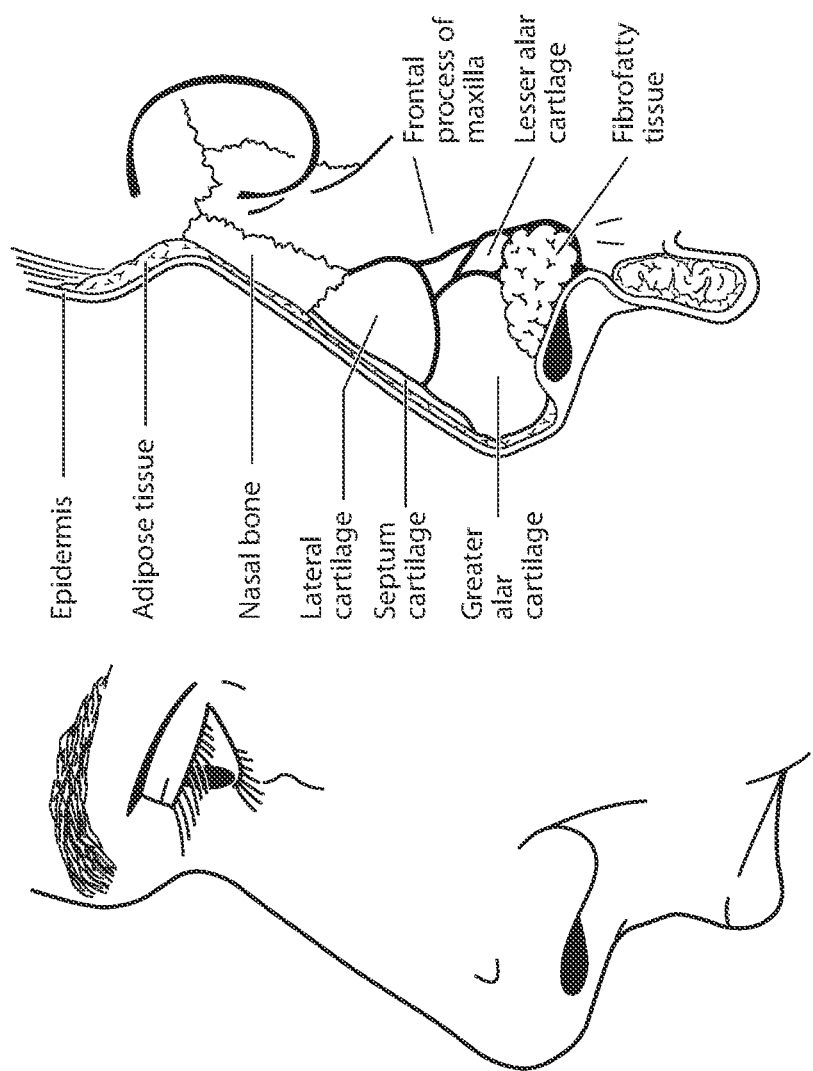
FIG. 2G
FIG. 2H
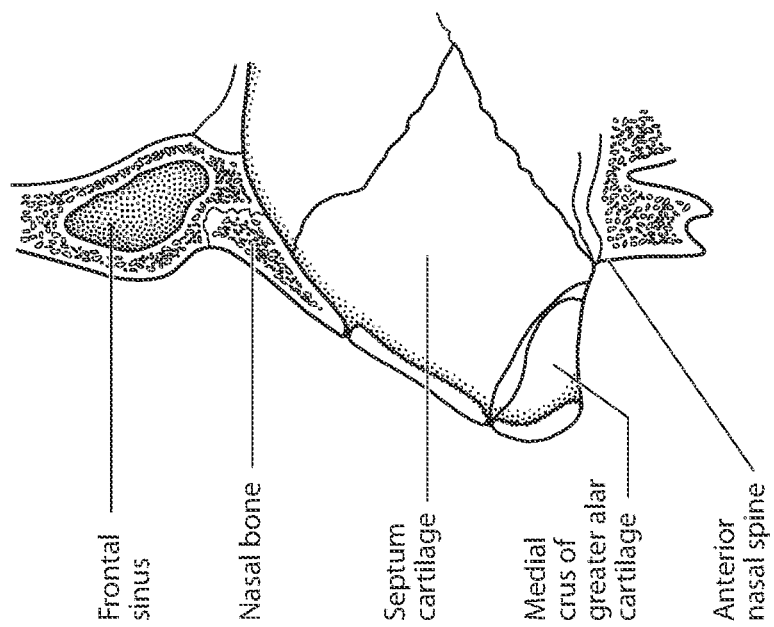
FIG. 2I

Relatively Large Positive Curvature

Relatively Small Positive Curvature

Zero Curvature

Relatively Small Negative Curvature

Relatively Large Negative Curvature

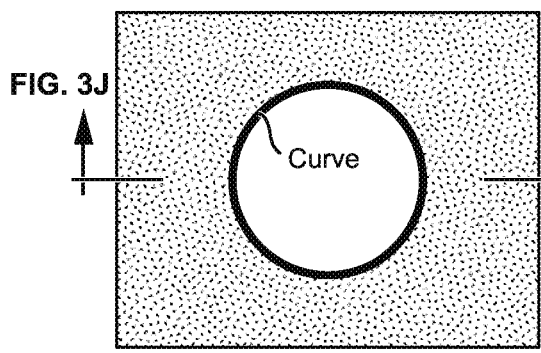
FIG. 3I
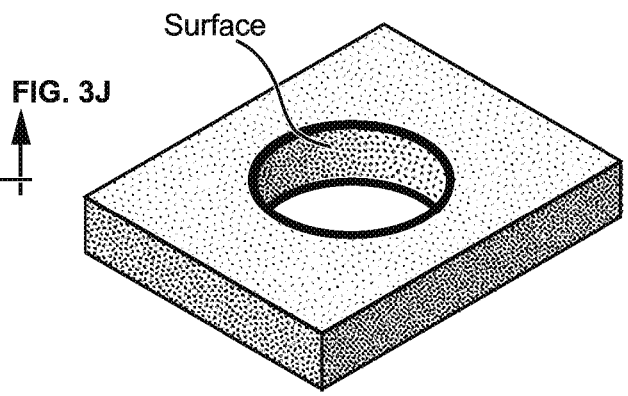
FIG. 3K
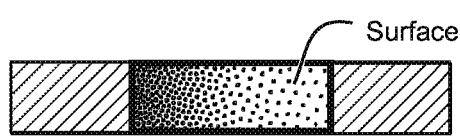
FIG. 3J
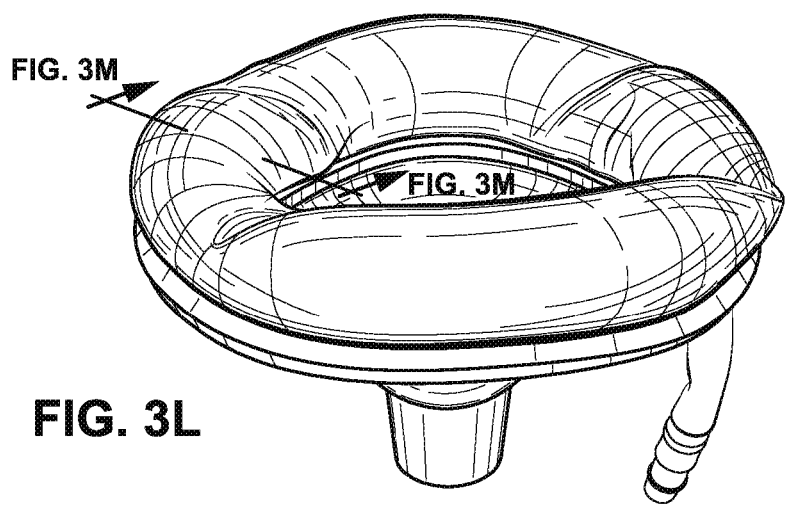
FIG. 3L
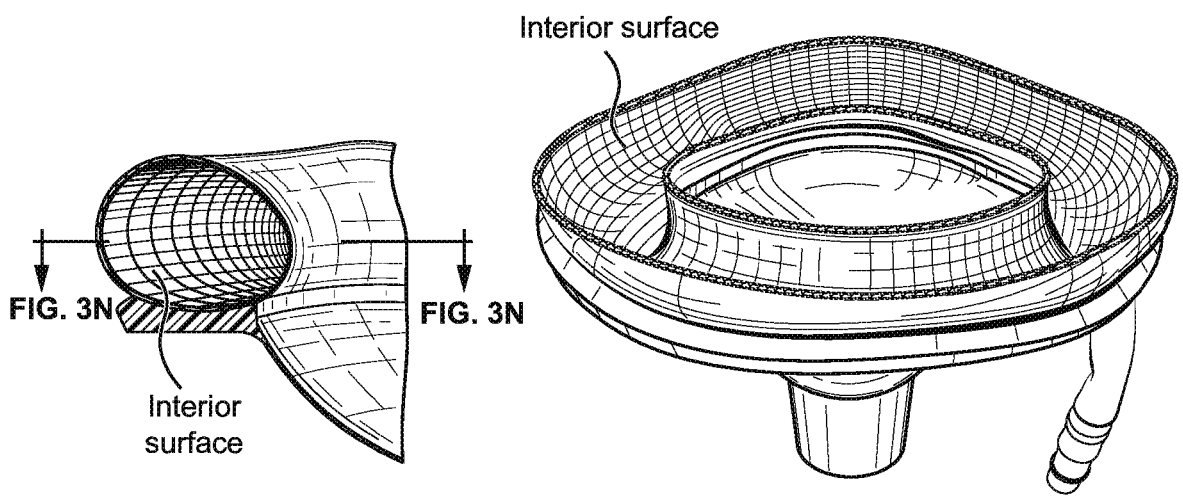
FIG. 3M  FIG. 3N

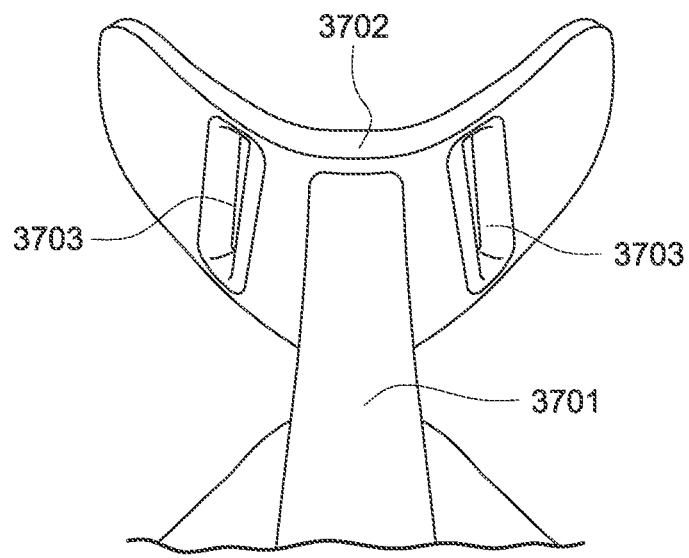
Fig. 22E
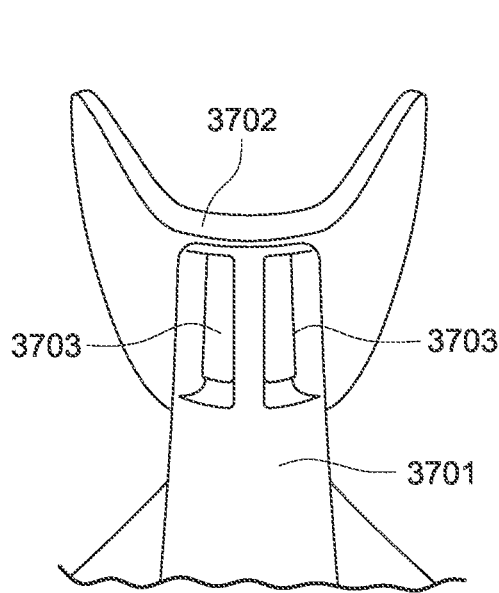 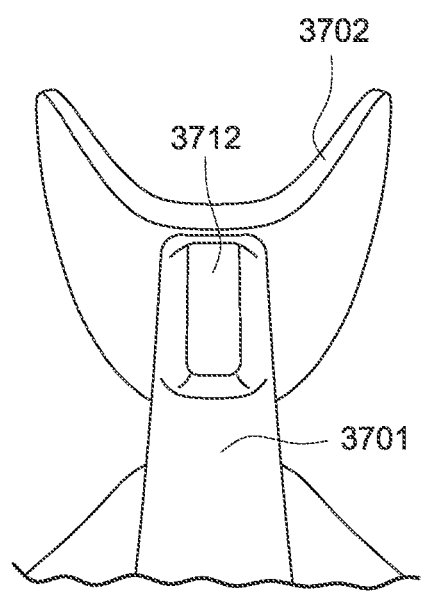
Fig. 22F    Fig. 22G

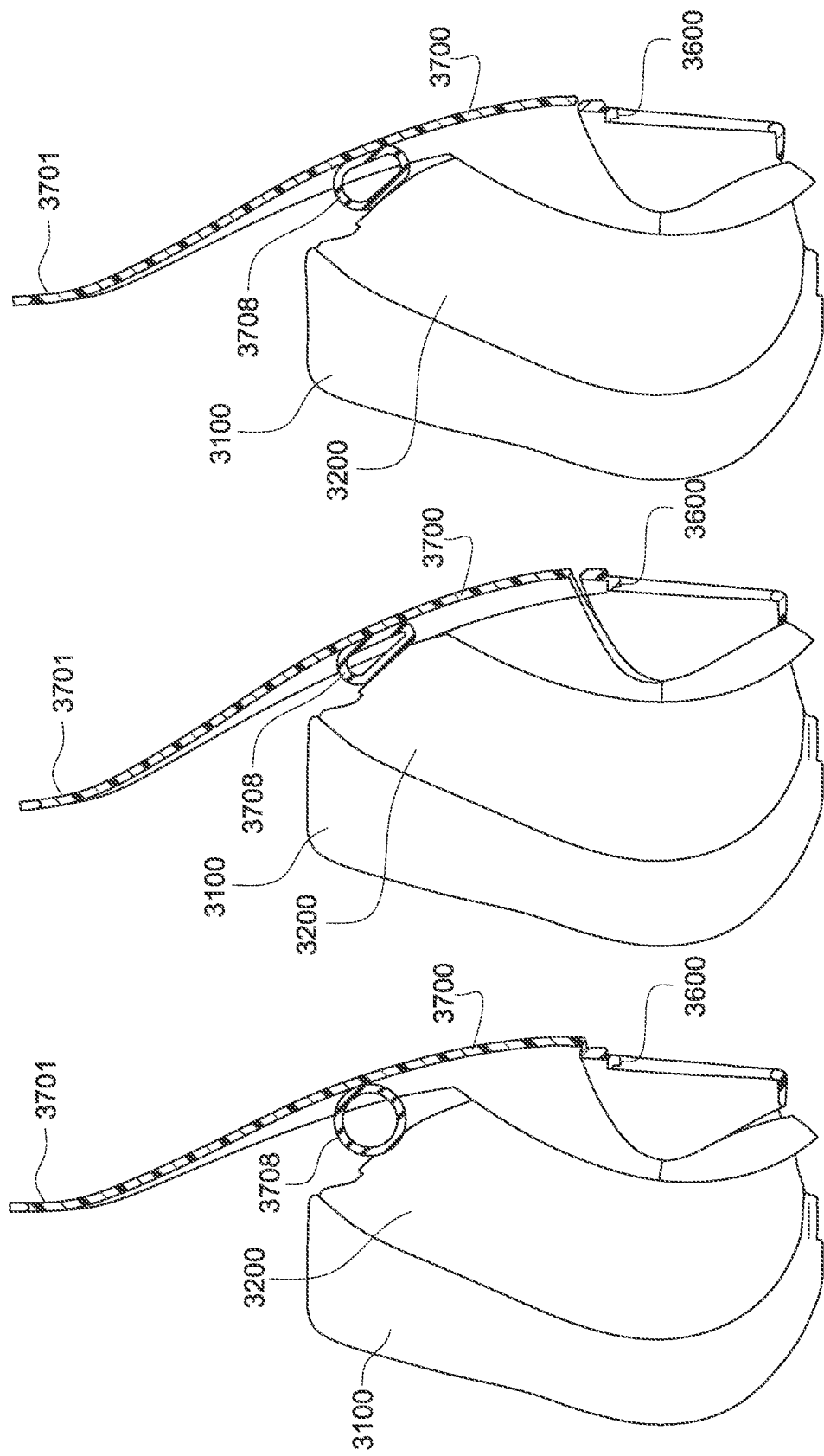

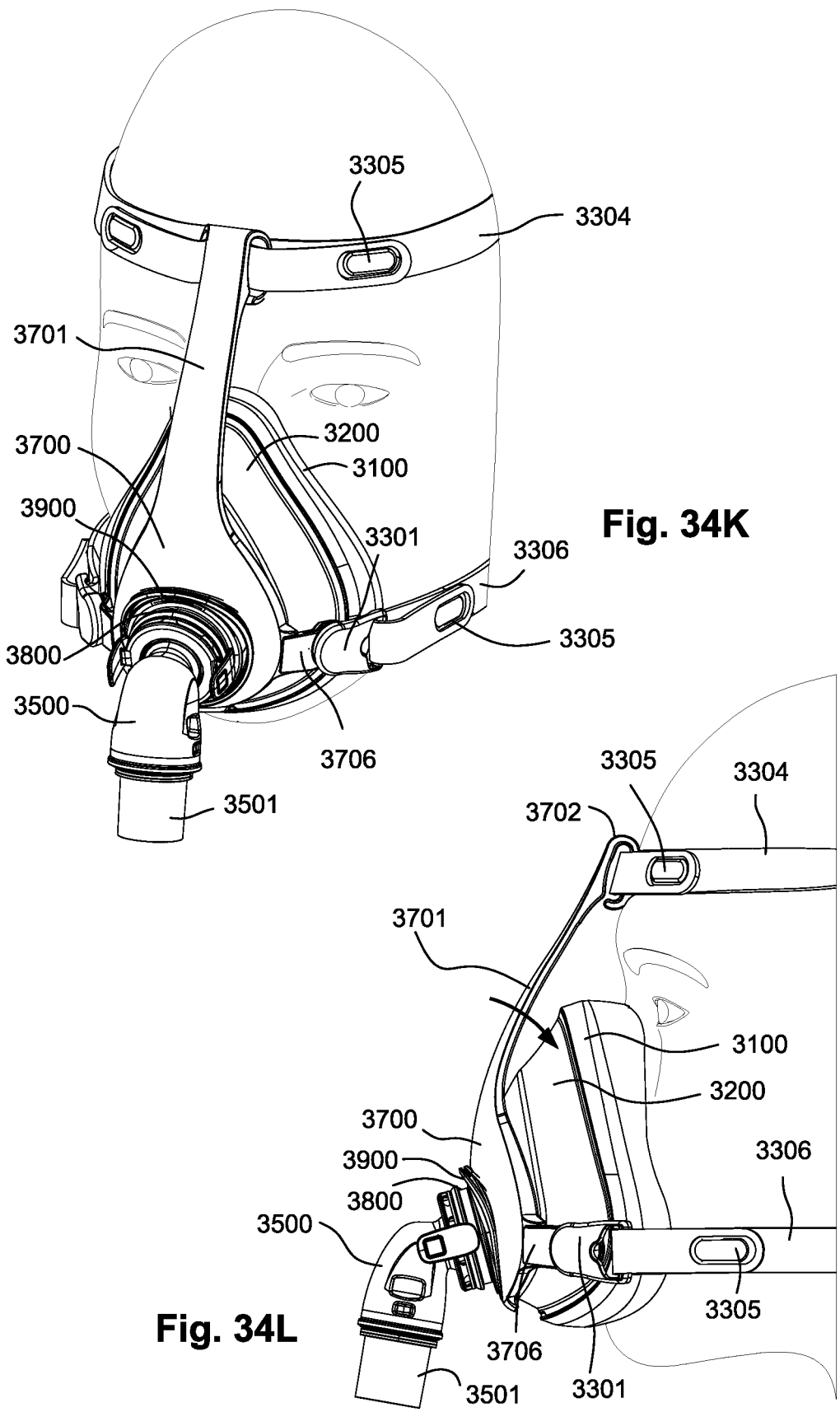

PATIENT INTERFACE WITH MOVABLE FRAME

1 CROSS-REFERENCE TO RELATED APPLICATIONS

This application is a continuation of U.S. application Ser. No. 16/339,168, filed Apr. 3, 2019, now U.S. Pat. No. 11,273,276, which is the U.S. national phase of International Application No. PCT/AU2017/050983 filed Sep. 8, 2017 which designated the U.S. and claims the benefit of U.S. Provisional Application No. 62/403,895, filed Oct. 4, 2016, the entire contents of each of which are incorporated herein by reference.

2 BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See *"Respiratory Physiology"*, by John B. West, Lippincott Williams & Wilkins, 9th edition published 2012.

A range of respiratory disorders exist. Certain disorders may be characterised by particular events, e.g., apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g., Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g., Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology, e.g., if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g., for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g., filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g., aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g., by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g., because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g., for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004310; WO 2006/074513; WO 2010/135785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063328 and WO 2006/130903 (describing amongst other things aspects of the ResMed Limited MIRAGE LIBERTY™ full-face mask); International Patent Application WO 2009/052560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See, for example, US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used to deliver one or more of a number of therapies described above, such as by generating a flow of air for delivery to an entrance to the airways. The flow of air may be pressurised. Examples of RPT devices include a CPAP device and a ventilator.

Air pressure generators are known in a range of applications, e.g., industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisde™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g., at a hospital). A medical humidifier for bedside placement may be small. A medical humidifier may be configured to only humidify and/or heat the flow of air delivered to the patient without humidifying and/or heating the patient's surroundings. Room-based systems (e.g., a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g., that the patient has used their RPT device according to certain a "compliance rule". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g., through noise or focused airflow.

ResMed Limited has developed a number of improved mask vent technologies. See International Patent Application Publication No. WO 1998/034665; International Patent Application Publication No. WO 2000/078381; U.S. Pat. No. 6,581,594; US Patent Application Publication No. US 2009/0050156; US Patent Application Publication No. 2009/0044808.

Table of noise of prior masks (ISO 17510-2:2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |

-continued

| Mask name | Mask type | A-weighted sound power level dB(A) (uncertainty) | A-weighted sound pressure dB(A) (uncertainty) | Year (approx.) |
|---|---|---|---|---|
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

((*) one specimen only, measured using test method specified in ISO 3744 in CPAP mode at 10 cmH₂O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

Another aspect of one form of the present technology is a patient interface that is moulded or otherwise constructed with a perimeter shape which is complementary to that of an intended wearer.

An aspect of one form of the present technology is a method of manufacturing an apparatus.

An aspect of certain forms of the present technology is a medical device that is easy to use, e.g., by a person who does not have medical training, by a person who has limited dexterity, vision, or by a person with limited experience in using this type of medical device.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

An aspect of the present technology is directed to a patient interface that comprises a plenum chamber pressurisable to a therapeutic pressure of at least 6 cmH₂O above ambient air pressure, said plenum chamber including a plenum chamber inlet port sized and structured to receive a flow of air at the therapeutic pressure for breathing by a patient; a seal-forming structure constructed and arranged to form a seal with a region of the patient's face surrounding an entrance to the patient's airways such that the flow of air at said therapeutic pressure is delivered to at least the entrance to the patient's nares, the seal-forming structure constructed and arranged to maintain said therapeutic pressure in the plenum chamber throughout the patient's respiratory cycle in use; a positioning and stabilising structure to provide an elastic force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use, a portion of the tie being dimensioned and structured to engage in use a portion of the patient's head in a region of a parietal bone, and the positioning and stabilising structure having a non-rigid decoupling portion; a vent structure to allow a continuous flow of gases exhaled by the patient from an interior of the plenum chamber to ambient, said vent structure being sized and shaped to maintain the therapeutic pressure in the plenum chamber in use; a decoupling structure configured to provide a fluid connection between the plenum chamber and an air circuit for the flow of air at the therapeutic pressure for breathing by the patient; a connector ring configured to connect to at least one of the decoupling structure and the plenum chamber; a frame having at least one tie attachment structure to receive the tie of the positioning and stabilising structure; and a flexible joint structure joining the connector ring and the frame, wherein the patient interface is configured to allow the patient to breath from ambient through their mouth in the absence of a flow of pressurised air through the plenum chamber inlet port or the patient interface is configured to leave the patient's mouth uncovered.

In examples, (a) the frame and the connector ring may be resiliently movable relative to one another, (b) the frame may comprise a first material, the connector ring may comprise a second material, and the flexible joint structure may comprise a third material, and the first material and the second material may be more rigid than the third material, (c) the third material may be a resiliently deformable material, (d) each of the first material, the second material, and the third material may have at least one different property, (e) the decoupling structure may be configured to be releasably connected to the connector ring, (f) the decoupling structure may comprise a button that is depressible to release the decoupling structure from the connector ring, (g) the connector ring may comprise an attachment lip and the button may comprise a retainer to releasably connect to the attachment lip, (h) the attachment lip may be shaped uniformly around at least a portion of the connector ring such that the decoupling structure is rotatable relative to the connector ring while the retainer is connected to the attachment lip, (i) the attachment lip may be shaped uniformly around the entire perimeter of the connector ring such that the decoupling structure is rotatable 360° relative to the connector ring while the retainer is connected to the attachment lip, (j) the plenum chamber may be configured to releasably connect to the connector ring, (k) the connector ring may comprise an attachment structure and the plenum chamber may comprise a neck having an outer rim, and the attachment structure may be configured to releasably connect to the outer rim with a snap fit, (l) the connector ring may comprise a notch and the plenum chamber may comprise a wing extending from the neck, and the wing may be configured to engage the notch to prevent rotation of the plenum chamber relative to the connector ring, (m) the flexible joint structure may be joined to the frame and the connector ring by overmoulding, (n) the frame may comprise a frame opening and the flexible joint structure may comprise a frame joining portion that is joined to the frame around the perimeter of the frame opening, (o) the flexible joint structure may comprise a connector ring joining portion that is joined to the connector ring such that the connector ring is suspended within the frame opening by the flexible joint structure, (p) the flexible joint structure may comprise a web connecting the frame joining portion and the connector ring joining portion, the web being relatively thinner than the frame joining portion and the connector ring joining portion such that the frame is resiliently movable relative to the connector ring, (q) the decoupling structure may comprise a proximal end and the plenum chamber may comprise a sealing lip, and the sealing lip may be configured to contact the proximal end of the decoupling structure to form a sealed flow path for the flow of air at the therapeutic pressure from the decoupling structure to the plenum chamber for breathing by the patient, (r) the connector ring may comprise a spacer configured to contact the plenum chamber to limit movement of the connector ring toward the plenum chamber, (s) the frame may comprise a forehead support, (t) a superior end of the forehead support may comprise at least one tie attachment structure, (u) the decoupling structure may comprise the vent structure, (v) the seal-forming structure may be configured to form a seal with a region of the patient's face surrounding an entrance to the patient's airways such that the flow of air at said therapeutic pressure is only delivered to the entrance to the patient's nares, or the seal-forming structure may be configured to form a seal with a region of the patient's face surrounding an entrance to the patient's airways such that the flow of air at said therapeutic pressure is delivered to the entrance to the patient's nares and the entrance to the patient's mouth, (w) the decoupling structure may be configured to rotate relative to the plenum chamber about a single axis, and the frame may be decoupled from the plenum chamber by the flexible joint structure such that the frame is movable in any direction relative to the plenum chamber, and/or (x) the frame may be resiliently movable relative to the connector ring from a neutral position to a deformed position due to deformation of the flexible joint structure, and the flexible joint structure may be configured to urge the frame from the deformed position to the neutral position.

An aspect of the present technology is directed to a patient interface that comprises a plenum chamber pressurisable to a therapeutic pressure, a frame, a flexible joint structure, and a decoupling structure, the decoupling structure may be configured to rotate relative to the plenum chamber about a single axis, and the frame may be decoupled from the plenum chamber by the flexible joint structure such that the frame is movable in at least one direction relative to the plenum chamber.

An aspect of the present technology is directed to a patient interface that comprises a plenum chamber pressurisable to a therapeutic pressure, a frame, a flexible joint structure, a connector ring, and a decoupling structure, the frame may be resiliently movable relative to the connector ring from a neutral position to a deformed position due to deformation of the flexible joint structure, and the flexible joint structure may be configured to urge the frame from the deformed position to the neutral position.

An aspect of the present technology is directed to a patient interface that comprises a plenum chamber pressurisable to a therapeutic pressure of at least 6 cmH$_2$O above ambient air pressure, said plenum chamber including a plenum chamber inlet port sized and structured to receive a flow of air at the therapeutic pressure for breathing by a patient; a seal-forming structure constructed and arranged to form a seal with a region of the patient's face surrounding an entrance to the patient's airways such that the flow of air at said therapeutic pressure is delivered to at least the entrance to the patient's nares, the seal-forming structure constructed and arranged to maintain said therapeutic pressure in the plenum chamber throughout the patient's respiratory cycle in use; a positioning and stabilising structure to provide an elastic force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use, a portion of the tie being dimensioned and structured to engage in use a portion of the patient's head in a region of a parietal bone, and the positioning and stabilising structure having a non-rigid decoupling portion; a vent structure to allow a continuous flow of gases exhaled by the patient from an interior of the plenum chamber to ambient, said vent structure being sized and shaped to maintain the therapeutic pressure in the plenum chamber in use; a decoupling structure configured to provide a fluid connection between the plenum chamber and an air circuit for the flow of air at the therapeutic pressure for breathing by the patient; a frame having at least one tie attachment structure to receive the tie of the positioning and stabilising structure; a connector ring configured to connect at least one of the decoupling structure and the plenum chamber to the frame such that the frame is movable relative to at least one of the decoupling structure and the plenum chamber; and a spring joined to the frame to limit movement of the frame toward the plenum chamber, wherein the patient interface is configured to allow the patient to breath from ambient through their mouth in the absence of a flow of pressurised air through the plenum chamber inlet port or the patient interface is configured to leave the patient's mouth uncovered.

In examples, (a) the frame and the connector ring may be movable relative to one another, (b) the frame may comprise a pivot post and the connector ring comprises a pivot hole, and the pivot hole may be configured to receive the pivot post such that the connector ring is connected to the frame and pivotable about the pivot post, (c) the connector ring may comprise a pivot hole support and the pivot hole extends through the pivot hole support, (d) the plenum chamber and the decoupling structure may be connected to the connector ring such that the frame is pivotable relative to the plenum chamber, the decoupling structure, and the connector ring, (e) the decoupling structure may be configured to be releasably connected to the connector ring, (f) the decoupling structure may comprise a button that is depressible to release the decoupling structure from the connector ring, (g) the connector ring may comprise an attachment lip and the button may comprise a retainer to releasably connect to the attachment lip, (h) the attachment lip may be shaped uniformly around at least a portion of the connector ring such that the decoupling structure is rotatable relative to the connector ring while the retainer is connected to the attachment lip, (i) the attachment lip may be shaped uniformly around the entire perimeter of the connector ring such that the decoupling structure is rotatable 360° relative to the connector ring while the retainer is connected to the attachment lip, (j) the plenum chamber may be configured to releasably connect to the connector ring, (k) the connector ring may comprise an attachment structure and the plenum chamber may comprise a neck having an outer rim, and the attachment structure may be configured to releasably connect to the outer rim with a snap fit, (l) the spring may comprise a resiliently deformable material, (m) the frame may comprise a spring opening and the spring may comprise a spring attachment structure, and the spring may be joined to the frame at the spring opening by the spring attachment structure, (n) the spring may be joined to the frame by overmoulding, (o) the spring may be an arcuately shaped fixed beam that is configured to deform toward the frame due to contact with the plenum chamber in use, (p) the decoupling structure may comprise a proximal end and the plenum chamber may comprise a sealing lip, and the sealing lip may be configured to contact the proximal end of the decoupling structure to form a sealed flow path for the flow of air at the therapeutic pressure from the decoupling structure to the plenum chamber for breathing by the patient, (q) the connector ring may comprise a spacer configured to contact the plenum chamber to limit movement of the connector ring toward the plenum chamber, (r) the frame may comprise a forehead support, (s) the spring may be attached to the frame on the forehead support, (t) a superior end of the forehead support may comprise at least one tie attachment structure, (u) the decoupling structure may comprise the vent structure, and/or (v) the seal-forming structure may be configured to form a seal with a region of the patient's face surrounding an entrance to the patient's airways such that the flow of air at said therapeutic pressure is only delivered to the entrance to the patient's nares, or the seal-forming structure may be configured to form a seal with a region of the patient's face surrounding an entrance to the patient's airways such that the flow of air at said therapeutic pressure is delivered to the entrance to the patient's nares and the entrance to the patient's mouth.

An aspect of the present technology is directed to a patient interface that comprises a plenum chamber pressurisable to a therapeutic pressure of at least 6 cmH$_2$O above ambient air pressure, said plenum chamber including a plenum chamber inlet port sized and structured to receive a flow of air at the therapeutic pressure for breathing by a patient; a seal-forming structure constructed and arranged to form a seal with a region of the patient's face surrounding an entrance to the patient's airways such that the flow of air at said therapeutic pressure is delivered to at least the entrance to the patient's nares, the seal-forming structure constructed and arranged to maintain said therapeutic pressure in the plenum chamber throughout the patient's respiratory cycle in use; a positioning and stabilising structure to provide an elastic force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use, a portion of the tie being dimensioned and structured to engage in use a portion of the patient's head in a region of a parietal bone, and the positioning and stabilising structure having a non-rigid decoupling portion; a vent structure to allow a continuous flow of gases exhaled by the patient from an interior of the plenum chamber to ambient, said vent structure being sized and shaped to maintain the therapeutic pressure in the plenum chamber in use; a decoupling structure configured to provide a fluid connection between the plenum chamber and an air circuit for the flow of air at the therapeutic pressure for breathing by the patient; and a frame having at least one tie attachment structure to receive the tie of the positioning and stabilising structure, wherein the frame is configured to be resiliently movable in any direction having at least one of a component parallel to the patient's sagittal plane, a component parallel to the patient's coronal plane, a component parallel to the patient's Frankfort horizontal plane, and wherein the patient interface is configured to allow the patient to breath from ambient through their mouth in the absence of a flow of pressurised air through the plenum chamber inlet port or the patient interface is configured to leave the patient's mouth uncovered.

In examples, (a) the patient interface may comprise a connector ring configured to connect to at least one of the decoupling structure and the plenum chamber to the frame, (b) the patient interface may comprise a flexible joint structure joining the connector ring and the frame such that the frame and the connector ring are resiliently movable relative to one another, (c) the frame may comprise a first material, the connector ring may comprise a second material, and the flexible joint structure may comprise a third material, and the first material and the second material may be more rigid than the third material, (d) the third material may be a resiliently deformable material, (e) each of the first material, the second material, and the third material may have at least one different property, (f) the plenum chamber may be configured to releasably connect to the connector ring, (g) the connector ring may comprise an attachment structure and the plenum chamber may comprise a neck having an outer rim, and the attachment structure may be configured to releasably connect to the outer rim with a snap fit, (h) the connector ring may comprise a notch and the plenum chamber may comprise a wing extending from the neck, and the wing may be configured to engage the notch to prevent rotation of the plenum chamber relative to the connector ring, (i) the flexible joint structure may be joined to the frame and the connector ring by overmoulding, (j) the frame may comprise a frame opening and the flexible joint structure may comprise a frame joining portion that is joined to the frame around the perimeter of the frame opening, (k) the flexible joint structure may comprise a connector ring joining portion that is joined to the connector ring such that the connector ring is suspended within the frame opening by the flexible joint structure, (l) the flexible joint structure may comprise a web connecting the frame joining portion and the connector ring joining portion, the web being relatively thinner than the frame joining portion and the connector ring joining portion such that the frame is resiliently movable relative to the connector ring, (m) the frame may comprise a pivot post and the connector ring may comprise a pivot hole, and the pivot hole may be configured to receive the pivot post such that the connector ring is connected to the frame and pivotable about the pivot post, (n) the connector ring may comprise a pivot hole support and the pivot hole may extend through the pivot hole support, (o) the plenum chamber and the decoupling structure may be connected to the connector ring such that the frame is pivotable relative to the plenum chamber, the decoupling structure, and the connector ring, (p) the frame may comprise a spring joined to the frame to limit movement of the frame toward the plenum chamber, (q) the spring may comprise a resiliently deformable material, (r) the frame may comprise a spring opening and the spring may comprise a spring attachment structure, and the spring may be joined to the frame at the spring opening by the spring attachment structure, (s) the spring may be joined to the frame by overmoulding, (t) the spring may be an arcuately shaped fixed beam that is configured to deform toward the frame due to contact with the plenum chamber in use, (u) the frame may comprise a forehead support, and the spring may be attached to the frame on the forehead support, (v) a superior end of the forehead support may comprise at least one tie attachment structure, (w) the decoupling structure may be configured to be releasably connected to the connector ring, (x) the decoupling structure may comprise a button that is depressible to release the decoupling structure from the connector ring, (y) the connector ring may comprise an attachment lip and the button may comprise a retainer to releasably connect to the attachment lip, (z) the attachment lip may be shaped uniformly around at least a portion of the connector ring such that the decoupling structure is rotatable relative to the connector ring while the retainer is connected to the attachment lip, (aa) the attachment lip may be shaped uniformly around the entire perimeter of the connector ring such that the decoupling structure is rotatable 360° relative to the connector ring while the retainer is connected to the attachment lip, (bb) the connector ring may comprise a spacer configured to contact the plenum chamber to limit movement of the connector ring toward the plenum chamber, (cc) the decoupling structure may comprise the vent structure, (dd) the decoupling structure may comprise a proximal end and the plenum chamber comprises a sealing lip, and the sealing lip may be configured to contact the proximal end of the decoupling structure to form a sealed flow path for the flow of air at the therapeutic pressure from the decoupling structure to the plenum chamber for breathing by the patient, and/or (ee) the seal-forming structure may be configured to form a seal with a region of the patient's face surrounding an entrance to the patient's airways such that the flow of air at said therapeutic pressure is only delivered to the entrance to the patient's nares, or the seal-forming structure may be configured to form a seal with a region of the patient's face surrounding an entrance to the patient's airways such that the flow of air at said therapeutic pressure is delivered to the entrance to the patient's nares and the entrance to the patient's mouth.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
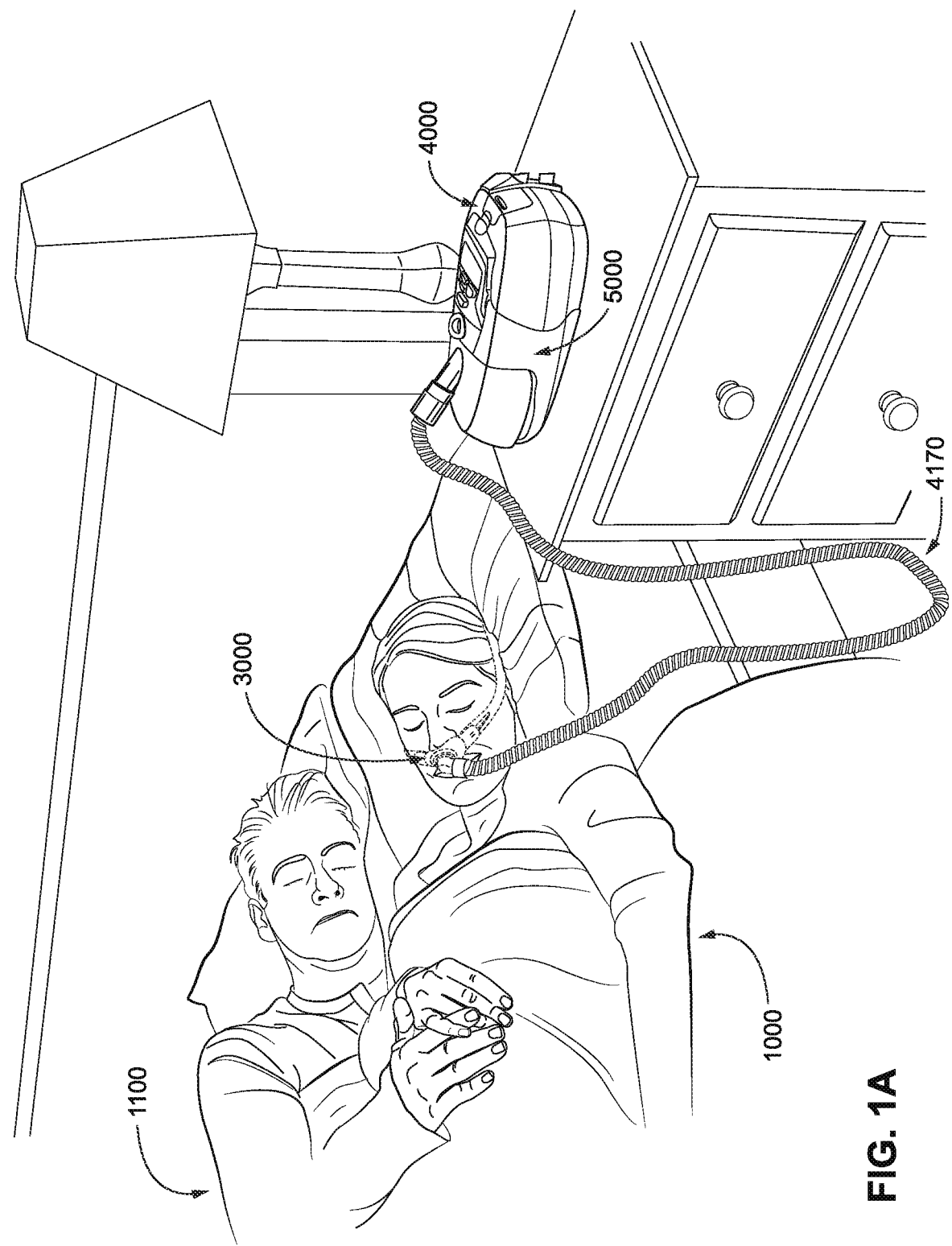
Figure 1B:
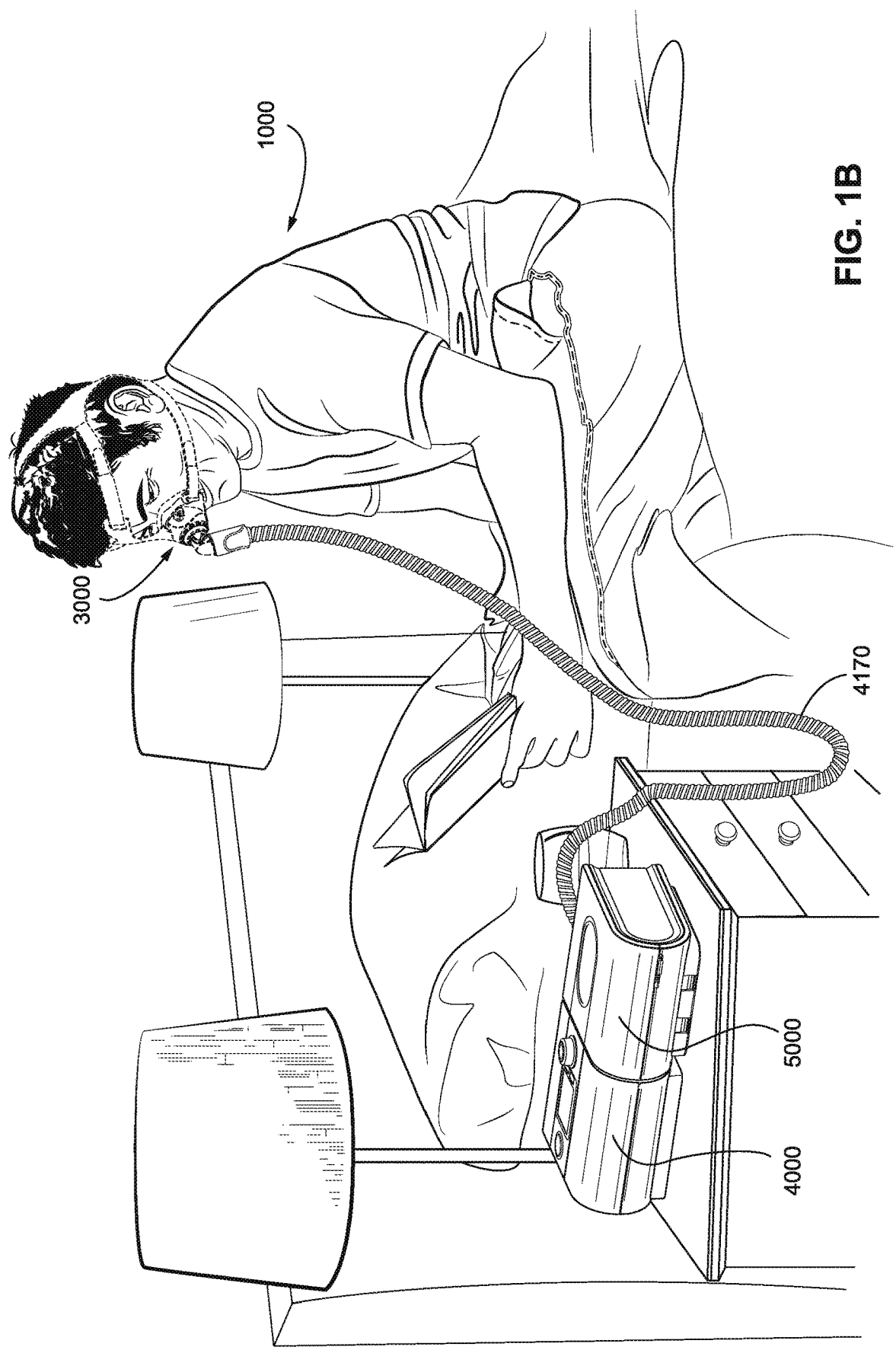
Figure 1C:
Figure 2A:
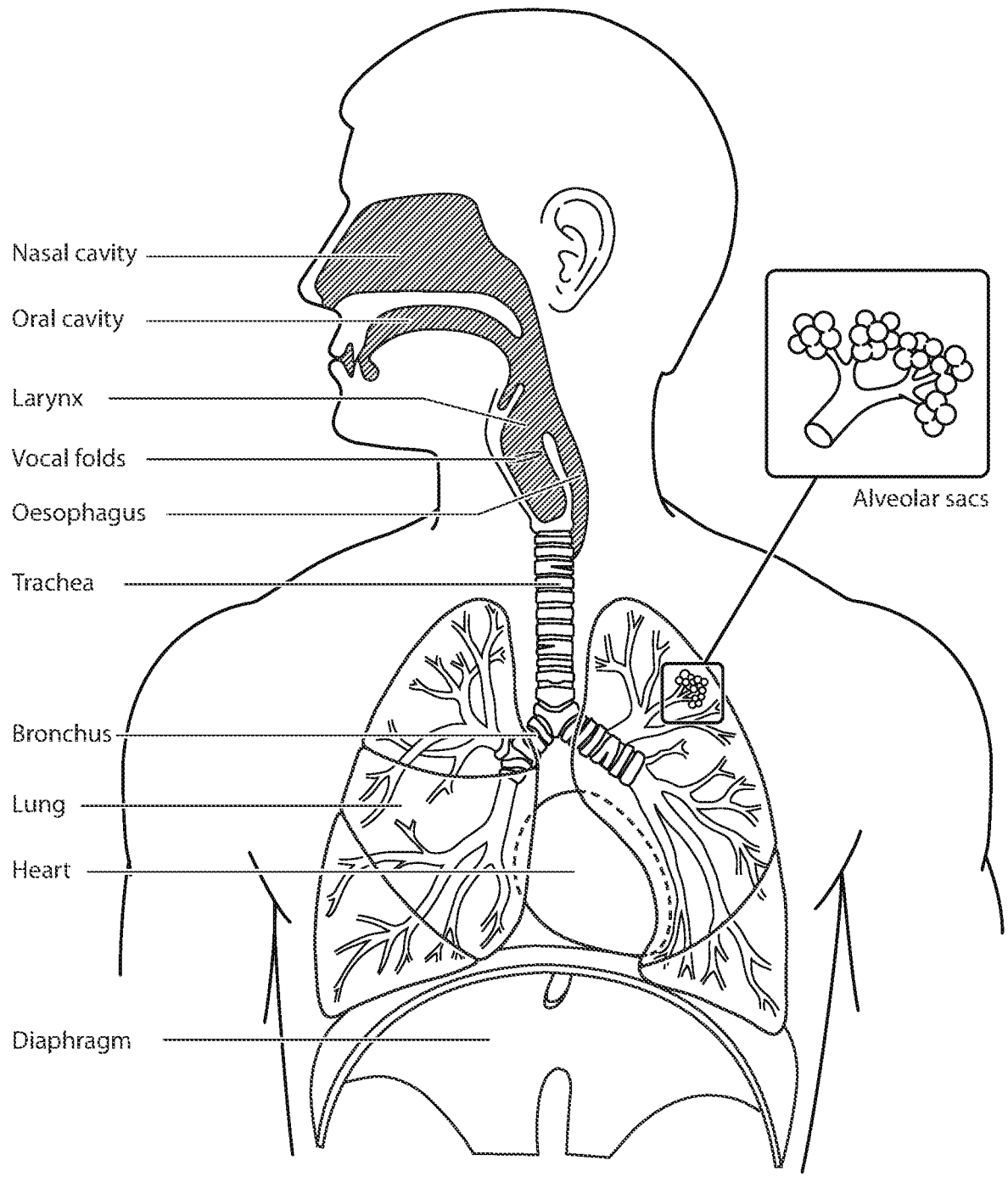
FIG. 2A shows an overview of a human respiratory system including the nasal and oral cavities, the larynx, vocal folds, oesophagus, trachea, bronchus, lung, alveolar sacs, heart and diaphragm.
Figure 2B:
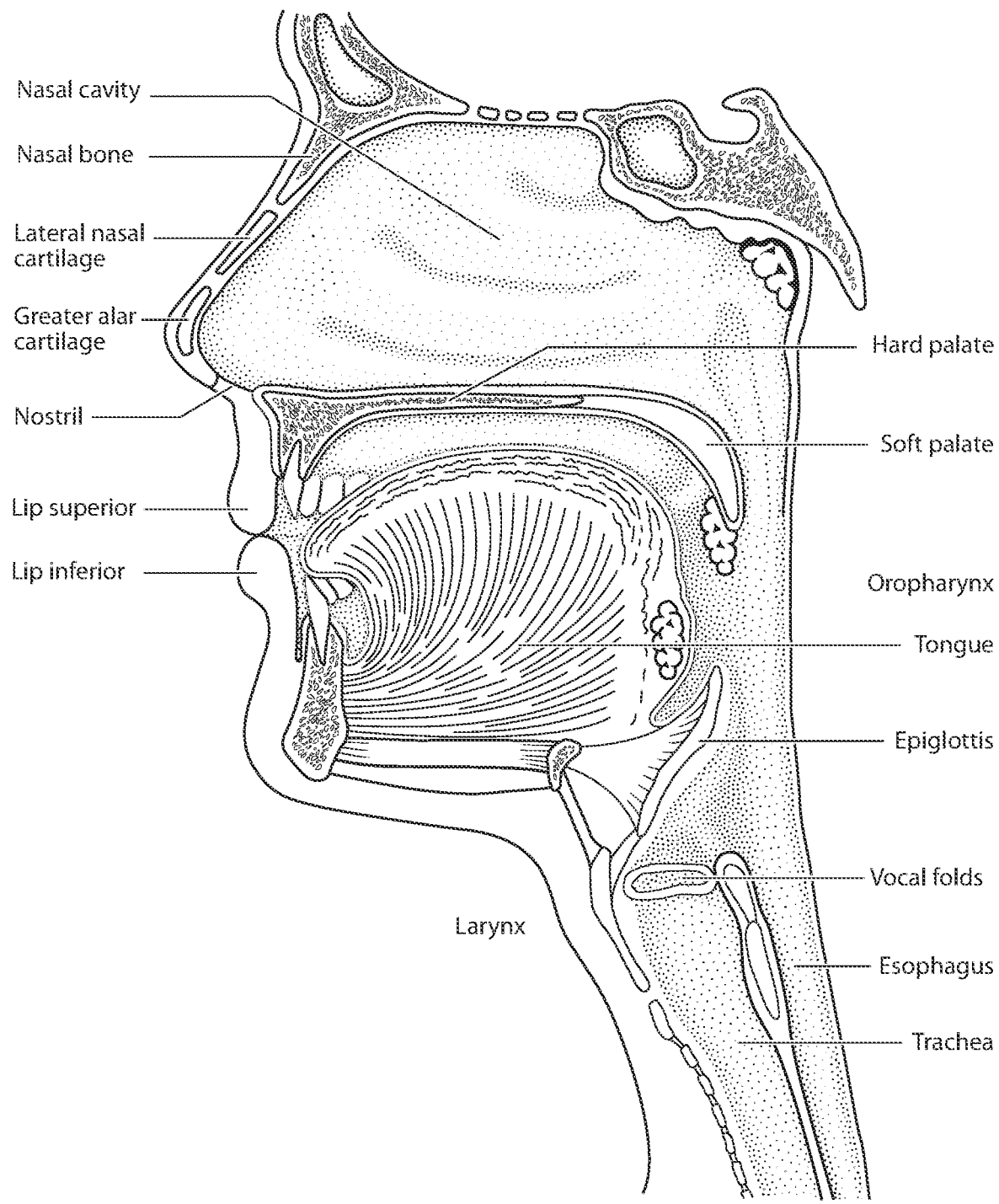
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
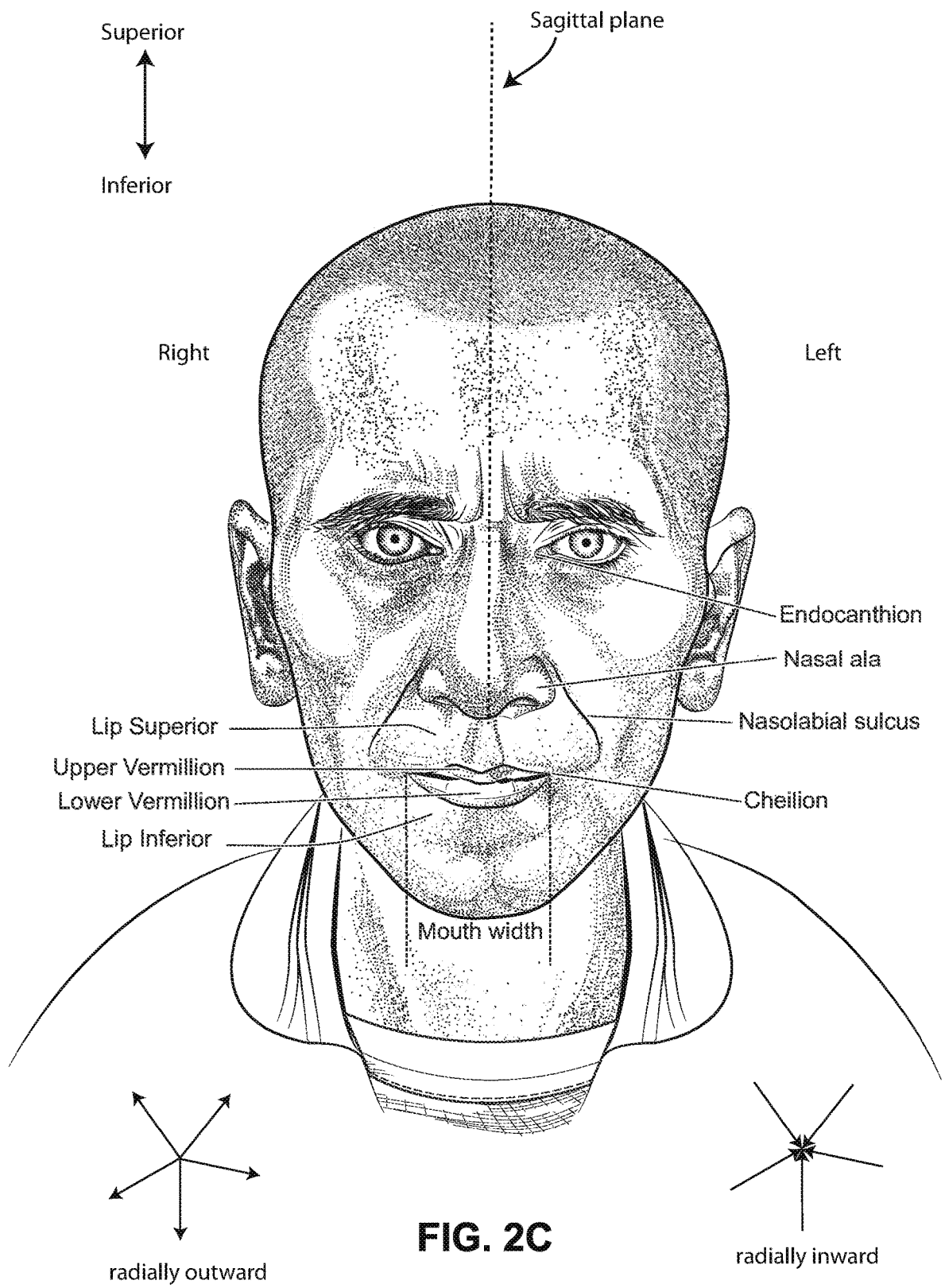
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
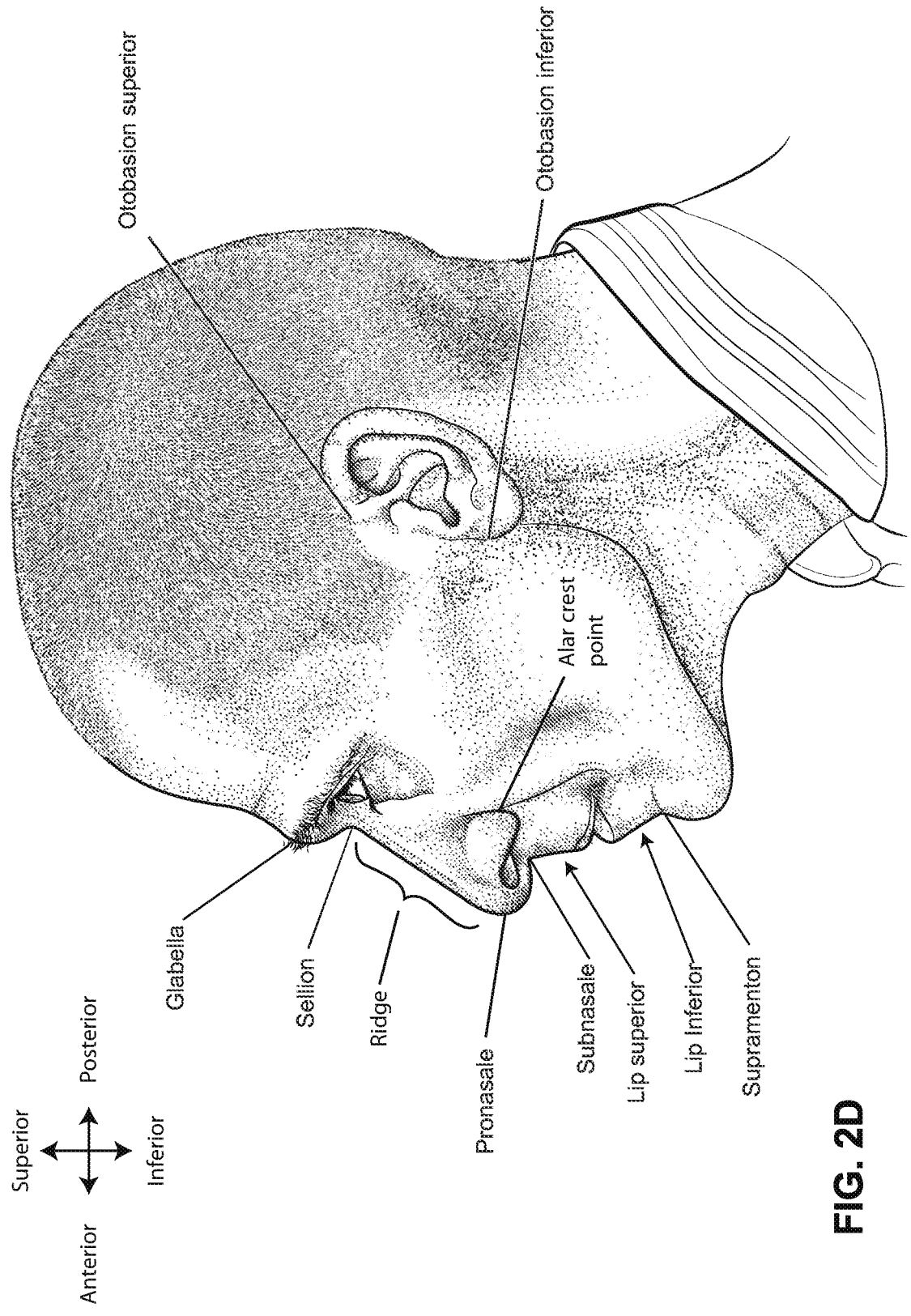
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
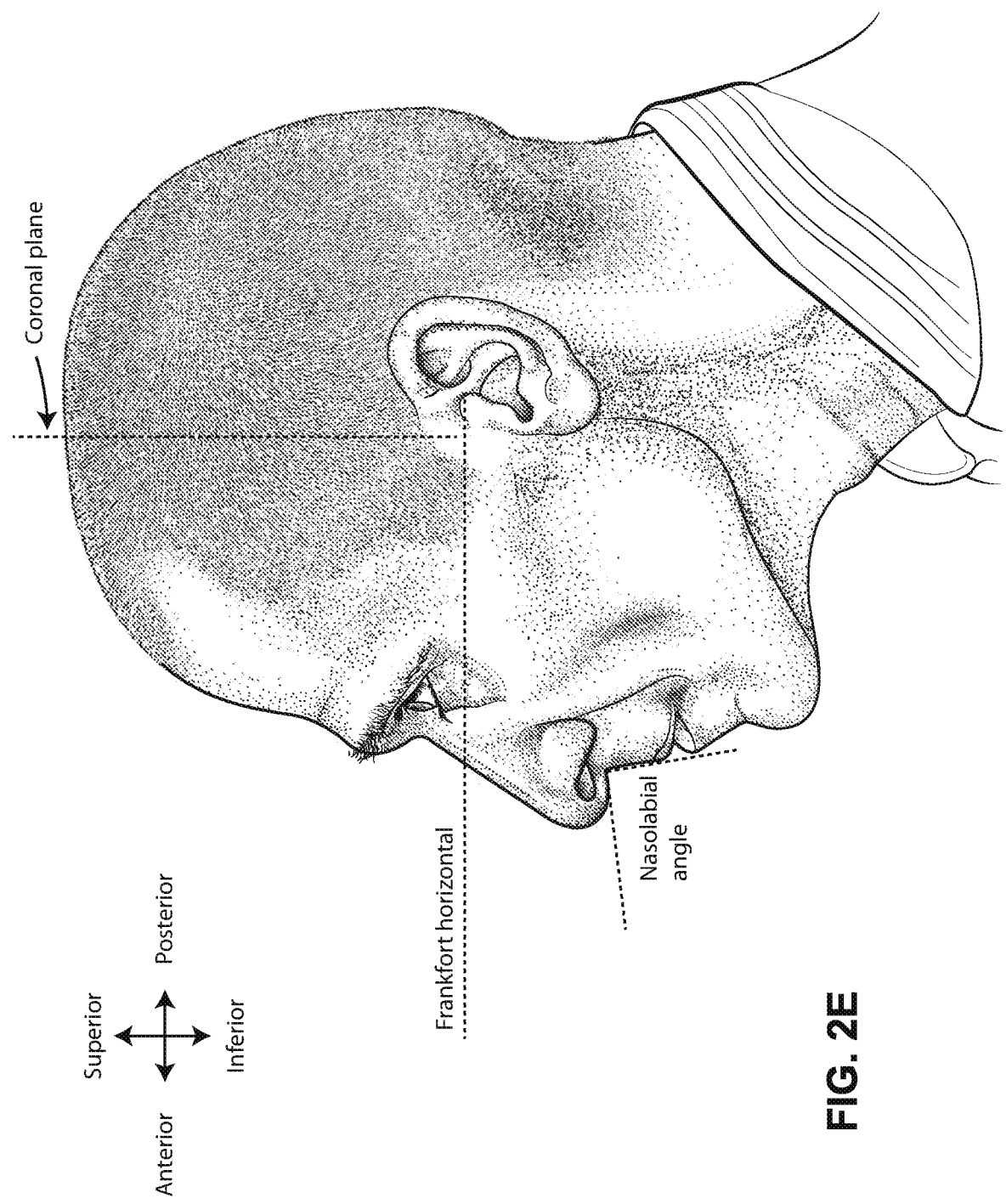

FIG. 2E is a further side view of a head. The approximate locations of the Frankfort horizontal and nasolabial angle are indicated. The coronal plane is also indicated.

Figure 2F:
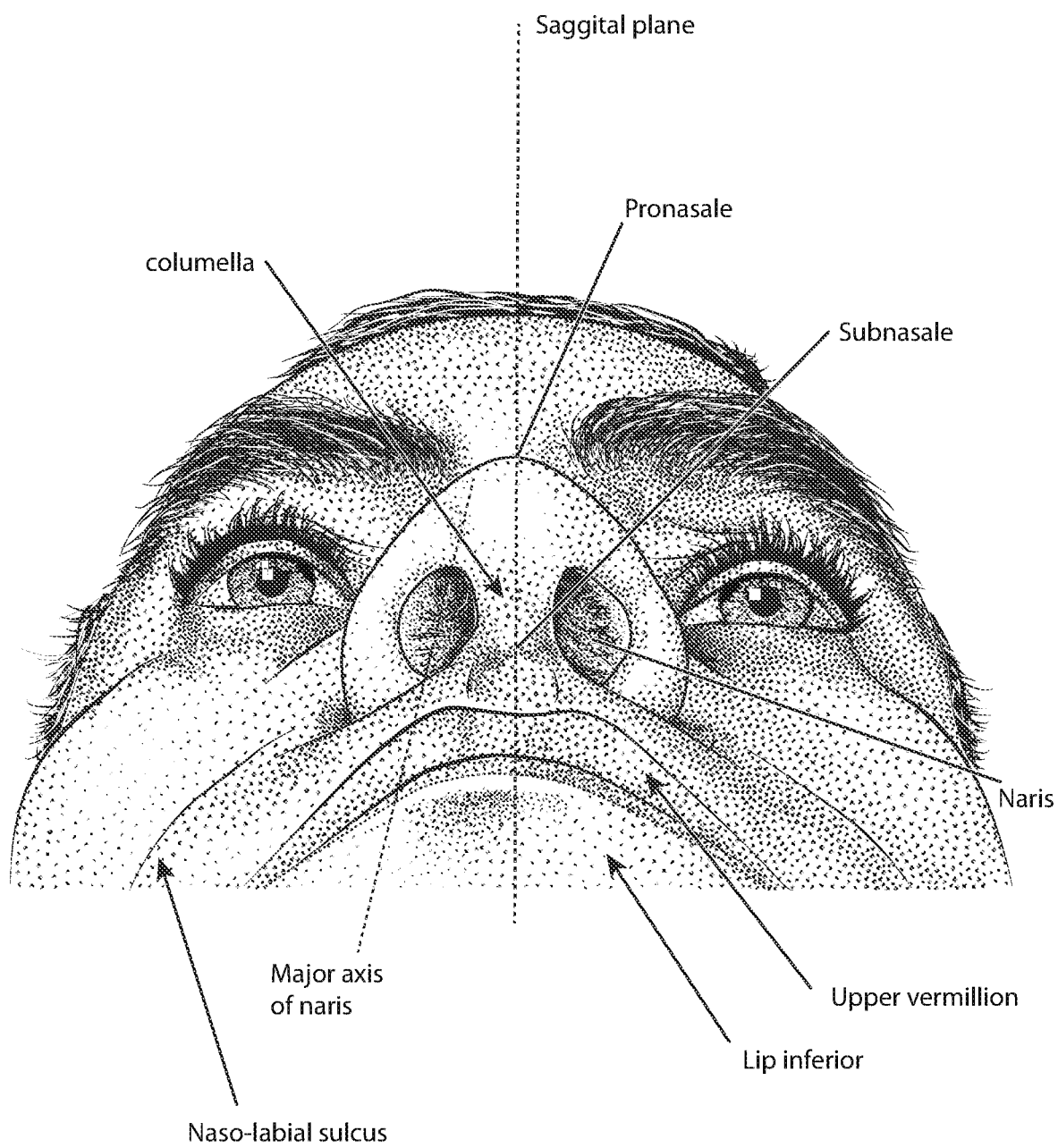

FIG. 2F shows a base view of a nose with several features identified including naso-labial sulcus, lip inferior, upper Vermilion, naris, subnasale, columella, pronasale, the major axis of a naris and the sagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from a sagittal plane, amongst other things showing the septum cartilage and medial crus of greater alar cartilage.

Figures 2J, 2K:
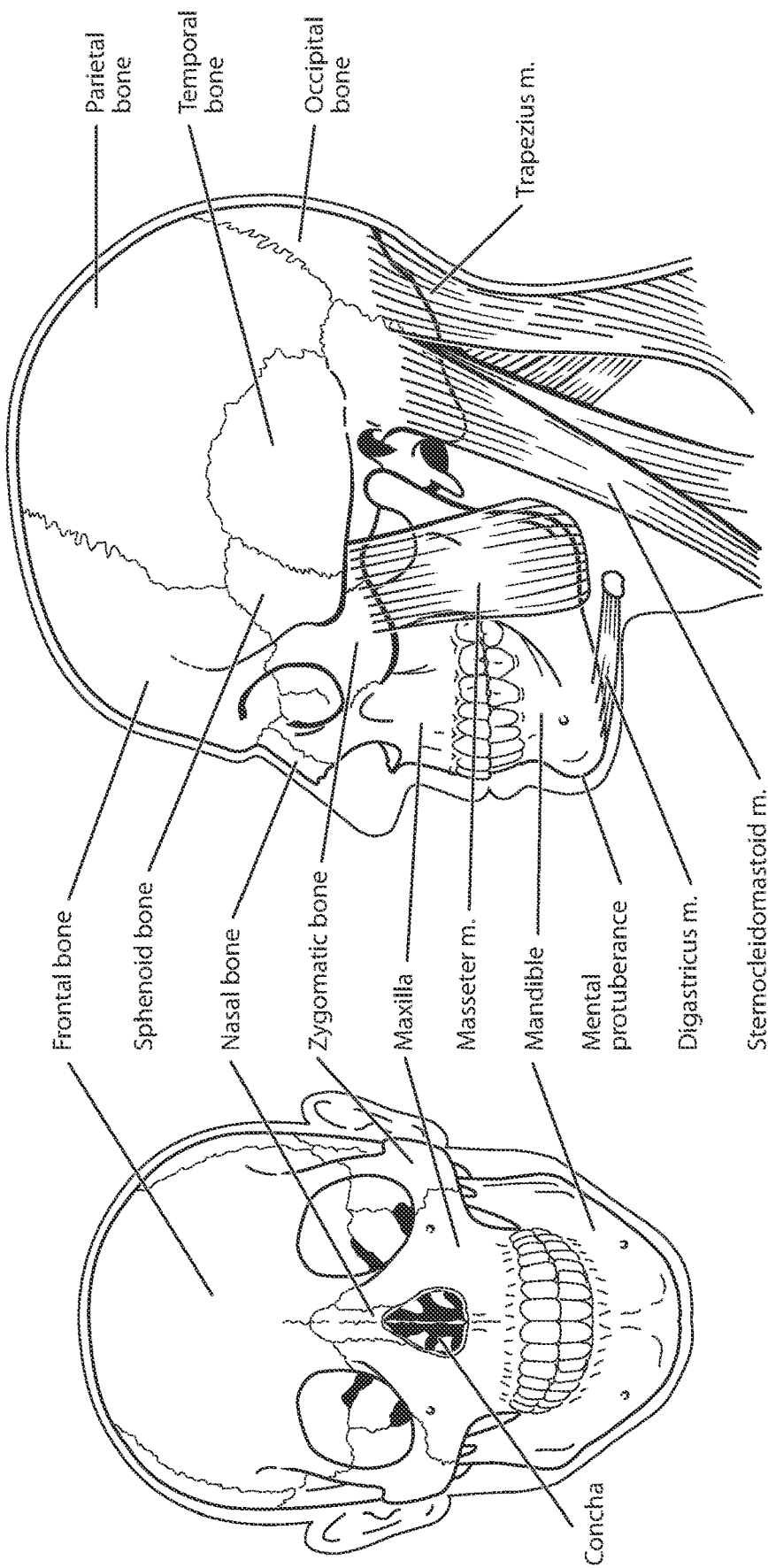

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
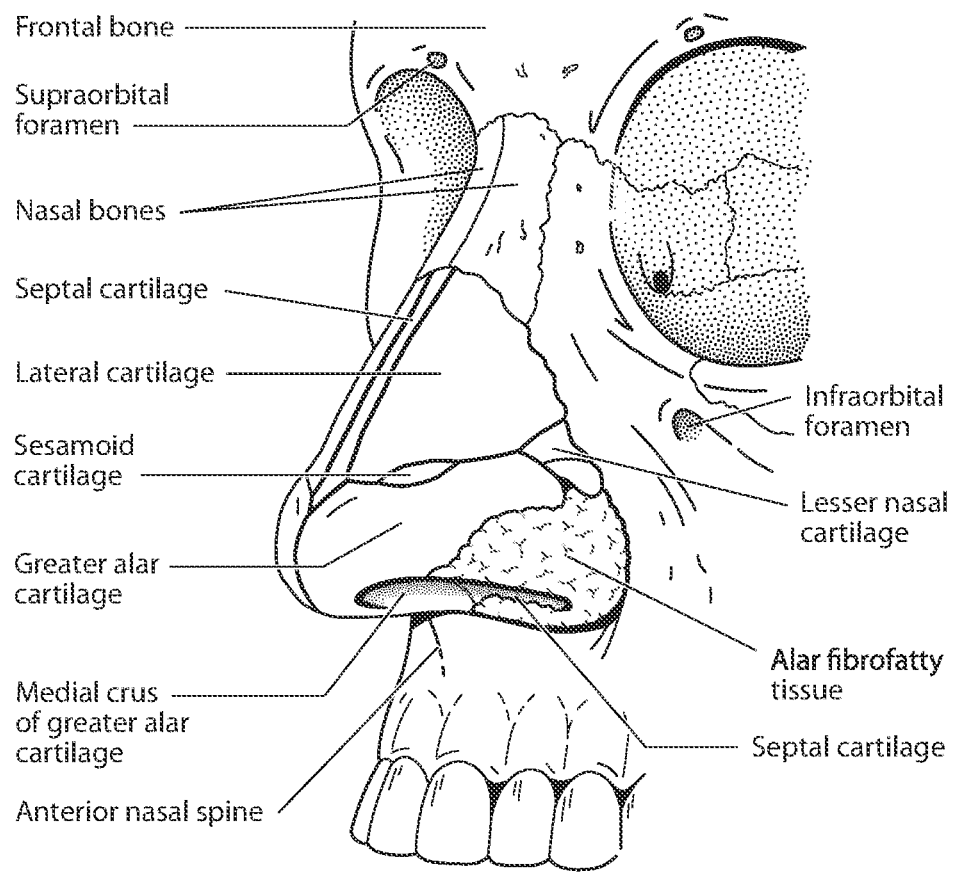

FIG. 2L shows an anterolateral view of a nose.

4.3 Patient Interface

Figure 3A:
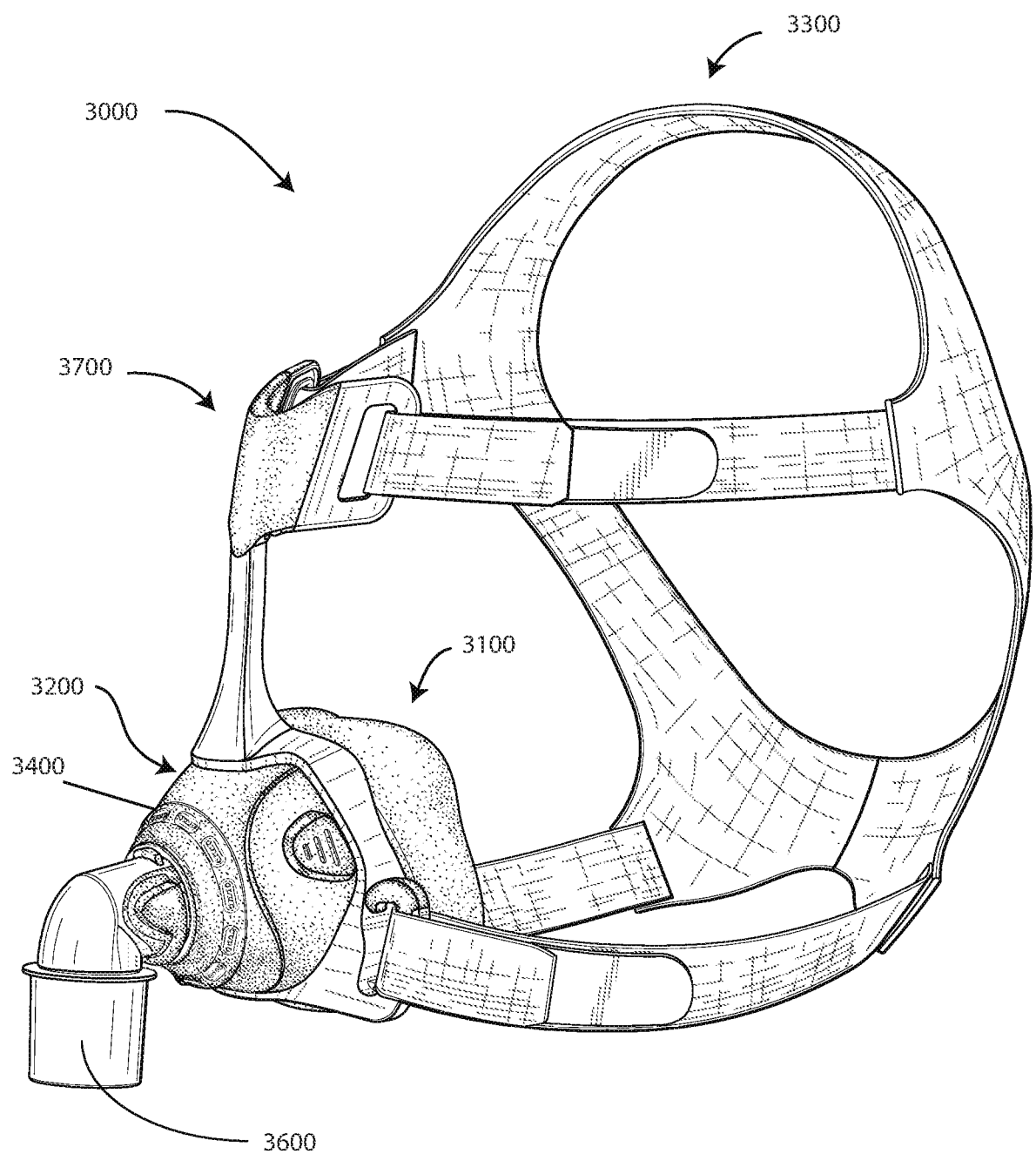

FIG. 3A shows a patient interface in the form of a nasal mask in accordance with one form of the present technology.

Figure 3B:
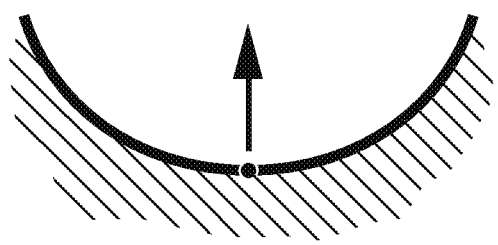

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
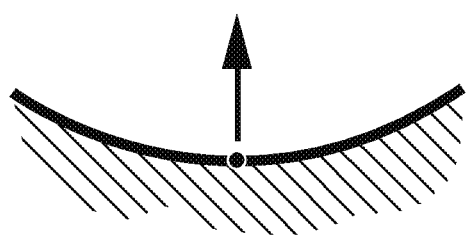

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
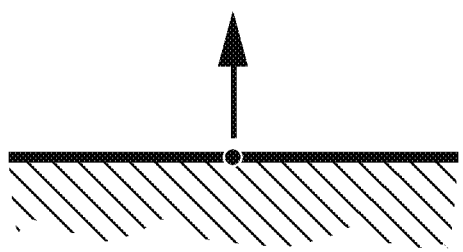

FIG. 3D shows a schematic of a cross-section through a structure at a point. An outward normal at the point is indicated. The curvature at the point has a value of zero.

Figure 3E:
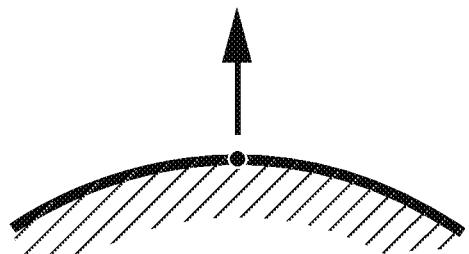

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
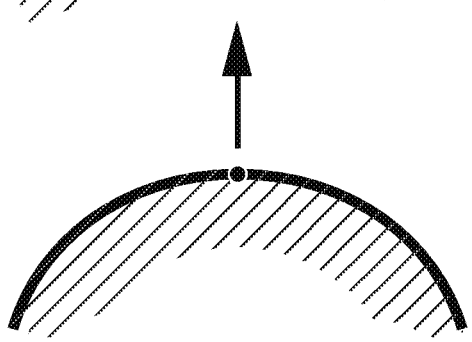

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
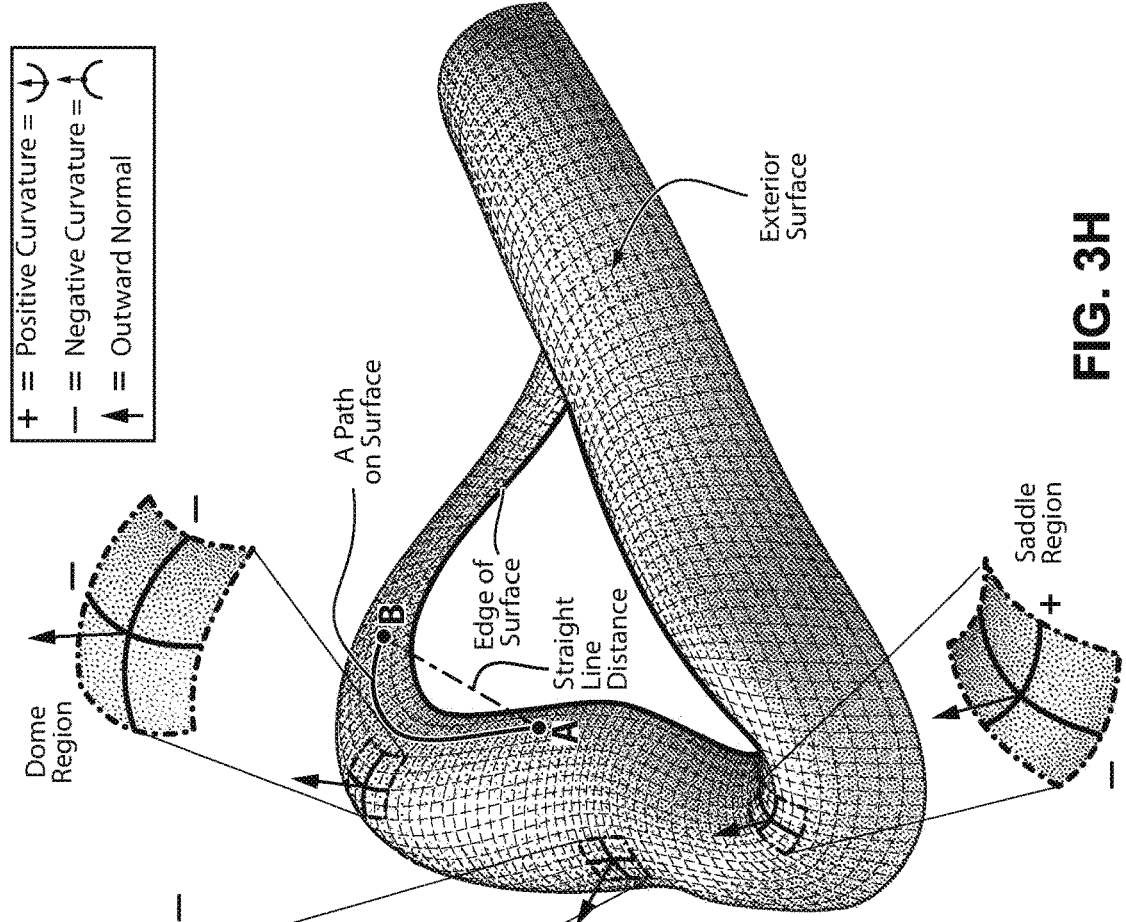
Figure 3G:
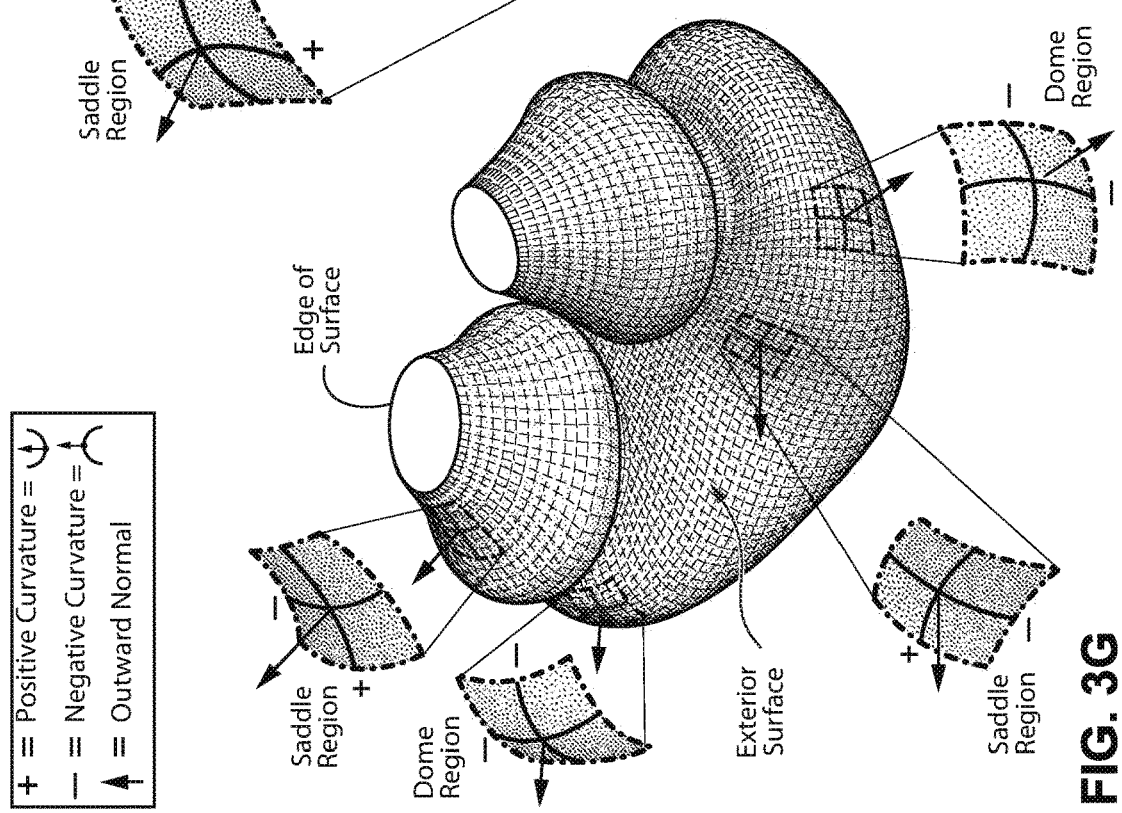

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

FIG. 3I shows the surface of a structure, with a one dimensional hole in the surface. The illustrated plane curve forms the boundary of a one dimensional hole.

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

FIG. 3L shows a mask having an inflatable bladder as a cushion.

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

Figure 3T:
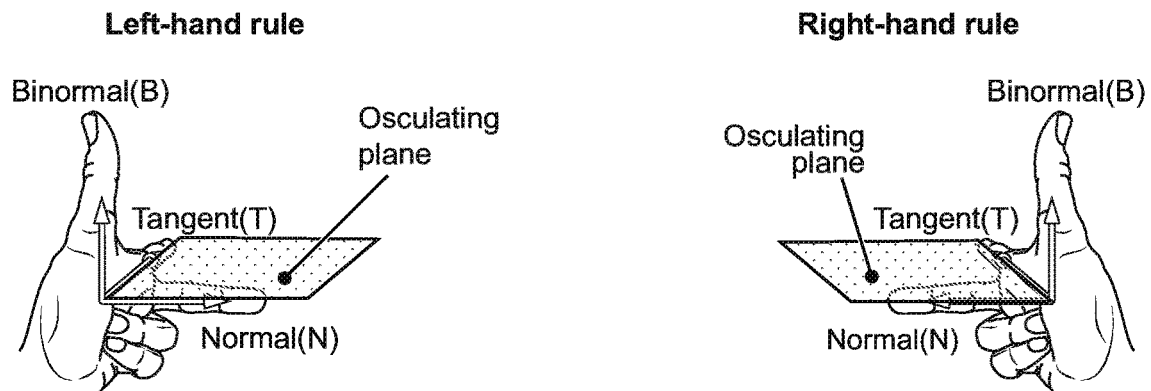
Figure 3T:
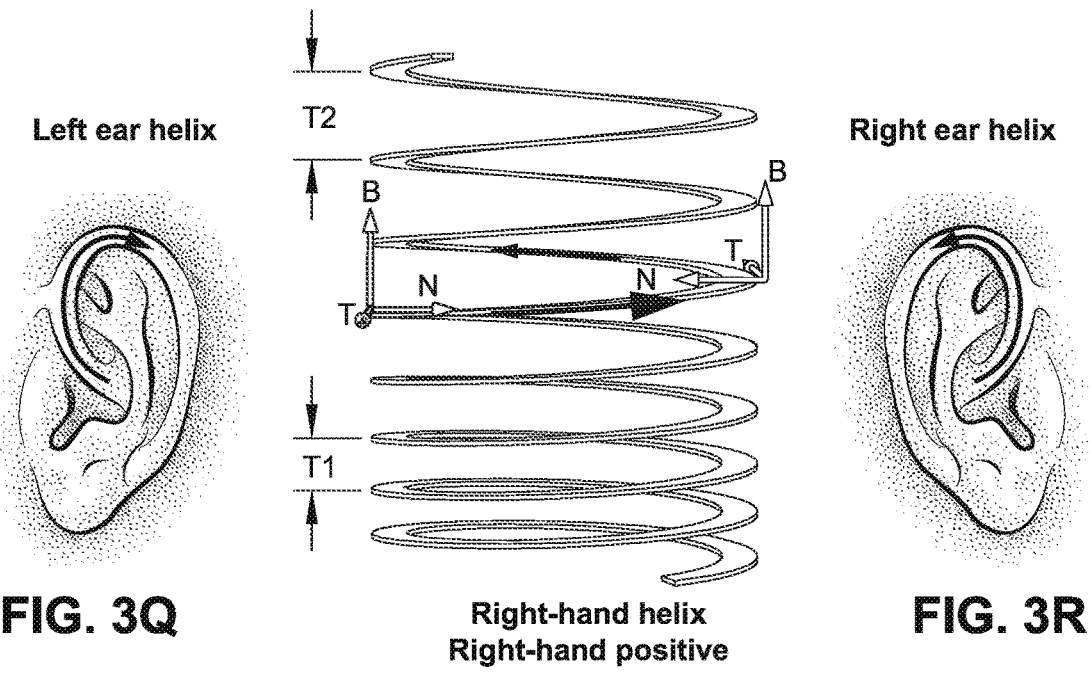
Figure 3T:
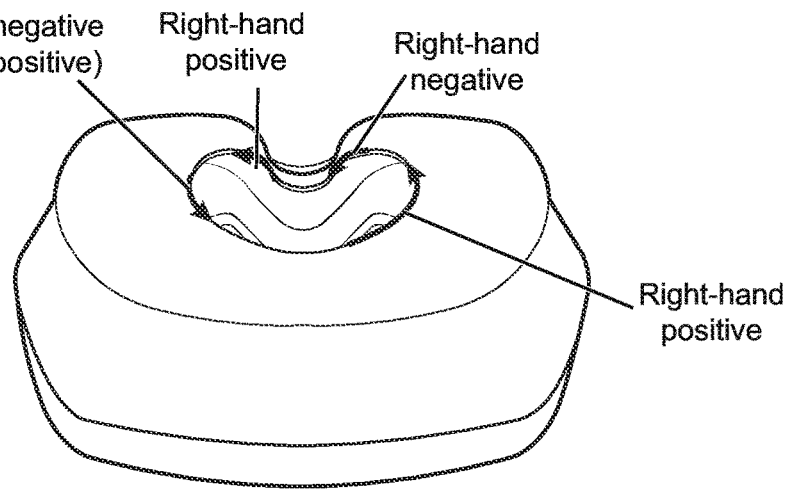

FIG. 3T shows a view of a mask, including the sign of the torsion of the space curve defined by the edge of the sealing membrane in different regions of the mask.

4.4 RPT Device

Figure 4A:
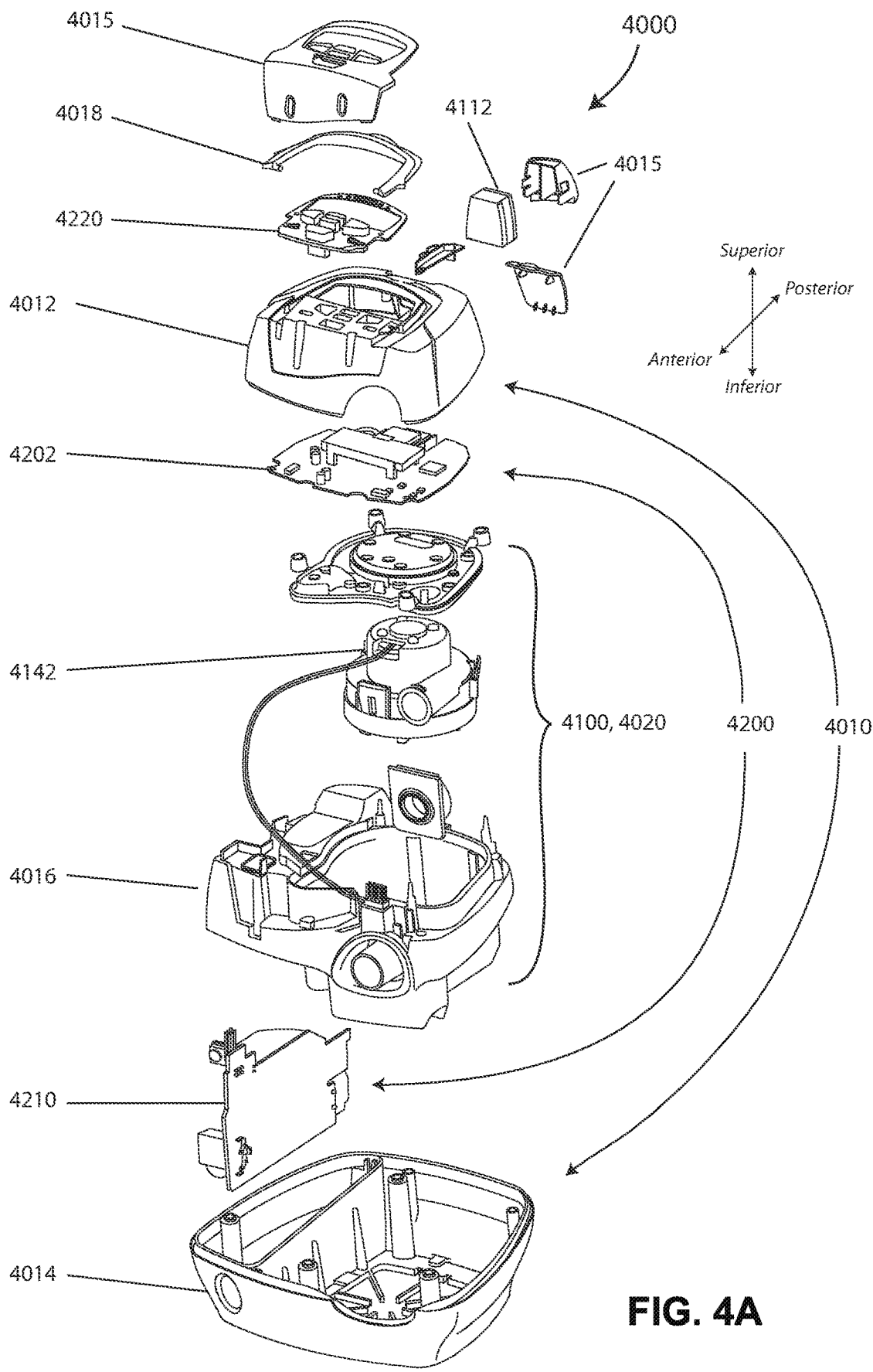

FIG. 4A shows an RPT device in accordance with one form of the present technology.

Figure 4B:
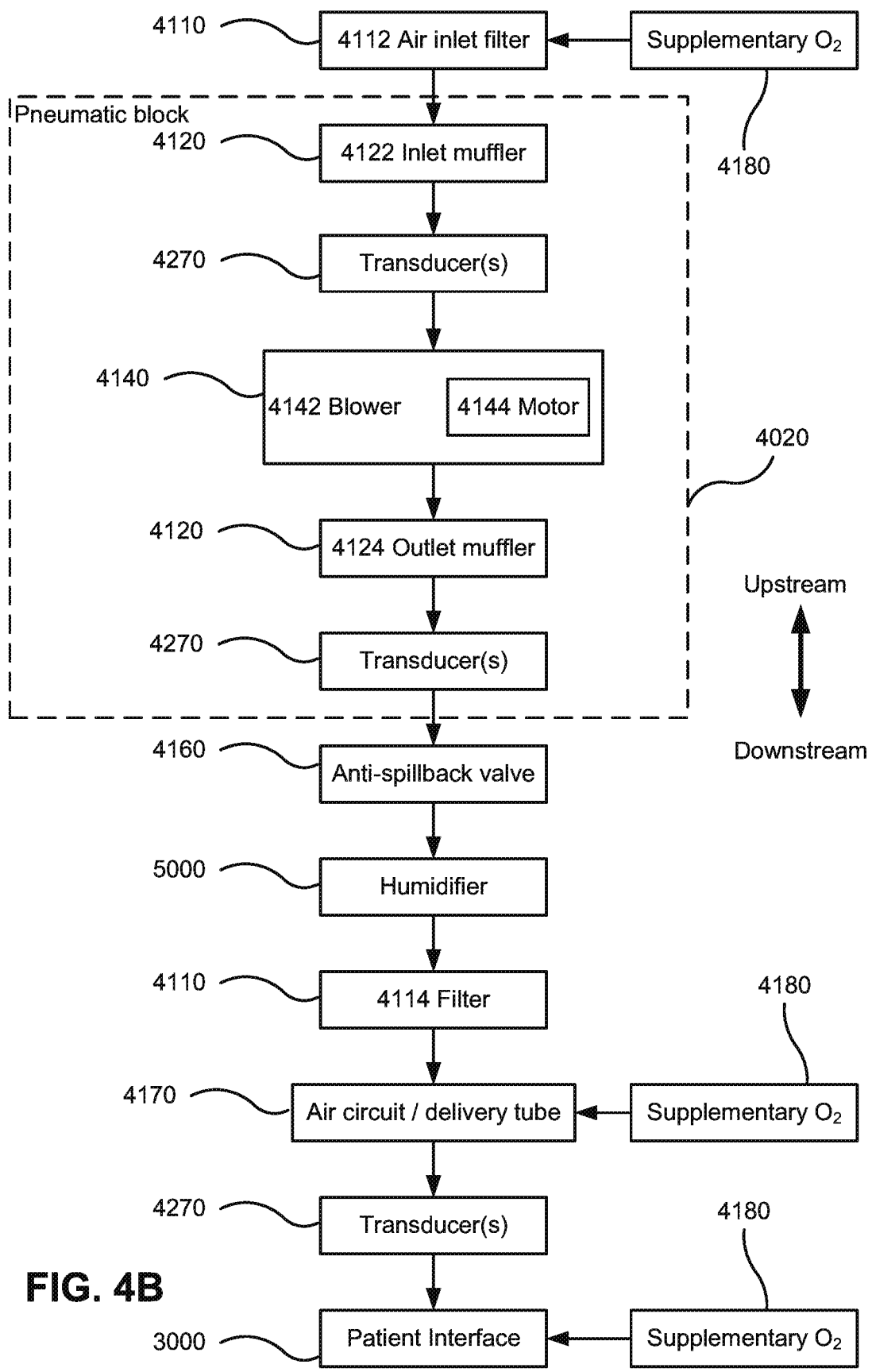

FIG. 4B is a schematic diagram of the pneumatic path of an RPT device in accordance with one form of the present technology. The directions of upstream and downstream are indicated.

4.5 Humidifier

Figure 5A:
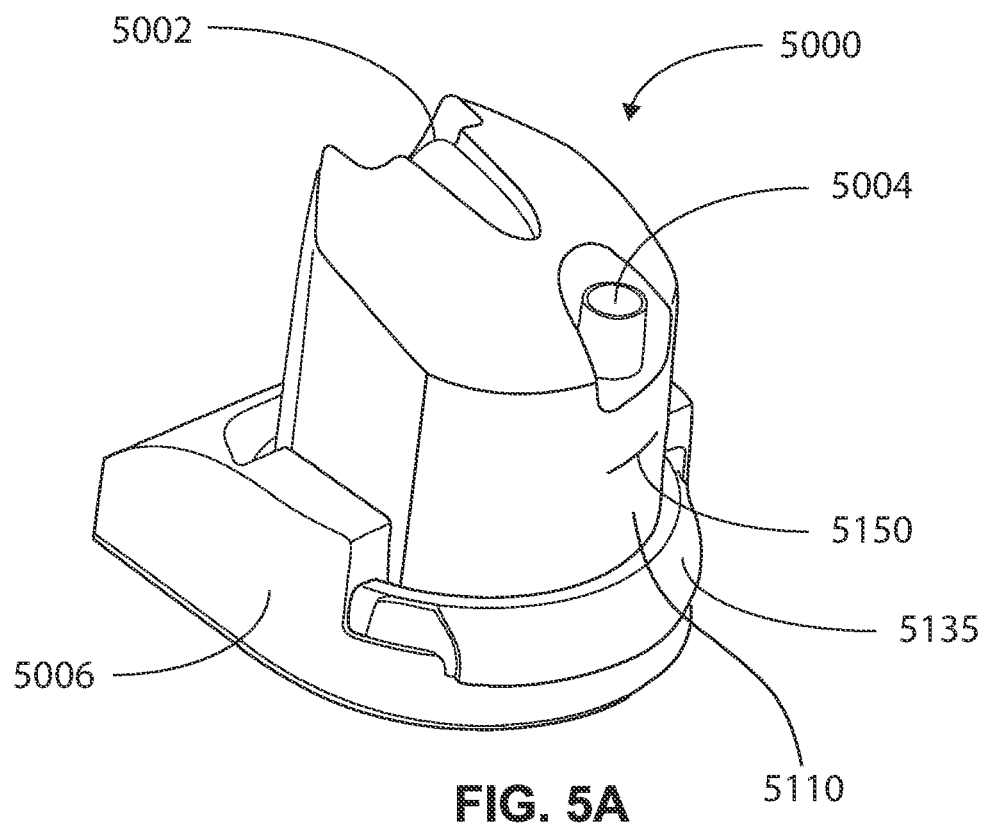

FIG. 5A shows an isometric view of a humidifier in accordance with one form of the present technology.

Figure 5B:
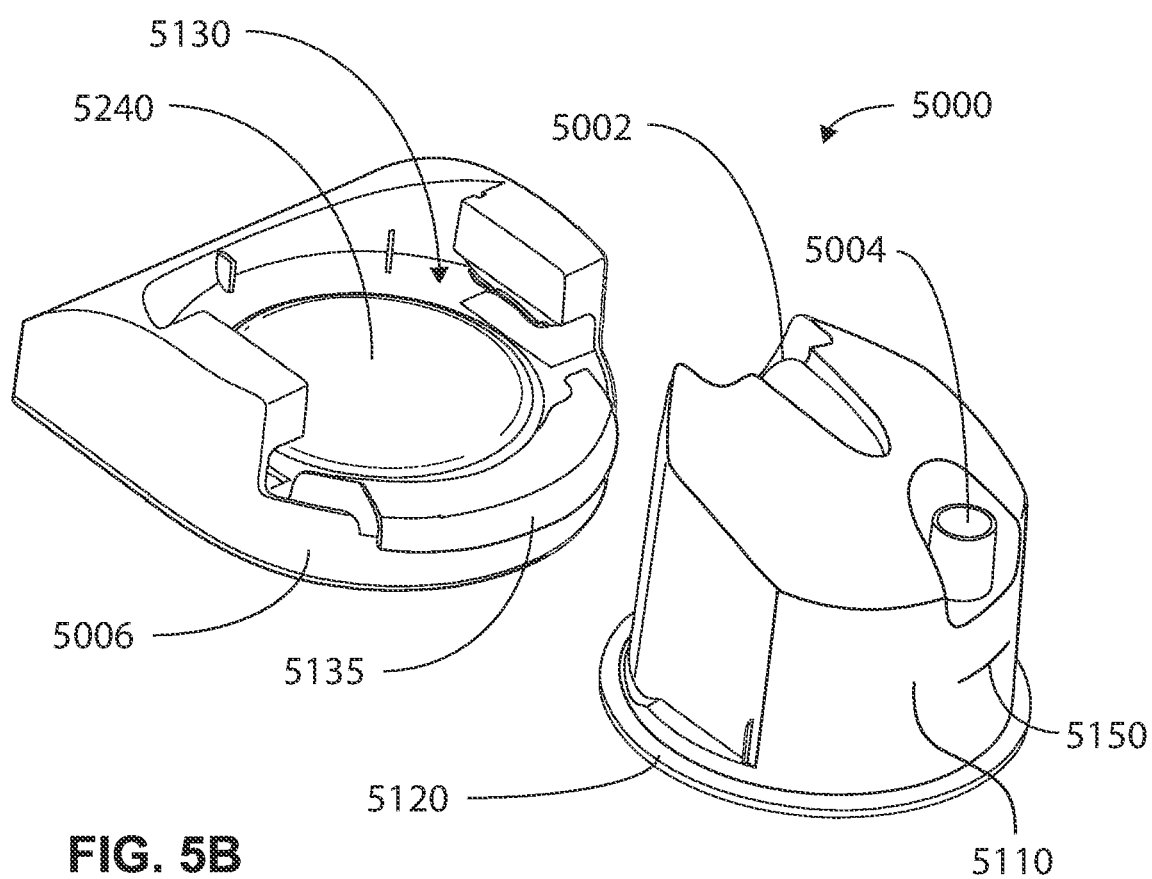

FIG. 5B shows an isometric view of a humidifier in accordance with one form of the present technology, showing a humidifier reservoir 5110 removed from the humidifier reservoir dock 5130.

4.6 Patient Interface of the Present Technology

Figure 6A:
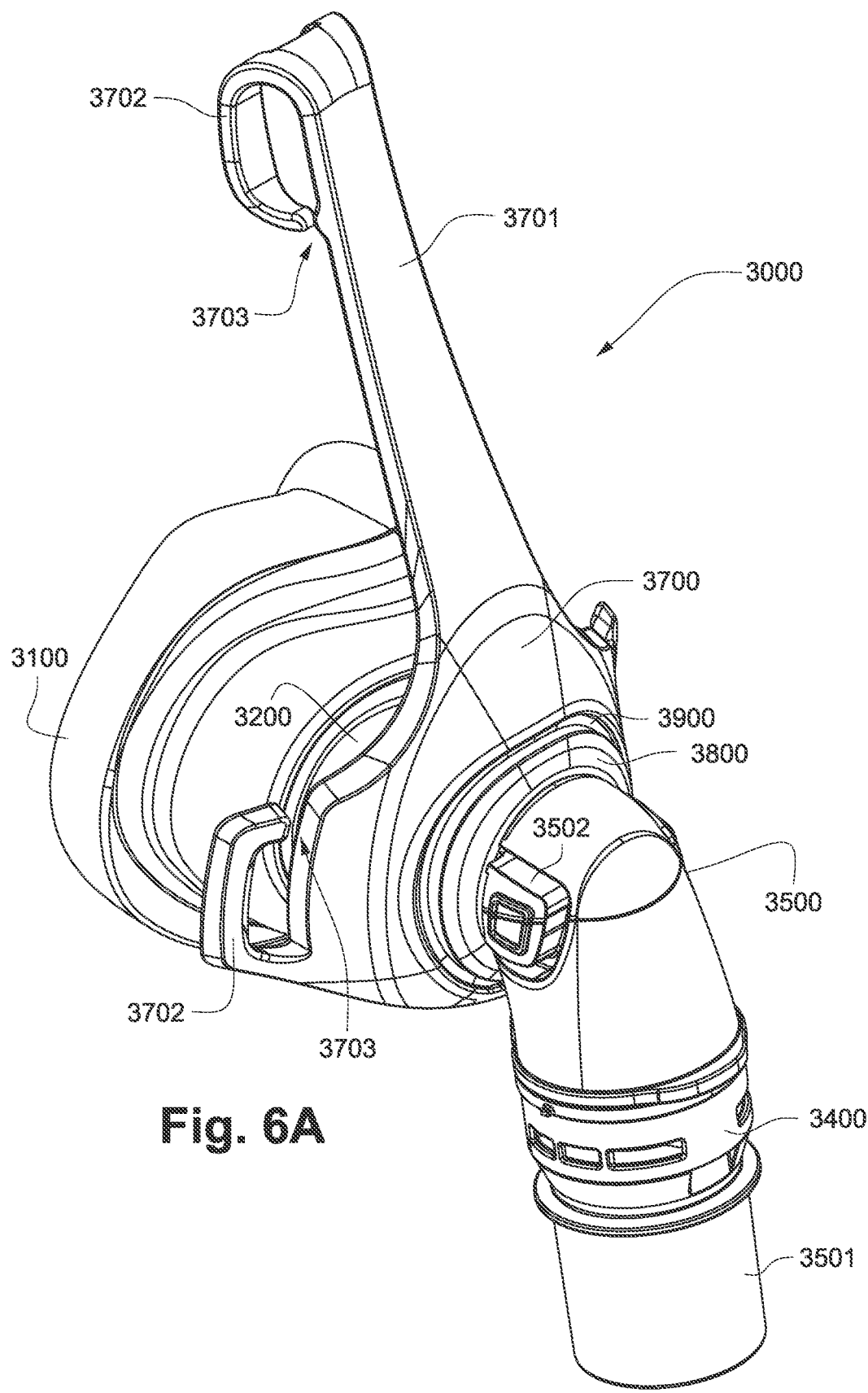

FIG. 6A depicts an anterior perspective view of a patient interface according to an example of the present technology.

Figure 6B:
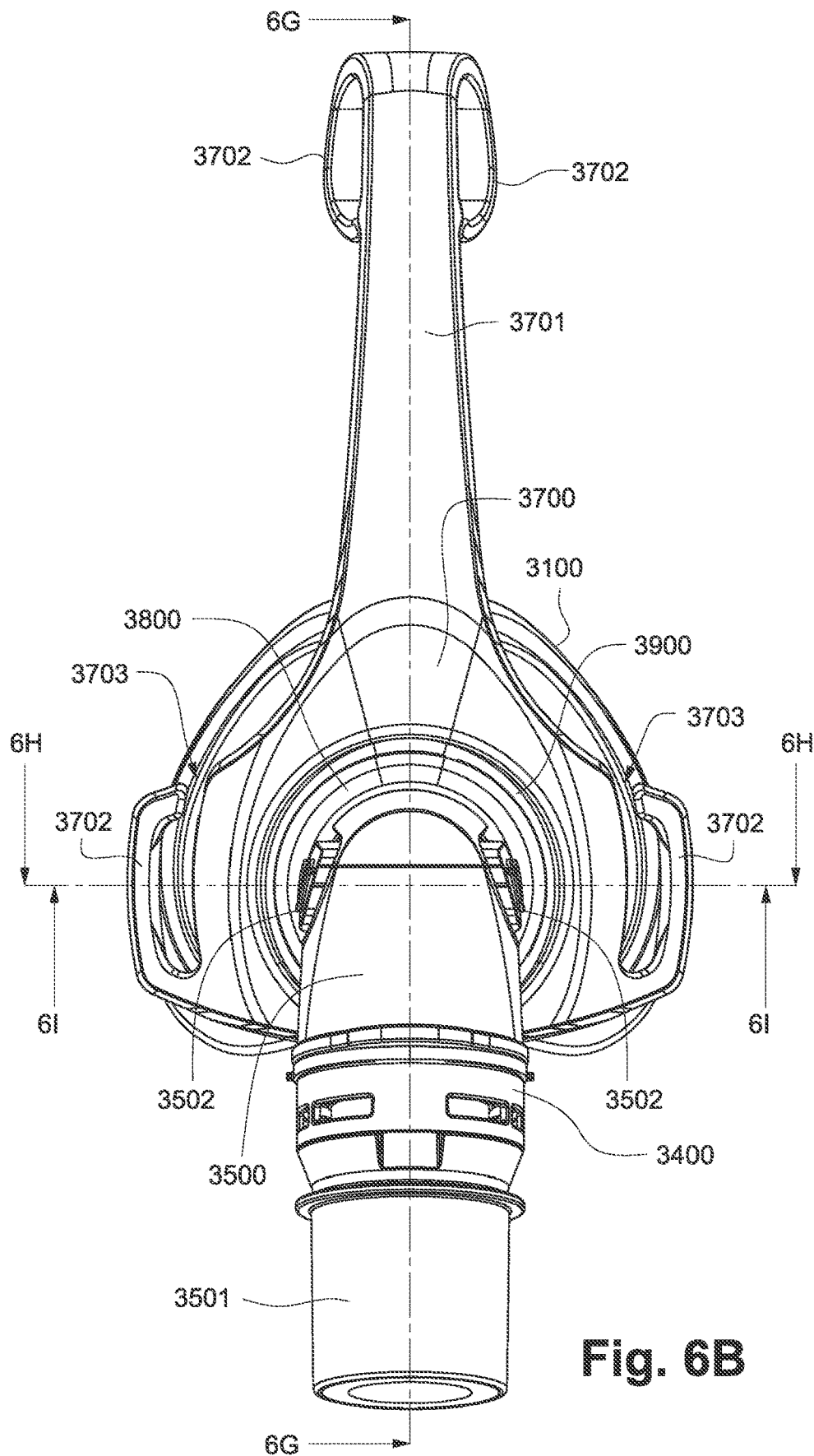

FIG. 6B depicts an anterior view of a patient interface according to an example of the present technology.

Figure 6C:
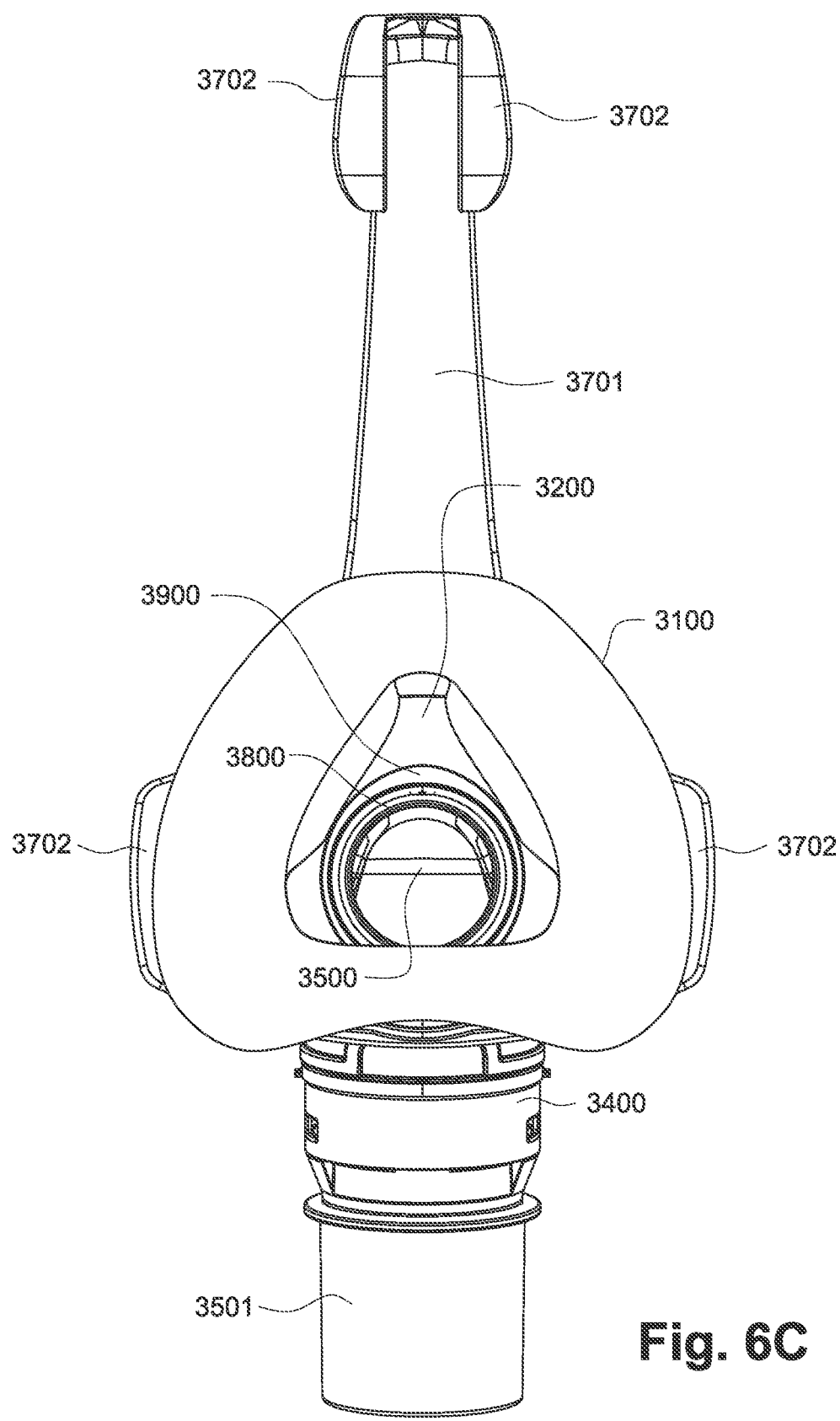

FIG. 6C depicts a posterior view of a patient interface according to an example of the present technology.

Figure 6D:
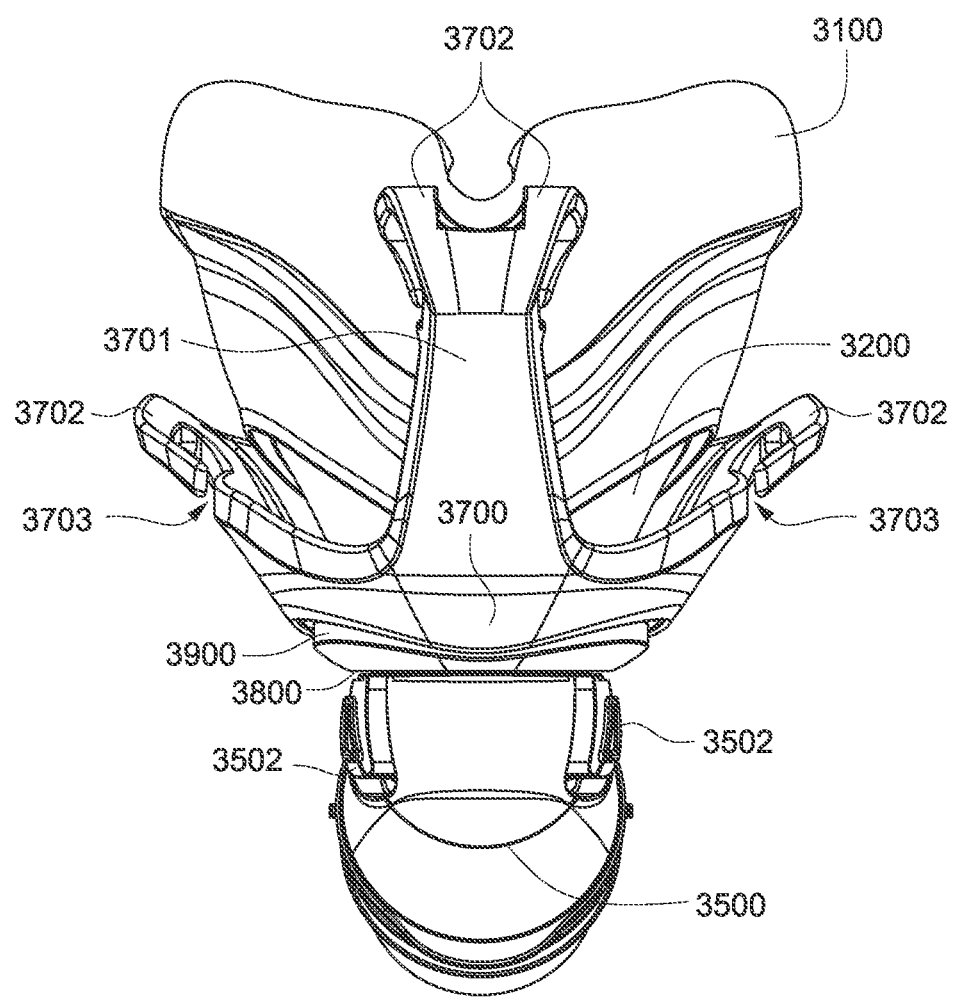

FIG. 6D depicts a superior view of a patient interface according to an example of the present technology.

Figure 6E:
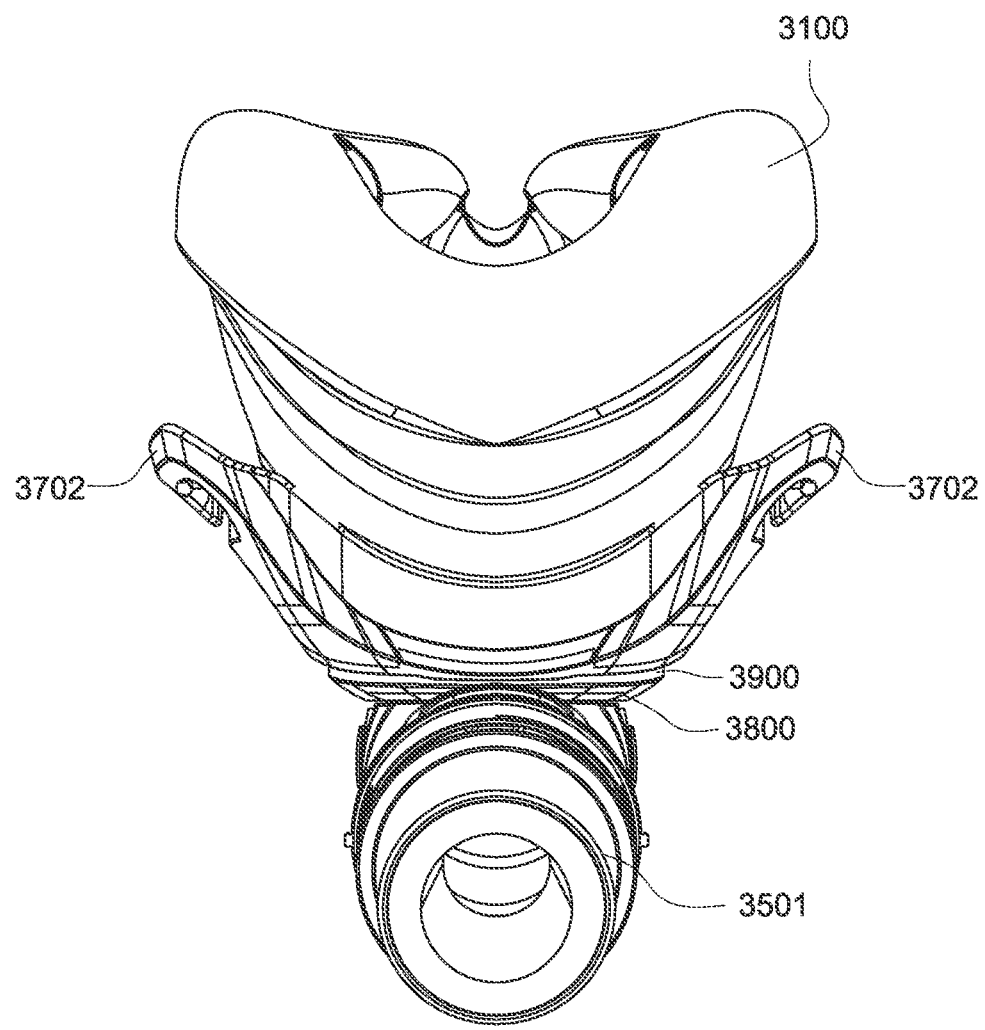

FIG. 6E depicts an inferior view of a patient interface according to an example of the present technology.

Figure 6F:
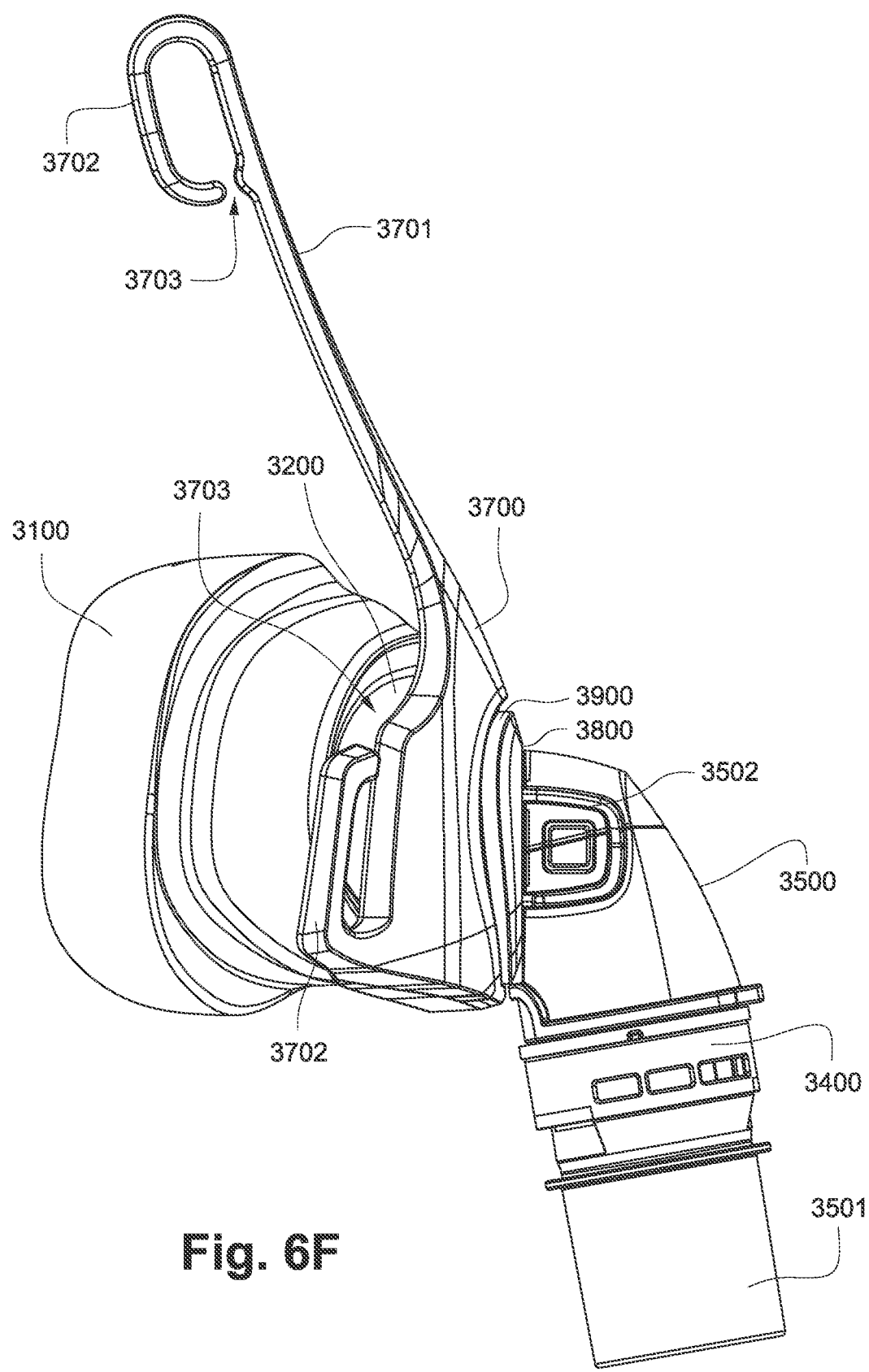

FIG. 6F depicts a lateral view of a patient interface according to an example of the present technology.

Figure 6G:
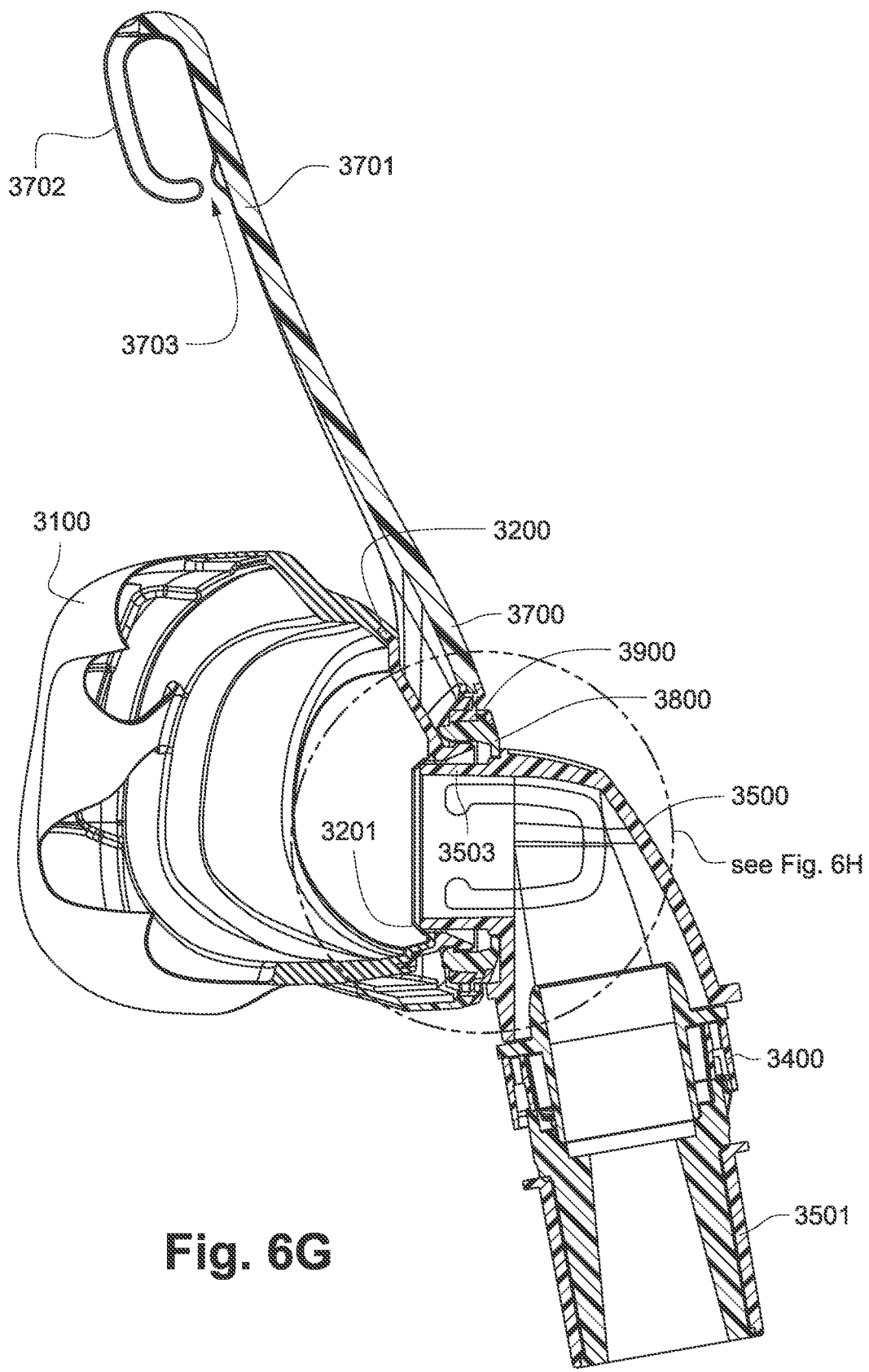

FIG. 6G depicts a cross-sectional view of a patient interface taken through line 6G-6G of FIG. 6B according to an example of the present technology.

Figure 6H:
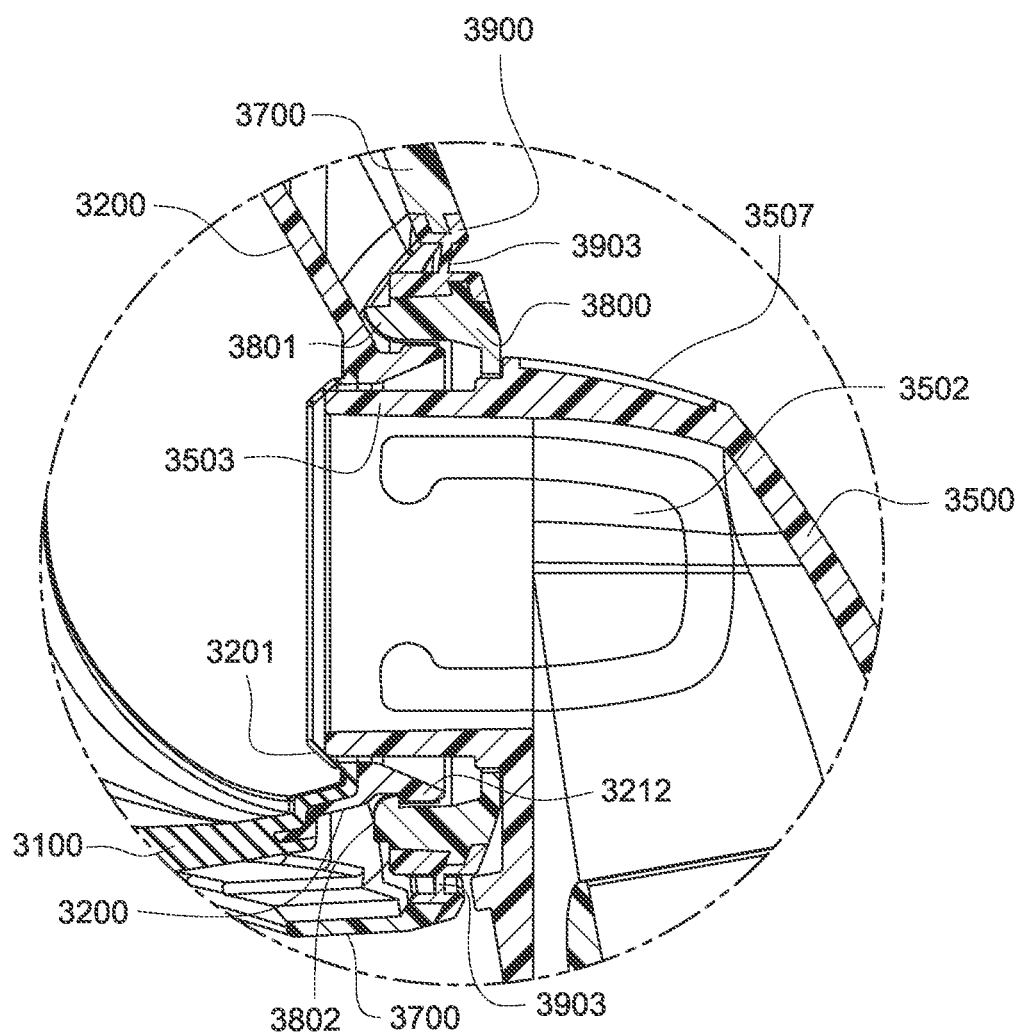

FIG. 6H depicts a detailed view of a portion of a patient interface depicted in FIG. 6G according to an example of the present technology.

Figure 6I:
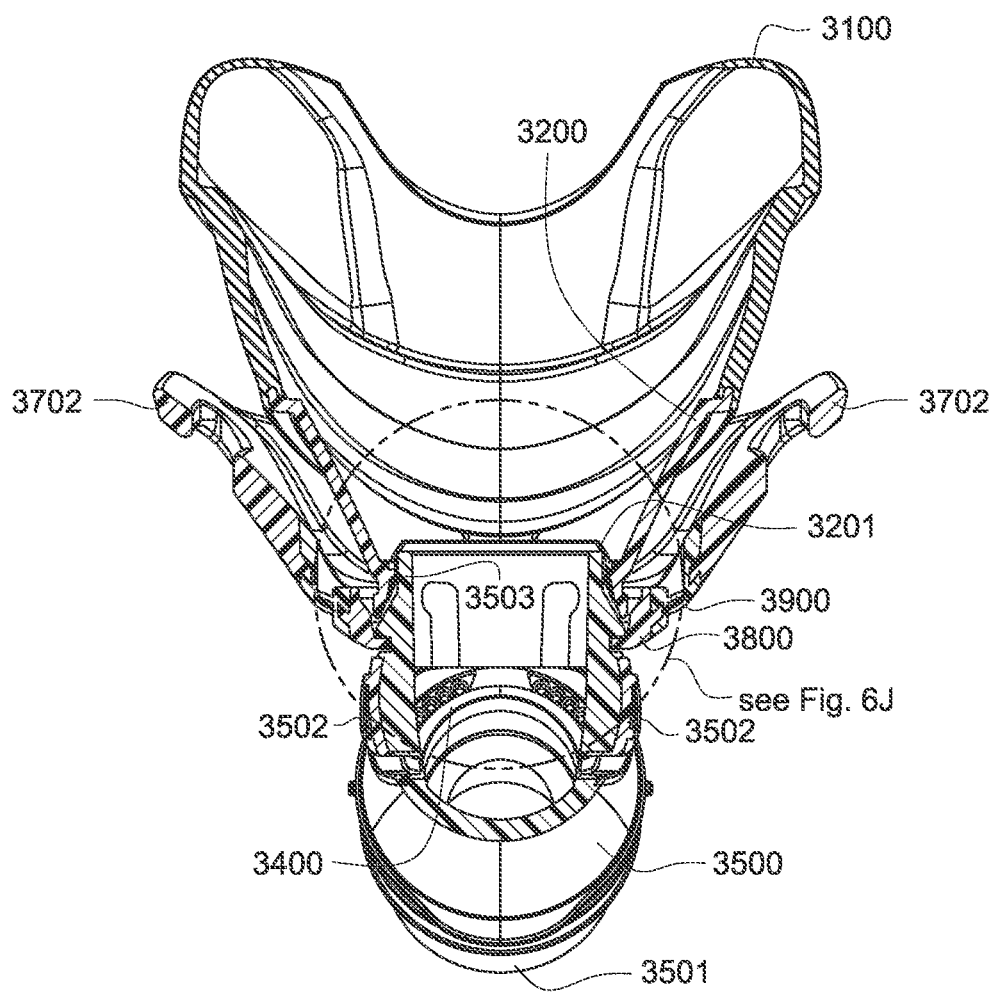

FIG. 6I depicts a cross-sectional view of a patient interface taken through line 6I-6I of FIG. 6B according to an example of the present technology.

Figure 6J:
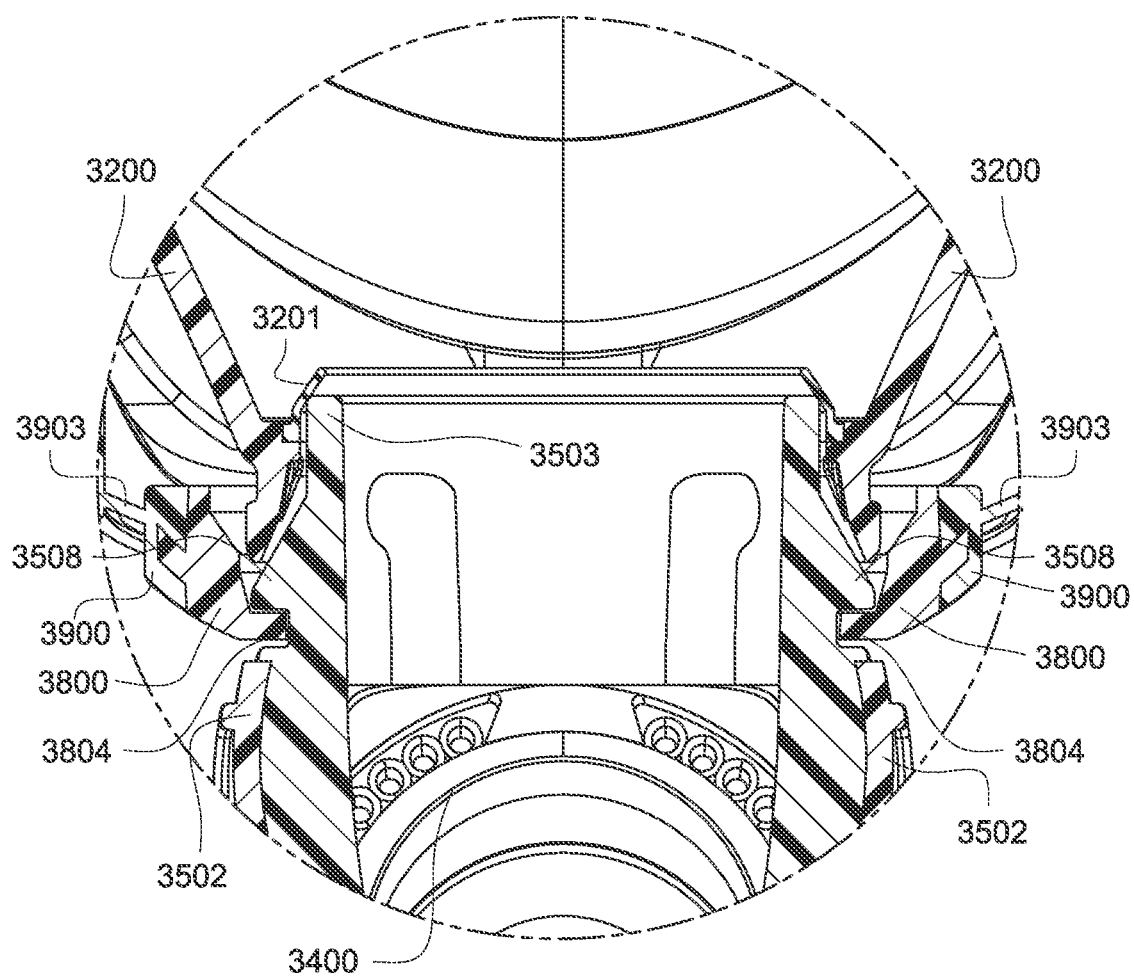

FIG. 6J depicts a detailed view of a portion of a patient interface depicted in FIG. 6I according to an example of the present technology.

Figure 6K:
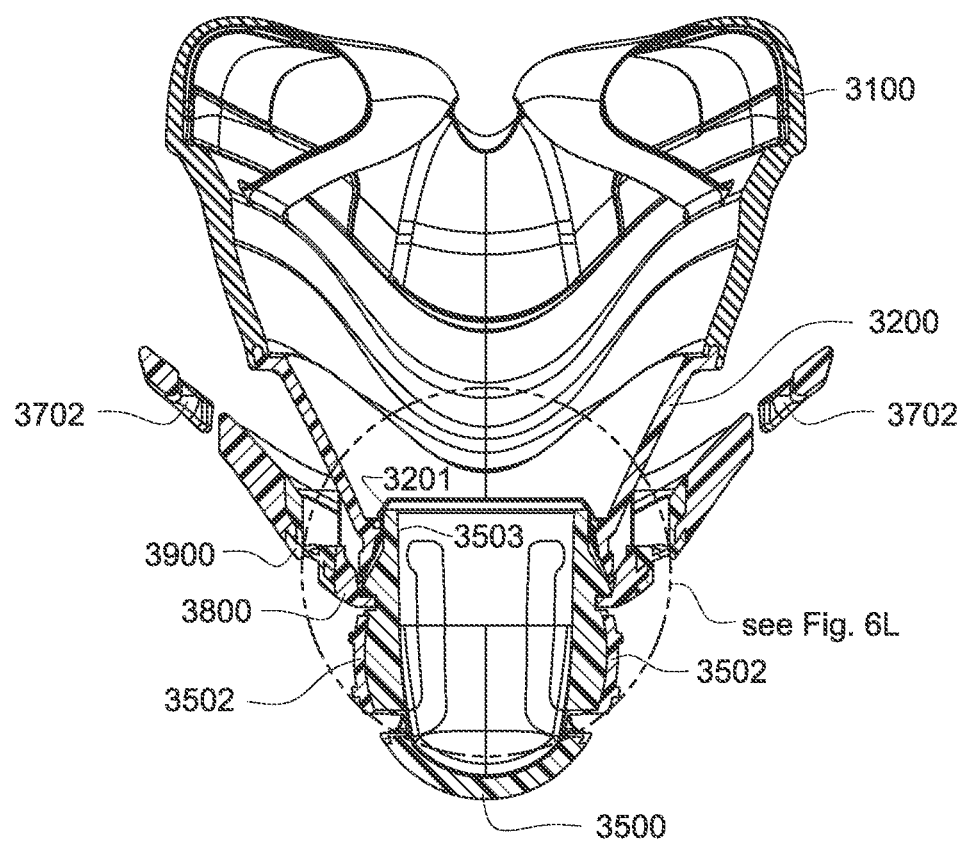

FIG. 6K depicts a cross-sectional view of a patient interface taken through line 6K-6K of FIG. 6B according to an example of the present technology.

Figure 6L:
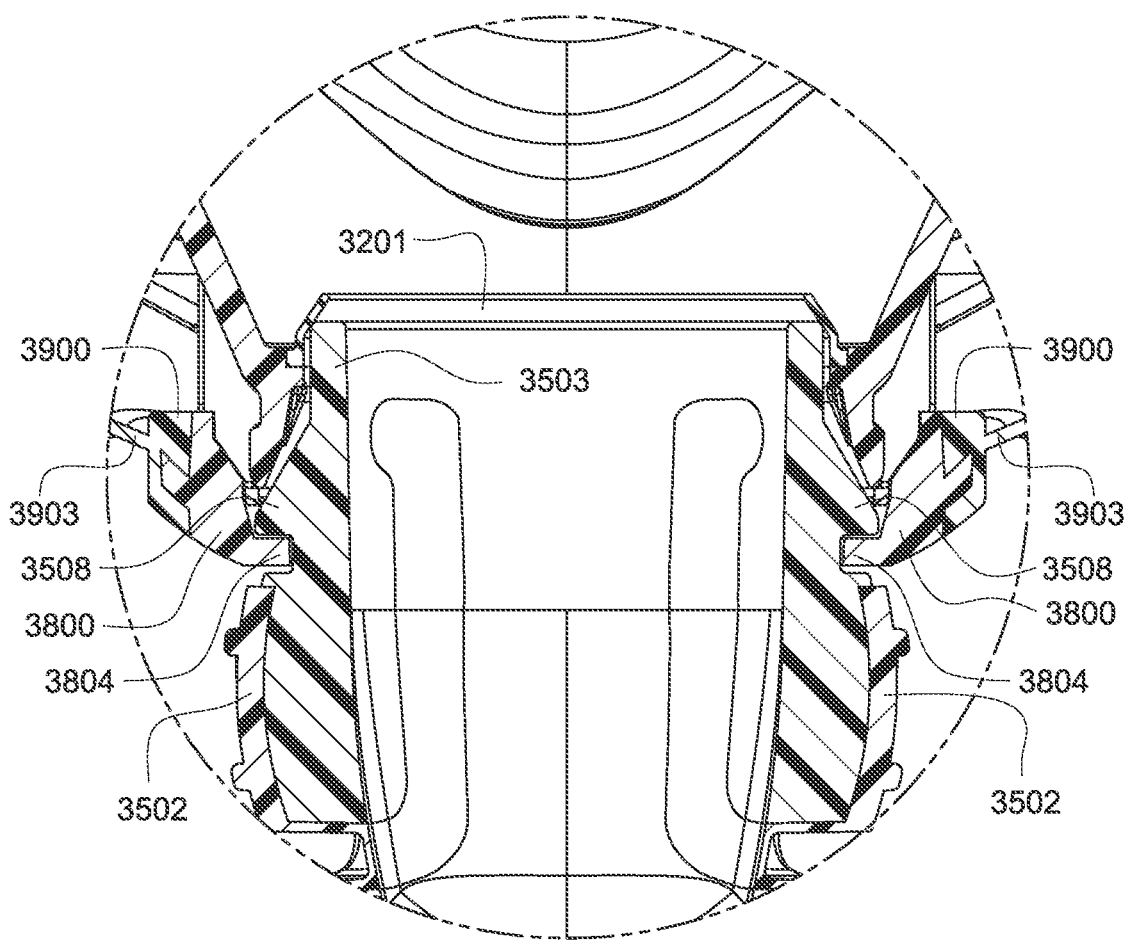

FIG. 6L depicts a detailed view of a portion of a patient interface depicted in FIG. 6K according to an example of the present technology.

Figure 6M:
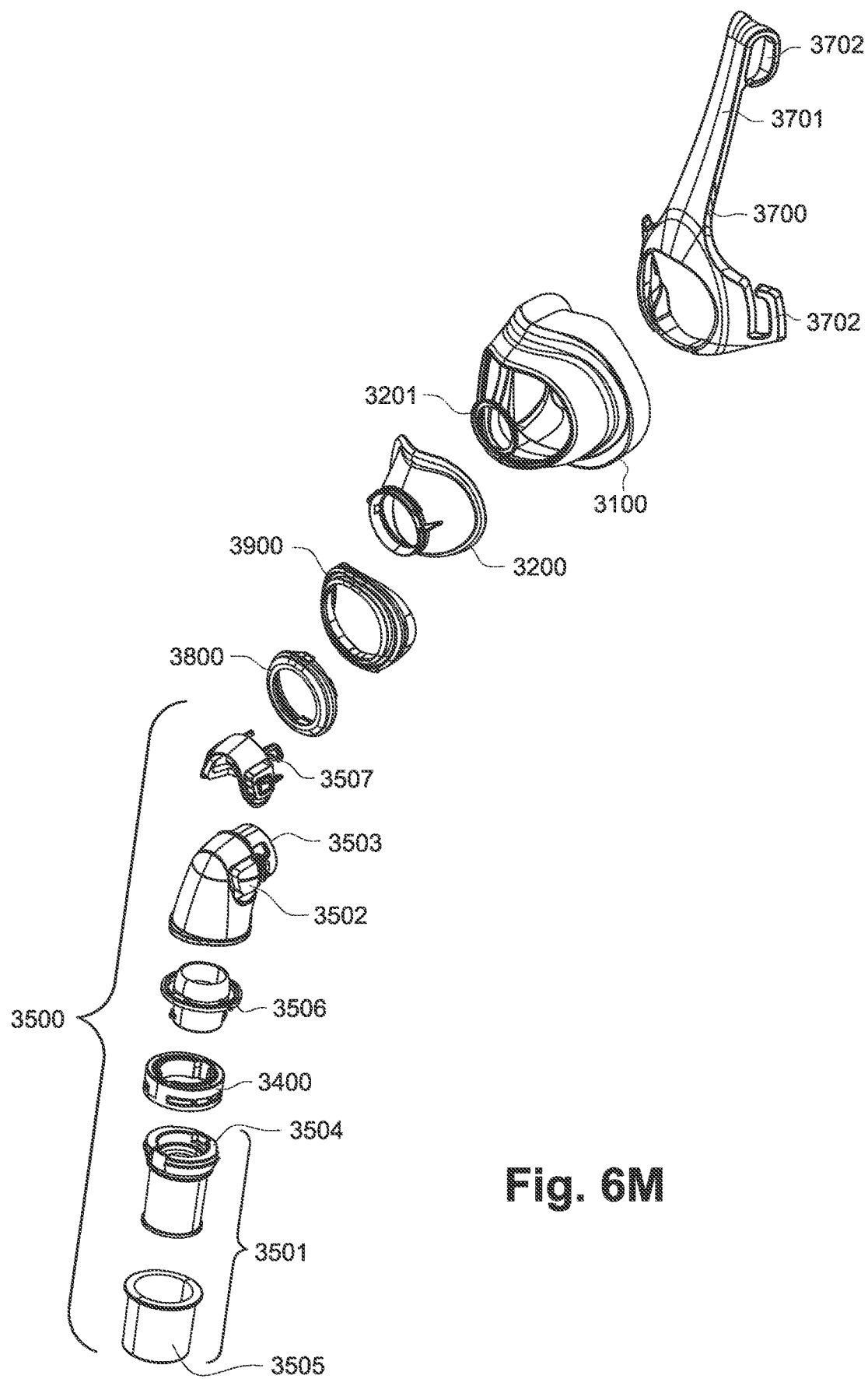

FIG. 6M depicts an exploded view of a patient interface according to an example of the present technology.

Figure 7A:
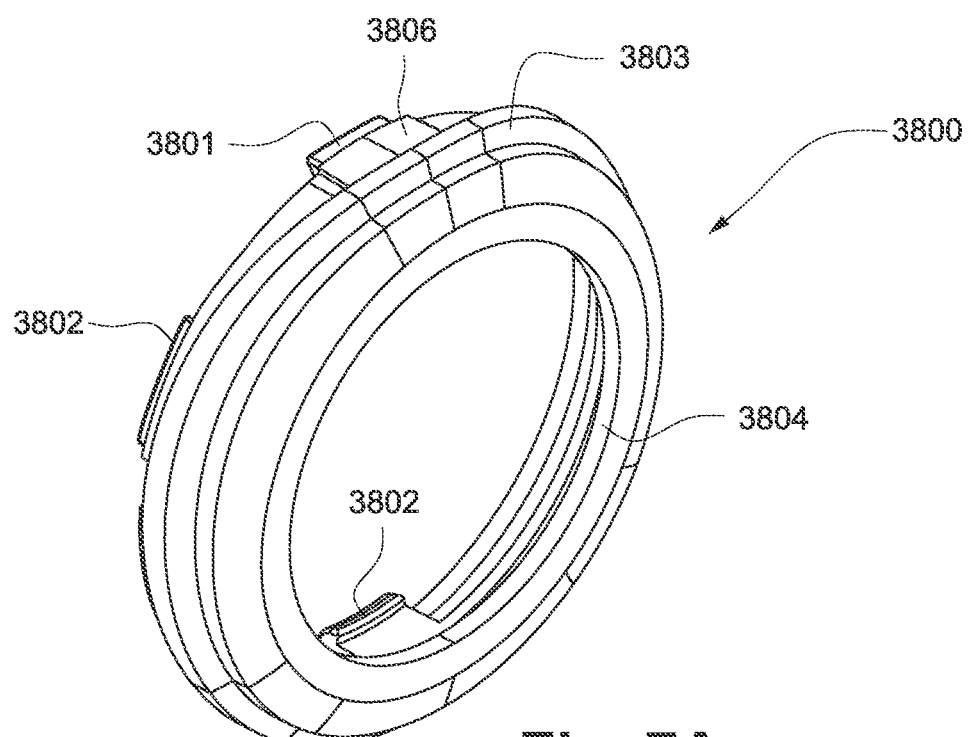

FIG. 7A depicts an anterior perspective view of a connector ring of a patient interface according to an example of the present technology.

Figure 7B:
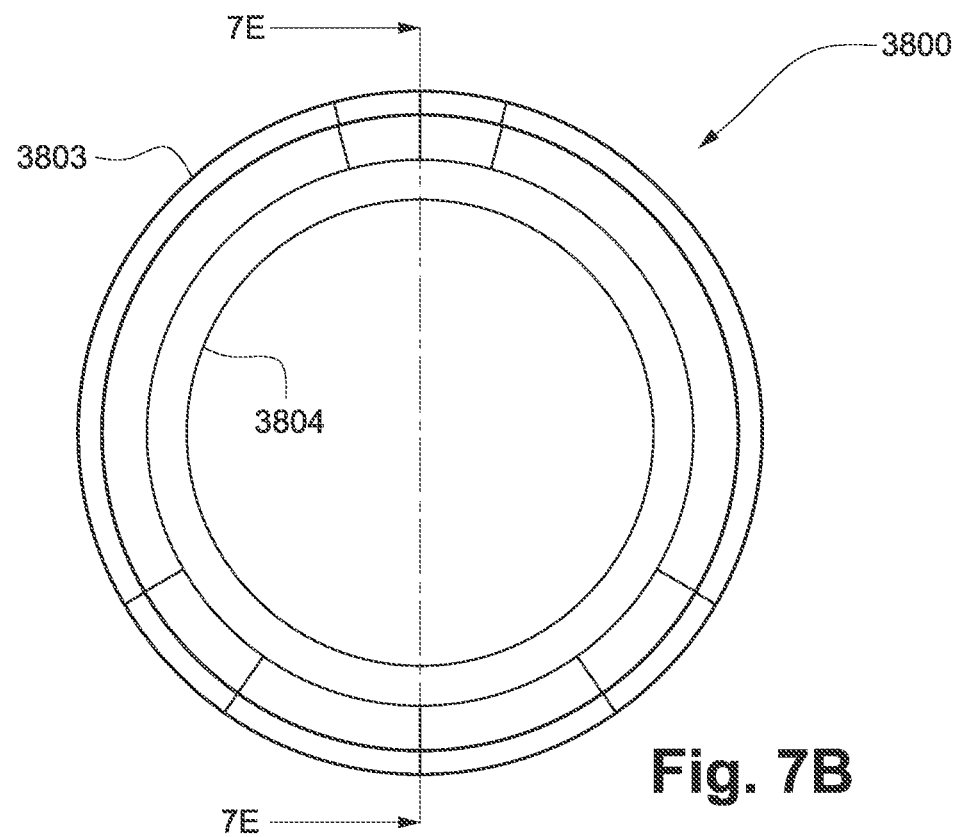

FIG. 7B depicts an anterior view of a connector ring of a patient interface according to an example of the present technology.

Figure 7C:
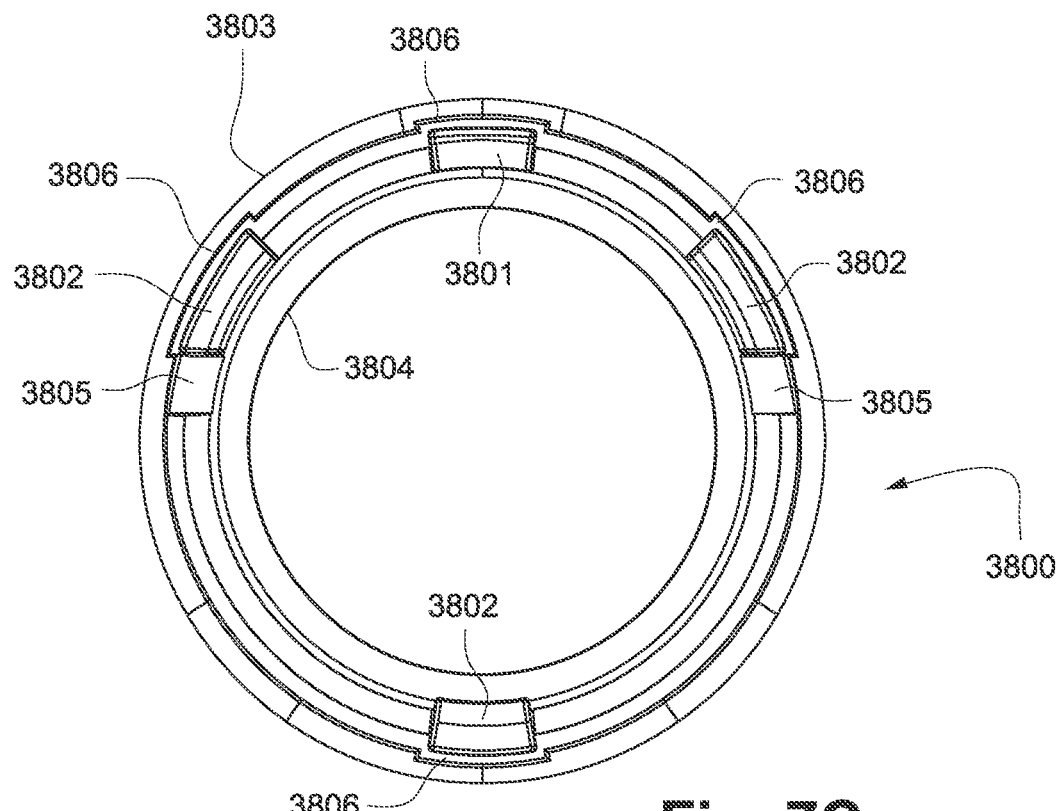

FIG. 7C depicts a posterior view of a connector ring of a patient interface according to an example of the present technology.

Figure 7D:
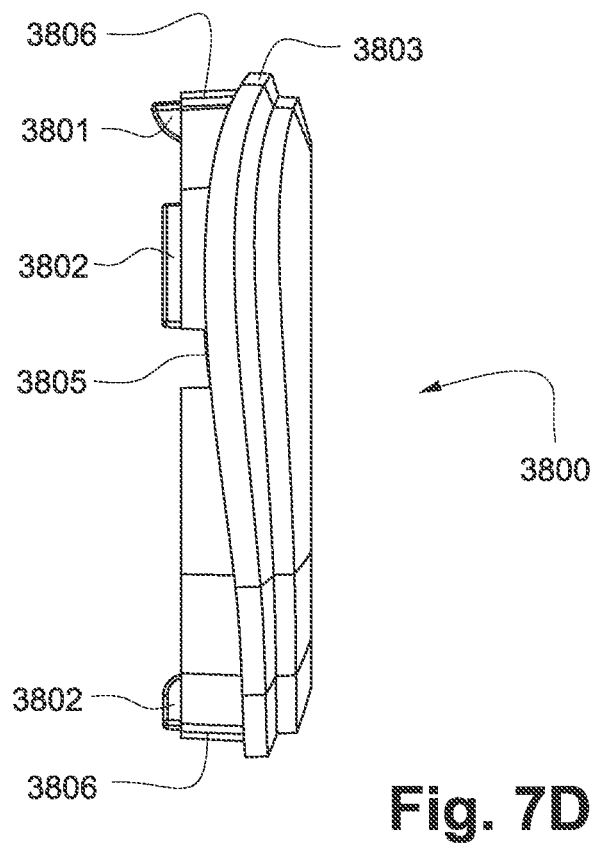

FIG. 7D depicts a lateral view of a connector ring of a patient interface according to an example of the present technology.

Figure 7E:
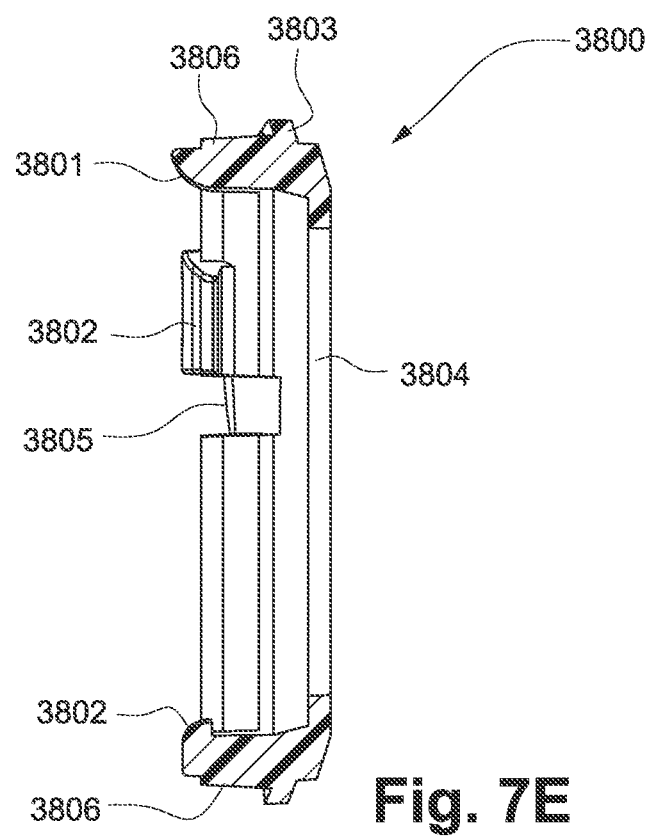

FIG. 7E depicts a cross-sectional view of a connector ring of a patient interface taken through line 7E-7E of FIG. 7B according to an example of the present technology.

Figure 7F:
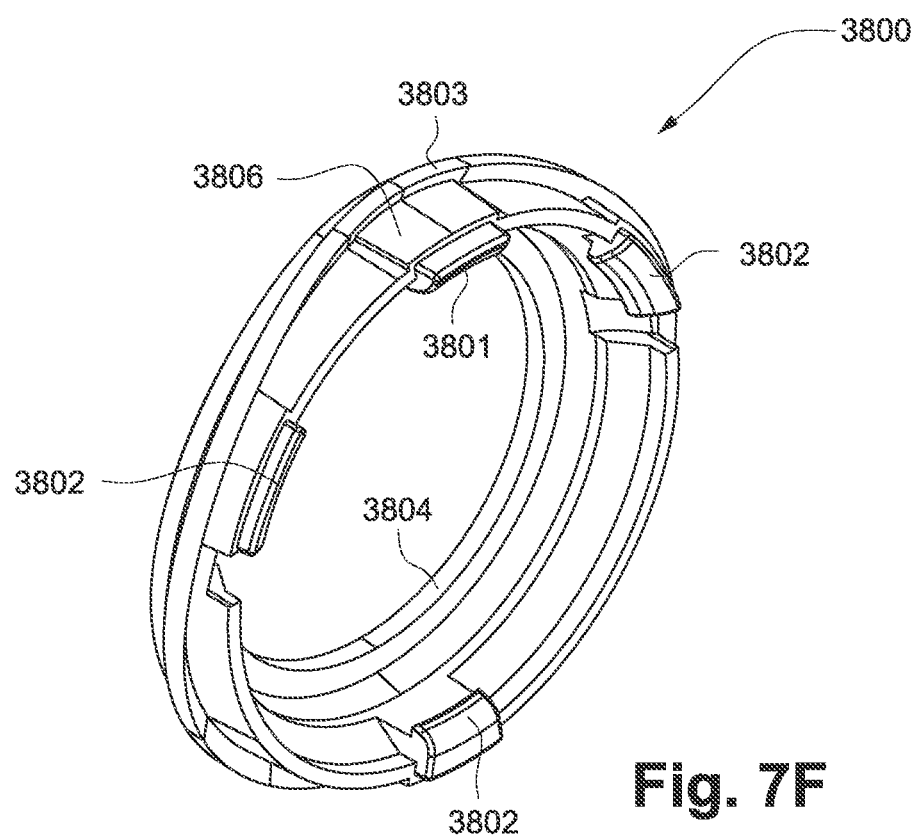

FIG. 7F depicts a posterior perspective view of a connector ring of a patient interface according to an example of the present technology.

Figure 8A:
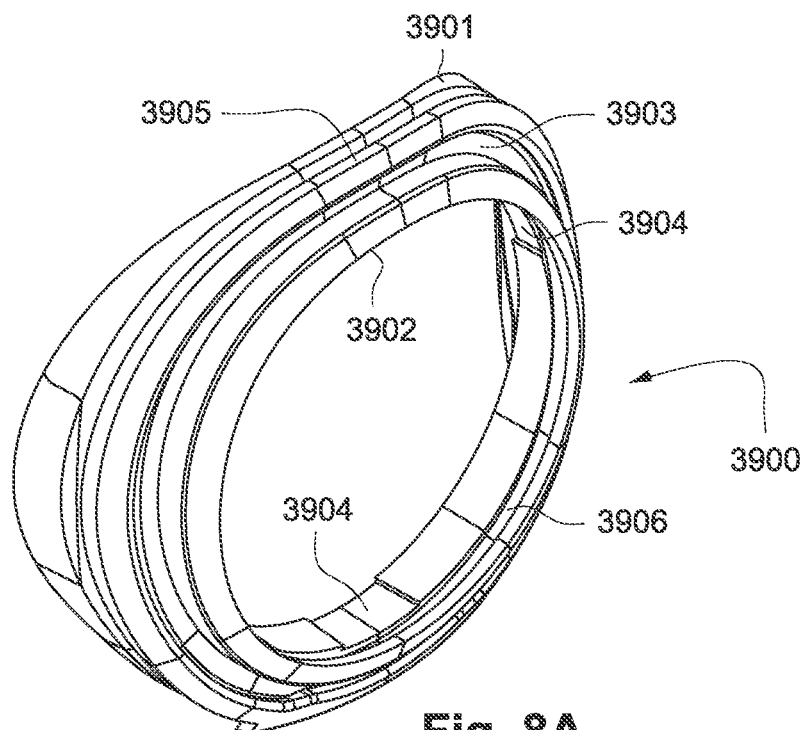

FIG. 8A depicts an anterior perspective view of a flexible joint structure of a patient interface according to an example of the present technology.

Figure 8B:
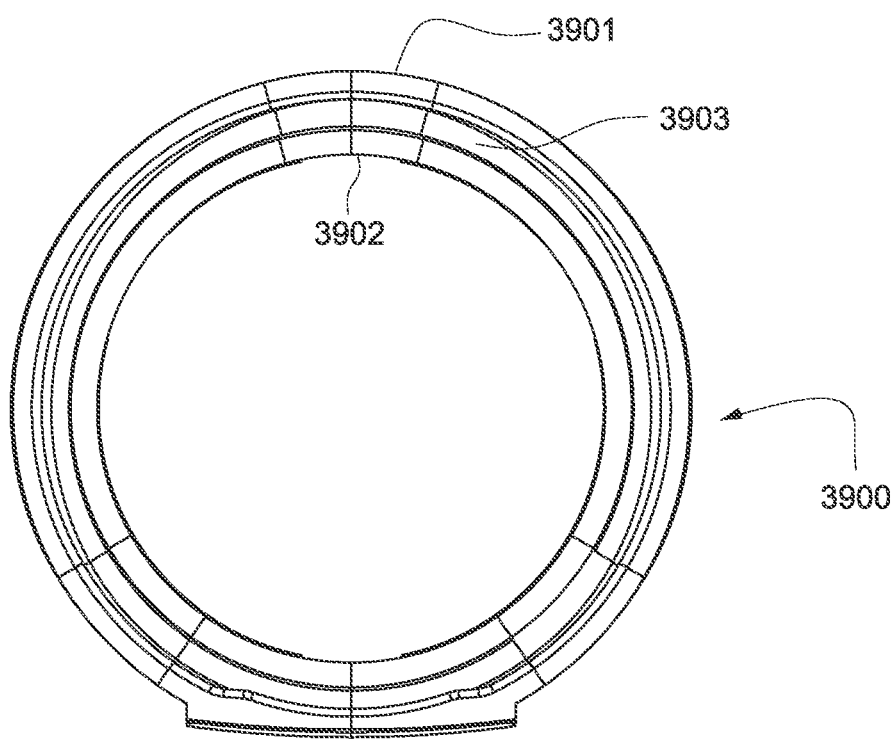

FIG. 8B depicts an anterior view of a flexible joint structure of a patient interface according to an example of the present technology.

Figure 8C:
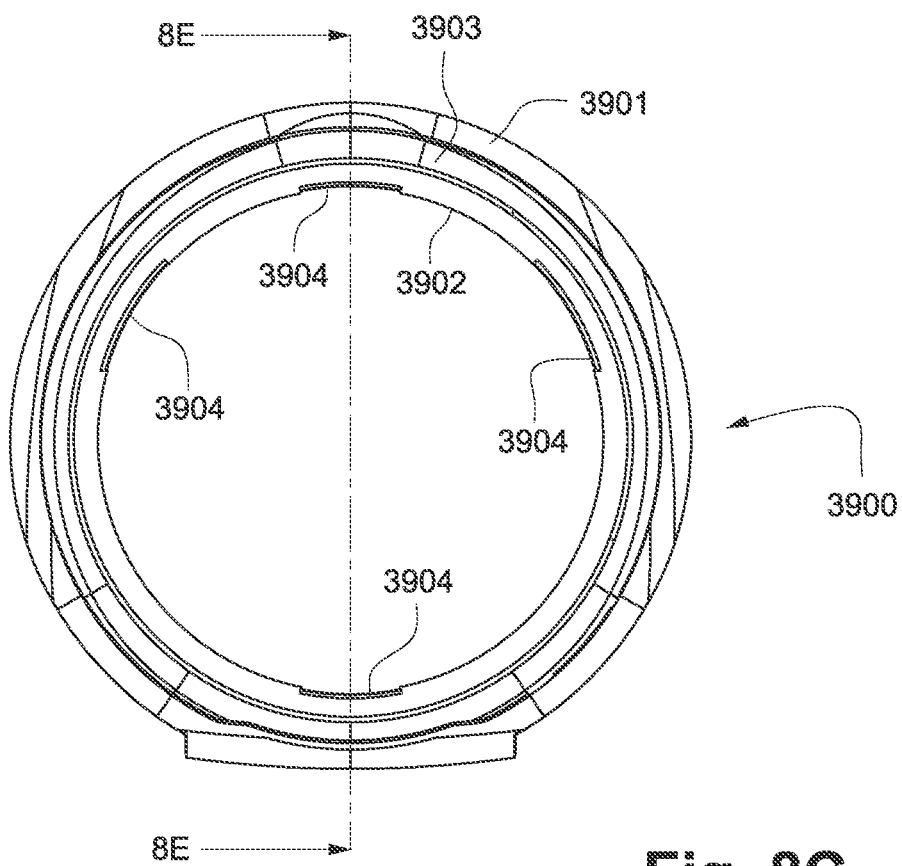

FIG. 8C depicts a posterior view of a flexible joint structure of a patient interface according to an example of the present technology.

Figure 8D:
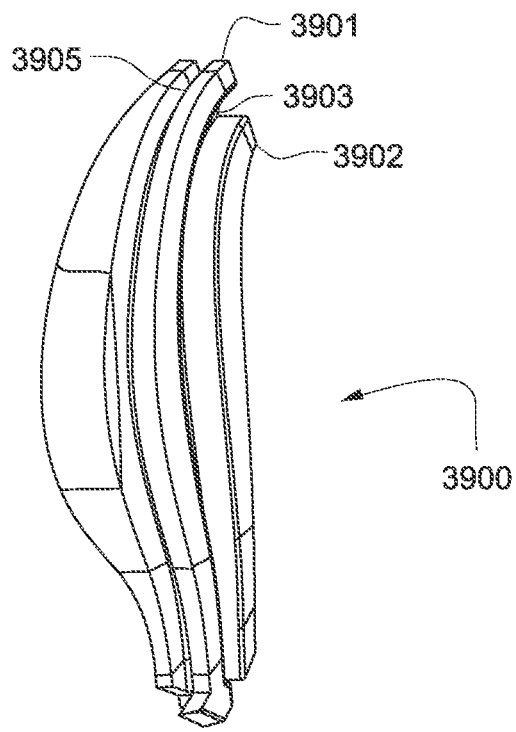

FIG. 8D depicts a lateral view of a flexible joint structure of a patient interface according to an example of the present technology.

Figure 8E:
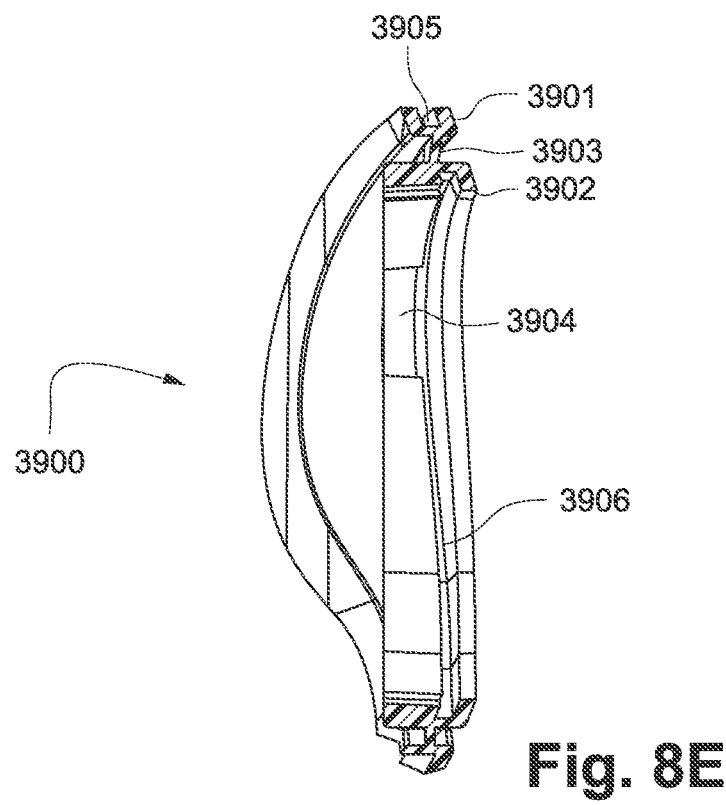

FIG. 8E depicts a cross-sectional view of a flexible joint structure of a patient interface taken through line 8E-8E of FIG. 8C according to an example of the present technology.

Figure 8F:
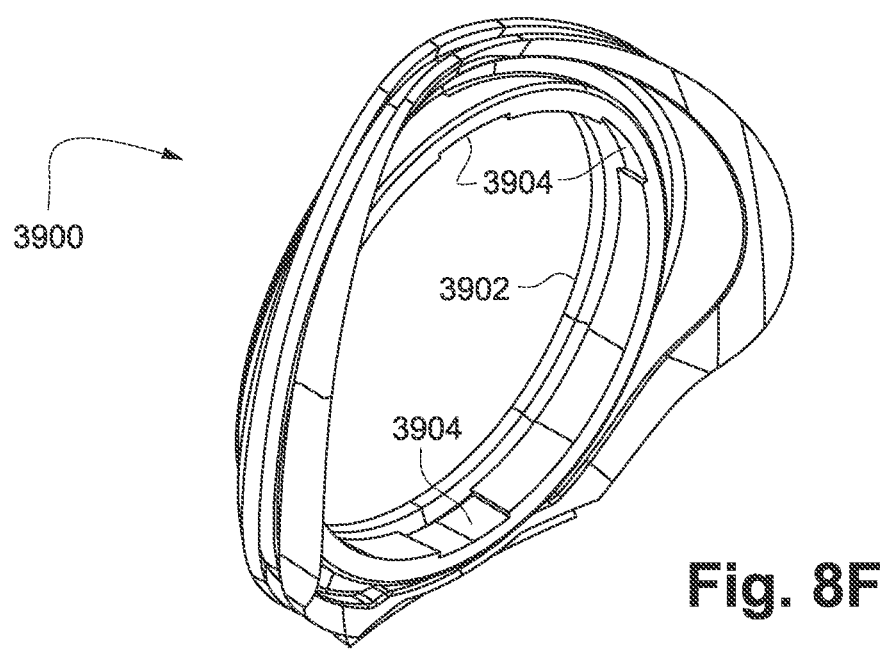

FIG. 8F depicts a posterior perspective view of a flexible joint structure of a patient interface according to an example of the present technology.

Figure 9A:
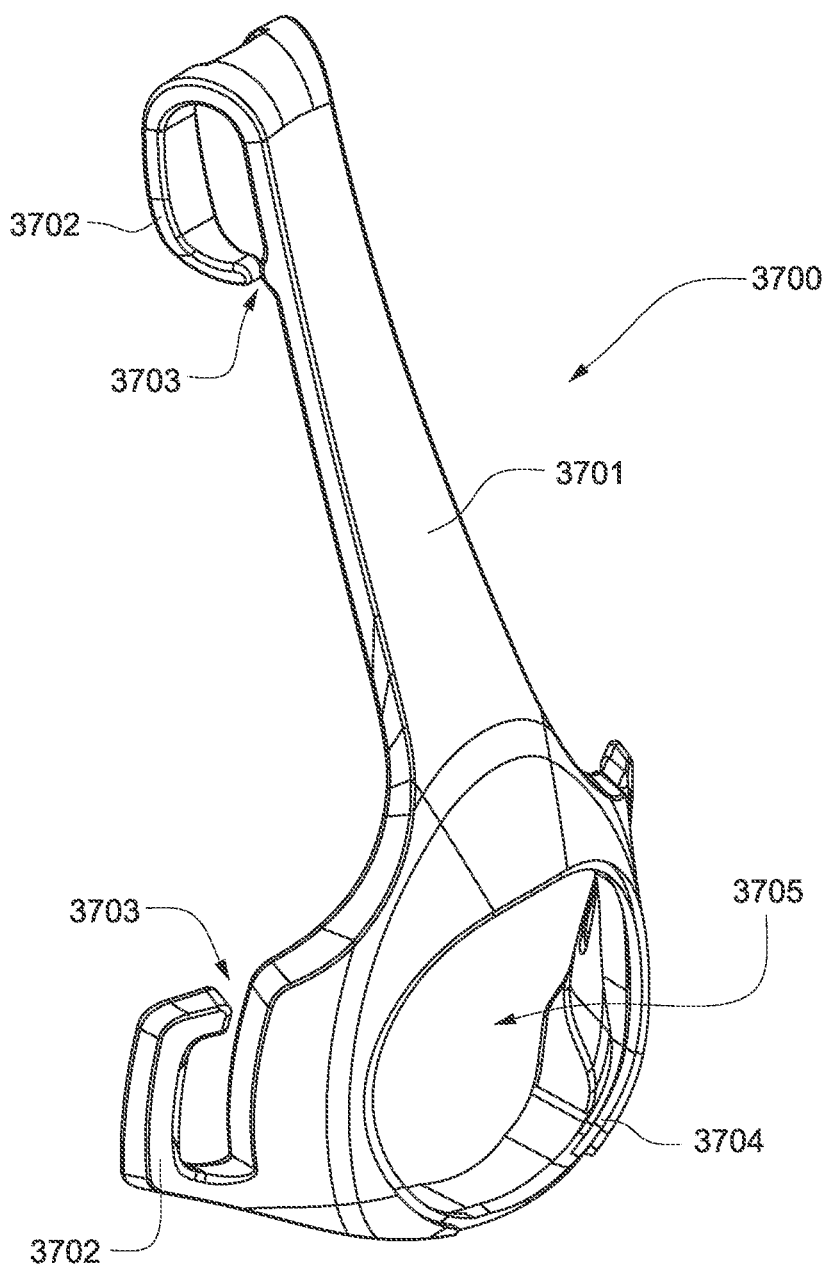

FIG. 9A depicts an anterior perspective view of a frame of a patient interface according to an example of the present technology.

Figure 9B:
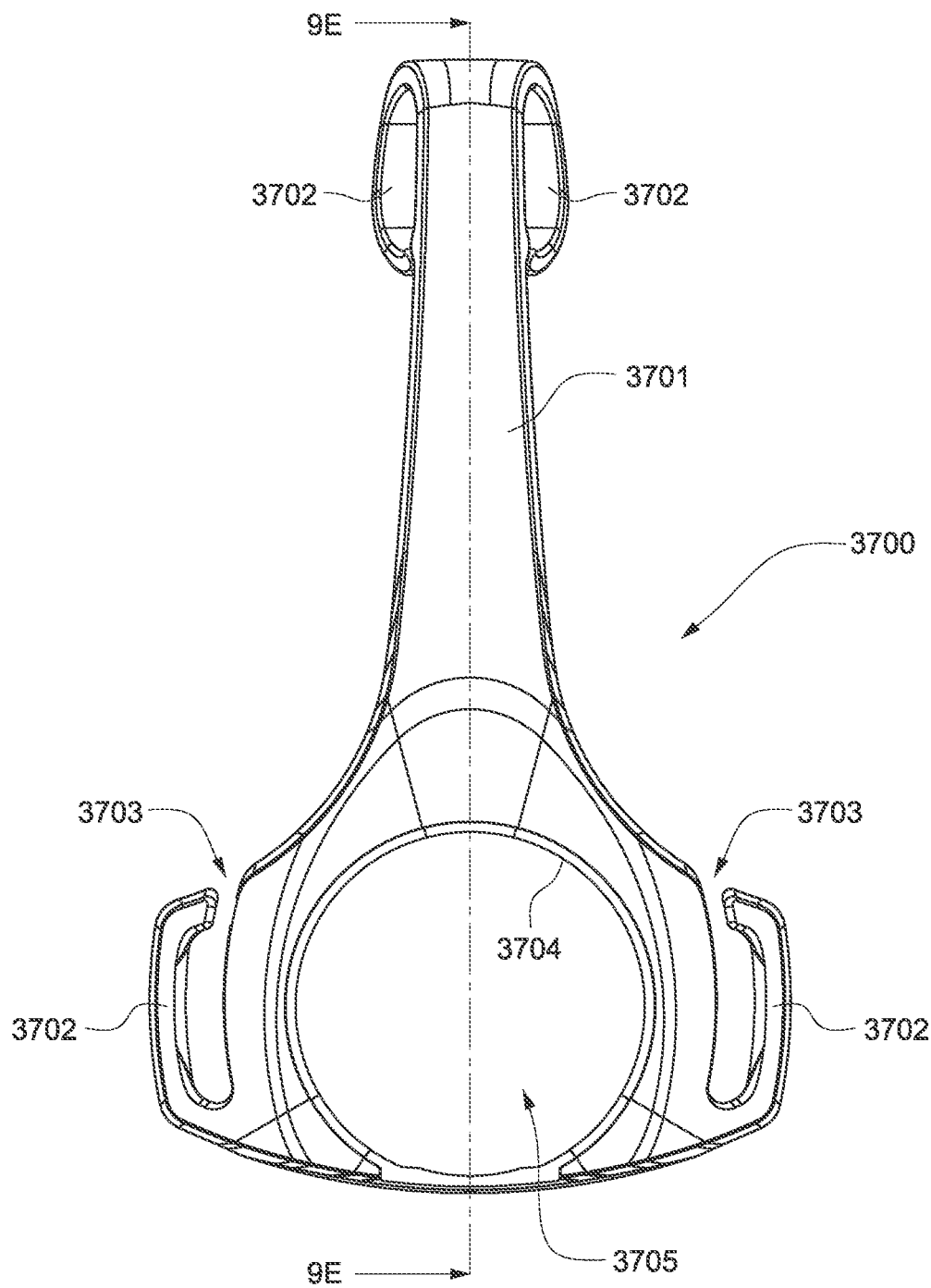

FIG. 9B depicts an anterior view of a frame of a patient interface according to an example of the present technology.

Figure 9C:
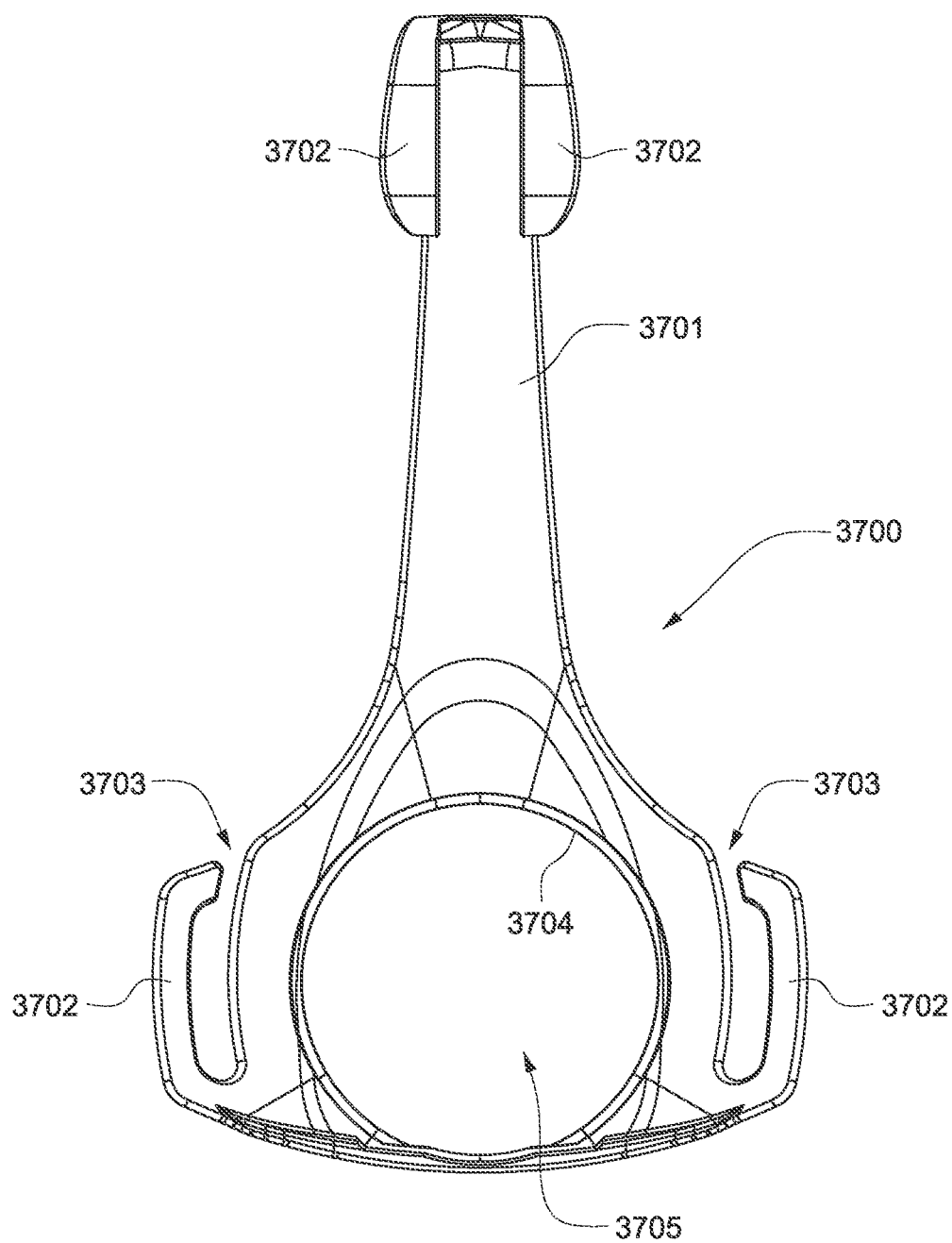

FIG. 9C depicts a posterior view of a frame of a patient interface according to an example of the present technology.

Figure 9D:
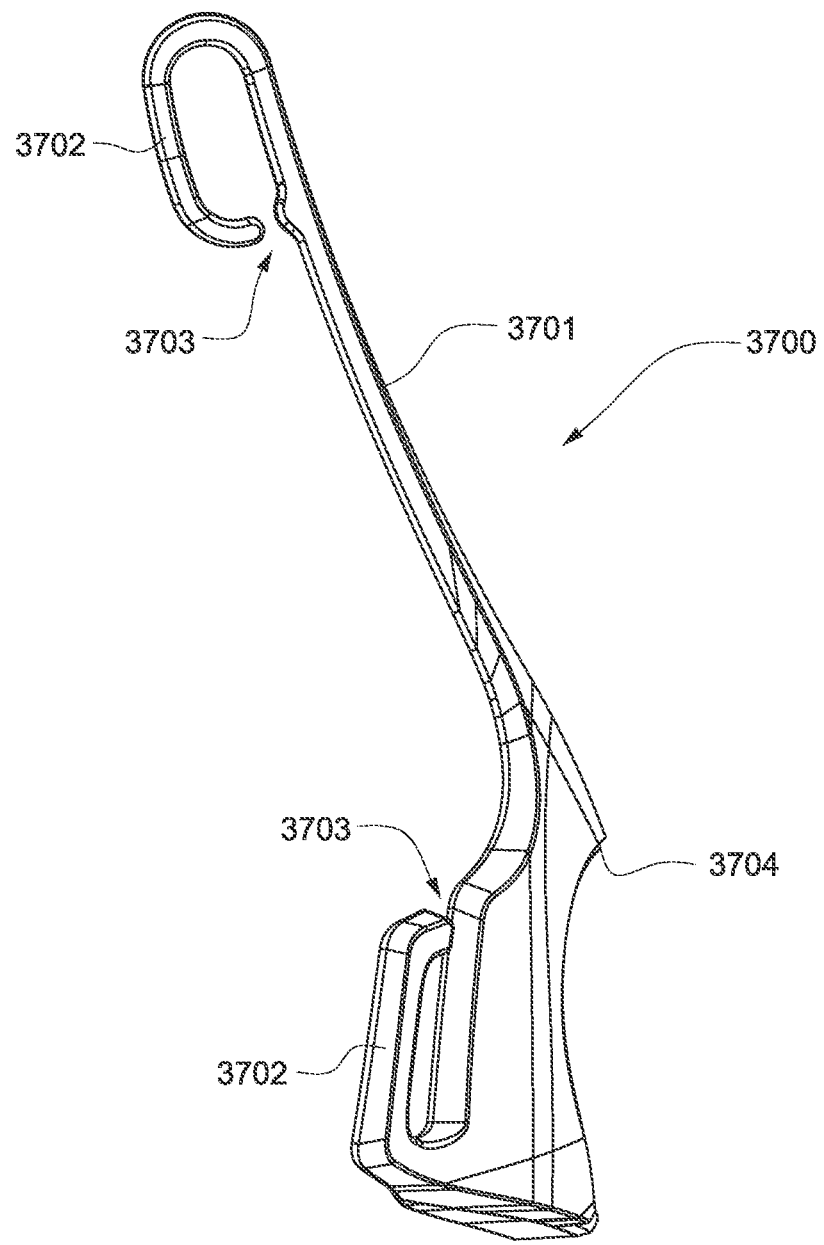

FIG. 9D depicts a lateral view of a frame of a patient interface according to an example of the present technology.

Figure 9E:
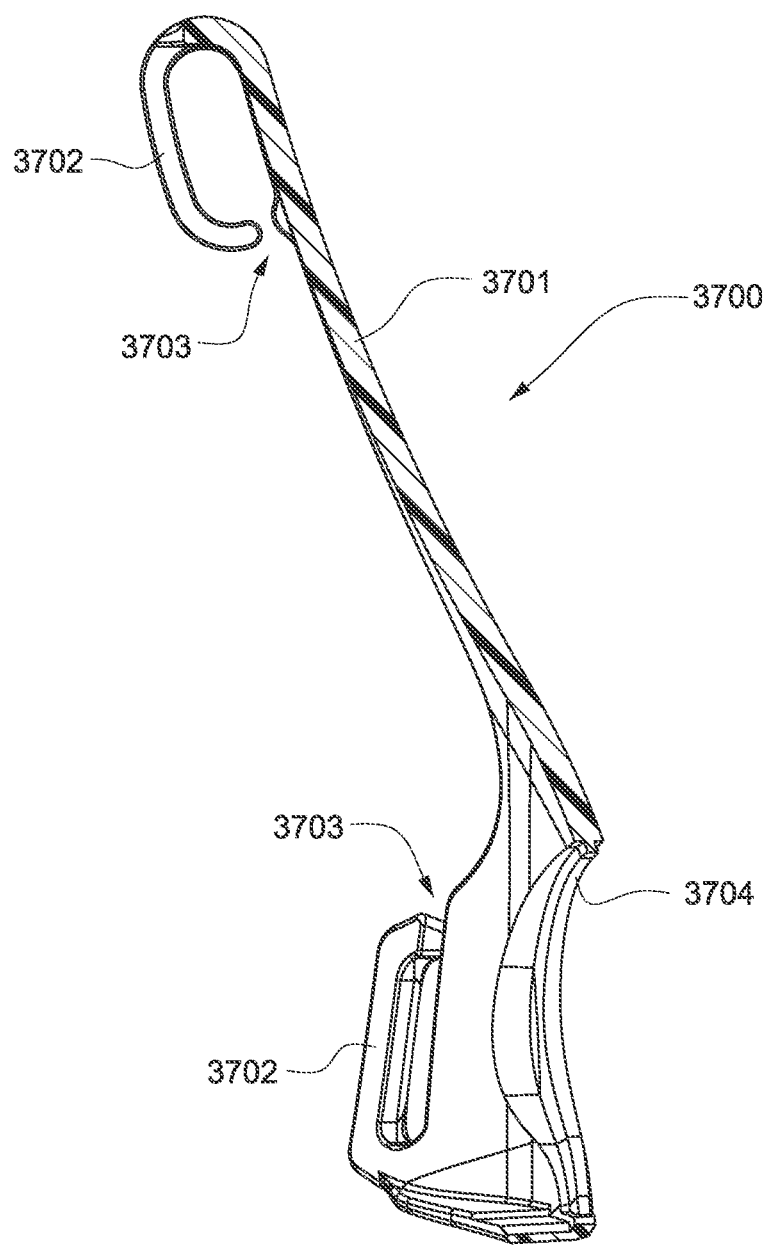

FIG. 9E depicts a cross-sectional view of a frame of a patient interface taken through line 9E-9E of FIG. 9B according to an example of the present technology.

Figure 10A:
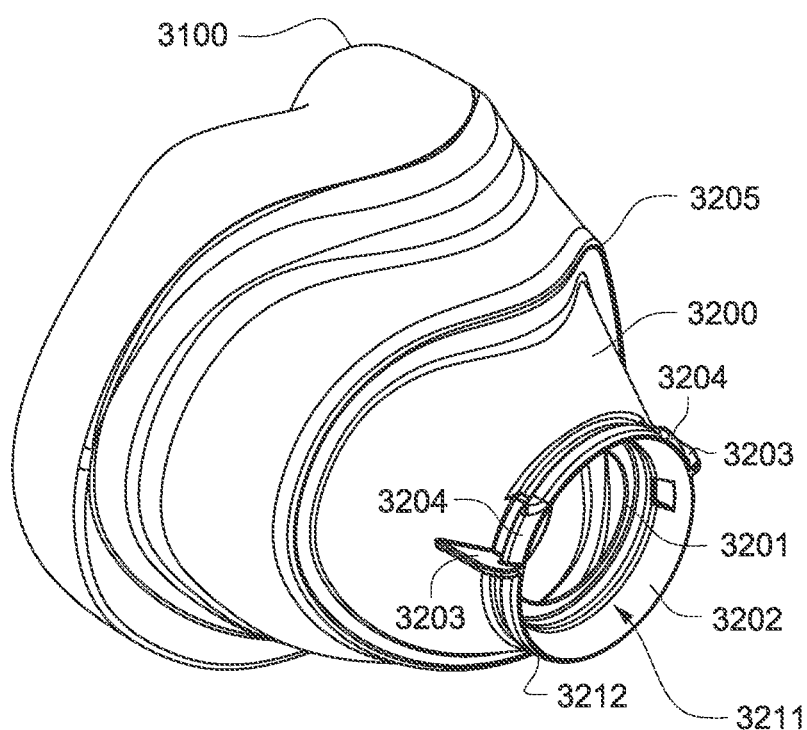

FIG. 10A depicts an anterior perspective view of a seal-forming structure and a plenum chamber of a patient interface according to an example of the present technology.

Figure 10B:
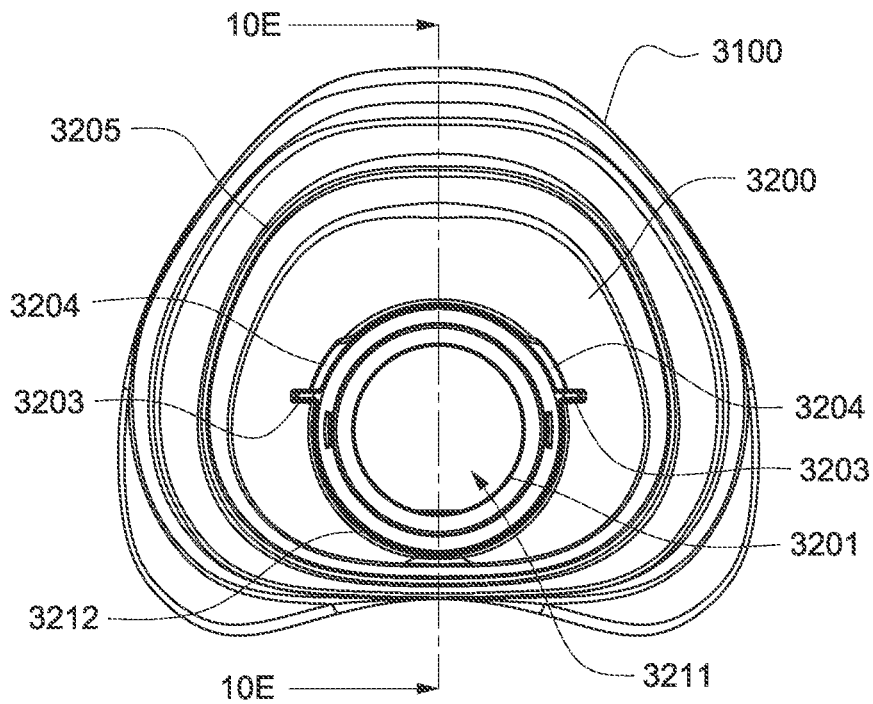

FIG. 10B depicts an anterior view of a seal-forming structure and a plenum chamber of a patient interface according to an example of the present technology.

Figure 10C:
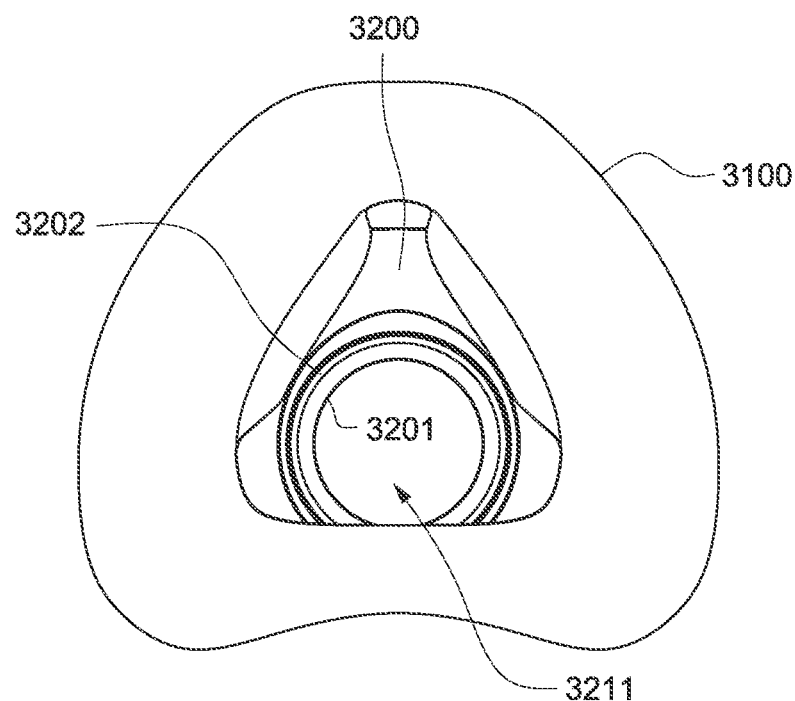

FIG. 10C depicts a posterior view of a seal-forming structure and a plenum chamber of a patient interface according to an example of the present technology.

Figure 10D:
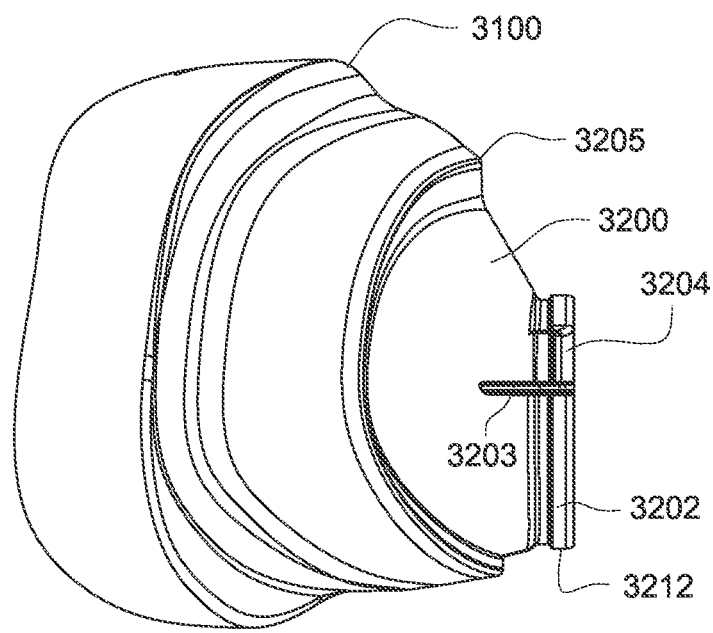

FIG. 10D depicts a lateral view of a seal-forming structure and a plenum chamber of a patient interface according to an example of the present technology.

Figure 10E:
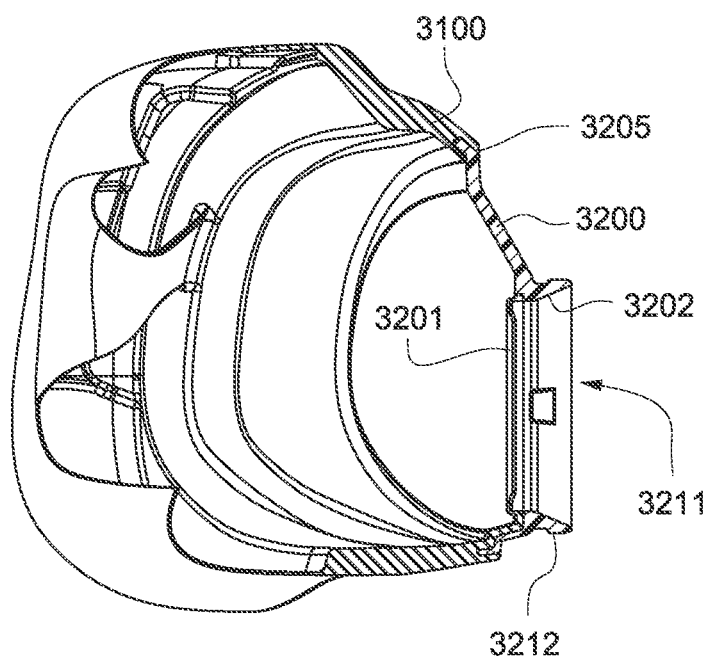

FIG. 10E depicts a cross-sectional view of a seal-forming structure and a plenum chamber of a patient interface taken through line 10E-10E of FIG. 10B according to an example of the present technology.

Figure 11A:
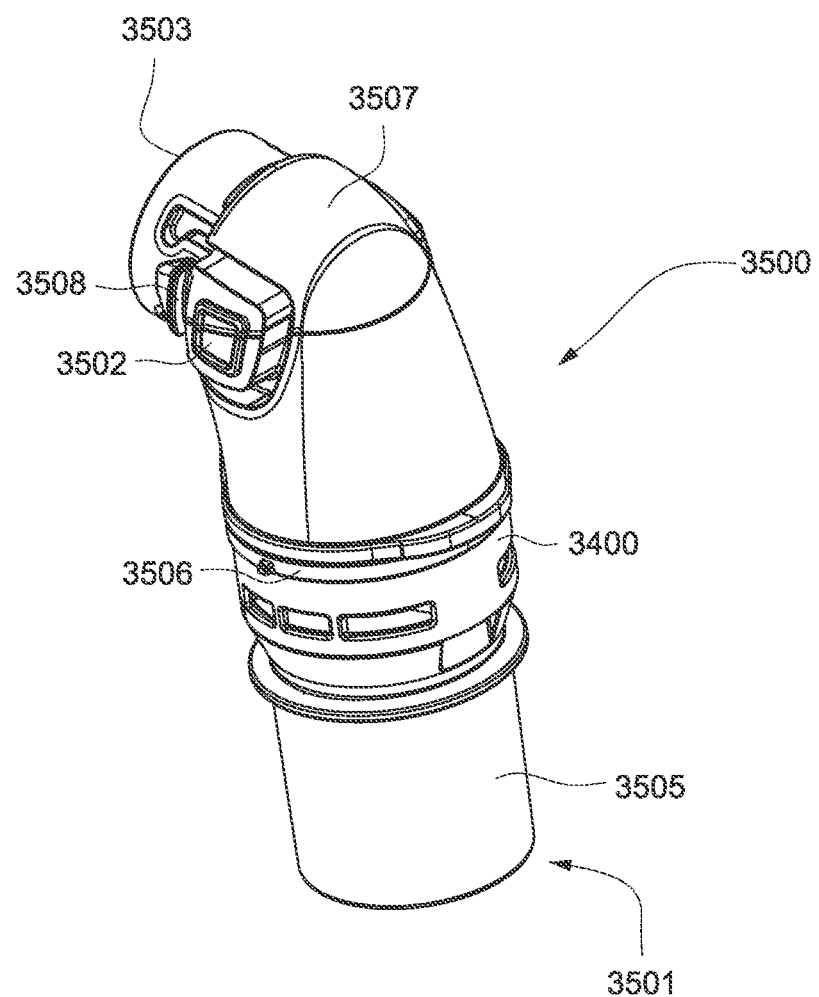

FIG. 11A depicts an anterior perspective view of a decoupling structure of a patient interface according to an example of the present technology.

Figures 11B, 11C:
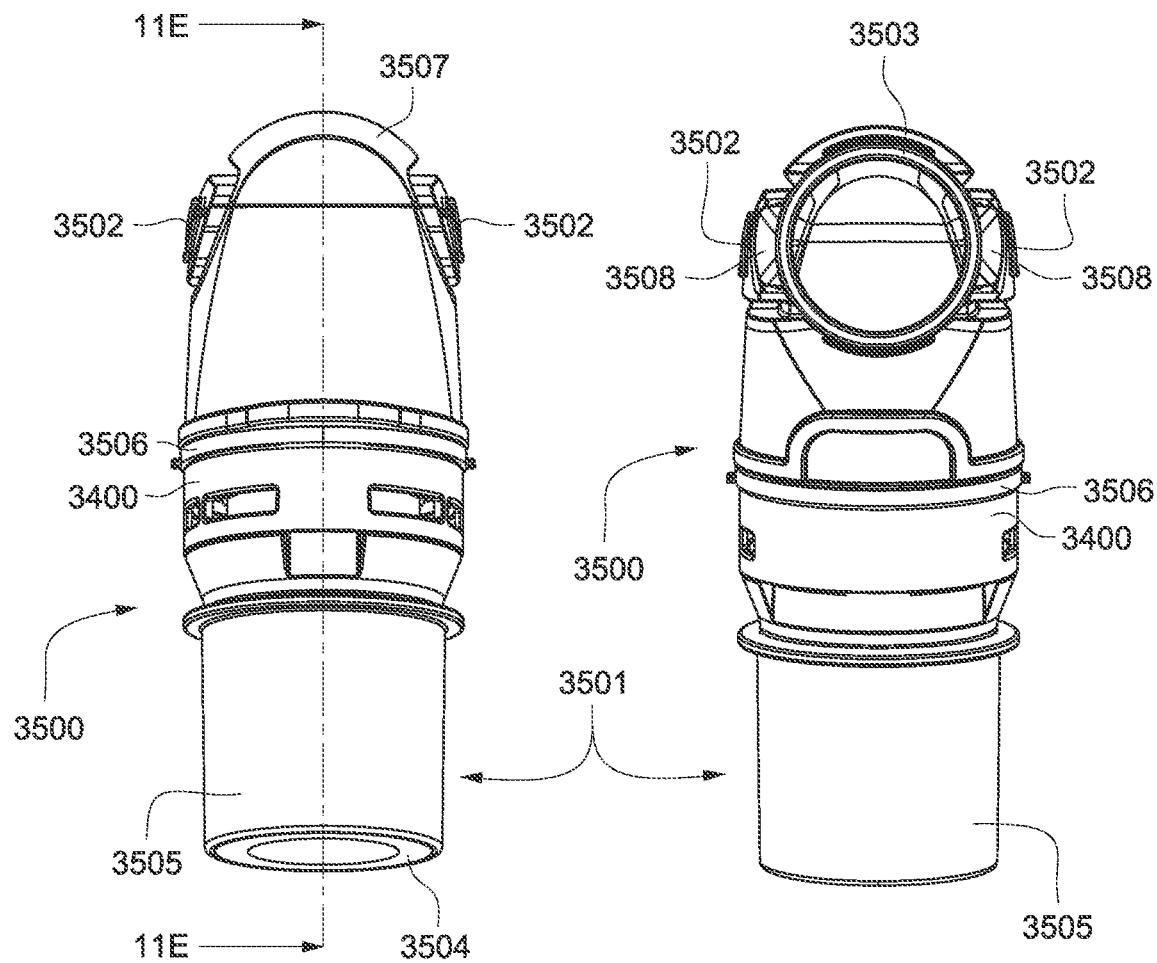

FIG. 11B depicts an anterior view of a decoupling structure of a patient interface according to an example of the present technology.

FIG. 11C depicts a posterior view of a decoupling structure of a patient interface according to an example of the present technology.

Figures 11D, 11E:
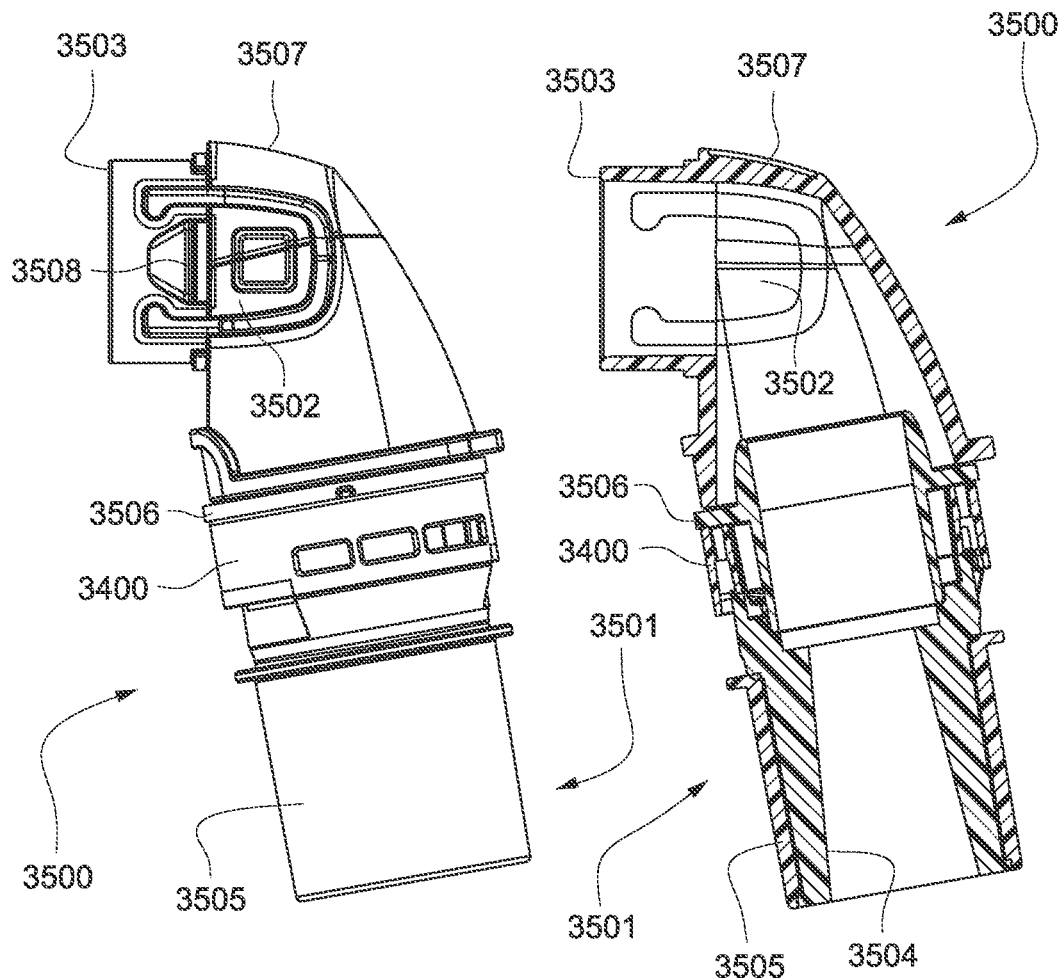

FIG. 11D depicts a lateral view of a decoupling structure of a patient interface according to an example of the present technology.

FIG. 11E depicts a cross-sectional view of a decoupling structure of a patient interface taken through line 11E-11E of FIG. 11B according to an example of the present technology.

Figure 12A:
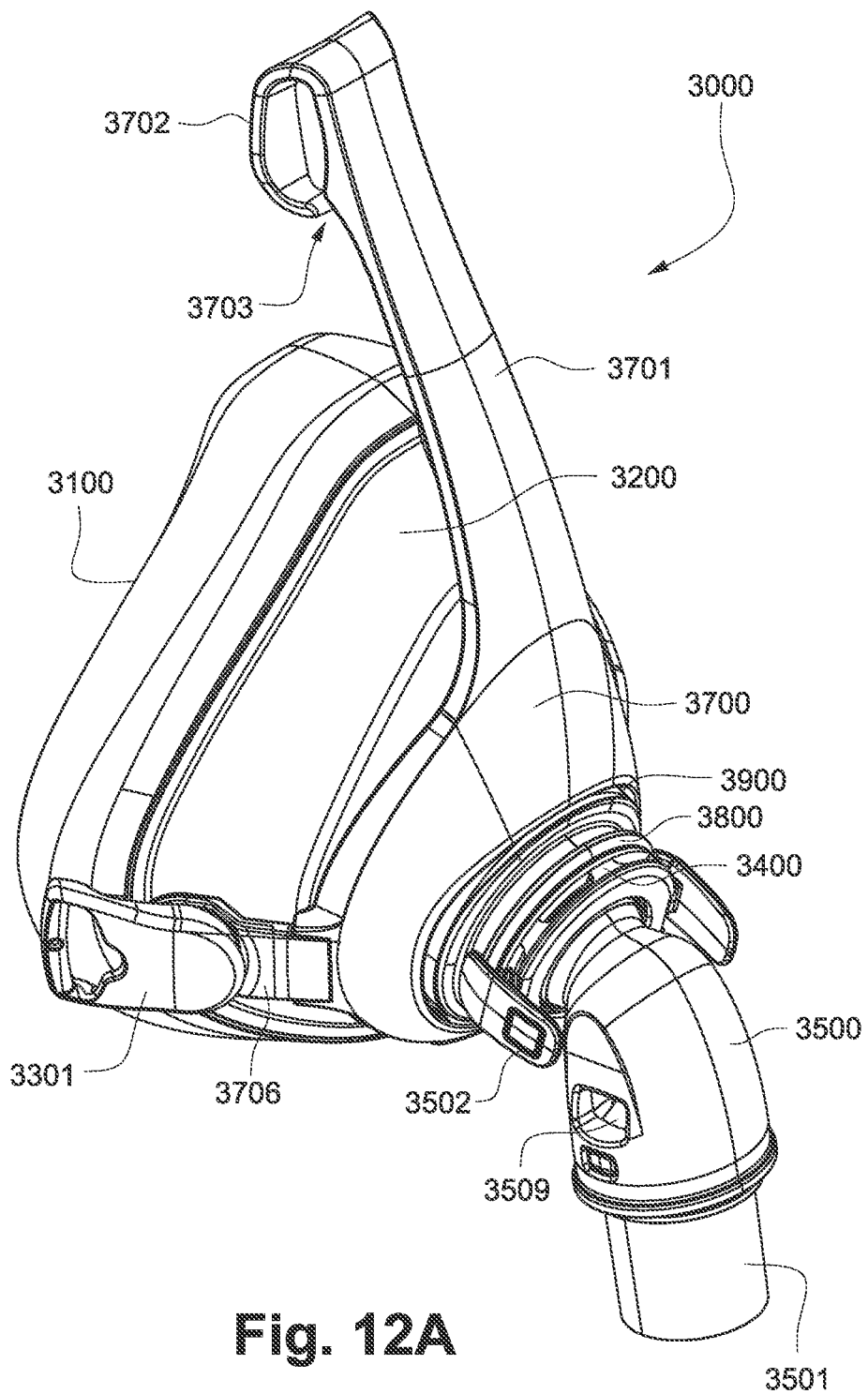

FIG. 12A depicts an anterior perspective view of a patient interface according to an example of the present technology.

Figure 12B:
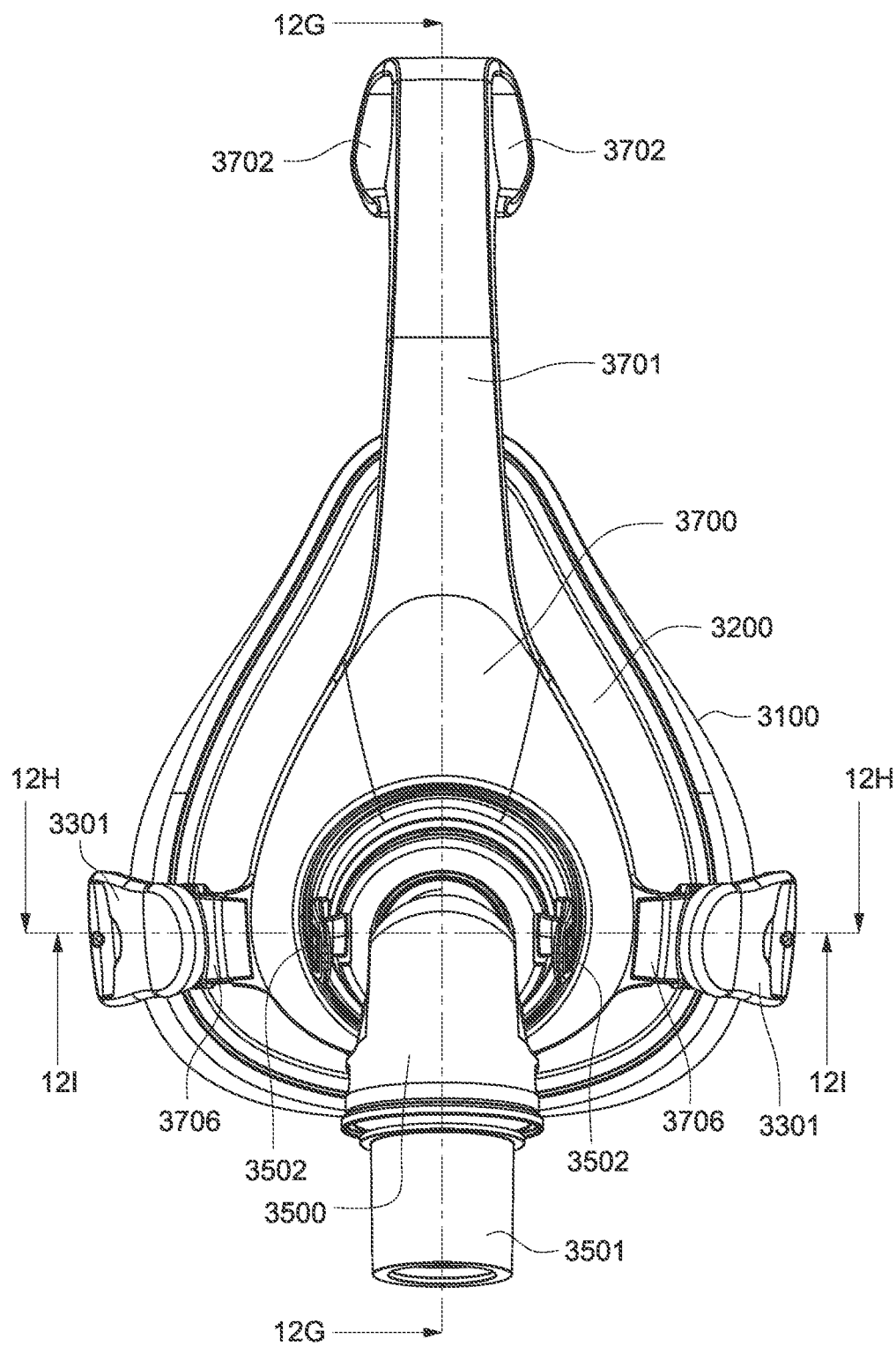

FIG. 12B depicts an anterior view of a patient interface according to an example of the present technology.

Figure 12C:
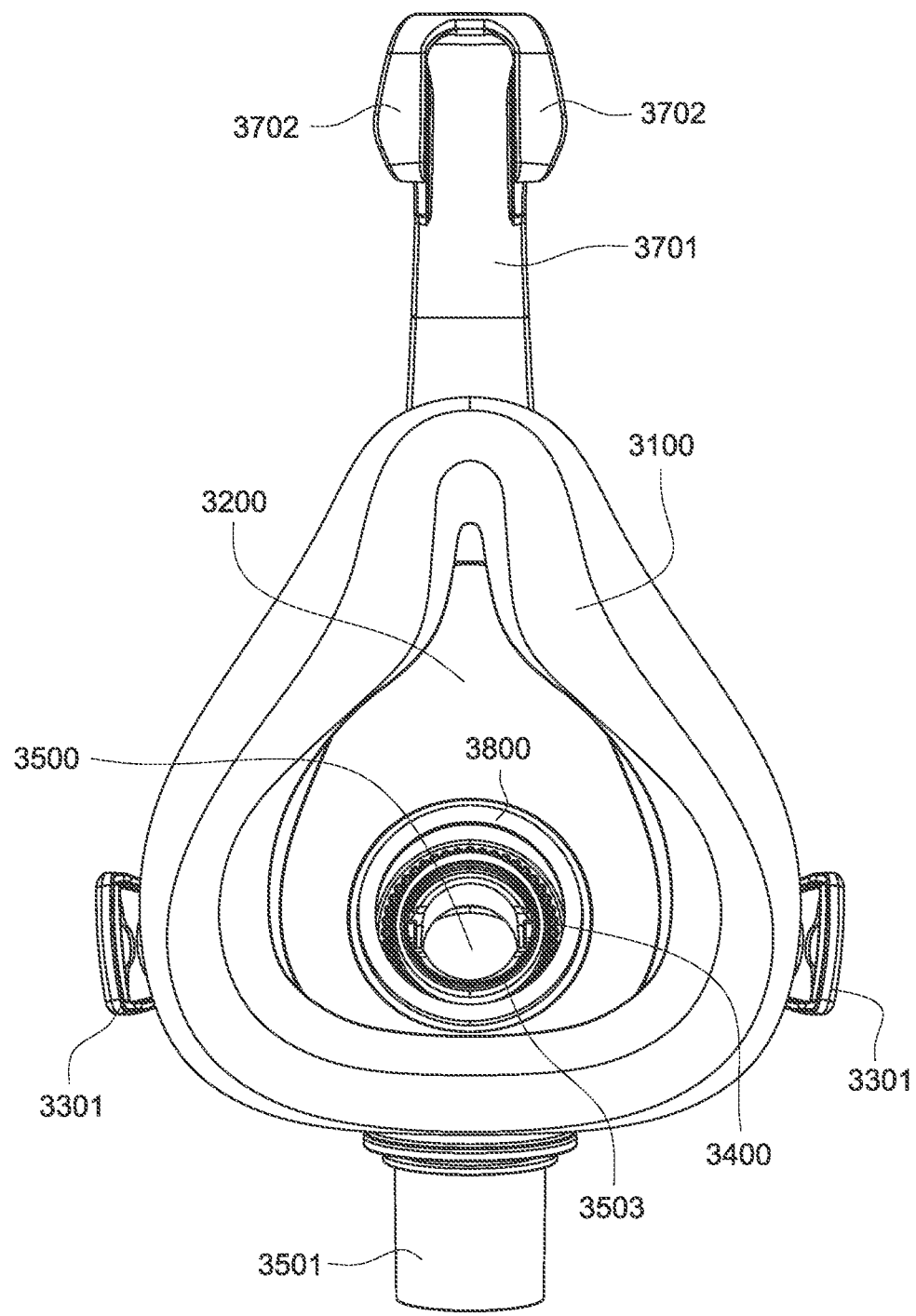

FIG. 12C depicts a posterior view of a patient interface according to an example of the present technology.

Figure 12D:
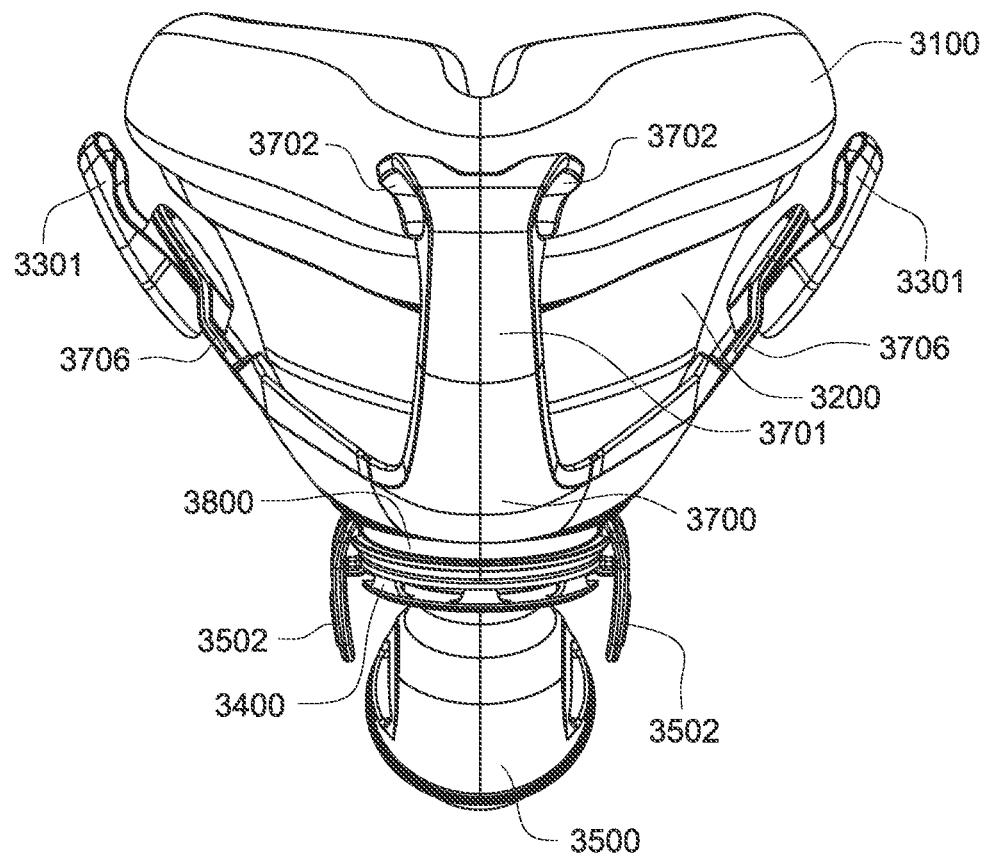

FIG. 12D depicts a superior view of a patient interface according to an example of the present technology.

Figure 12E:
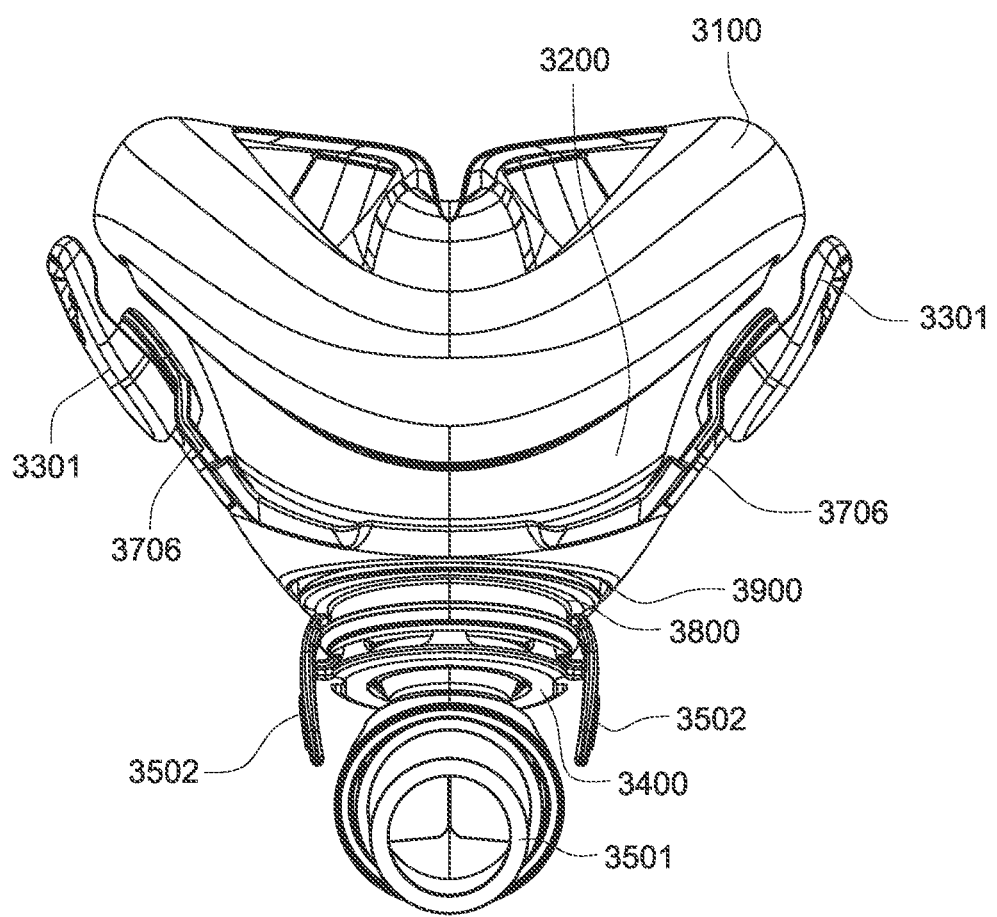

FIG. 12E depicts an inferior view of a patient interface according to an example of the present technology.

Figure 12F:
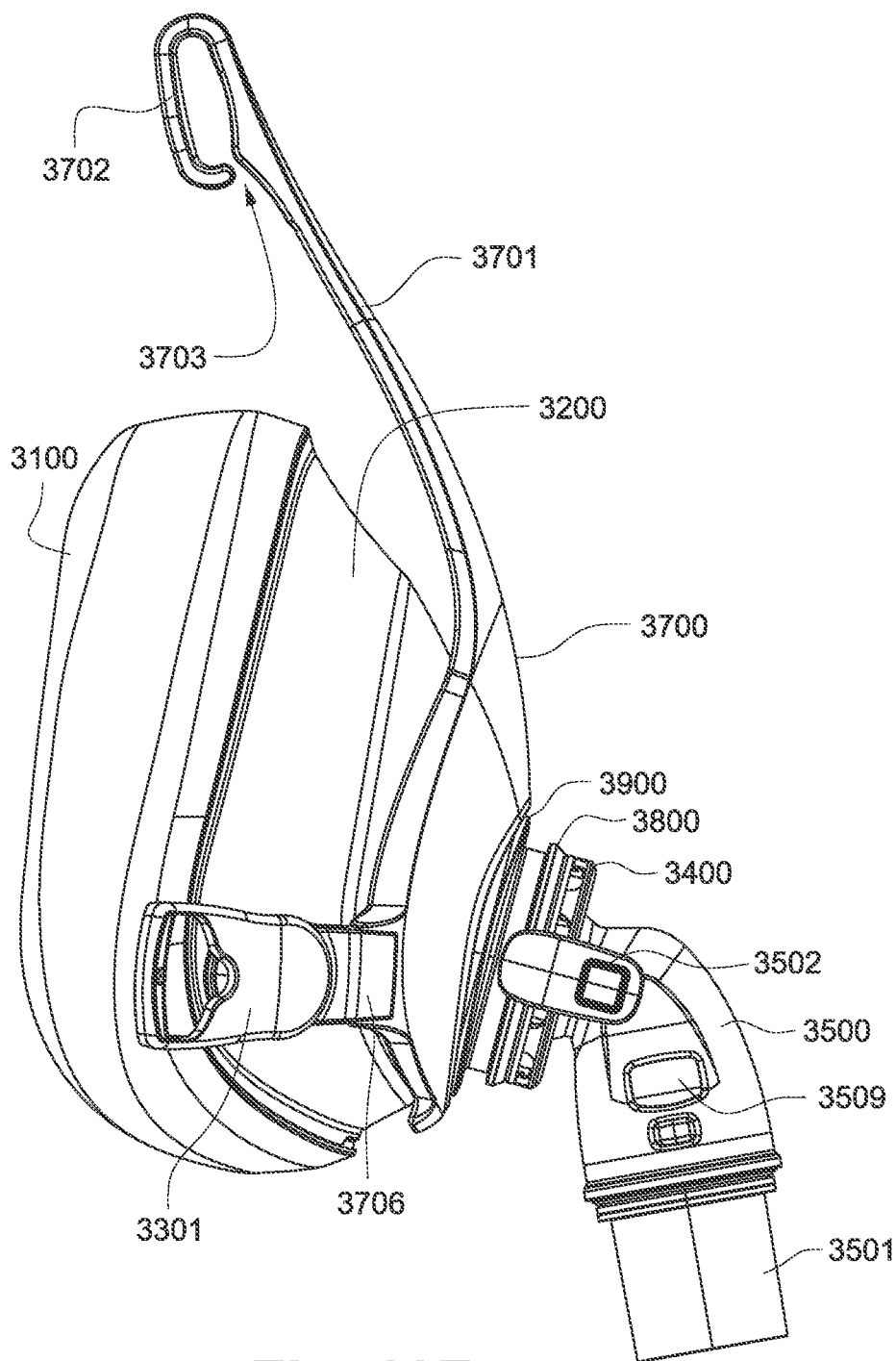

FIG. 12F depicts a lateral view of a patient interface according to an example of the present technology.

Figure 12G:
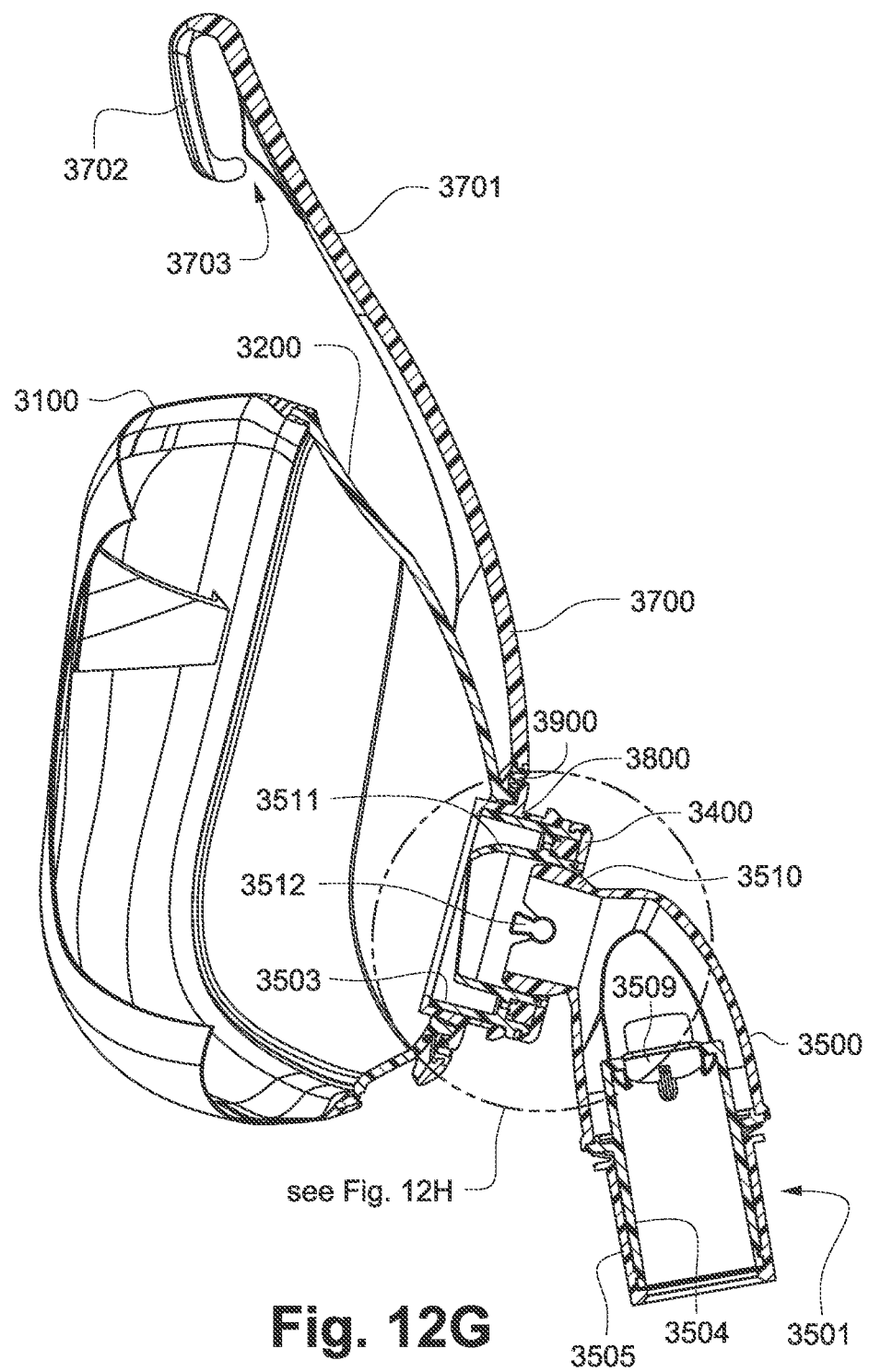

FIG. 12G depicts a cross-sectional view of a patient interface taken through line 12G-12G of FIG. 12B according to an example of the present technology.

Figure 12H:
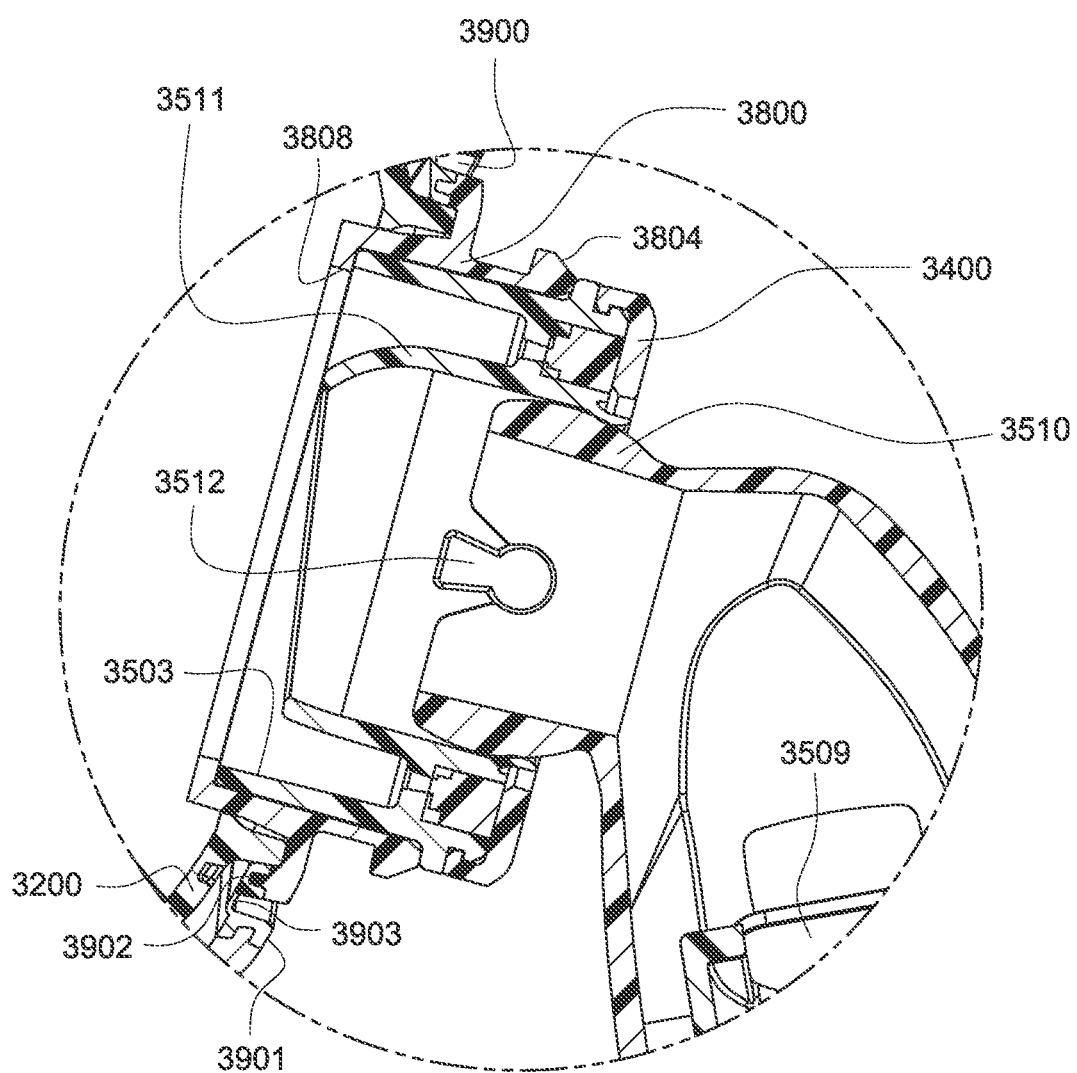

FIG. 12H depicts a detailed view of a portion of a patient interface depicted in FIG. 12G according to an example of the present technology.

Figure 12I:
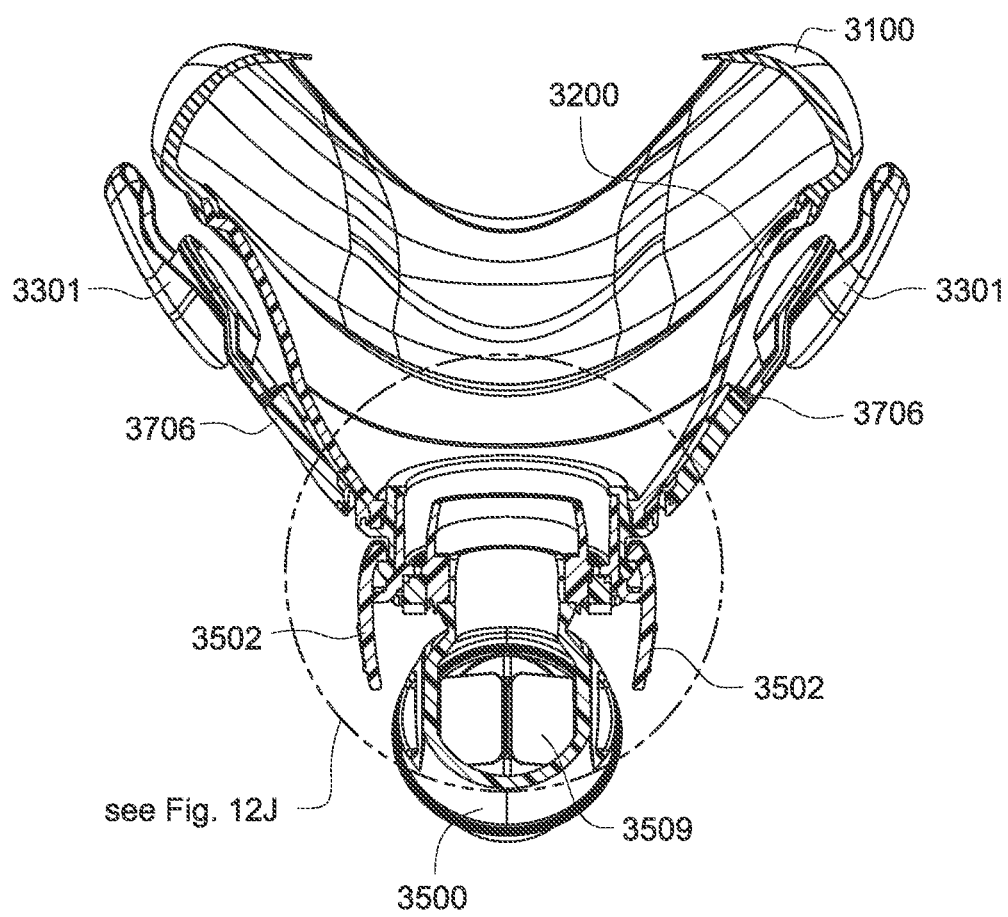

FIG. 12I depicts a cross-sectional view of a patient interface taken through line 12I-12I of FIG. 12B according to an example of the present technology.

Figure 12J:
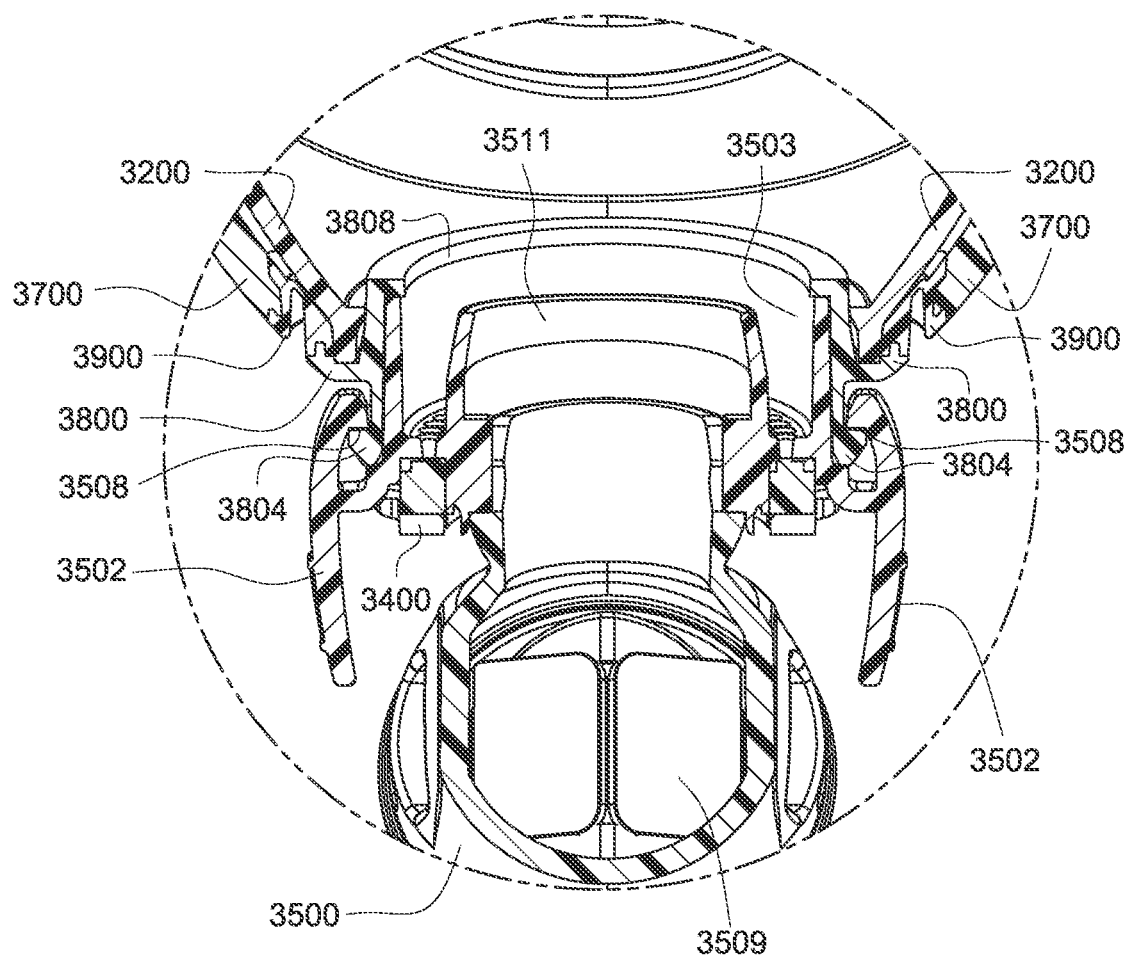

FIG. 12J depicts a detailed view of a portion of a patient interface depicted in FIG. 12I according to an example of the present technology.

Figure 12K:
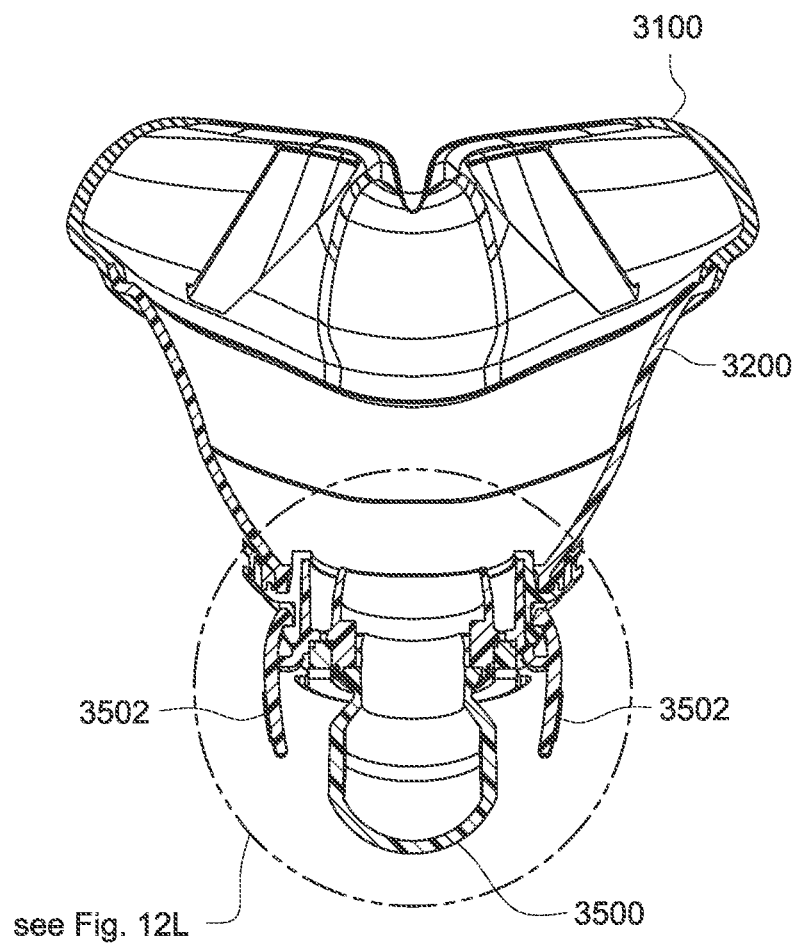

FIG. 12K depicts a cross-sectional view of a patient interface taken through line 12K-12K of FIG. 12B according to an example of the present technology.

Figure 12L:
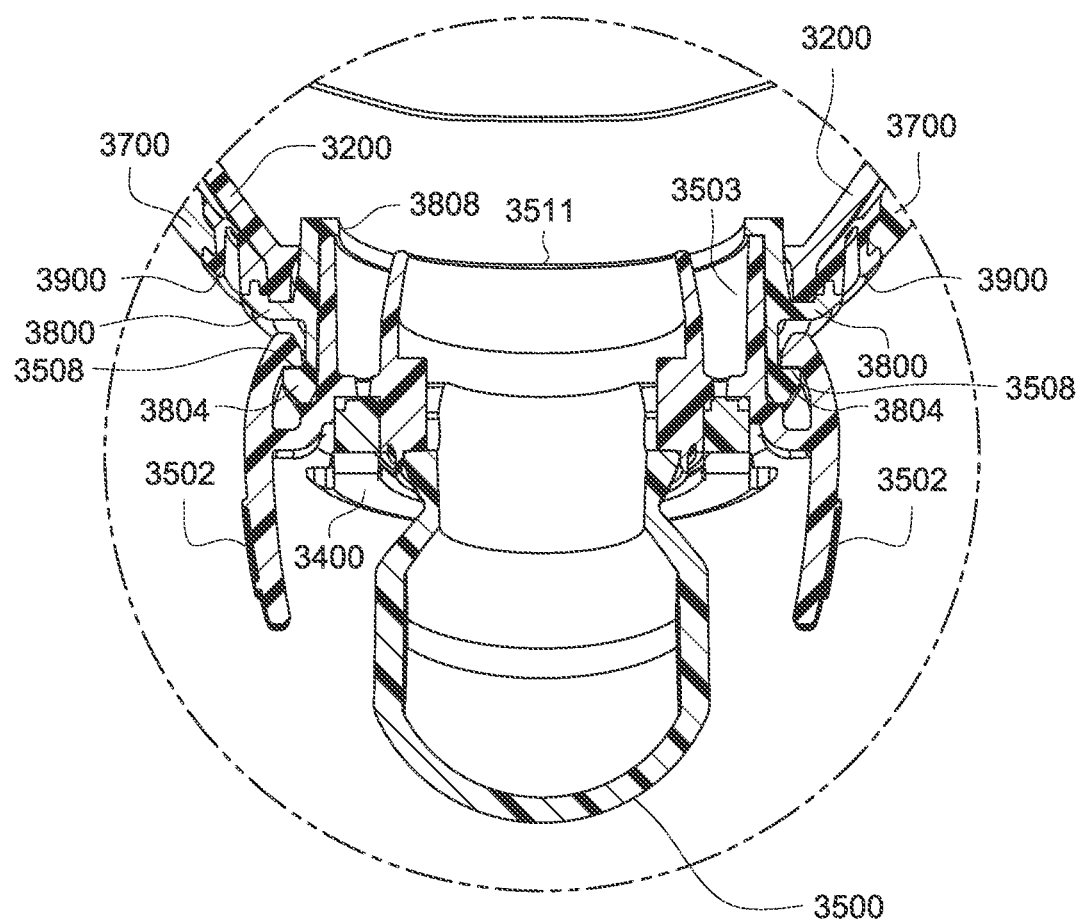

FIG. 12L depicts a detailed view of a portion of a patient interface depicted in FIG. 12K according to an example of the present technology.

Figure 12M:
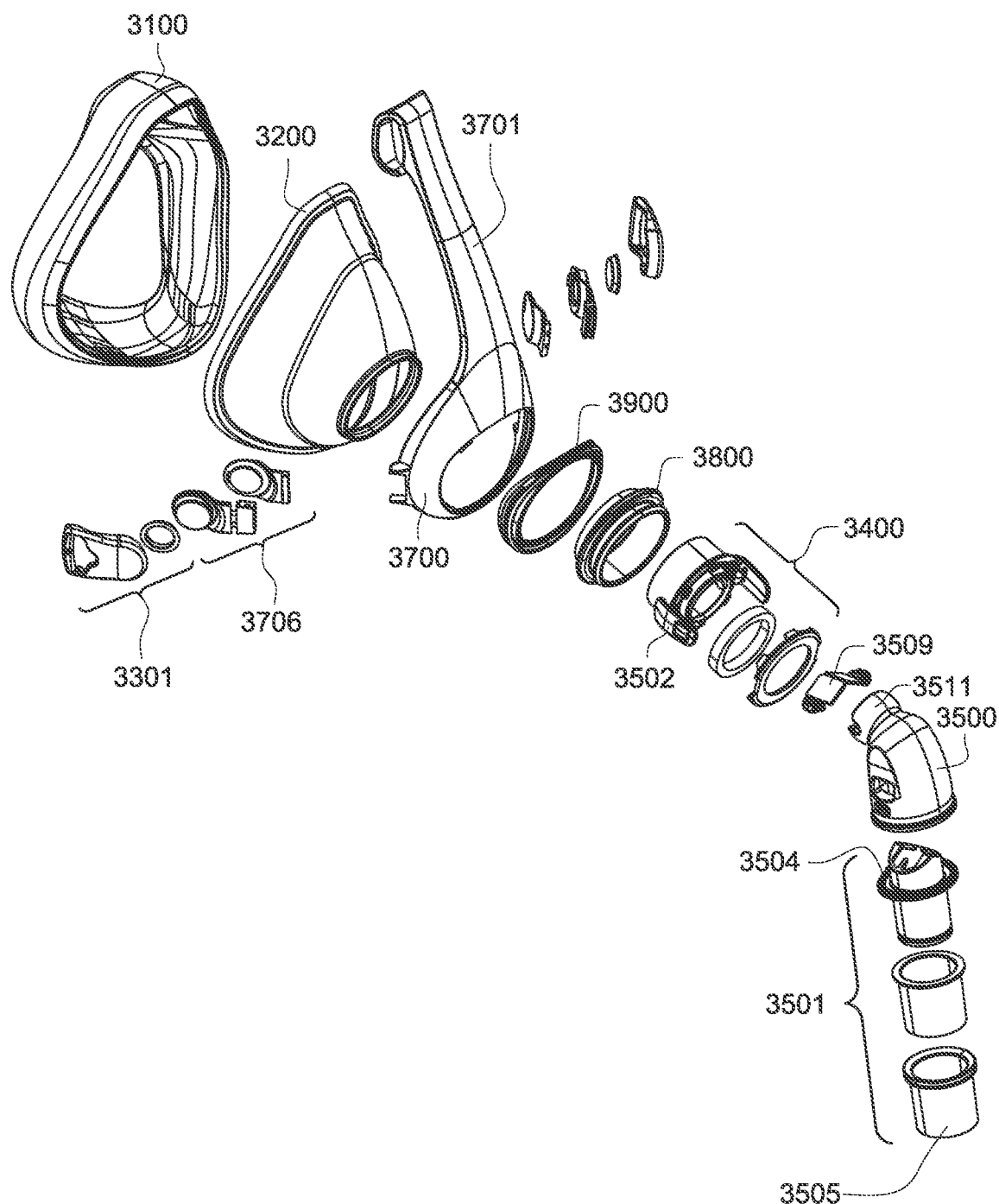

FIG. 12M depicts an exploded view of a patient interface according to an example of the present technology.

Figure 13A:
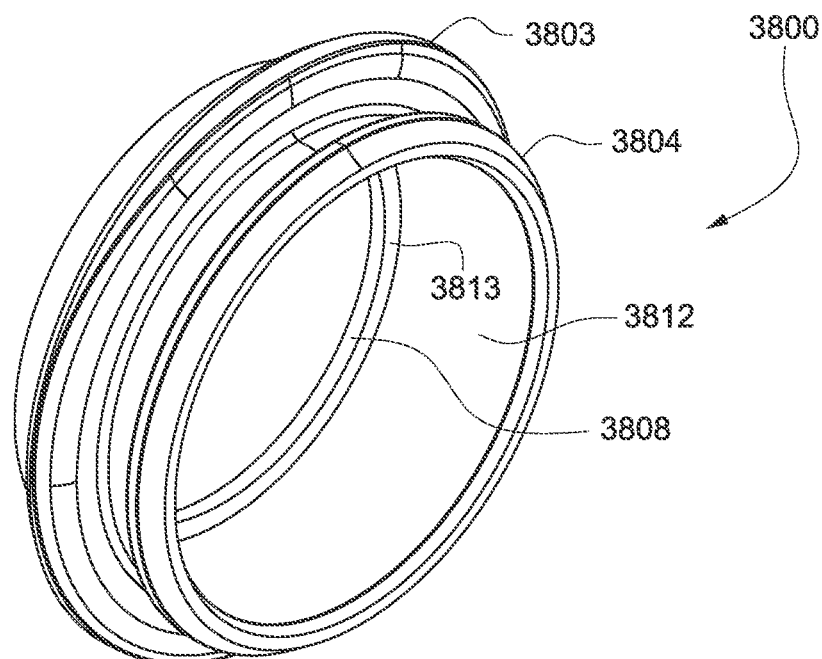

FIG. 13A depicts an anterior perspective view of a connector ring of a patient interface according to an example of the present technology.

Figure 13B:
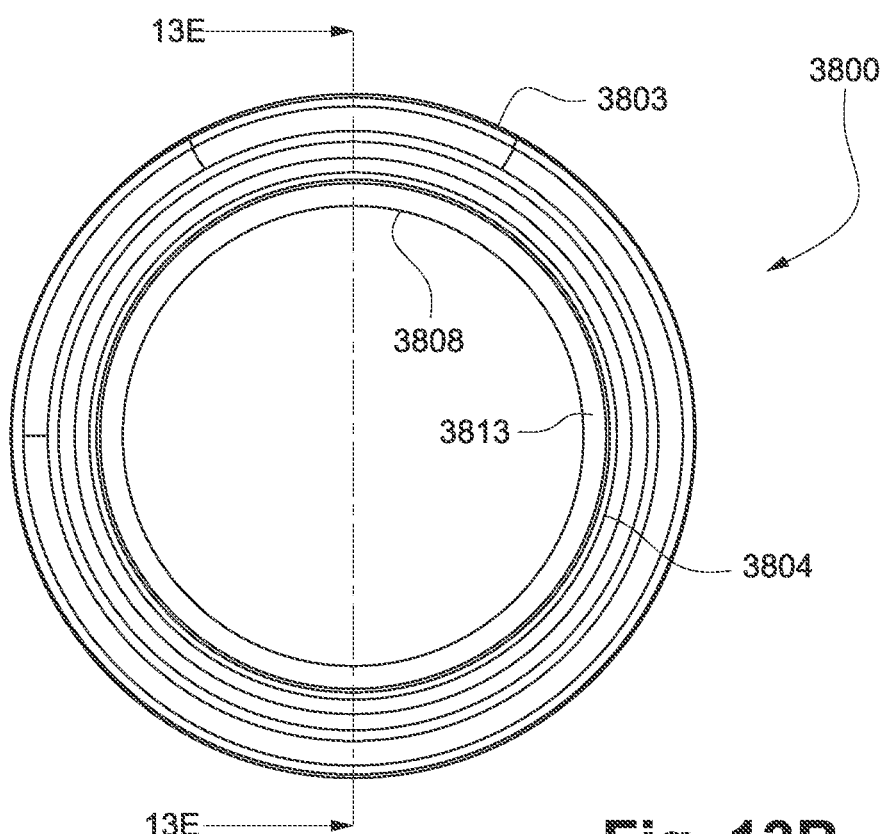

FIG. 13B depicts an anterior view of a connector ring of a patient interface according to an example of the present technology.

Figure 13C:
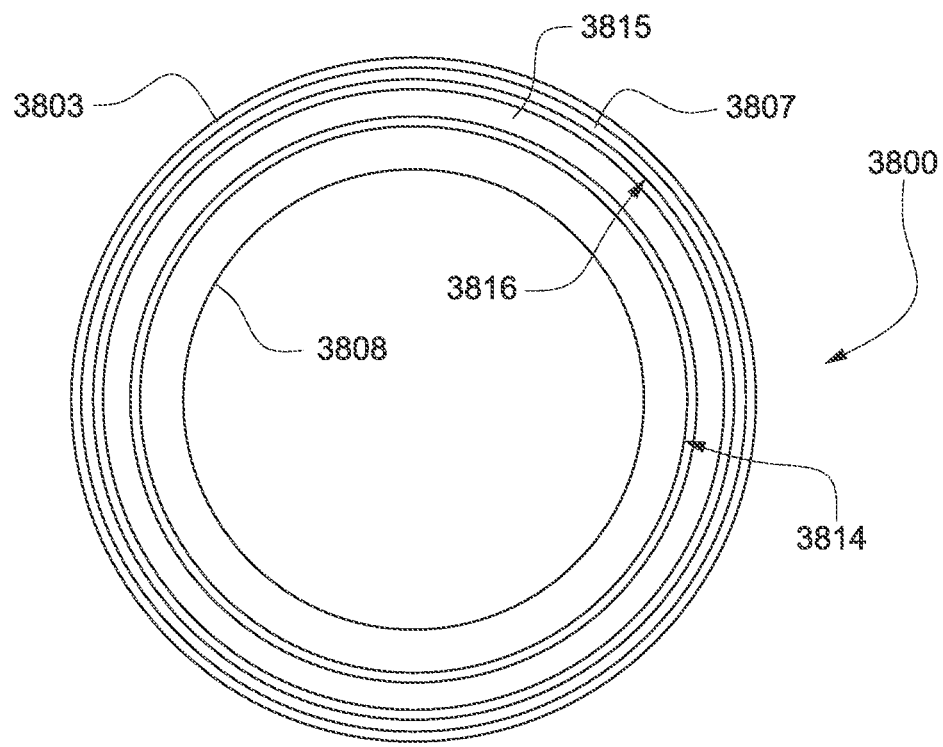

FIG. 13C depicts a posterior view of a connector ring of a patient interface according to an example of the present technology.

Figure 13D:
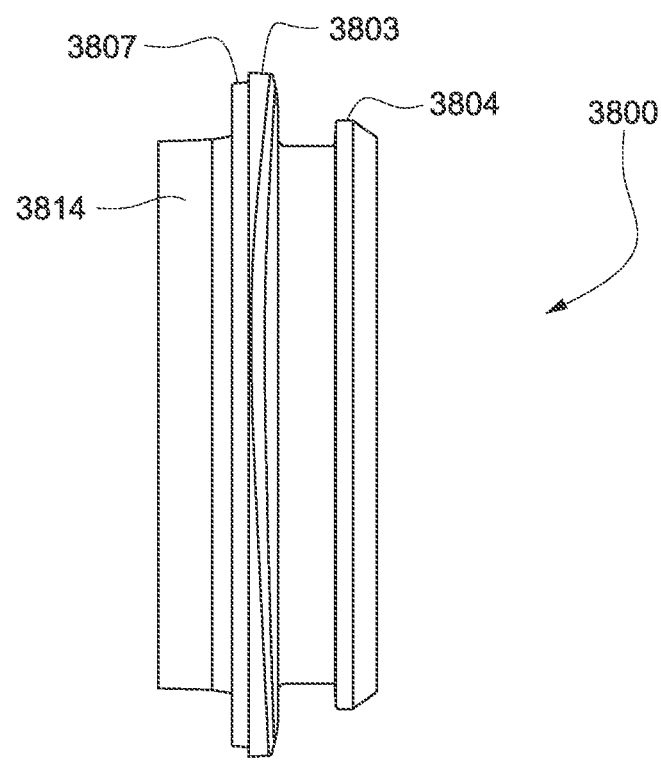

FIG. 13D depicts a lateral view of a connector ring of a patient interface according to an example of the present technology.

Figure 13E:
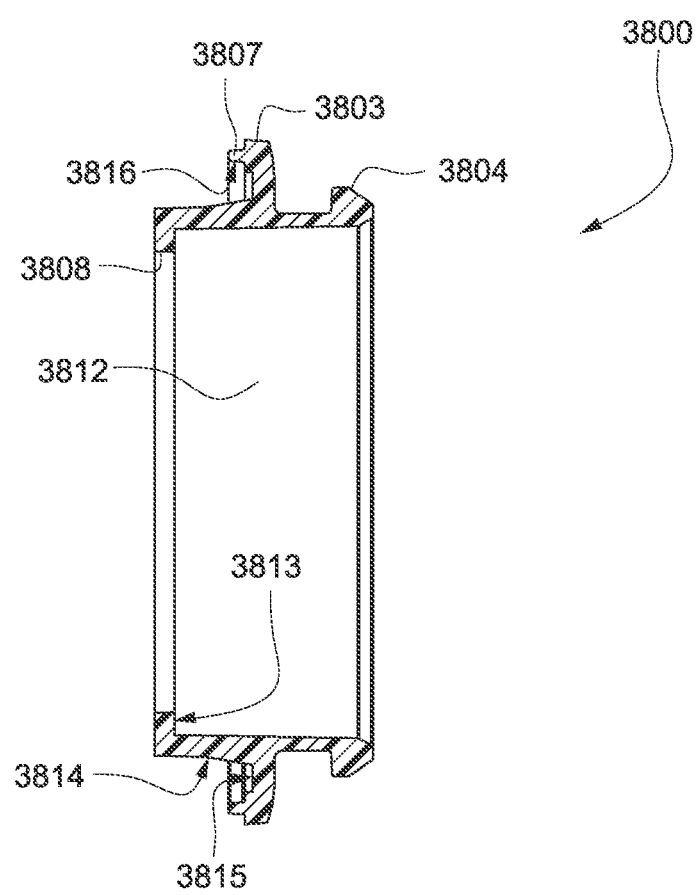

FIG. 13E depicts a cross-sectional view of a connector ring of a patient interface taken through line 13E-13E of FIG. 13B according to an example of the present technology.

Figure 14A:
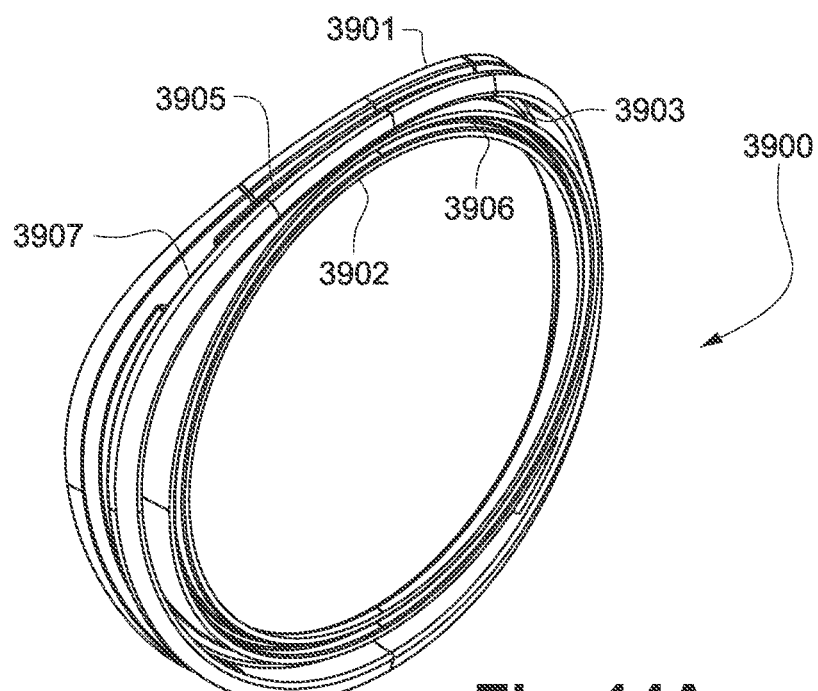

FIG. 14A depicts an anterior perspective view of a flexible joint structure of a patient interface according to an example of the present technology.

Figure 14B:
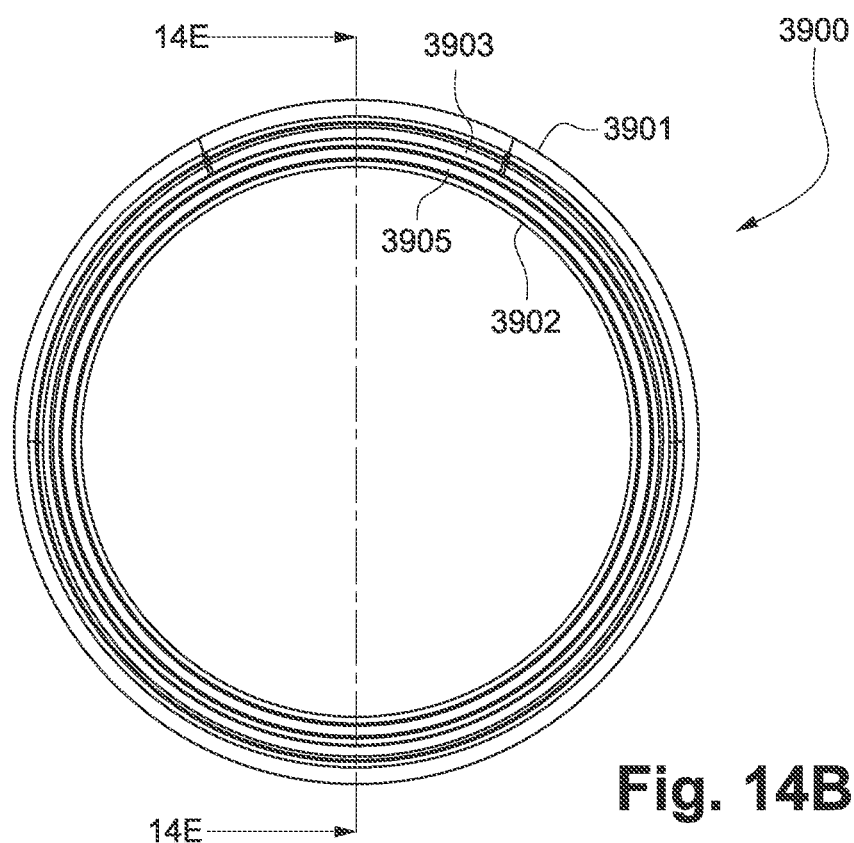

FIG. 14B depicts an anterior view of a flexible joint structure of a patient interface according to an example of the present technology.

Figure 14C:
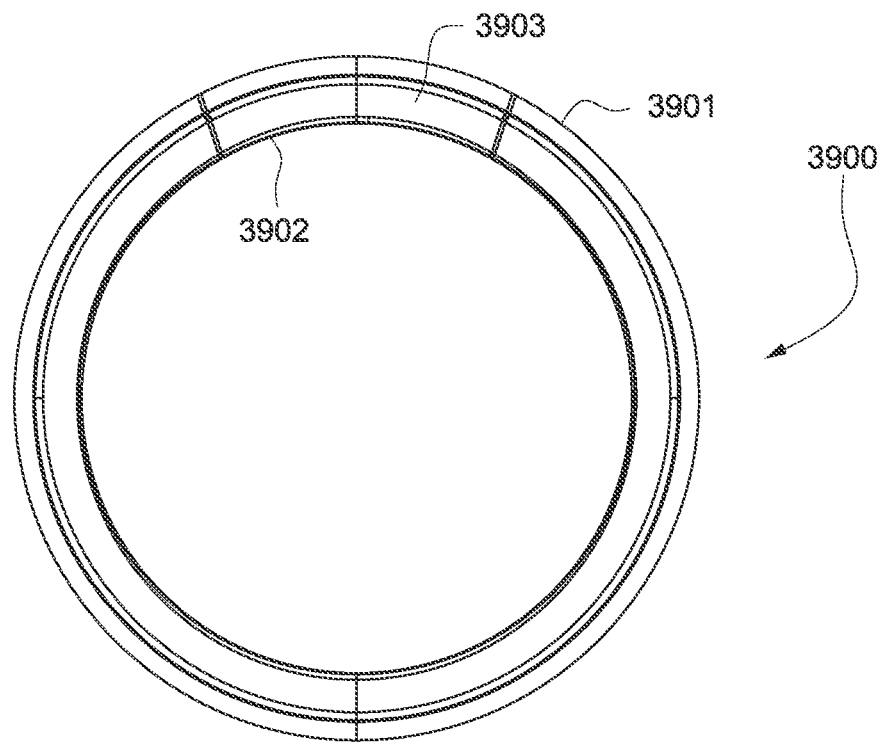

FIG. 14C depicts a posterior view of a flexible joint structure of a patient interface according to an example of the present technology.

Figure 14D:
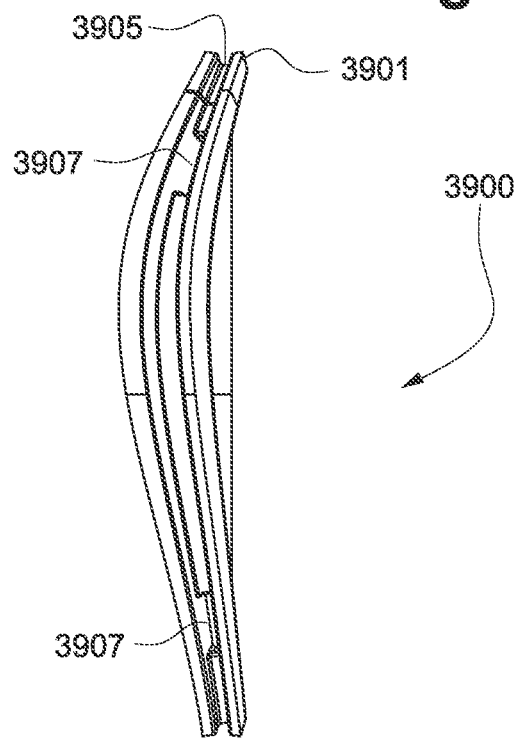

FIG. 14D depicts a lateral view of a flexible joint structure of a patient interface according to an example of the present technology.

Figure 14E:
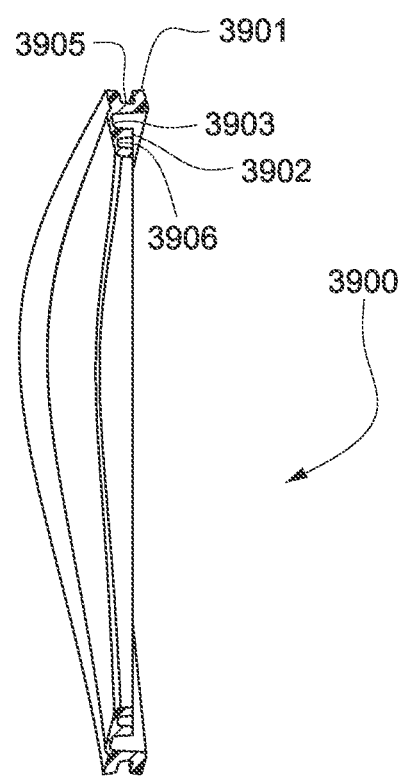

FIG. 14E depicts a cross-sectional view of a flexible joint structure of a patient interface taken through line 14E-14E of FIG. 14B according to an example of the present technology.

Figure 15A:
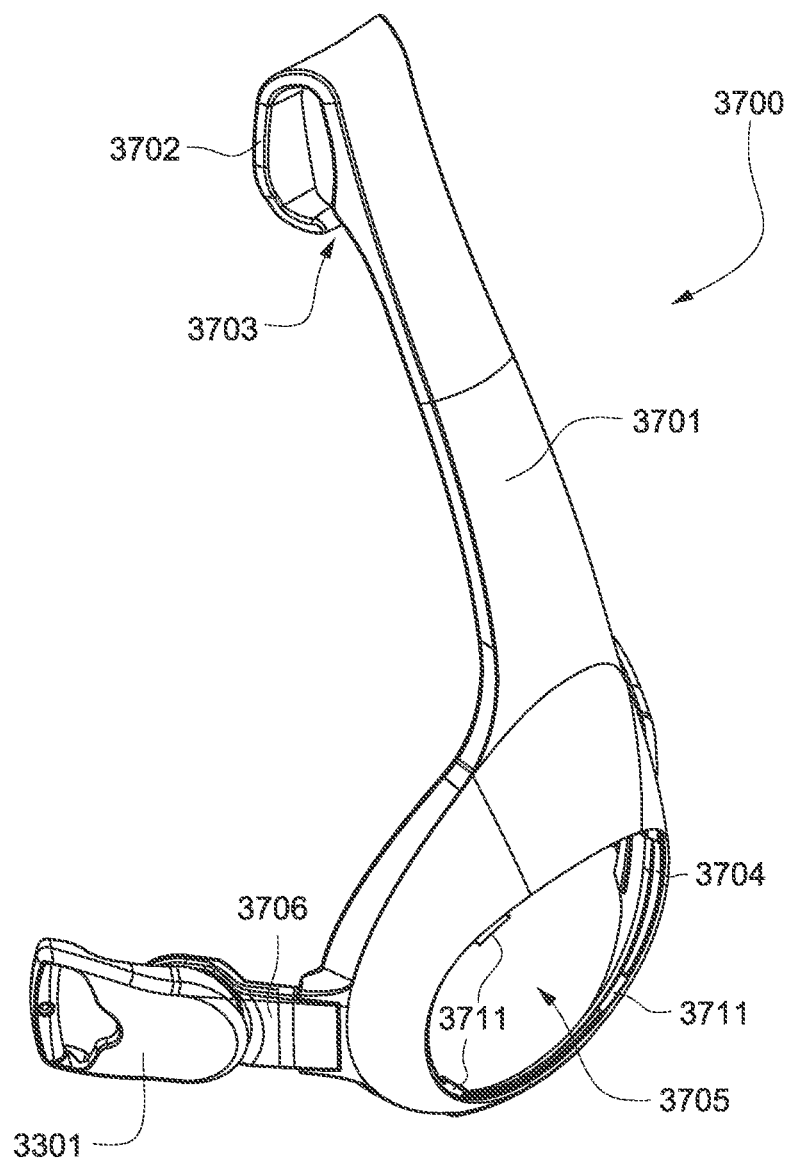

FIG. 15A depicts an anterior perspective view of a frame of a patient interface according to an example of the present technology.

Figure 15B:
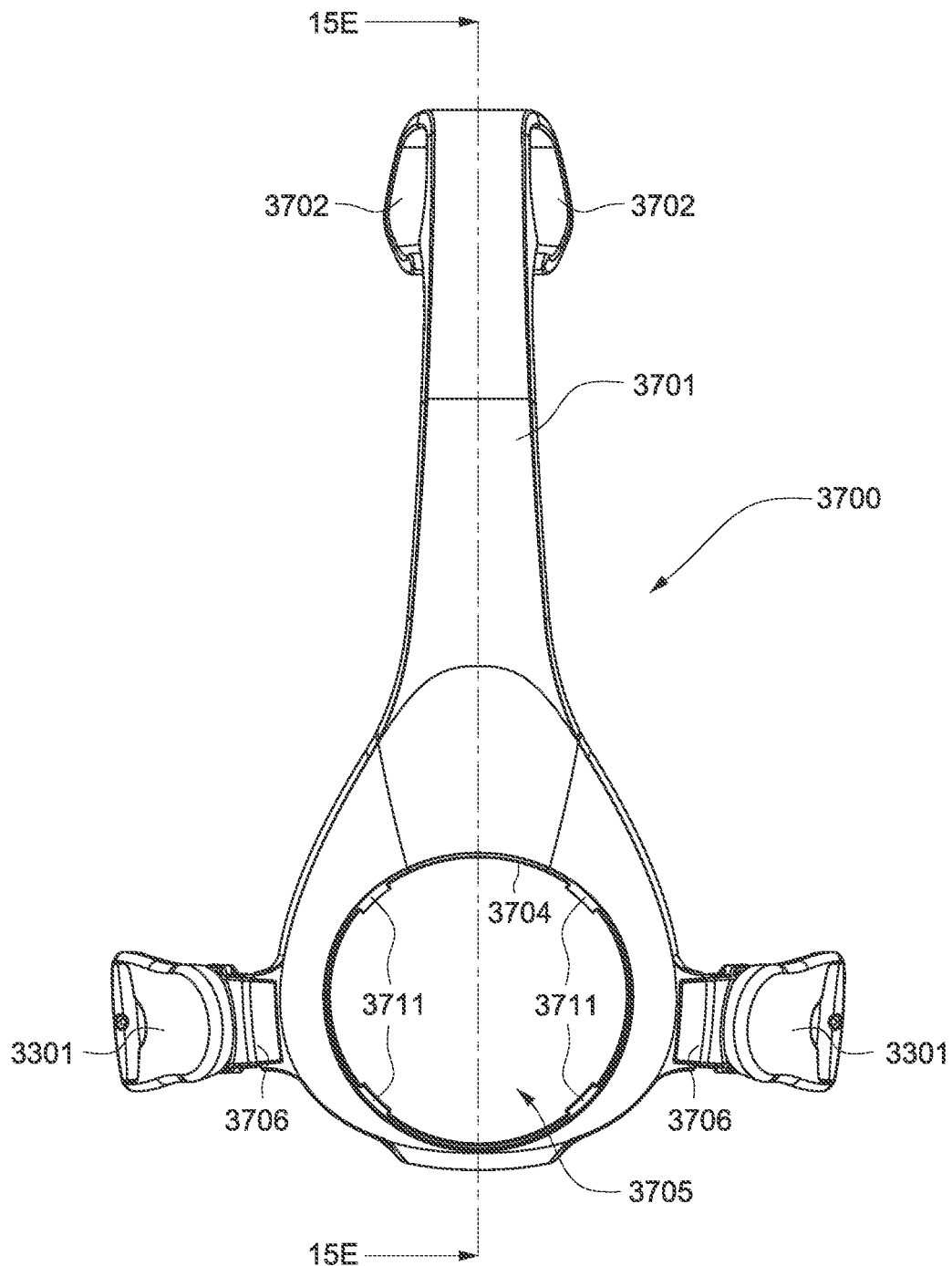

FIG. 15B depicts an anterior view of a frame of a patient interface according to an example of the present technology.

Figure 15C:
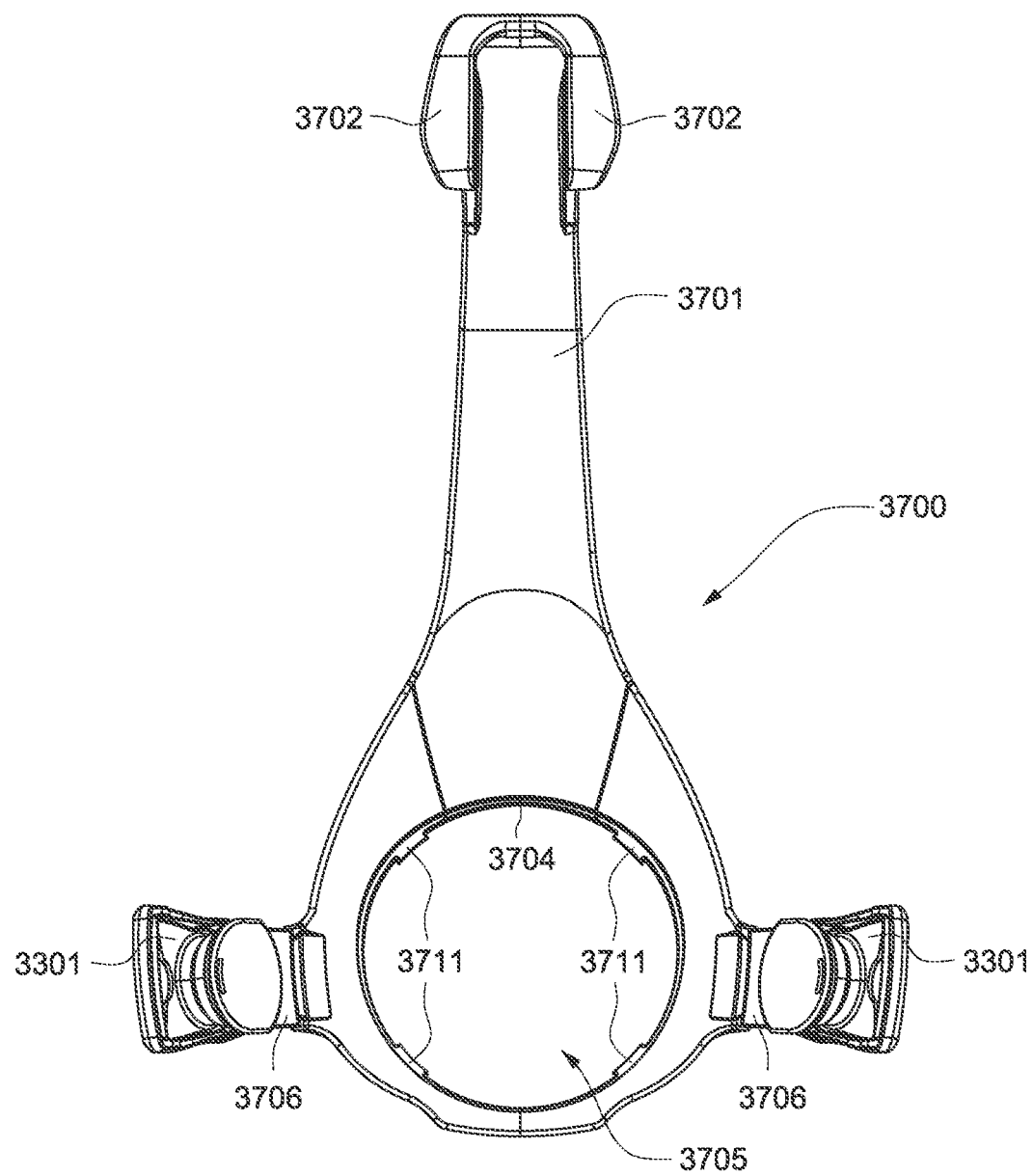

FIG. 15C depicts a posterior view of a frame of a patient interface according to an example of the present technology.

Figure 15D:
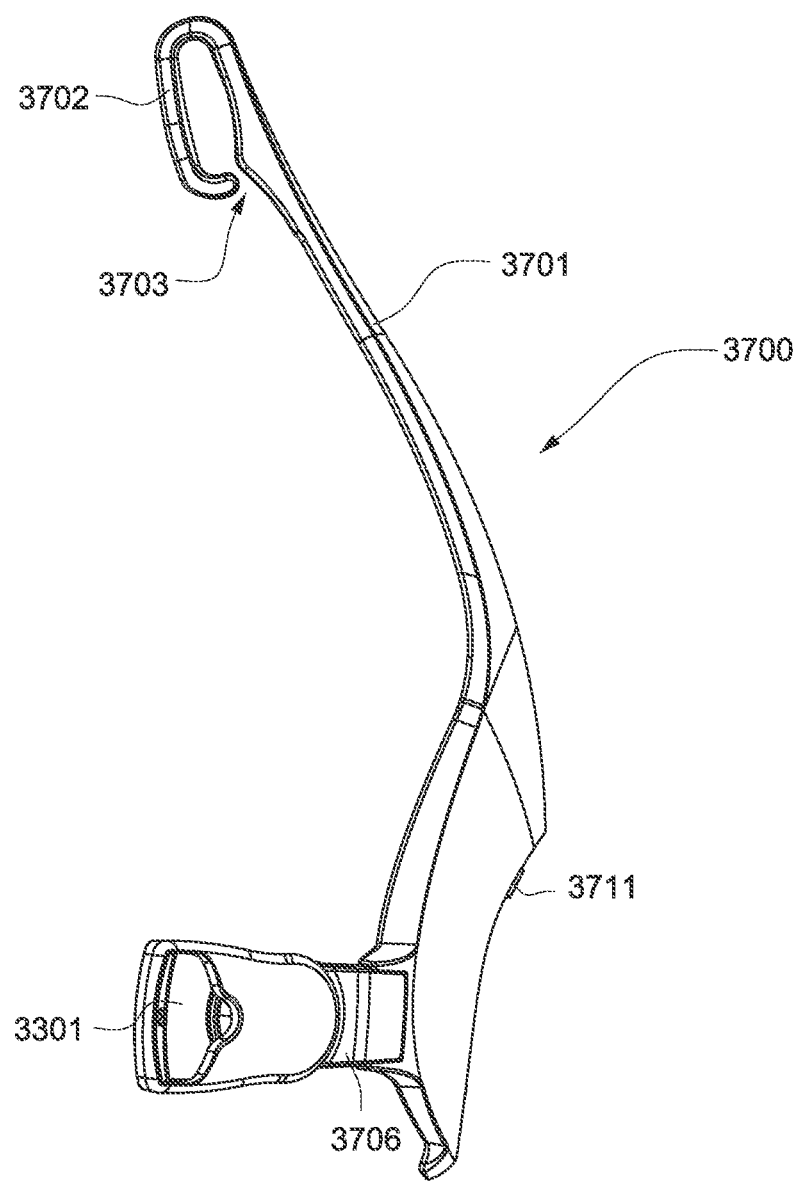

FIG. 15D depicts a lateral view of a frame of a patient interface according to an example of the present technology.

Figure 15E:
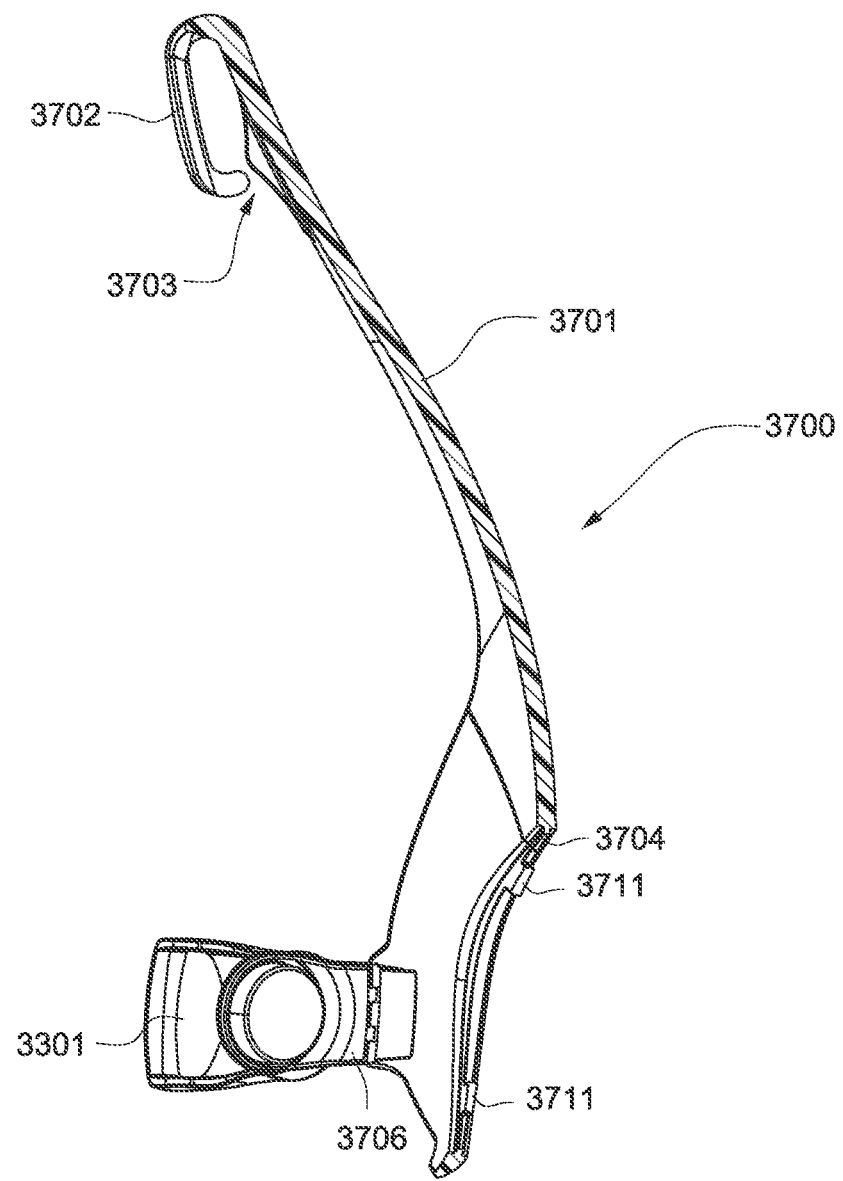

FIG. 15E depicts a cross-sectional view of a frame of a patient interface taken through line 15E-15E of FIG. 15B according to an example of the present technology.

Figure 16A:
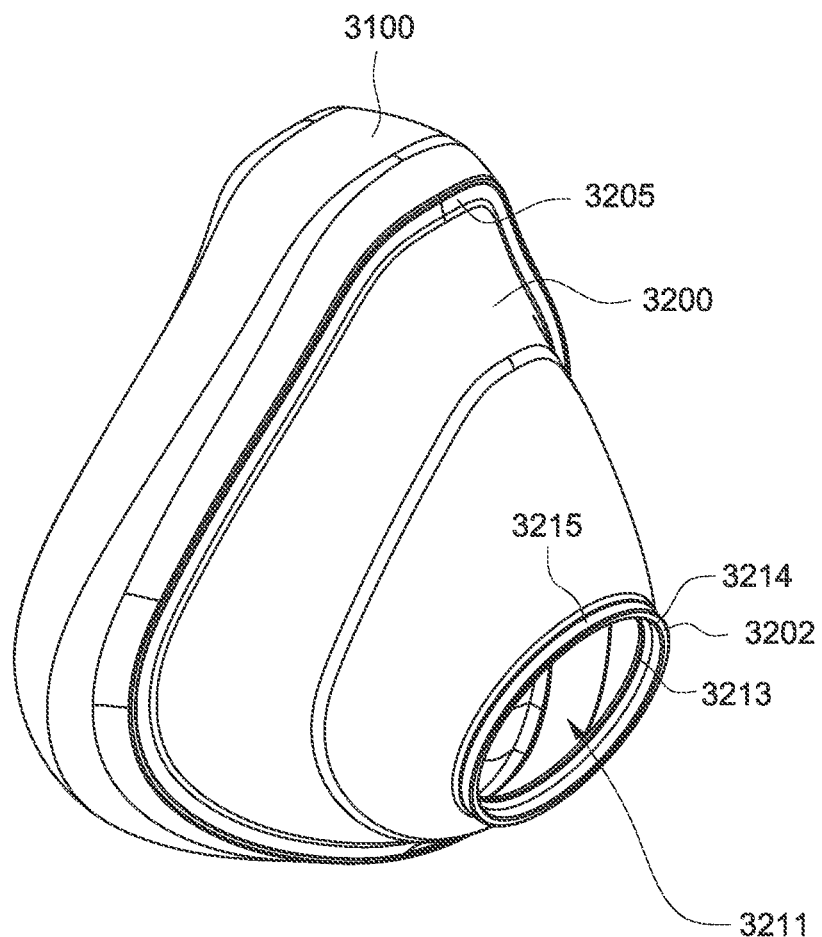

FIG. 16A depicts an anterior perspective view of a seal-forming structure and a plenum chamber of a patient interface according to an example of the present technology.

Figure 16B:
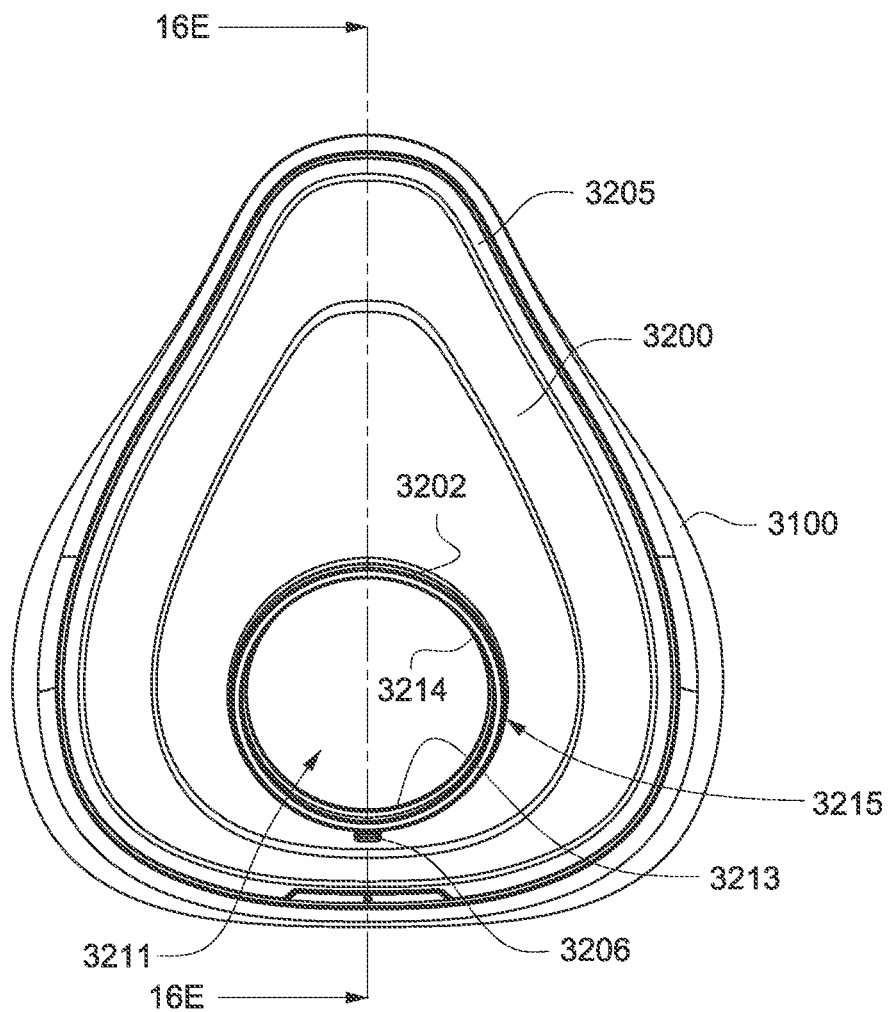

FIG. 16B depicts an anterior view of a seal-forming structure and a plenum chamber of a patient interface according to an example of the present technology.

Figure 16C:
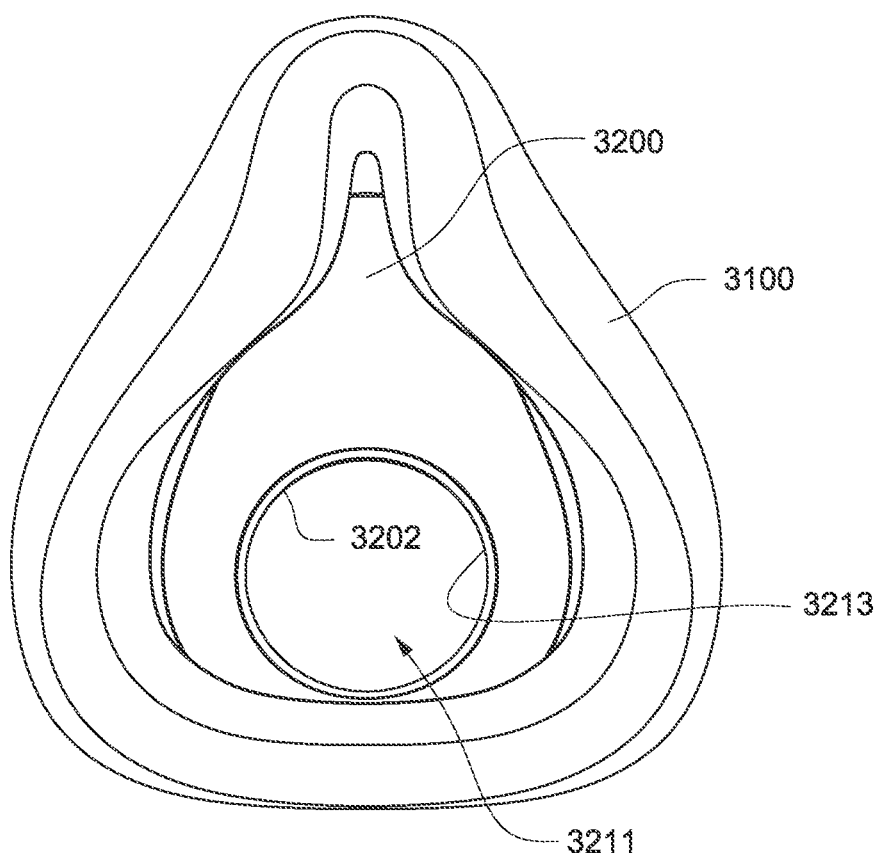

FIG. 16C depicts a posterior view of a seal-forming structure and a plenum chamber of a patient interface according to an example of the present technology.

Figure 16D:
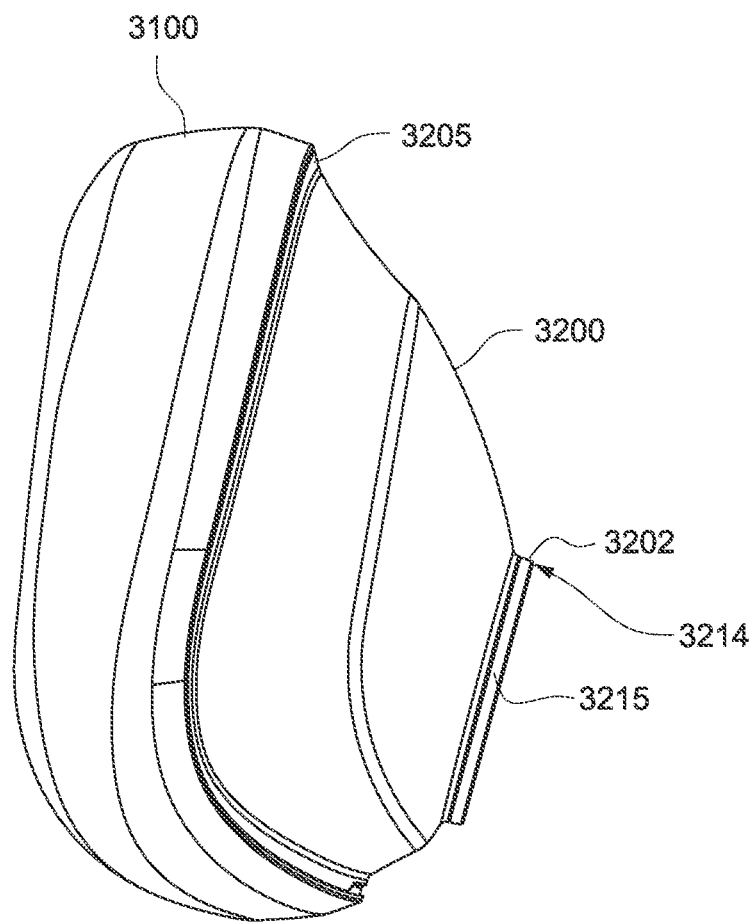

FIG. 16D depicts a lateral view of a seal-forming structure and a plenum chamber of a patient interface according to an example of the present technology.

Figure 16E:
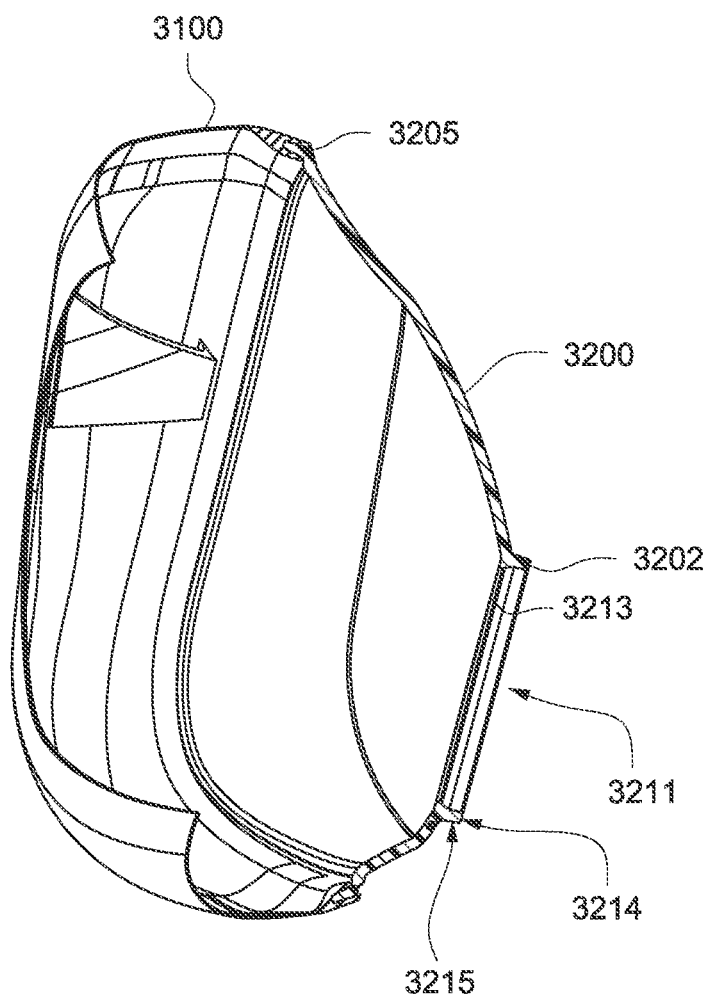

FIG. 16E depicts a cross-sectional view of a seal-forming structure and a plenum chamber of a patient interface taken through line 16E-16E of FIG. 16B according to an example of the present technology.

Figure 17A:
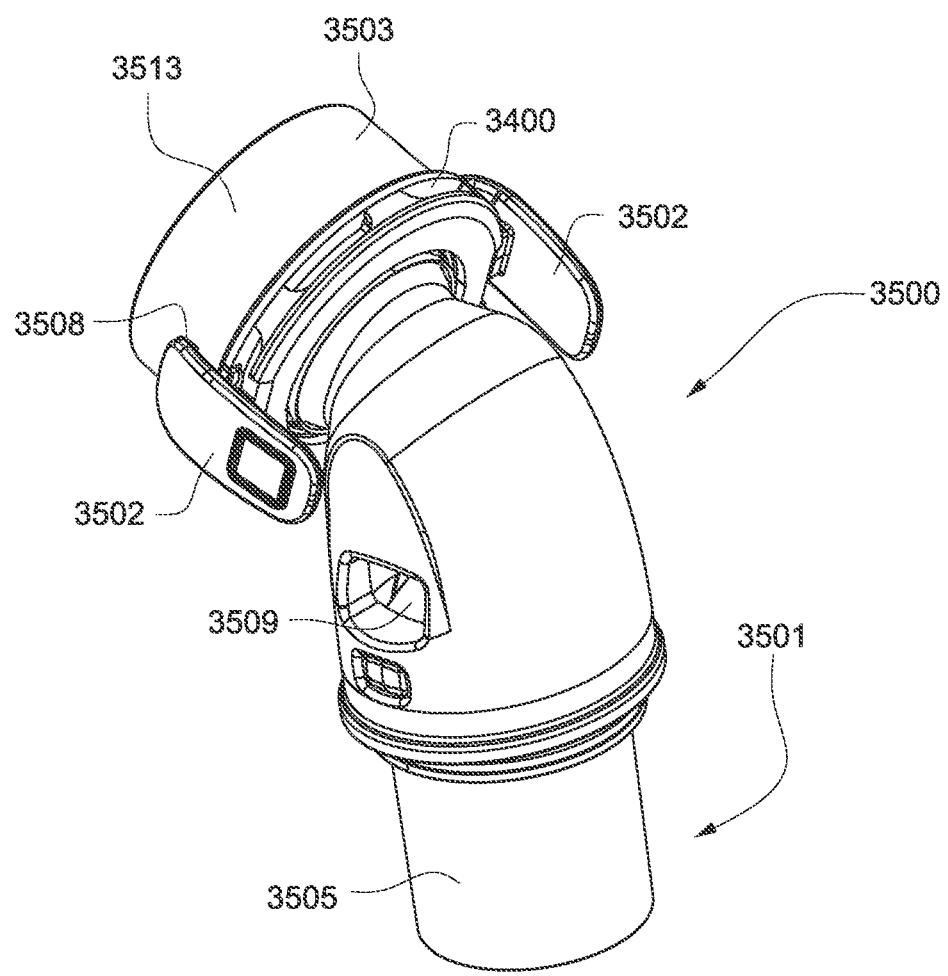

FIG. 17A depicts an anterior perspective view of a decoupling structure of a patient interface according to an example of the present technology.

Figures 17B, 17C:
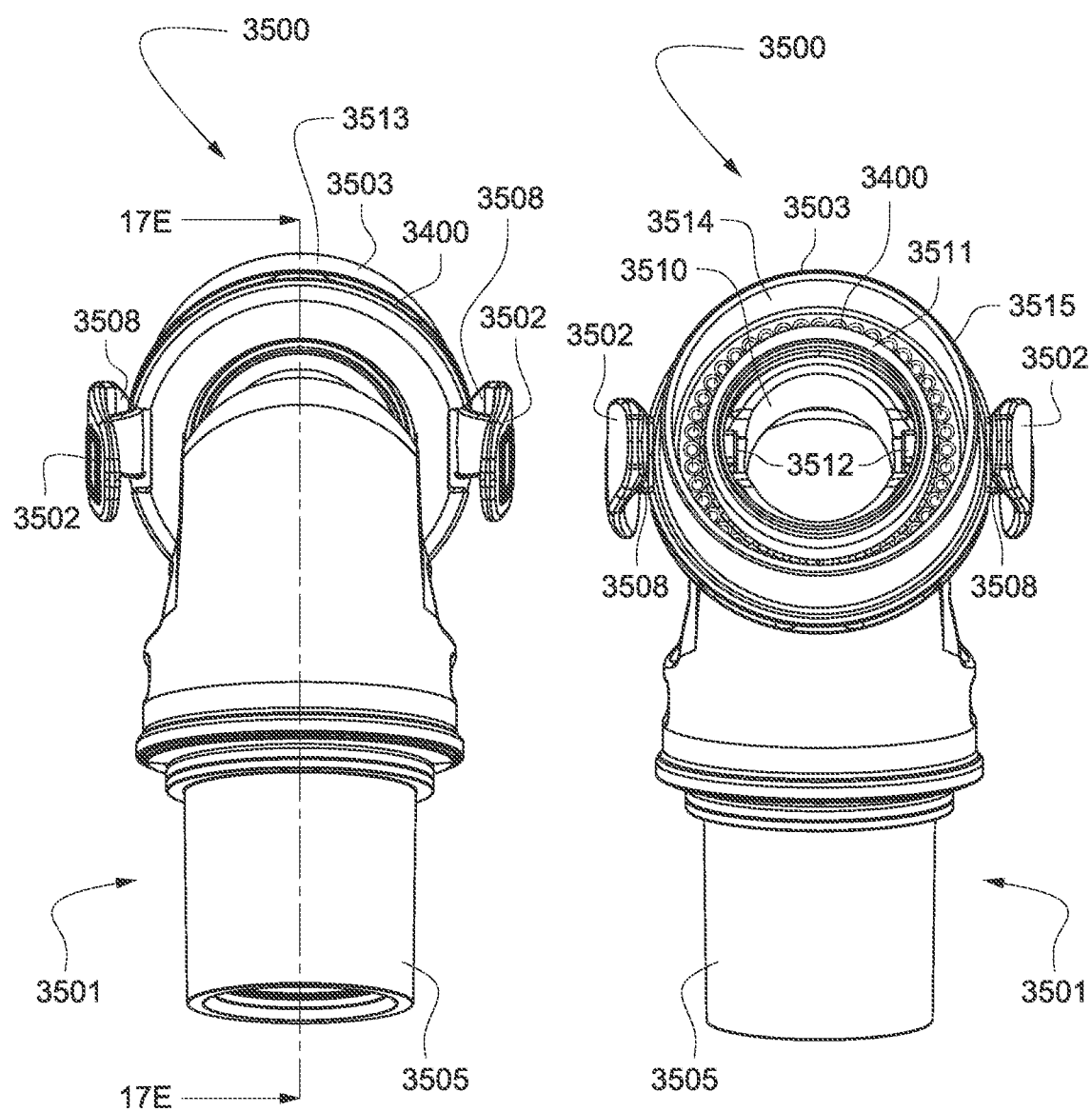

FIG. 17B depicts an anterior view of a decoupling structure of a patient interface according to an example of the present technology.

FIG. 17C depicts a posterior view of a decoupling structure of a patient interface according to an example of the present technology.

Figure 17E:
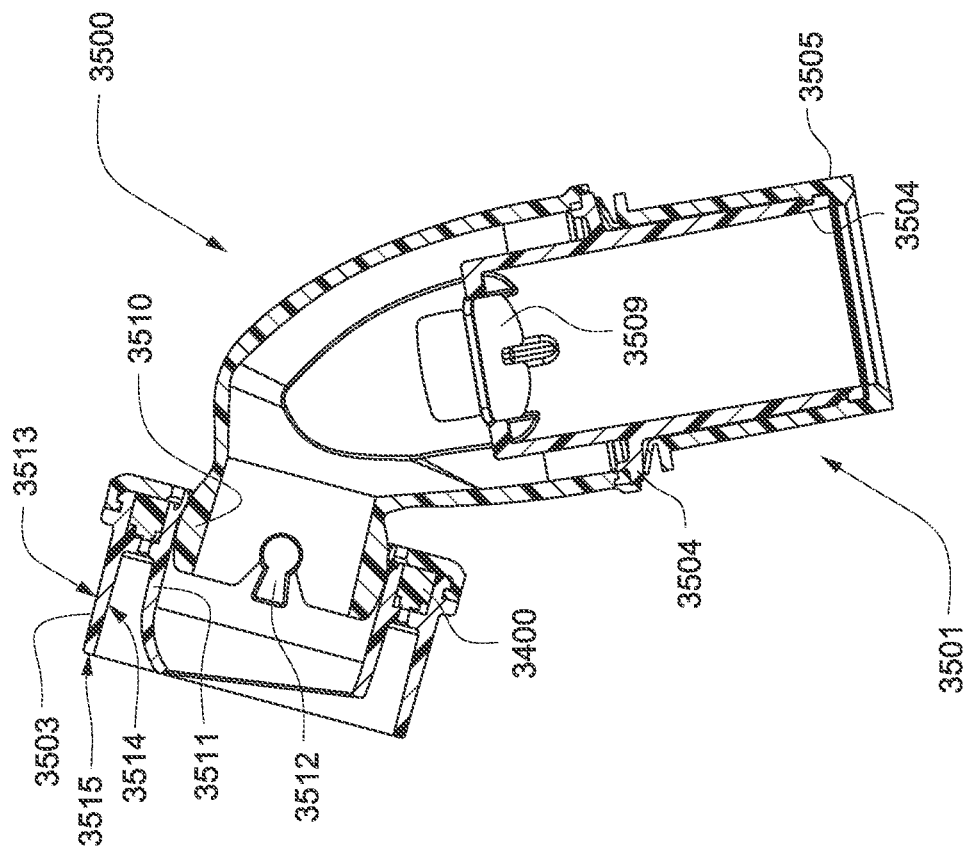
Figure 17D:
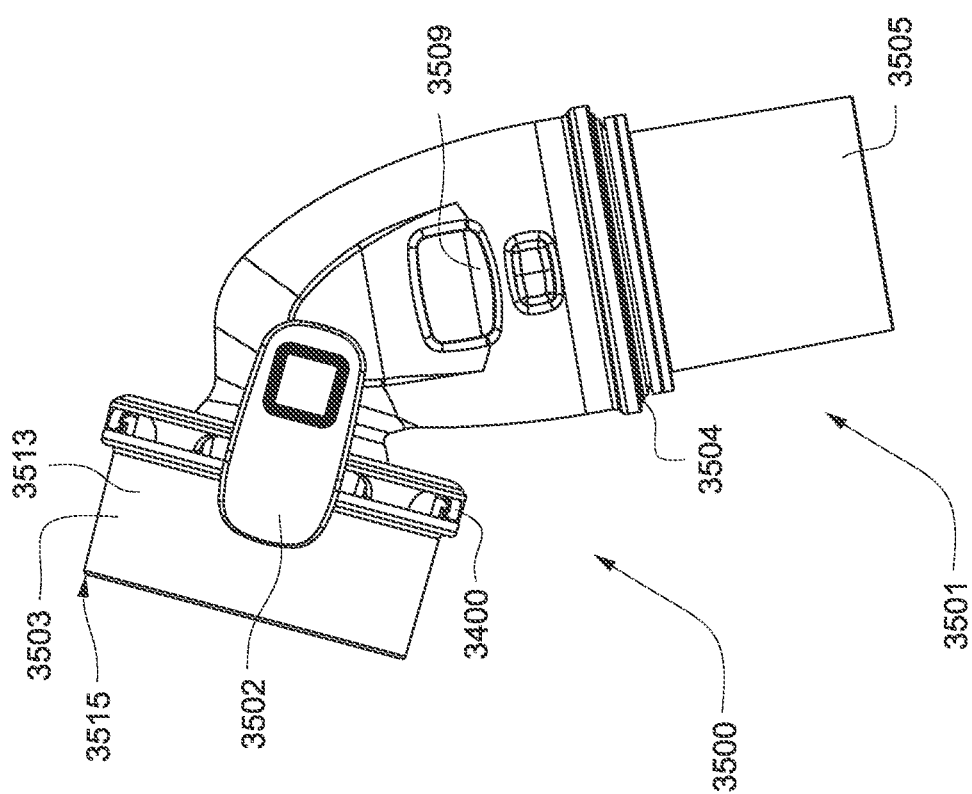

FIG. 17D depicts a lateral view of a decoupling structure of a patient interface according to an example of the present technology.

FIG. 17E depicts a cross-sectional view of a decoupling structure of a patient interface taken through line 17E-17E of FIG. 17B according to an example of the present technology.

Figure 18A:
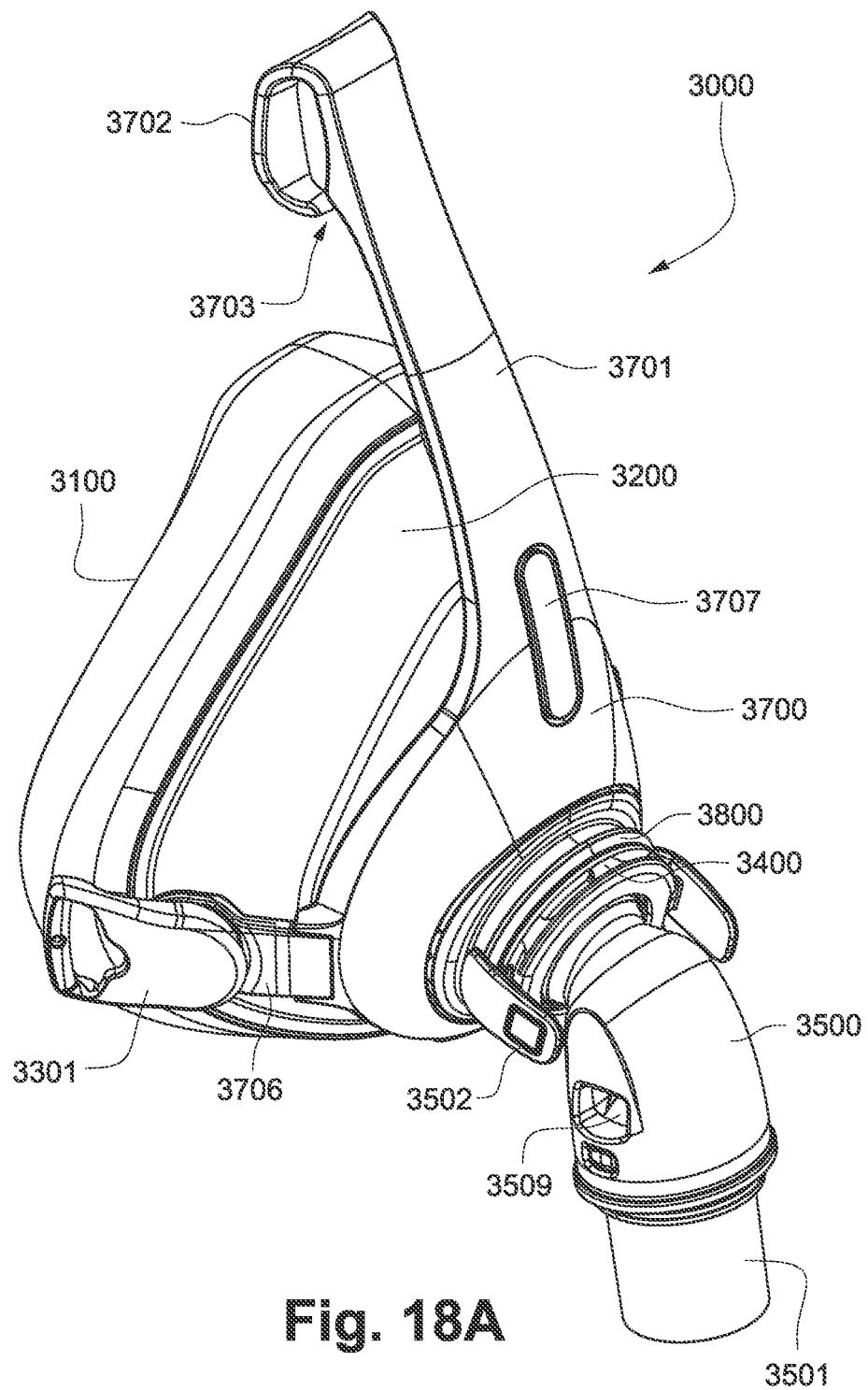

FIG. 18A depicts an anterior perspective view of a patient interface according to an example of the present technology.

Figure 18B:
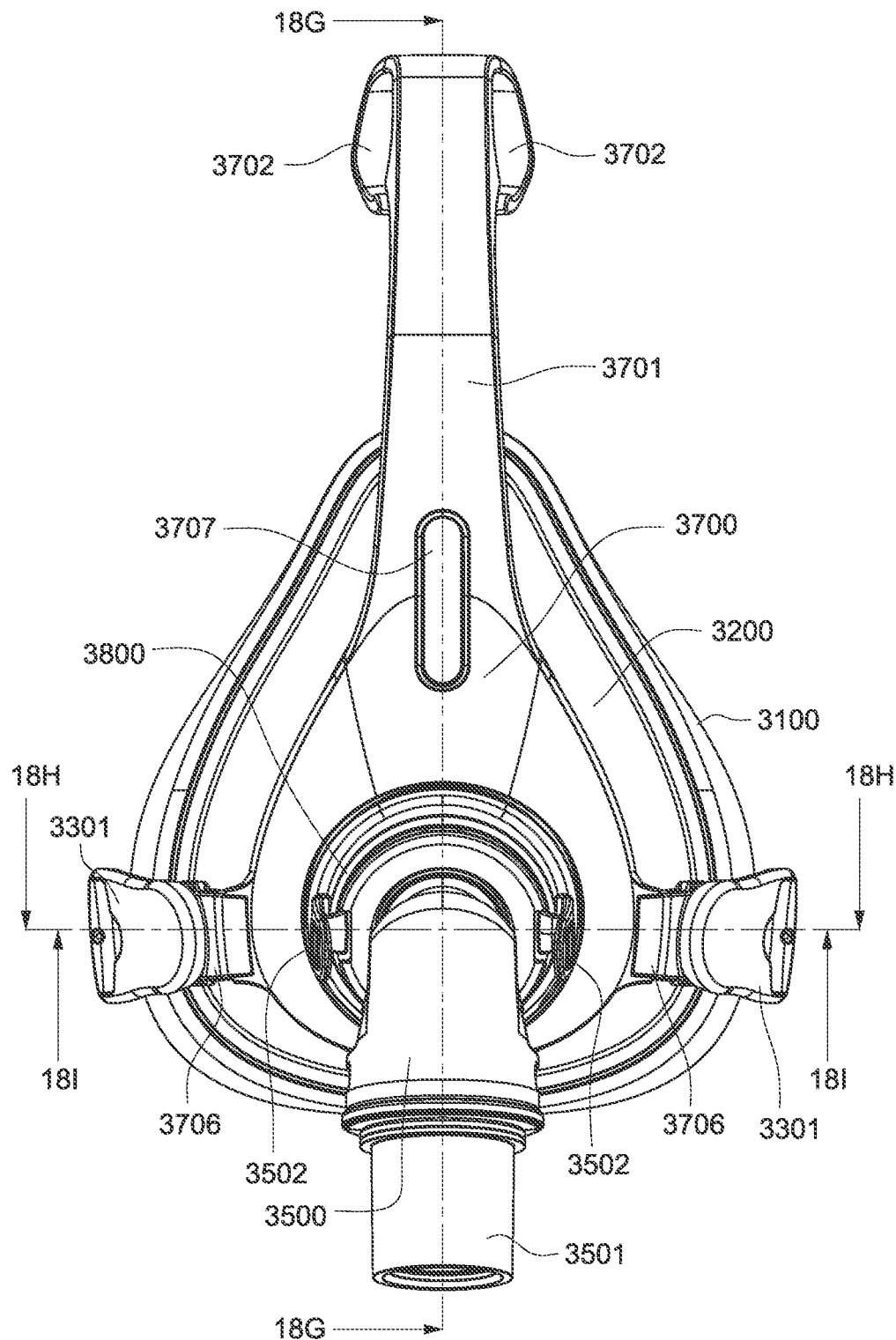

FIG. 18B depicts an anterior view of a patient interface according to an example of the present technology.

Figure 18C:
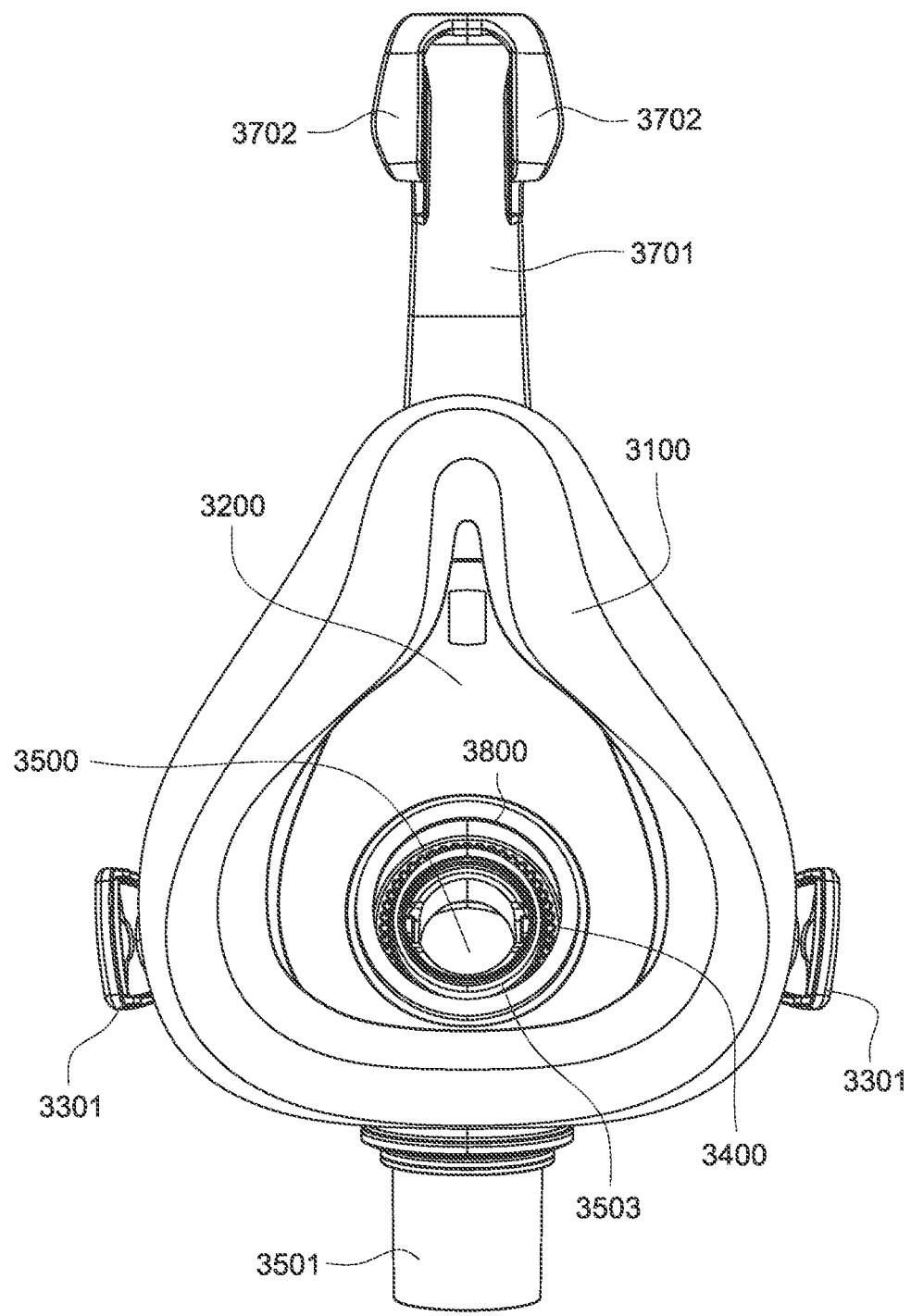

FIG. 18C depicts a posterior view of a patient interface according to an example of the present technology.

Figure 18D:
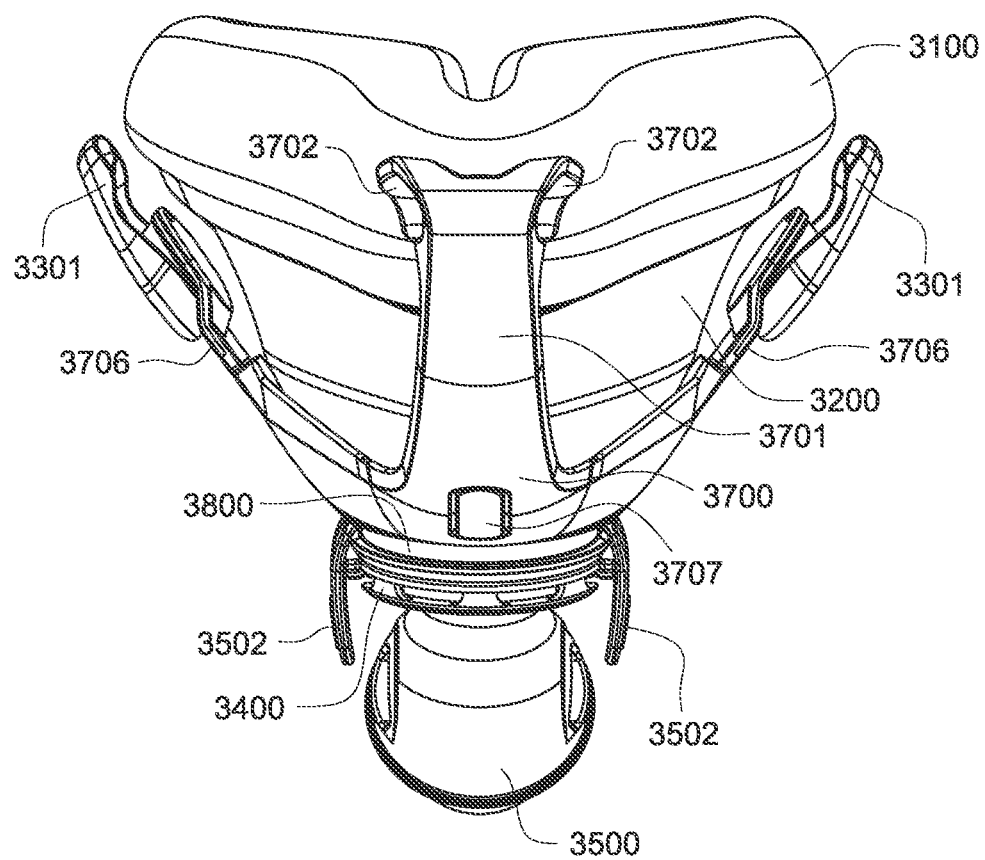

FIG. 18D depicts a superior view of a patient interface according to an example of the present technology.

Figure 18E:
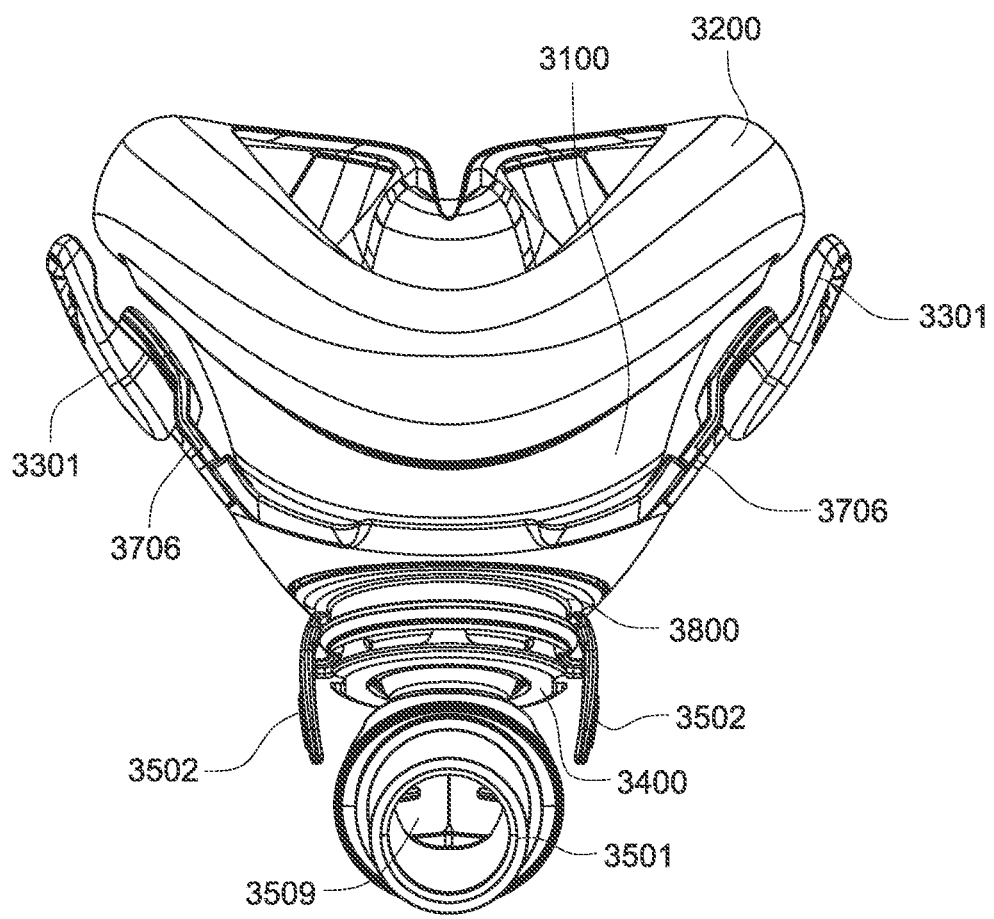

FIG. 18E depicts an inferior view of a patient interface according to an example of the present technology.

Figure 18F:
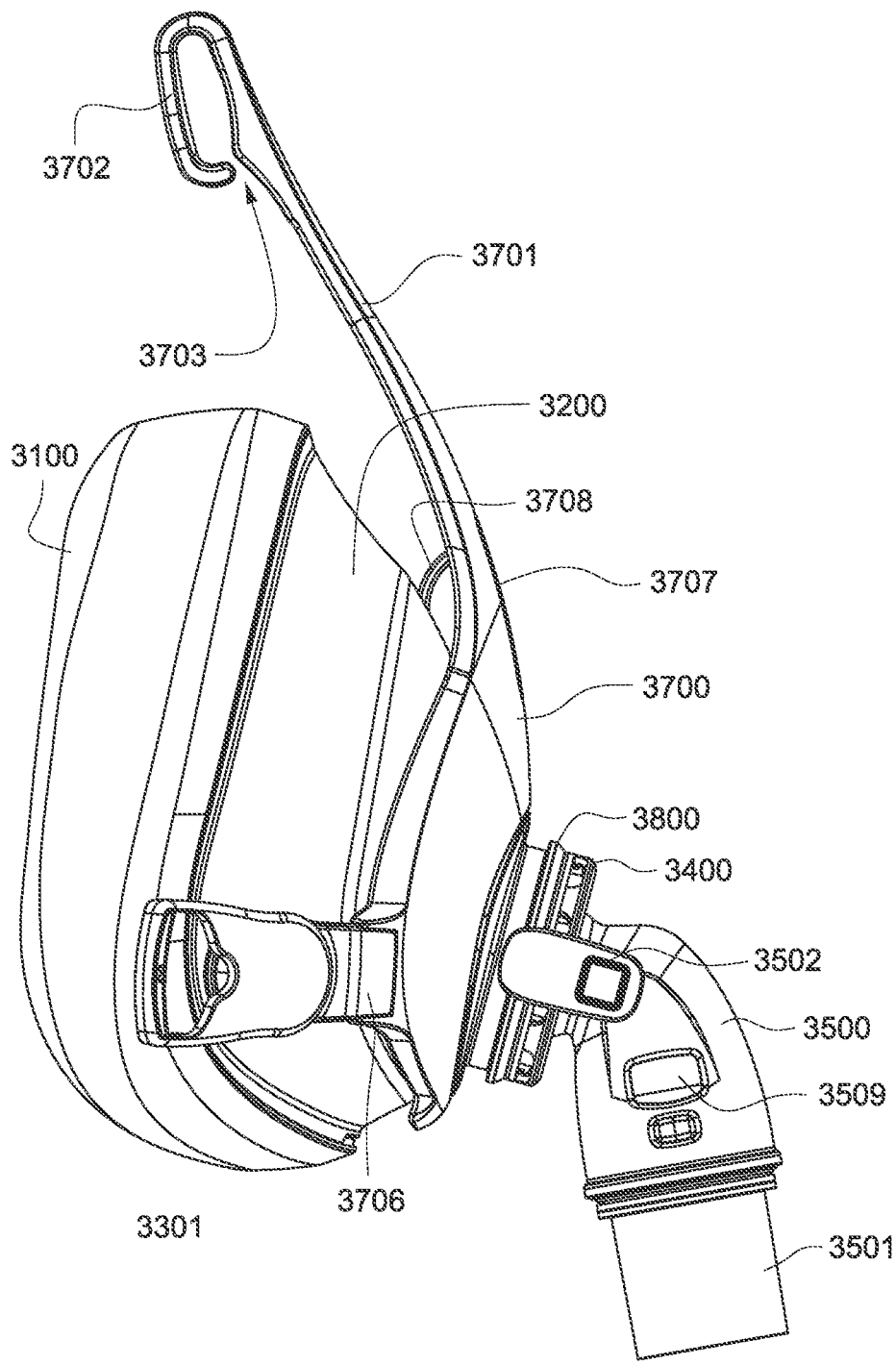

FIG. 18F depicts a lateral view of a patient interface according to an example of the present technology.

Figure 18G:
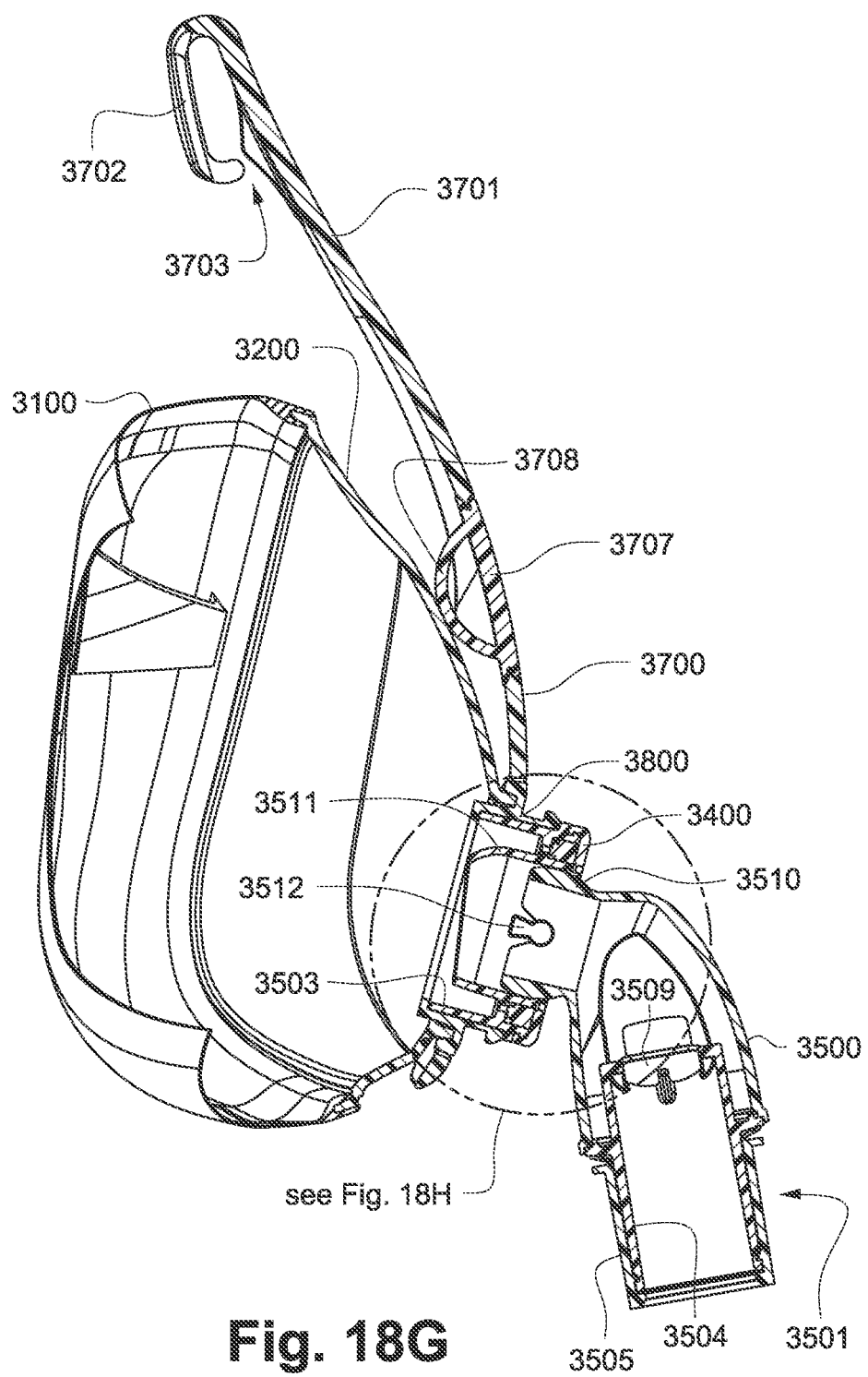

FIG. 18G depicts a cross-sectional view of a patient interface taken through line 18G-18G of FIG. 18B according to an example of the present technology.

Figure 18H:
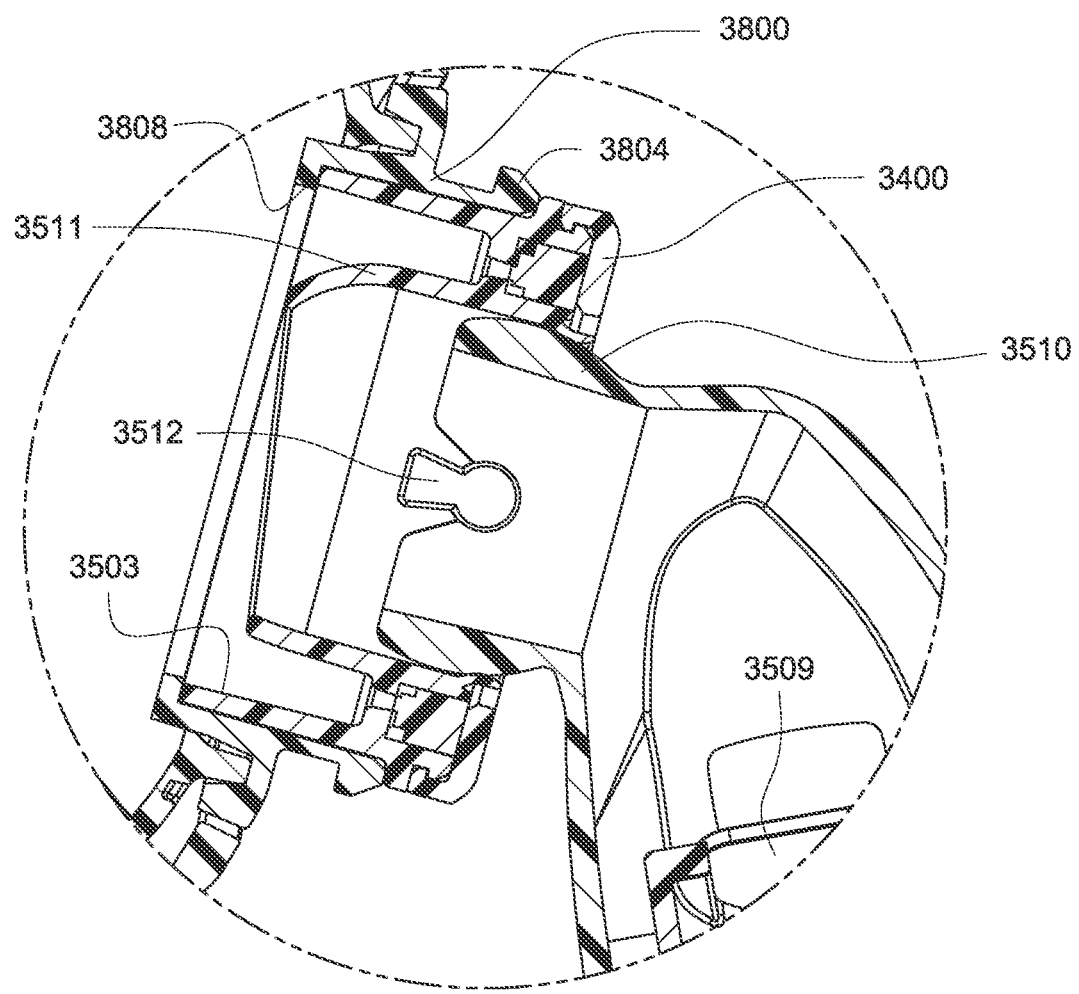

FIG. 18H depicts a detailed view of a portion of a patient interface depicted in FIG. 18G according to an example of the present technology.

Figure 18I:
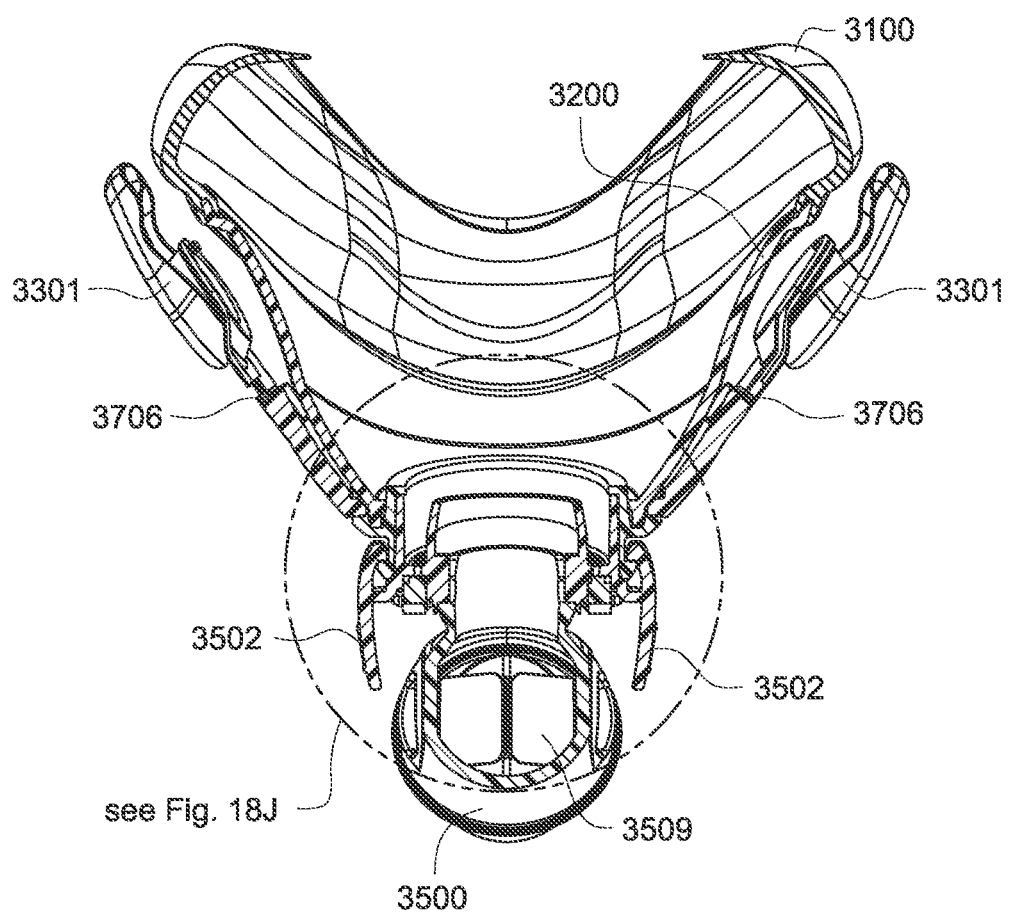

FIG. 18I depicts a cross-sectional view of a patient interface taken through line 18I-18I of FIG. 18B according to an example of the present technology.

Figure 18J:
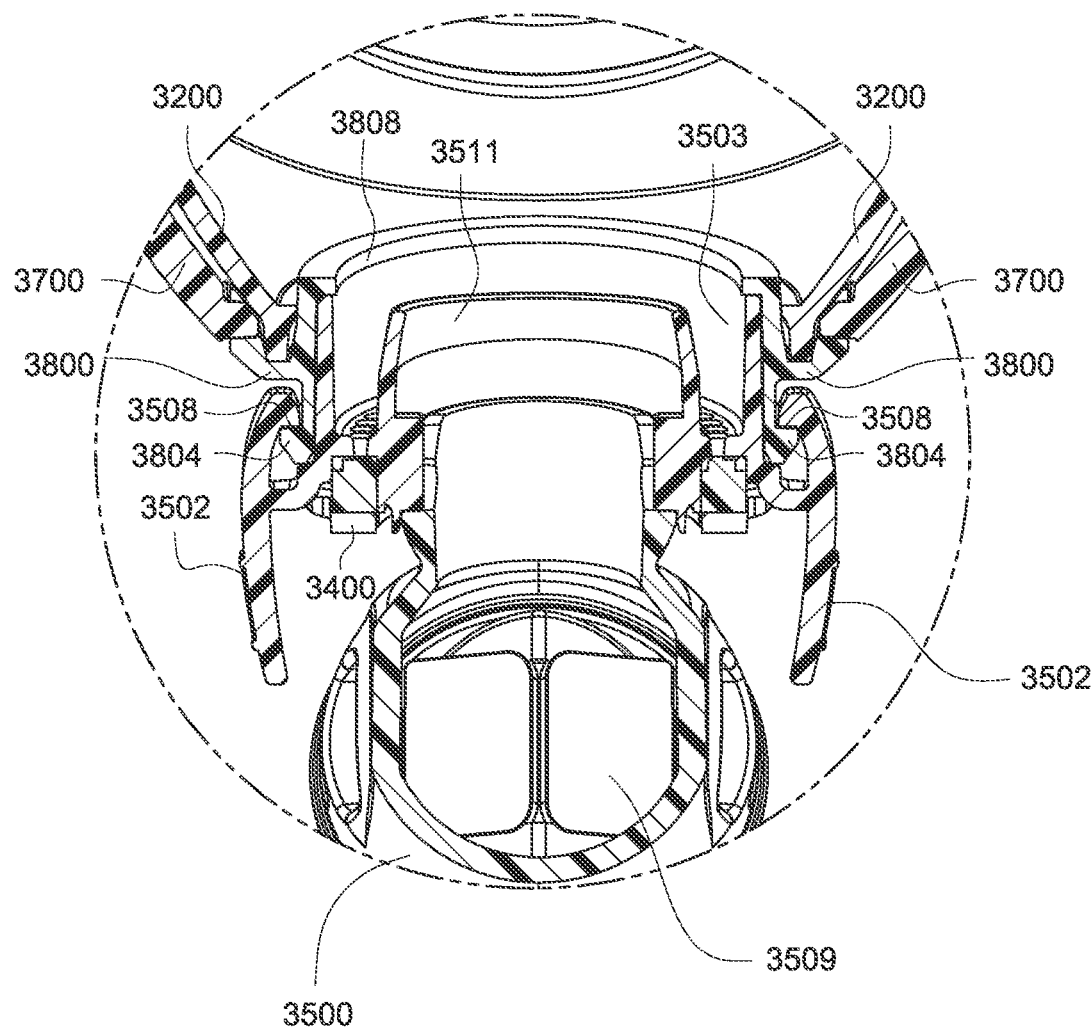

FIG. 18J depicts a detailed view of a portion of a patient interface depicted in FIG. 18I according to an example of the present technology.

Figure 18K:
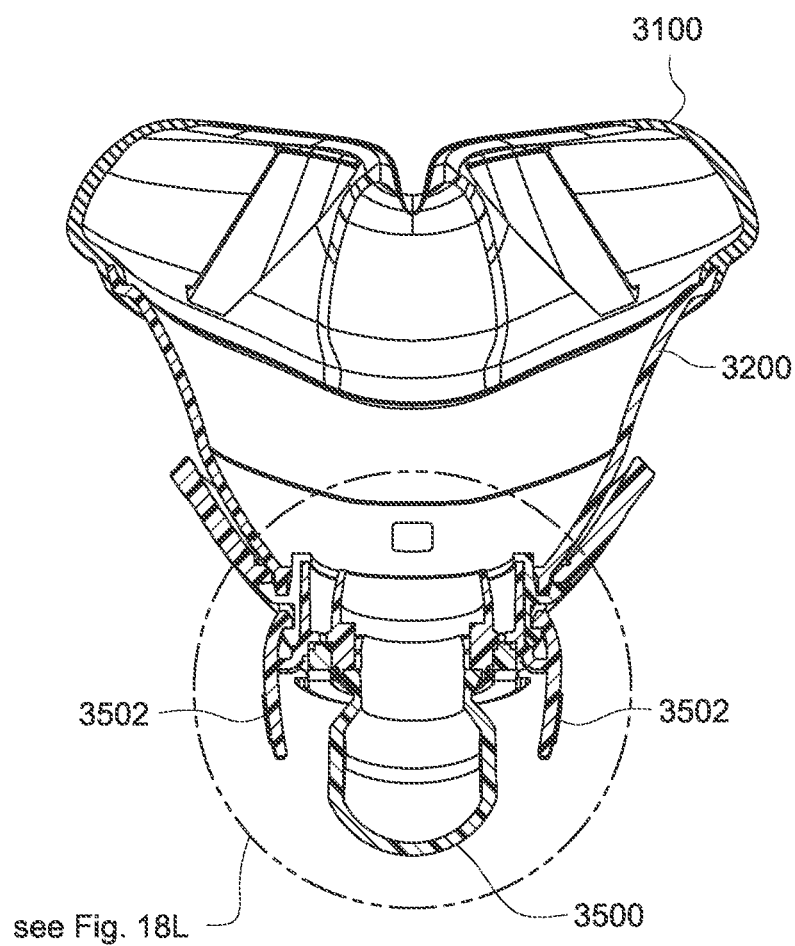

FIG. 18K depicts a cross-sectional view of a patient interface taken through line 18K-18K of FIG. 18B according to an example of the present technology.

Figure 18L:
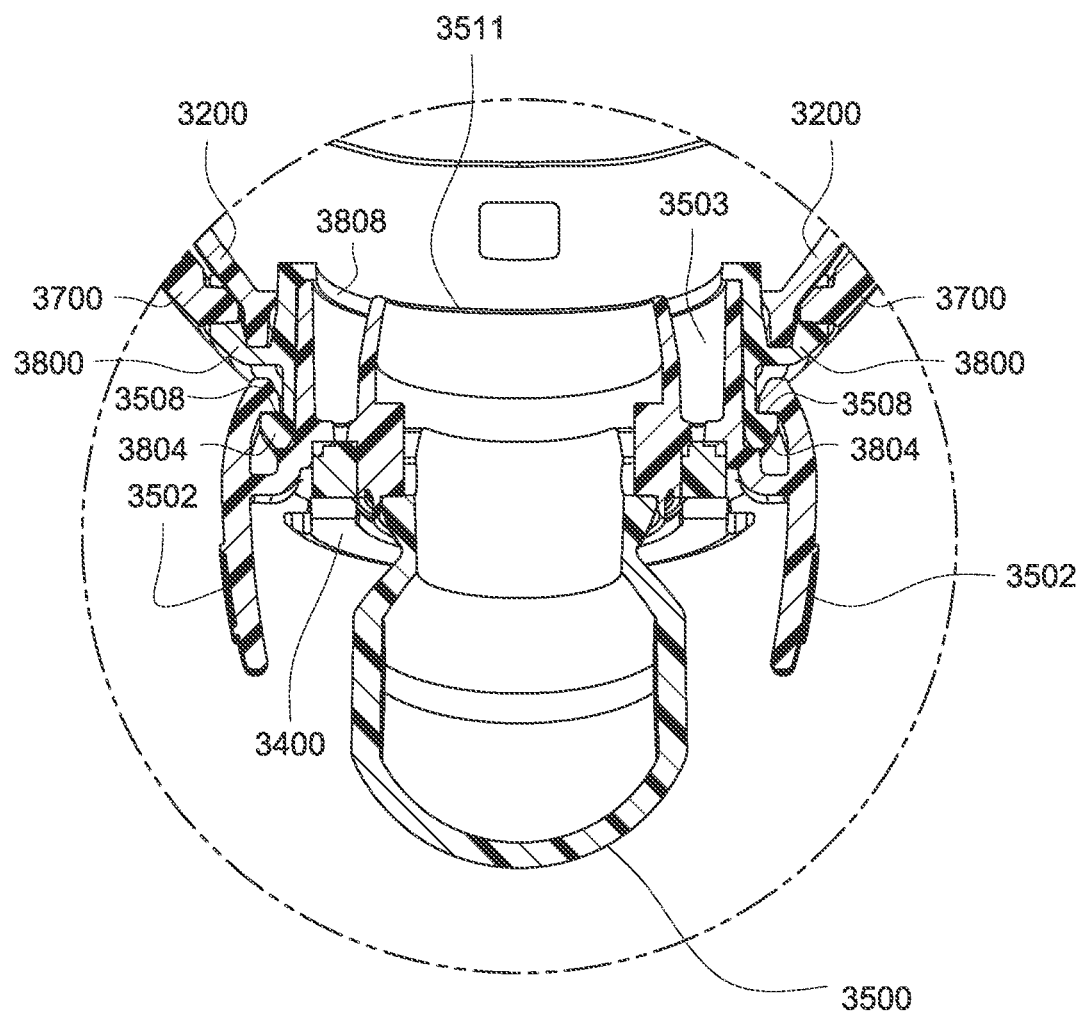

FIG. 18L depicts a detailed view of a portion of a patient interface depicted in FIG. 18K according to an example of the present technology.

Figure 18M:
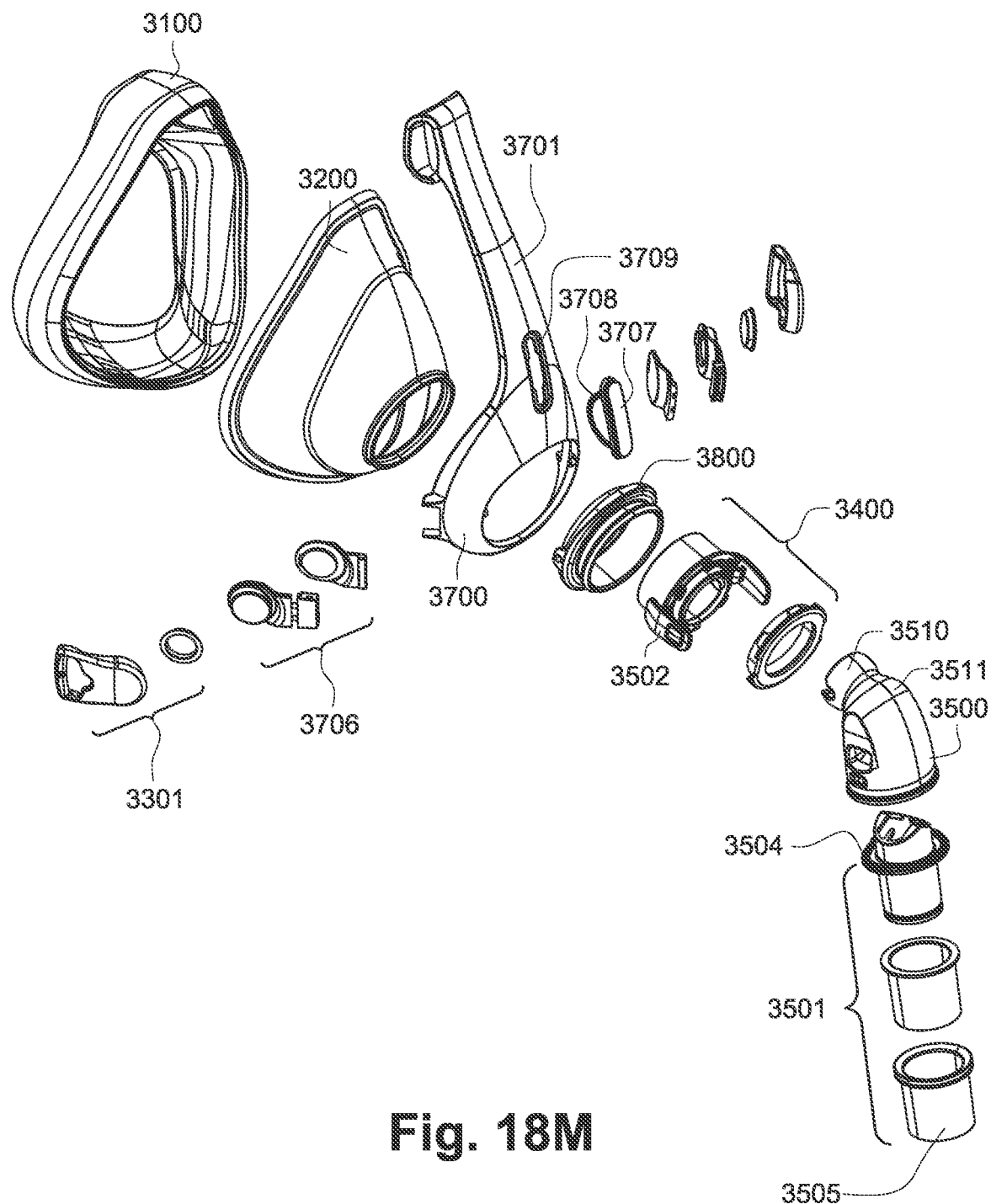

FIG. 18M depicts an exploded view of a patient interface according to an example of the present technology.

Figure 19A:
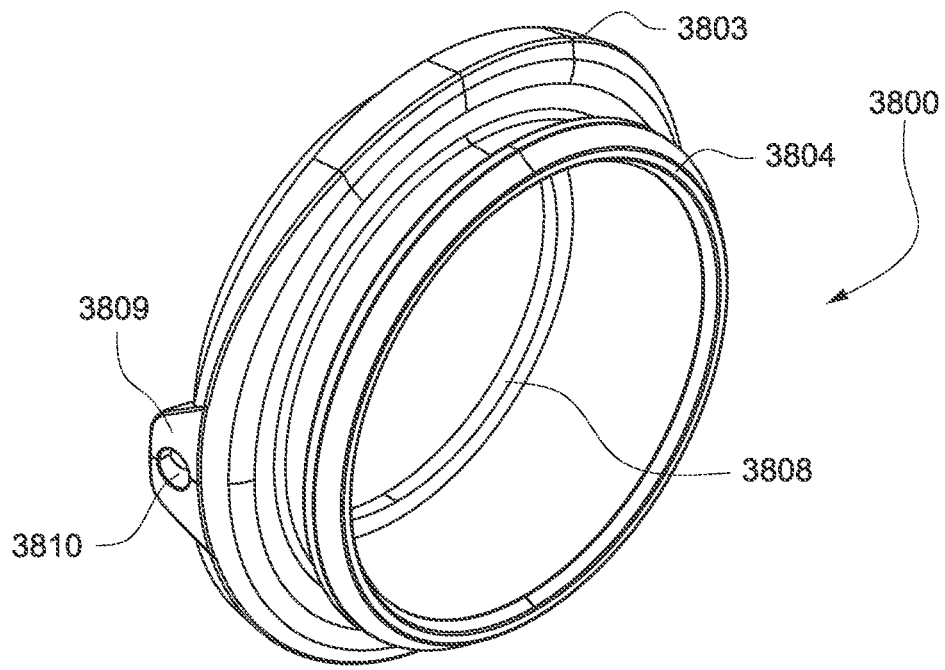

FIG. 19A depicts an anterior perspective view of a connector ring of a patient interface according to an example of the present technology.

Figure 19B:
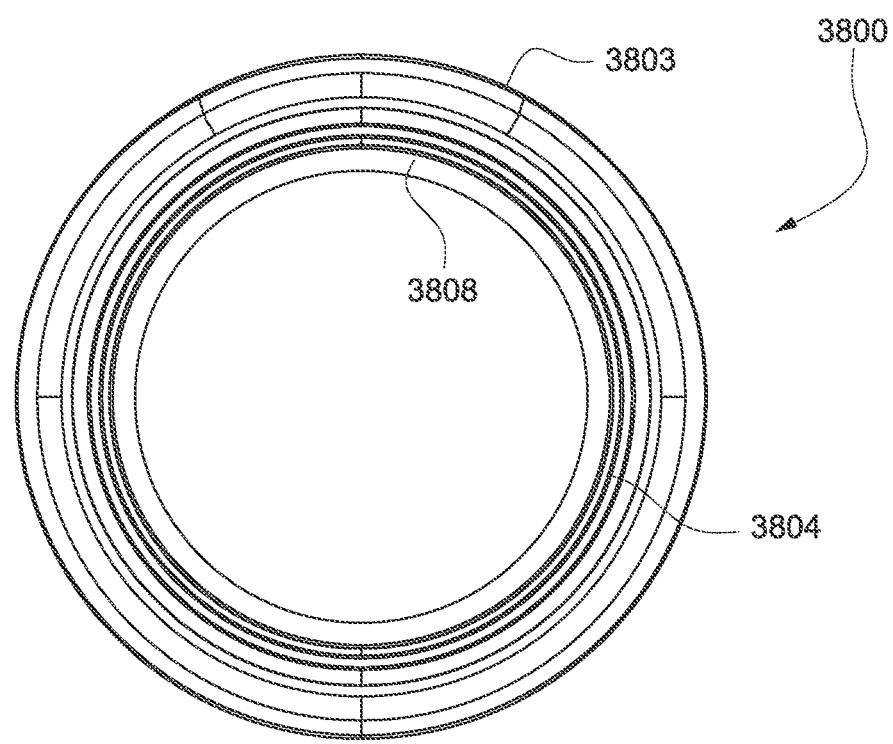

FIG. 19B depicts an anterior view of a connector ring of a patient interface according to an example of the present technology.

Figure 19C:
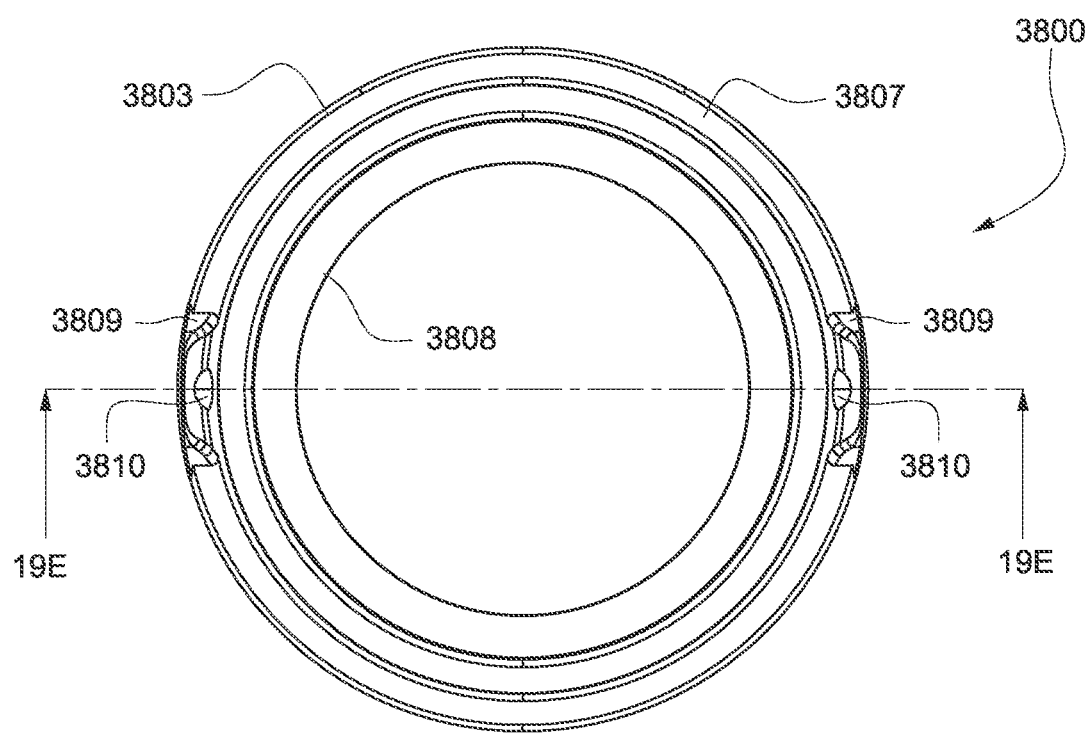

FIG. 19C depicts a posterior view of a connector ring of a patient interface according to an example of the present technology.

Figure 19D:
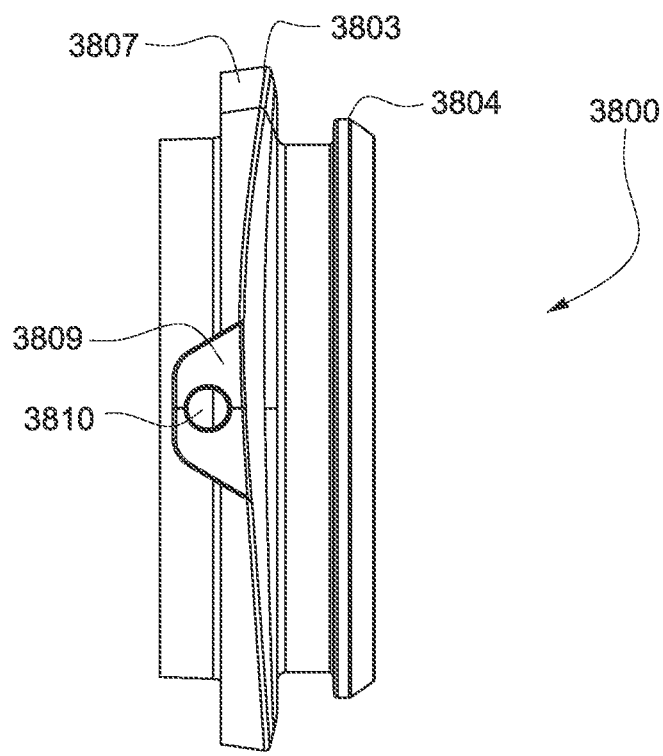

FIG. 19D depicts a lateral view of a connector ring of a patient interface according to an example of the present technology.

Figure 19E:
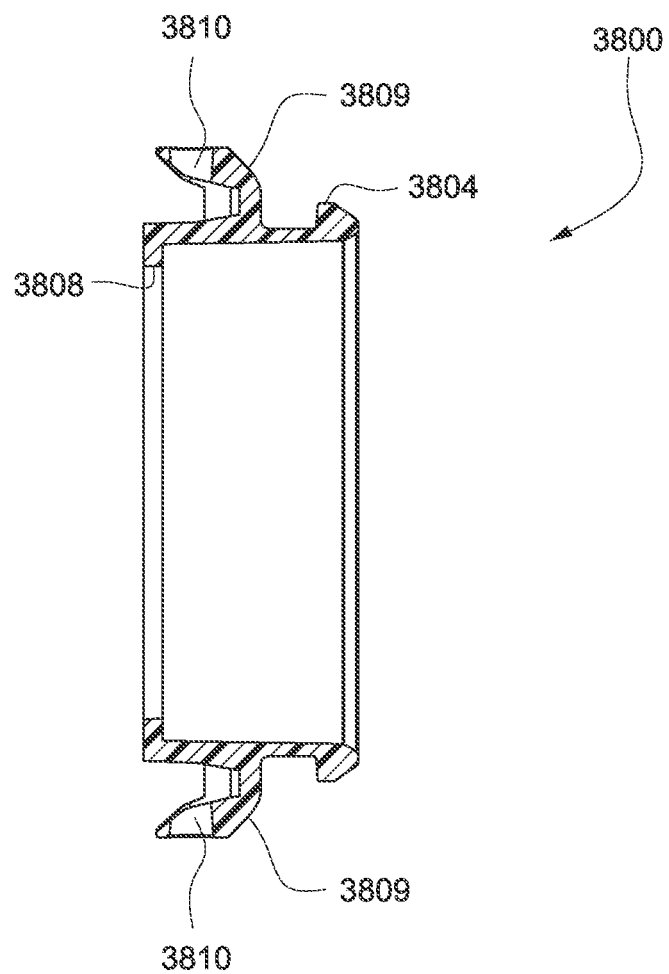

FIG. 19E depicts a cross-sectional view of a connector ring of a patient interface taken through line 19E-19E of FIG. 19C according to an example of the present technology.

Figure 20A:
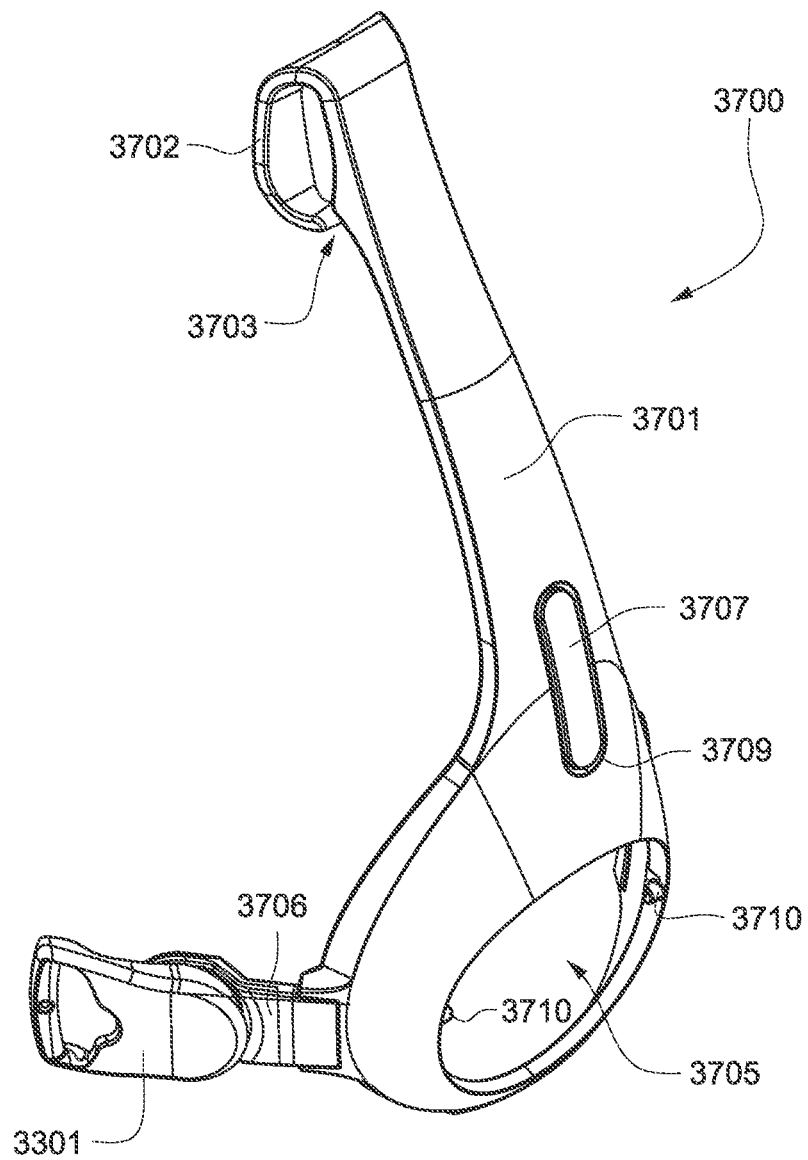

FIG. 20A depicts an anterior perspective view of a frame of a patient interface according to an example of the present technology.

Figure 20B:
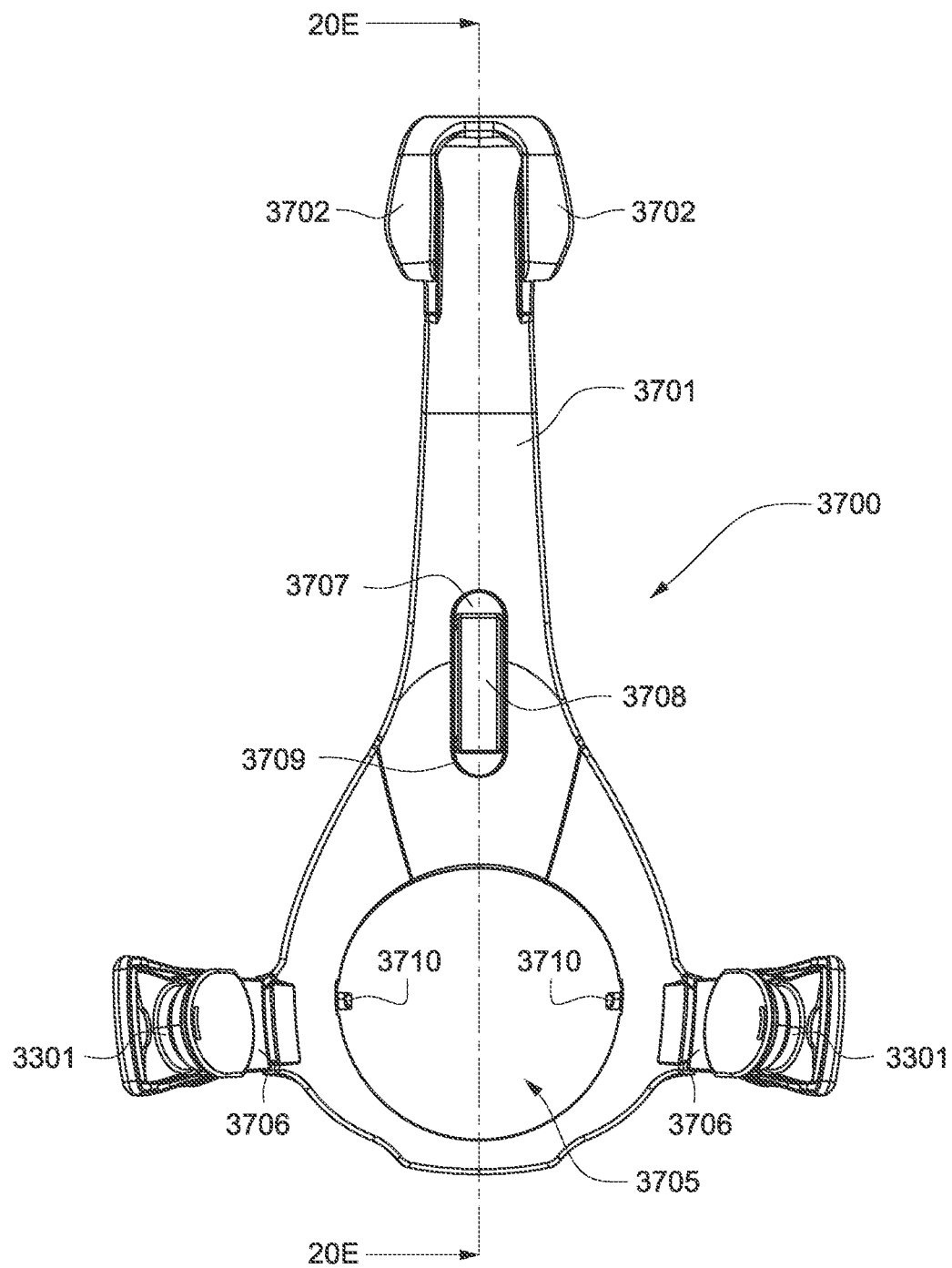

FIG. 20B depicts an anterior view of a frame of a patient interface according to an example of the present technology.

Figure 20C:
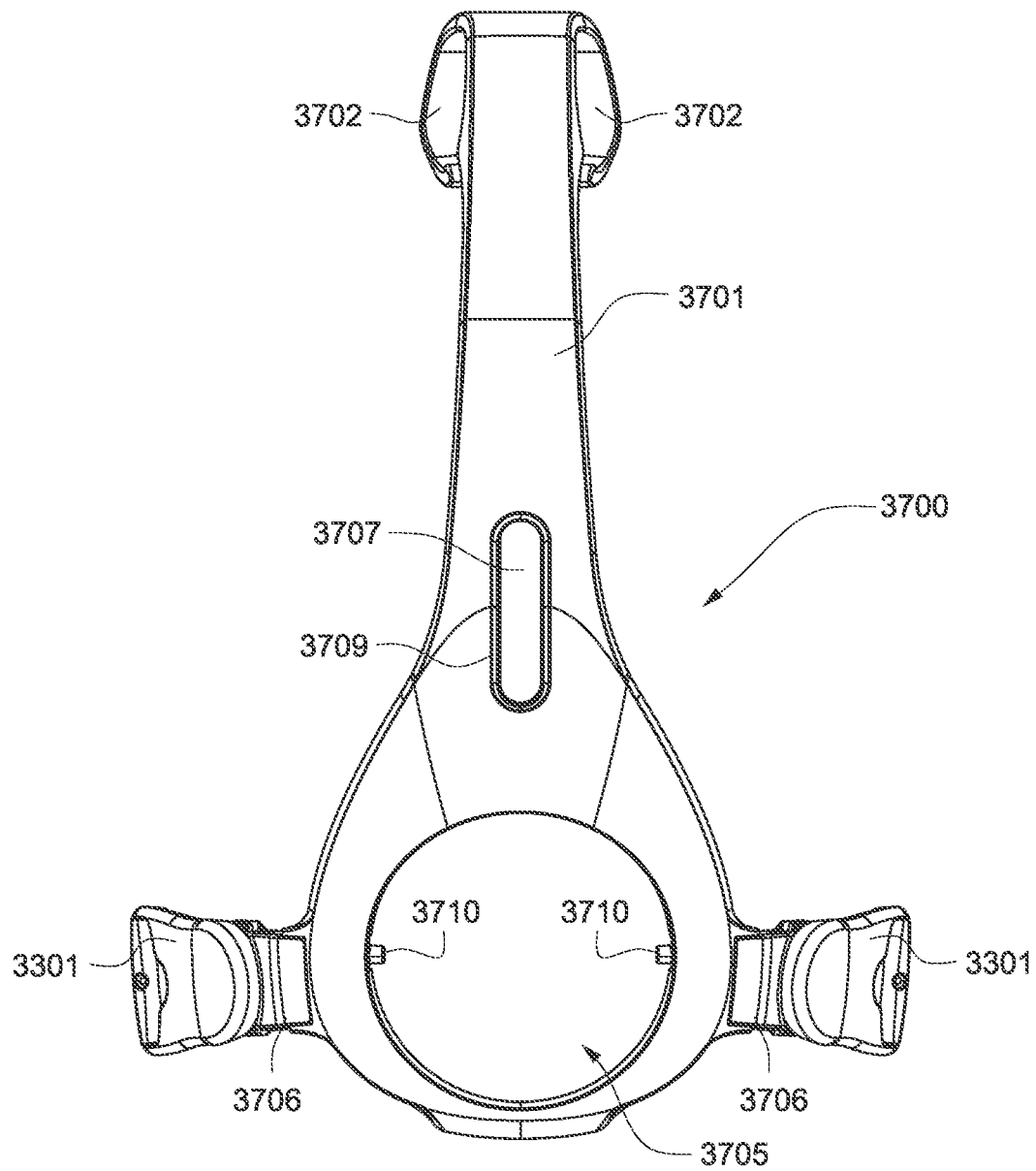

FIG. 20C depicts a posterior view of a frame of a patient interface according to an example of the present technology.

Figure 20D:
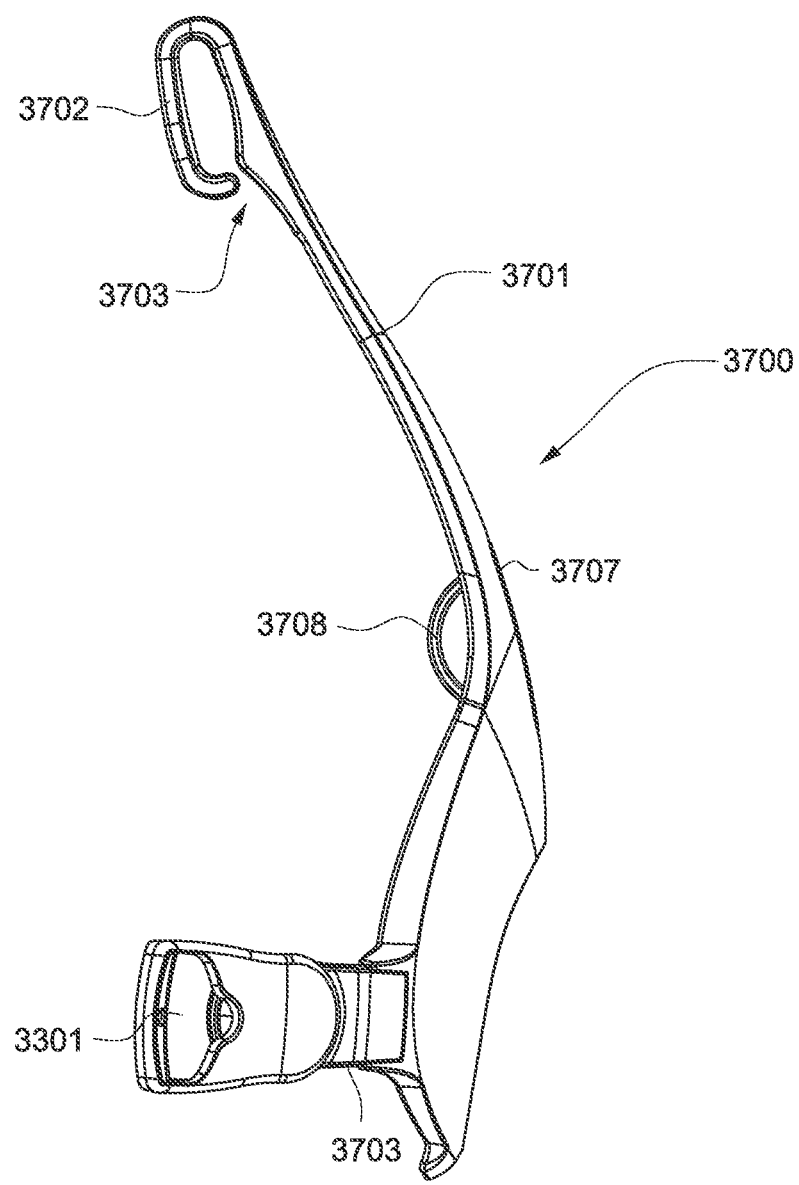

FIG. 20D depicts a lateral view of a frame of a patient interface according to an example of the present technology.

Figure 20E:
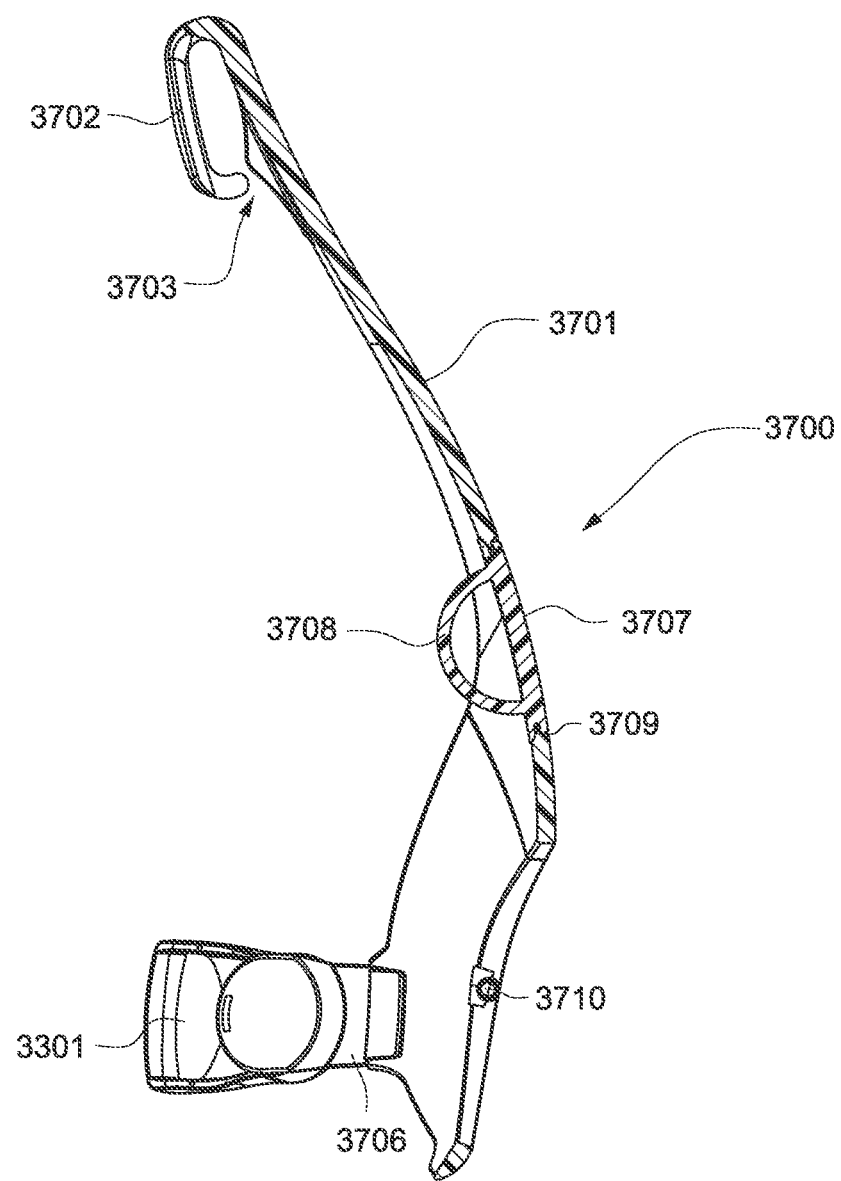

FIG. 20E depicts a cross-sectional view of a frame of a patient interface taken through line 20E-20E of FIG. 20B according to an example of the present technology.

Figure 21A:
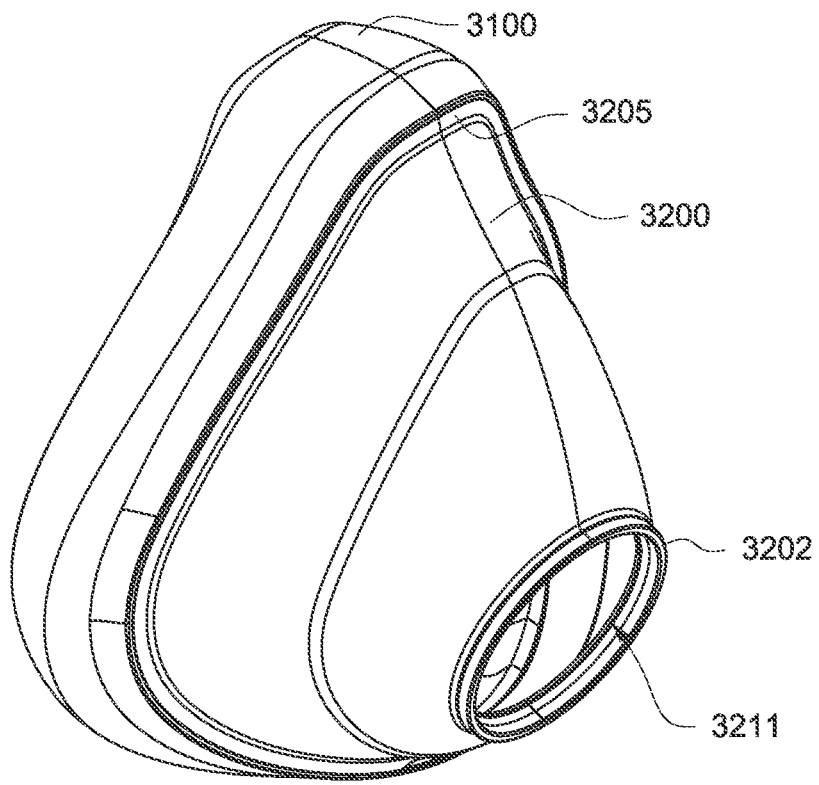

FIG. 21A depicts an anterior perspective view of a seal-forming structure and a plenum chamber of a patient interface according to an example of the present technology.

Figure 21B:
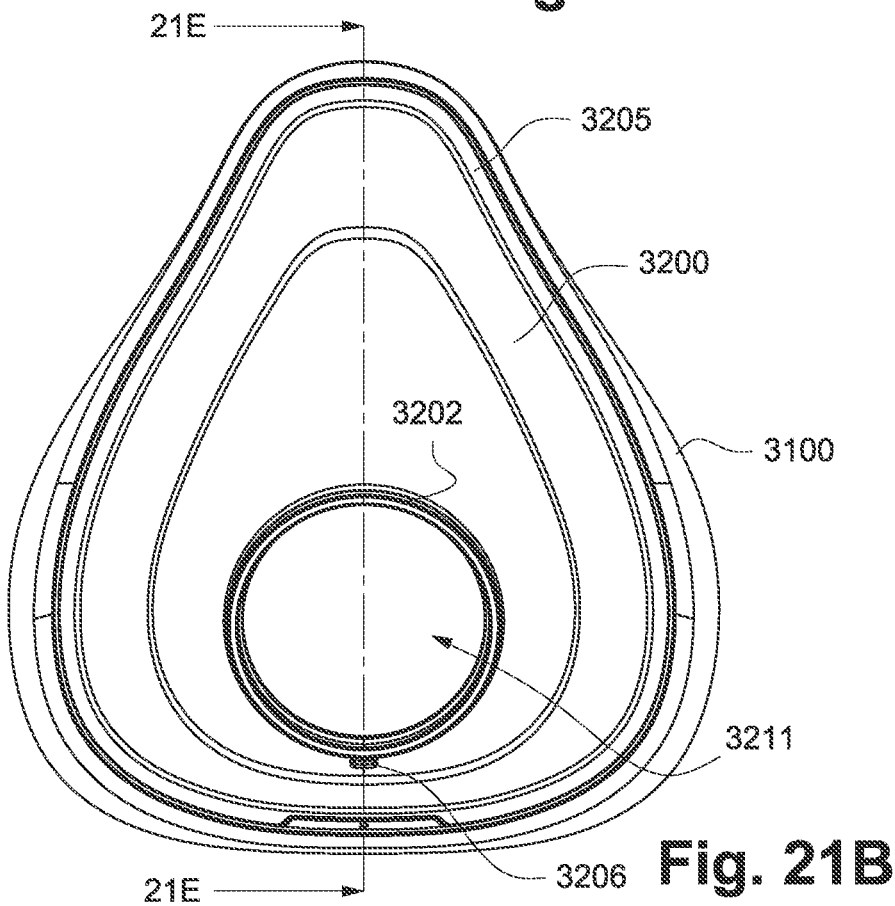

FIG. 21B depicts an anterior view of a seal-forming structure and a plenum chamber of a patient interface according to an example of the present technology.

Figure 21C:
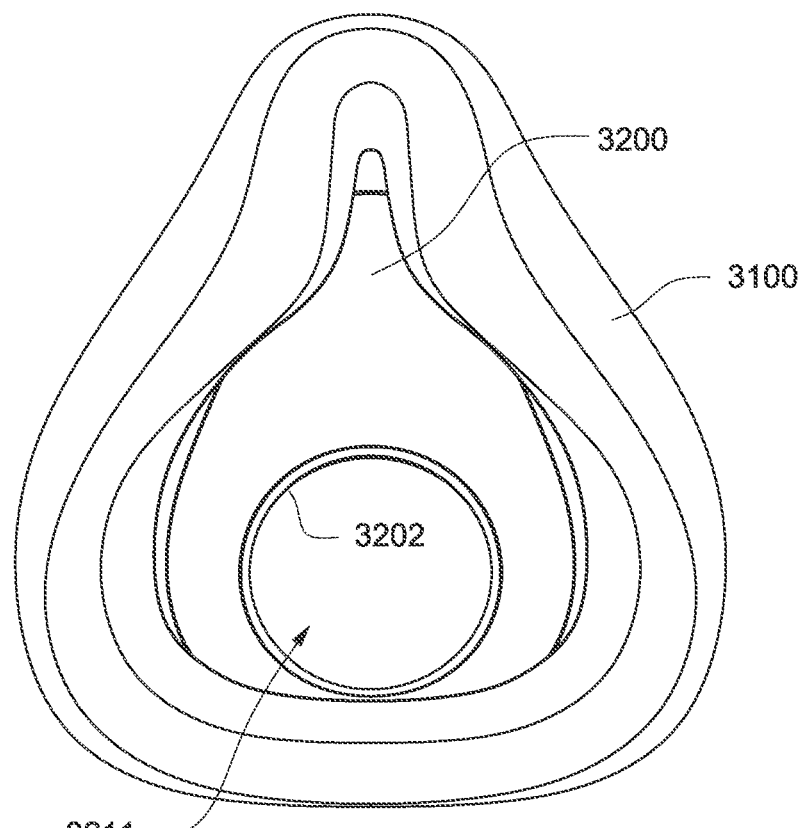

FIG. 21C depicts a posterior view of a seal-forming structure and a plenum chamber of a patient interface according to an example of the present technology.

Figure 21D:
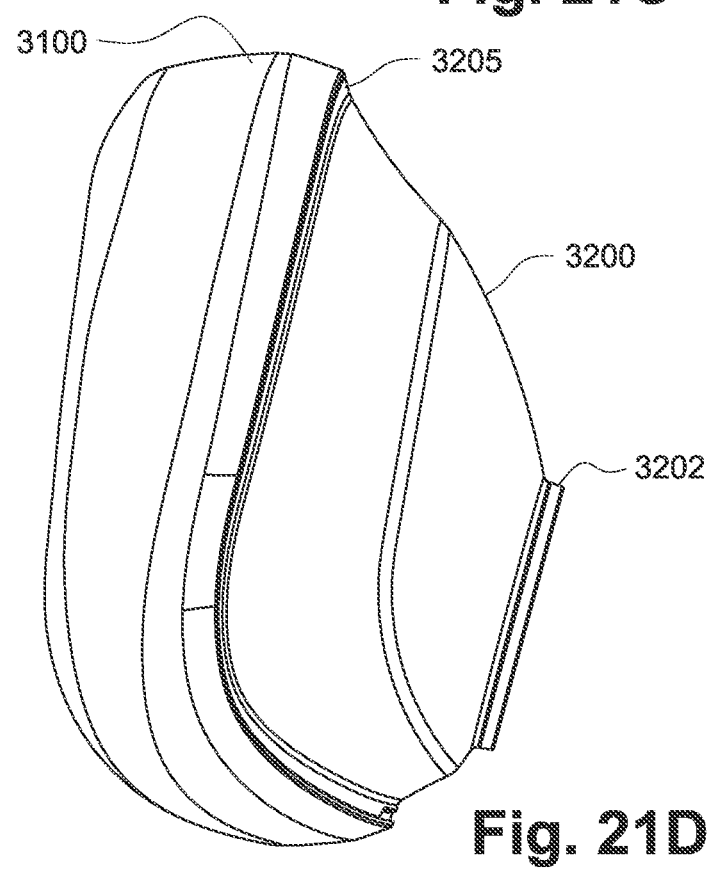

FIG. 21D depicts a lateral view of a seal-forming structure and a plenum chamber of a patient interface according to an example of the present technology.

Figure 21E:
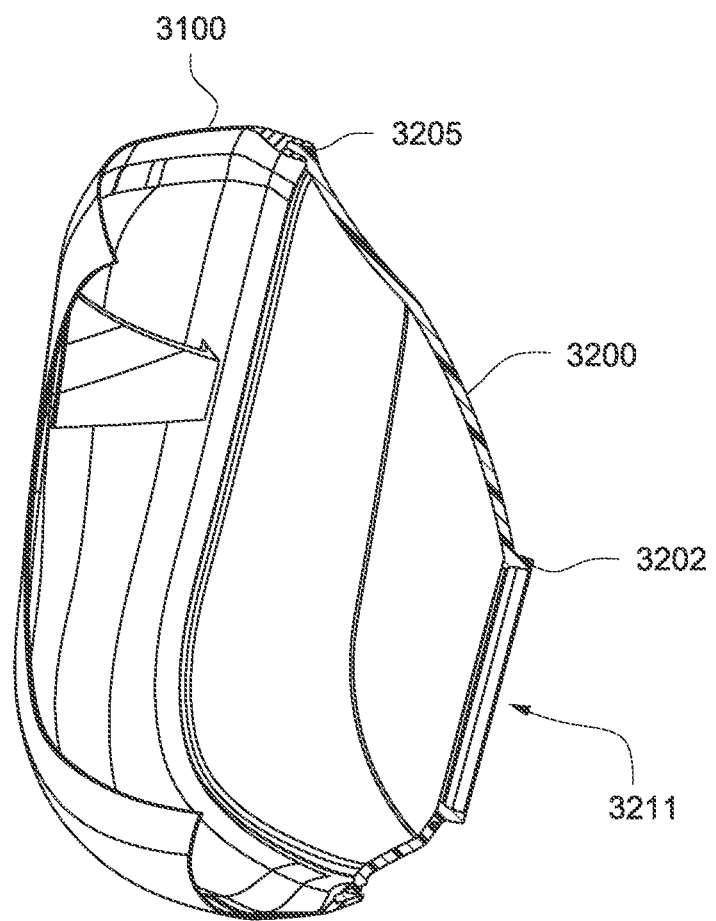

FIG. 21E depicts a cross-sectional view of a seal-forming structure and a plenum chamber of a patient interface taken through line 21E-21E of FIG. 21B according to an example of the present technology.

Figure 22A:
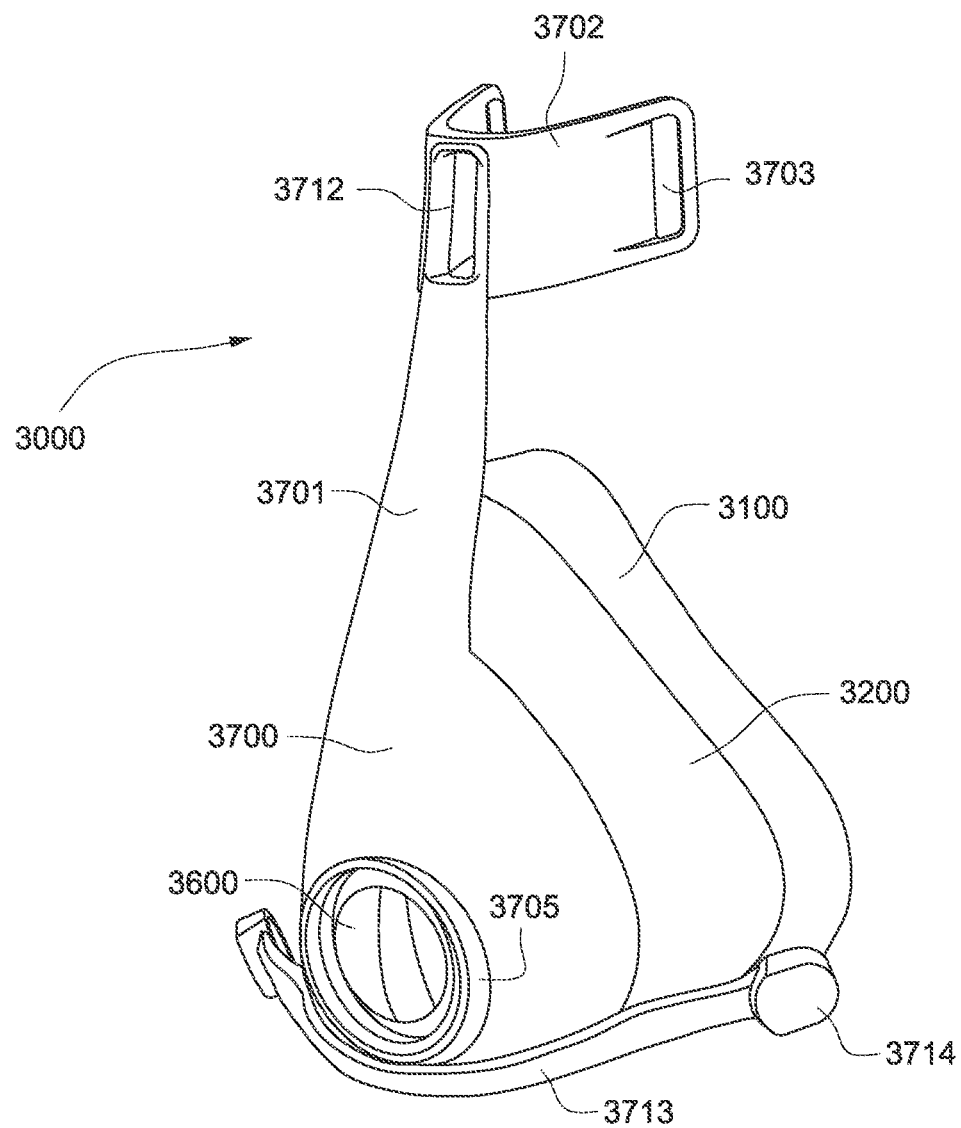

FIG. 22A depicts an anterior perspective view of a patient interface according to an example of the present technology.

Figure 22B:
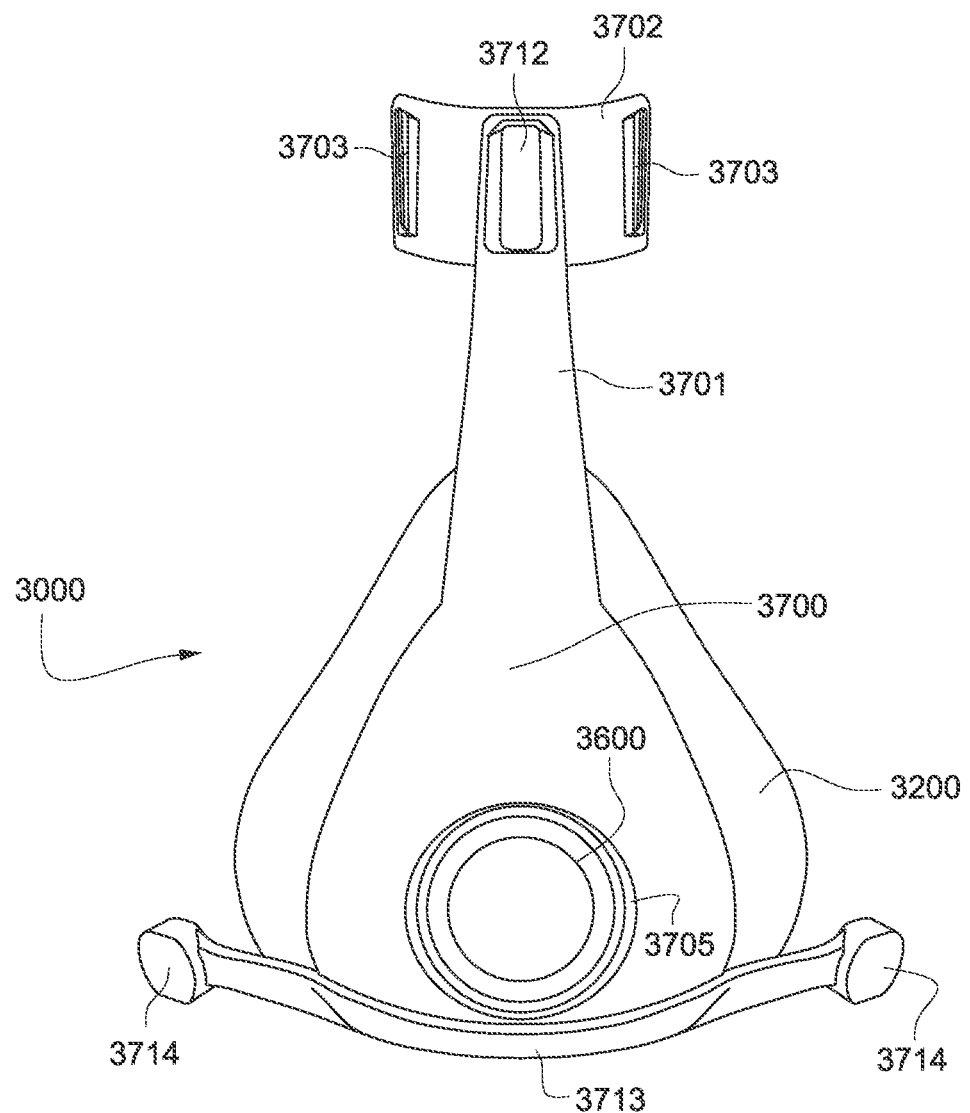

FIG. 22B depicts an anterior view of a patient interface according to an example of the present technology.

Figure 22C:
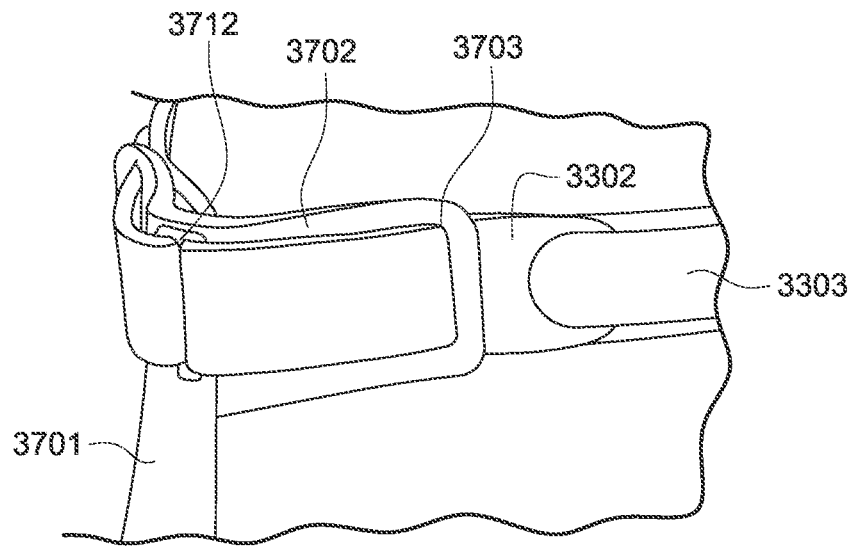

FIG. 22C depicts a detailed front perspective view of a patient interface according to an example of the present technology.

Figure 22D:
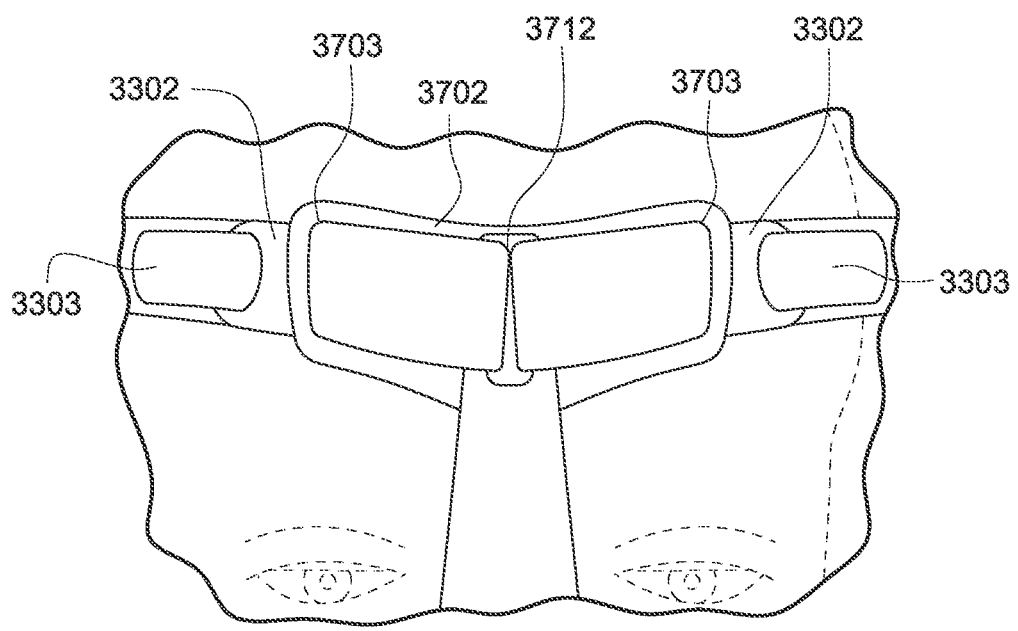

FIG. 22D depicts a detailed front view of a patient interface according to an example of the present technology.

FIG. 22E depicts a detailed front view of a patient interface according to an example of the present technology.

FIG. 22F depicts a detailed front view of a patient interface according to an example of the present technology.

FIG. 22G depicts a detailed front view of a patient interface according to an example of the present technology.

Figure 23A:
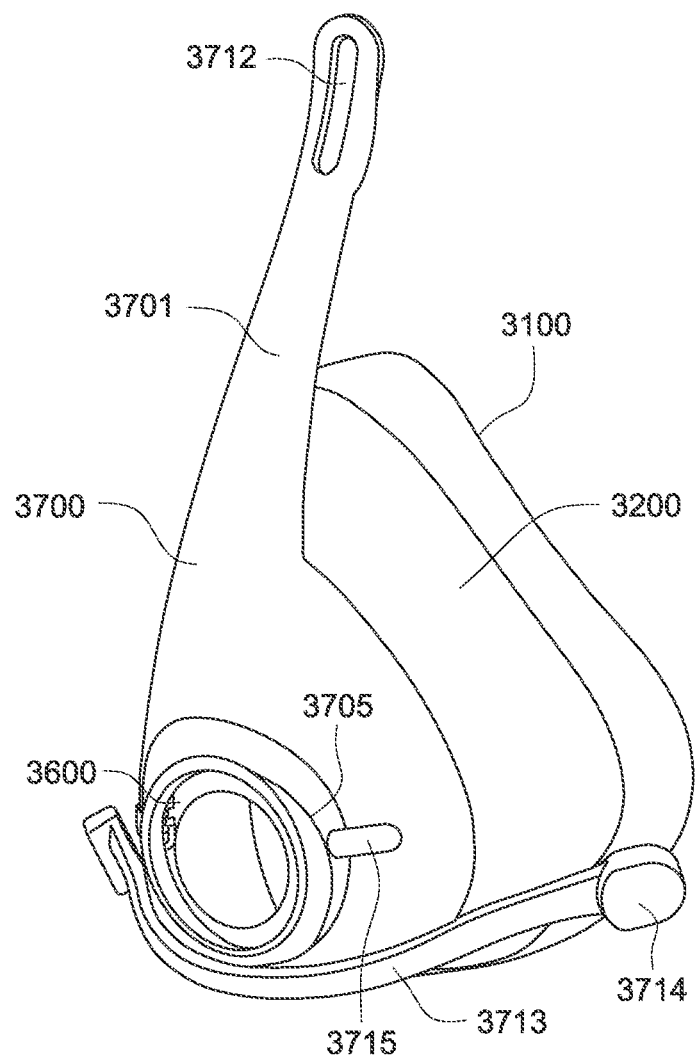

FIG. 23A depicts an anterior perspective view of a patient interface according to an example of the present technology.

Figure 23B:
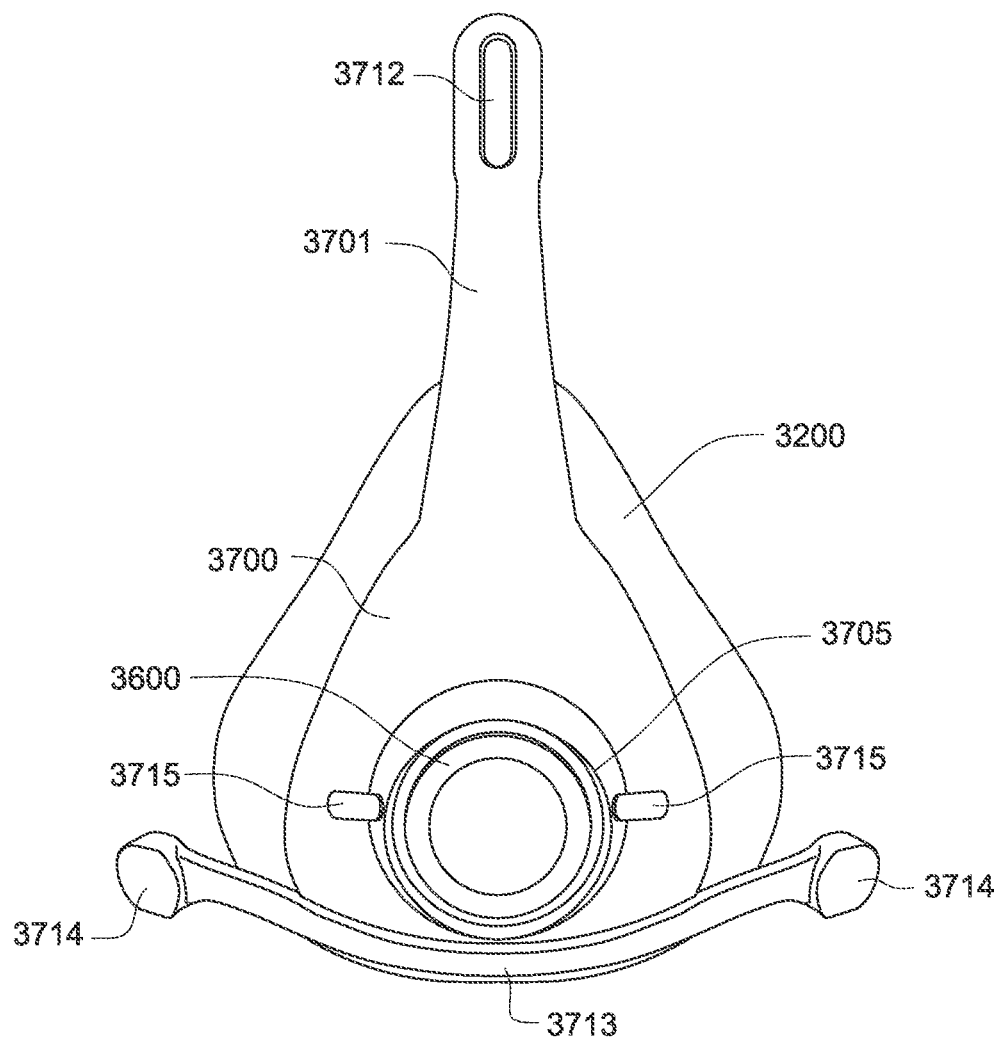

FIG. 23B depicts an anterior view of a patient interface according to an example of the present technology.

Figure 23C:
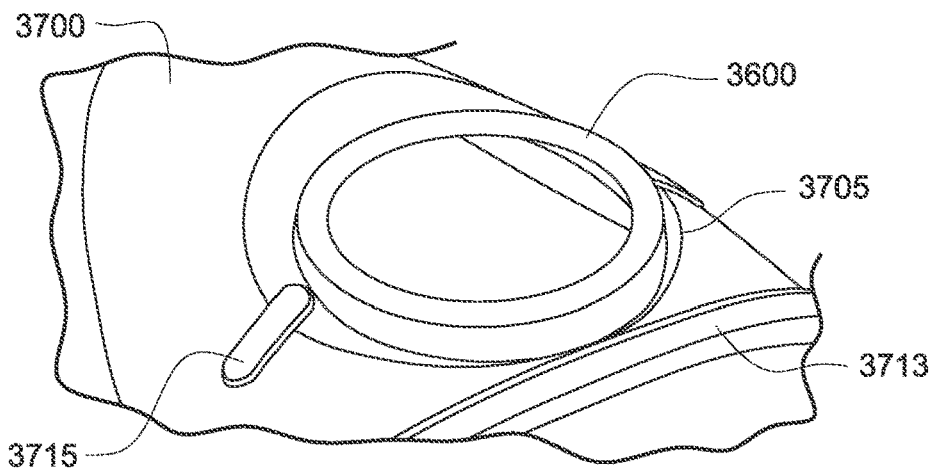

FIG. 23C depicts a detailed front perspective view of a patient interface according to an example of the present technology.

Figure 23D:
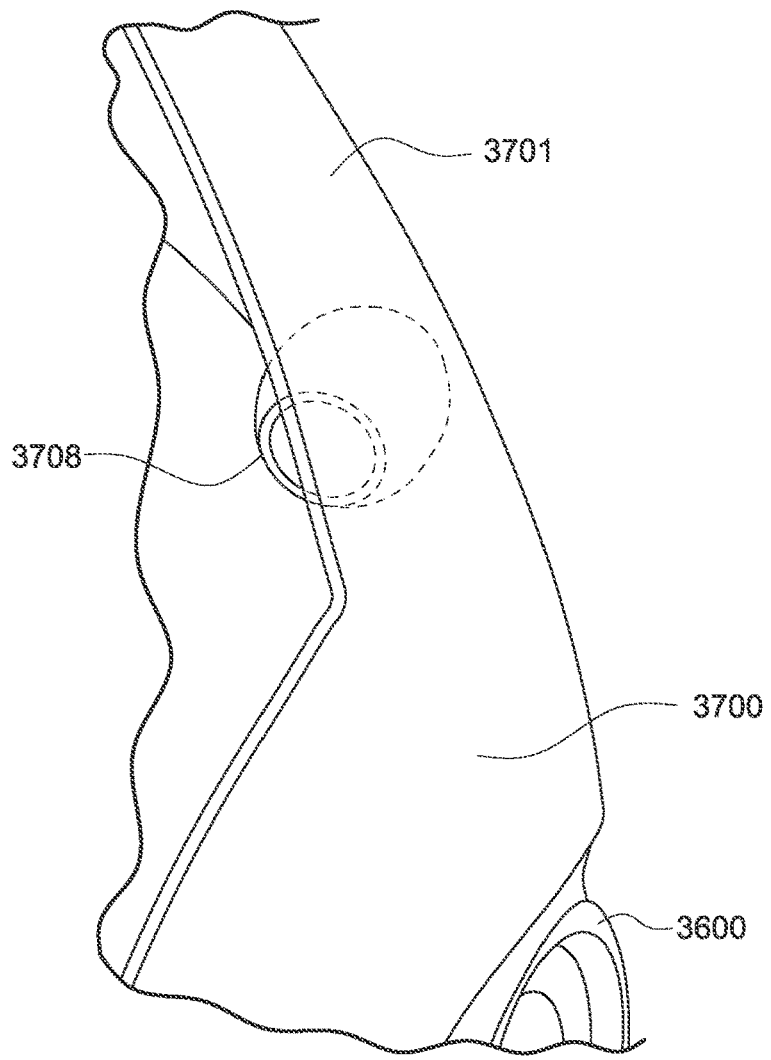

FIG. 23D depicts a detailed front perspective view of a patient interface according to an example of the present technology.

FIG. 23E depicts a lateral view of a patient interface according to an example of the present technology.

FIG. 23F depicts a lateral view of a patient interface according to an example of the present technology.

FIG. 23G depicts a lateral view of a patient interface according to an example of the present technology.

Figure 24A:
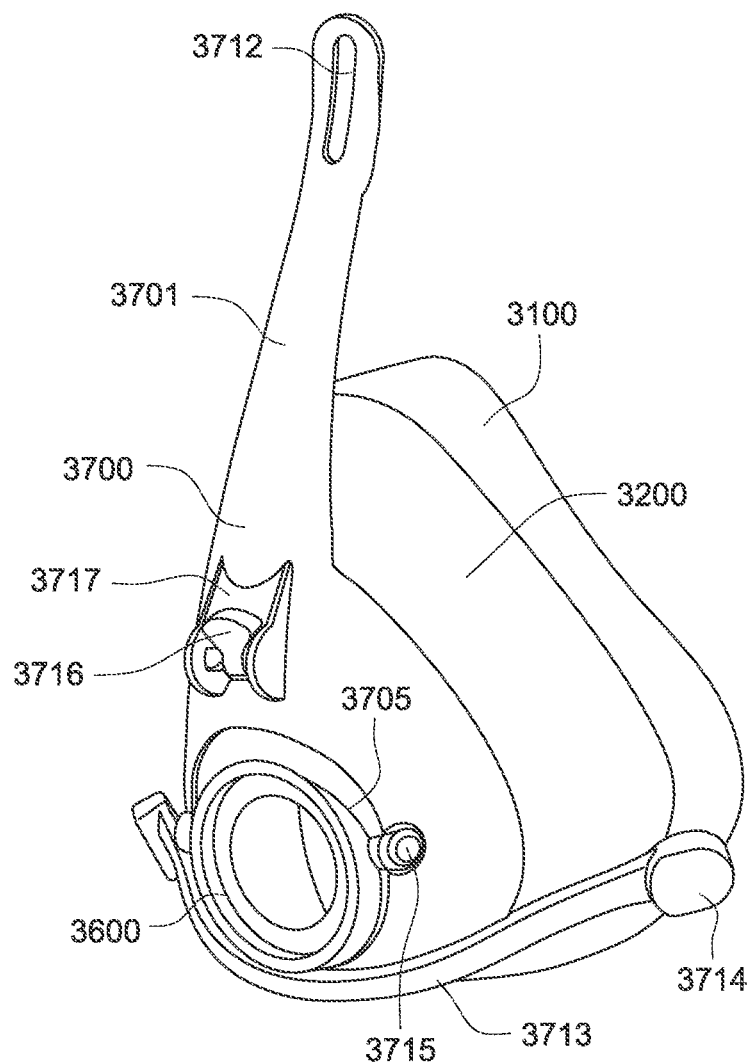

FIG. 24A depicts an anterior perspective view of a patient interface according to an example of the present technology.

Figure 24B:
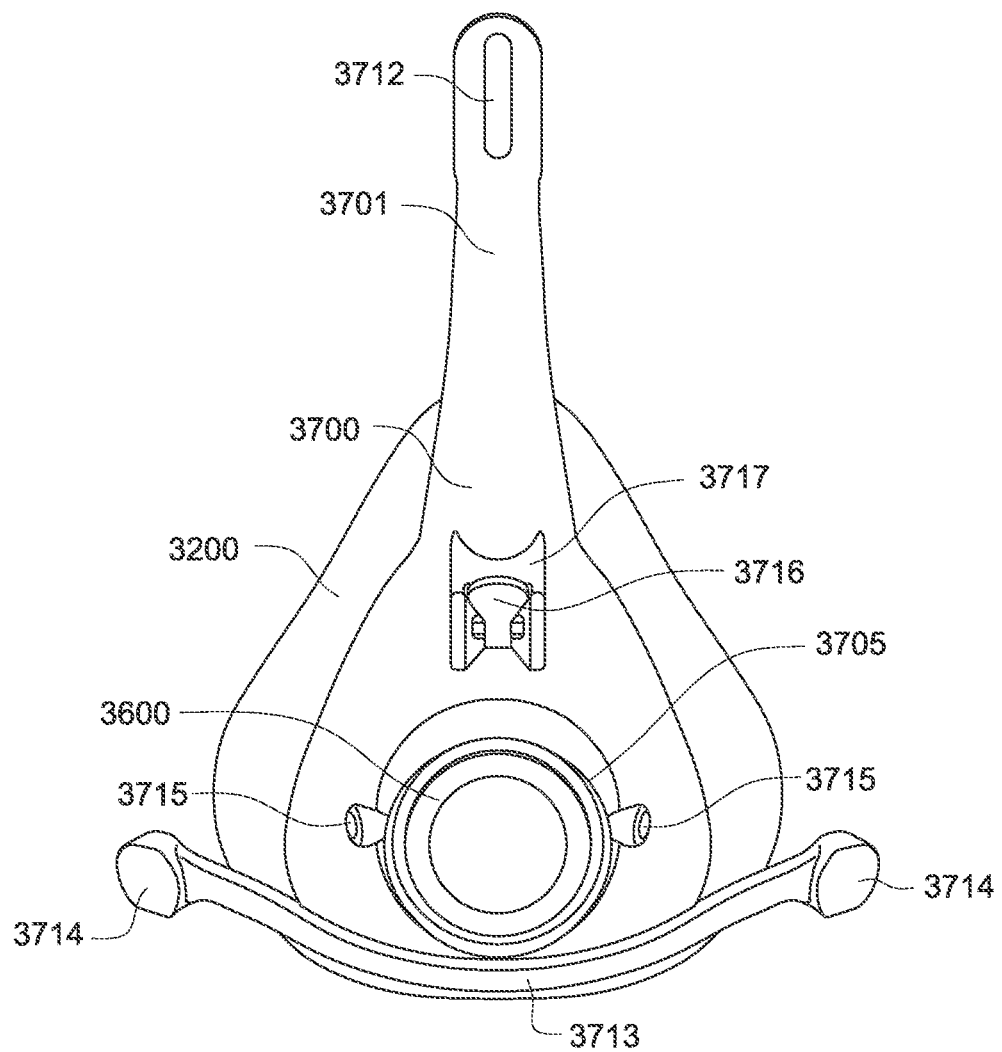

FIG. 24B depicts an anterior view of a patient interface according to an example of the present technology.

Figure 24C:
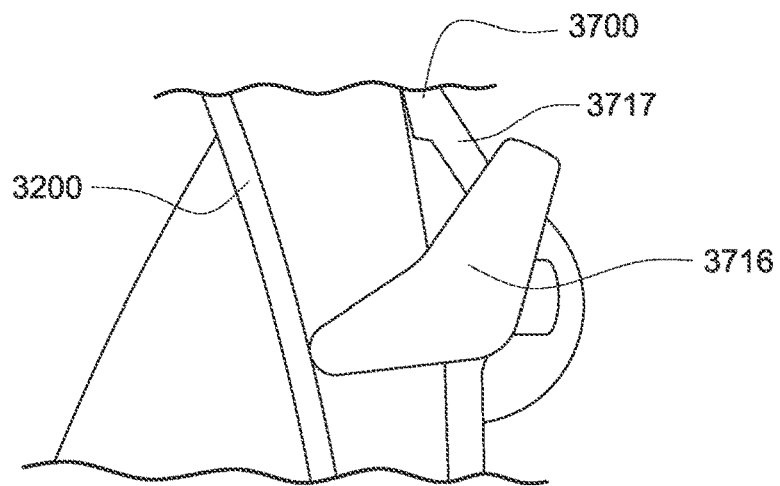

FIG. 24C depicts a detailed lateral view of a patient interface according to an example of the present technology.

Figure 24D:
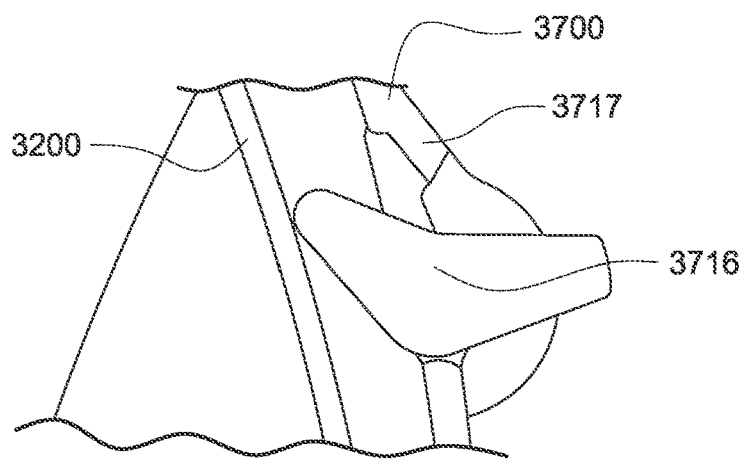

FIG. 24D depicts a detailed lateral view of a patient interface according to an example of the present technology.

Figure 24E:
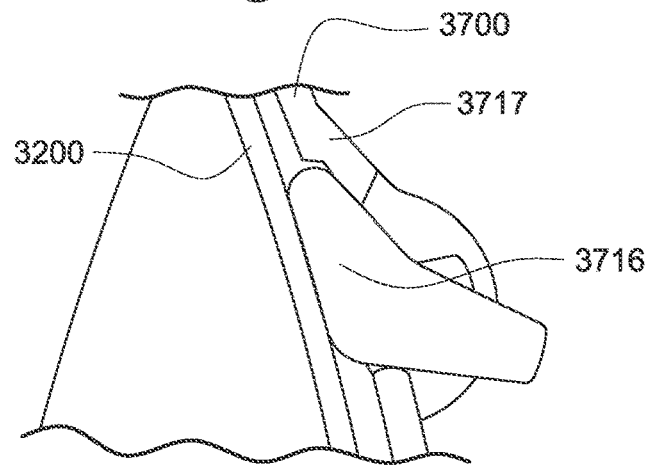

FIG. 24E depicts a detailed lateral view of a patient interface according to an example of the present technology.

Figure 24G:
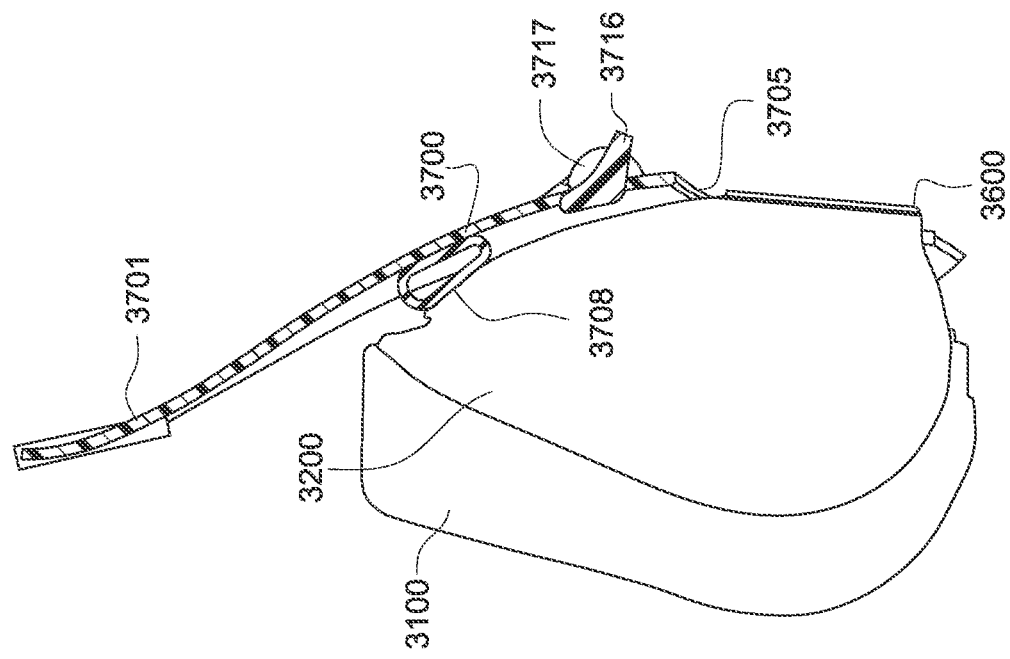
Figure 24F:
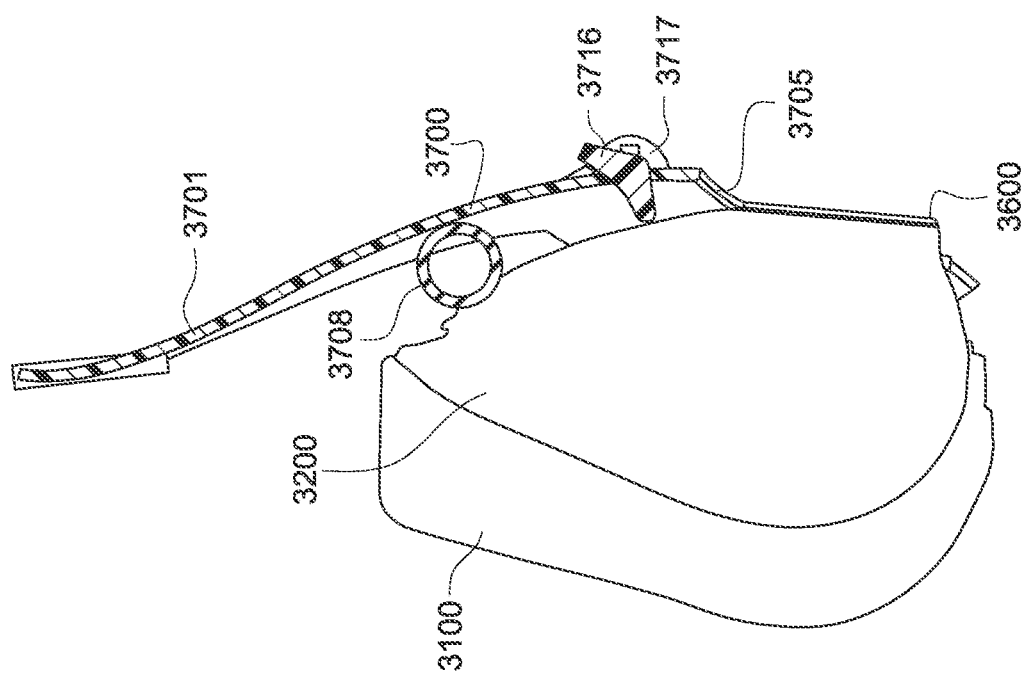

FIG. 24F depicts a lateral view of a patient interface according to an example of the present technology.

FIG. 24G depicts a lateral view of a patient interface according to an example of the present technology.

Figure 25A:
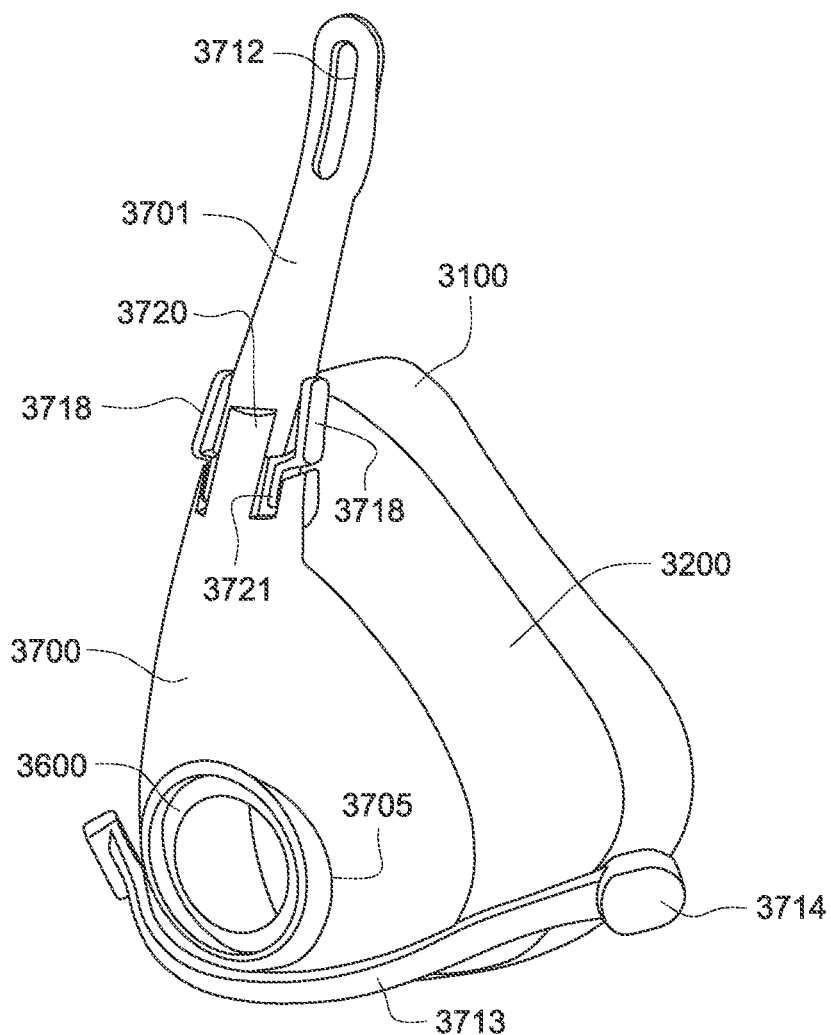

FIG. 25A depicts an anterior perspective view of a patient interface according to an example of the present technology.

Figure 25B:
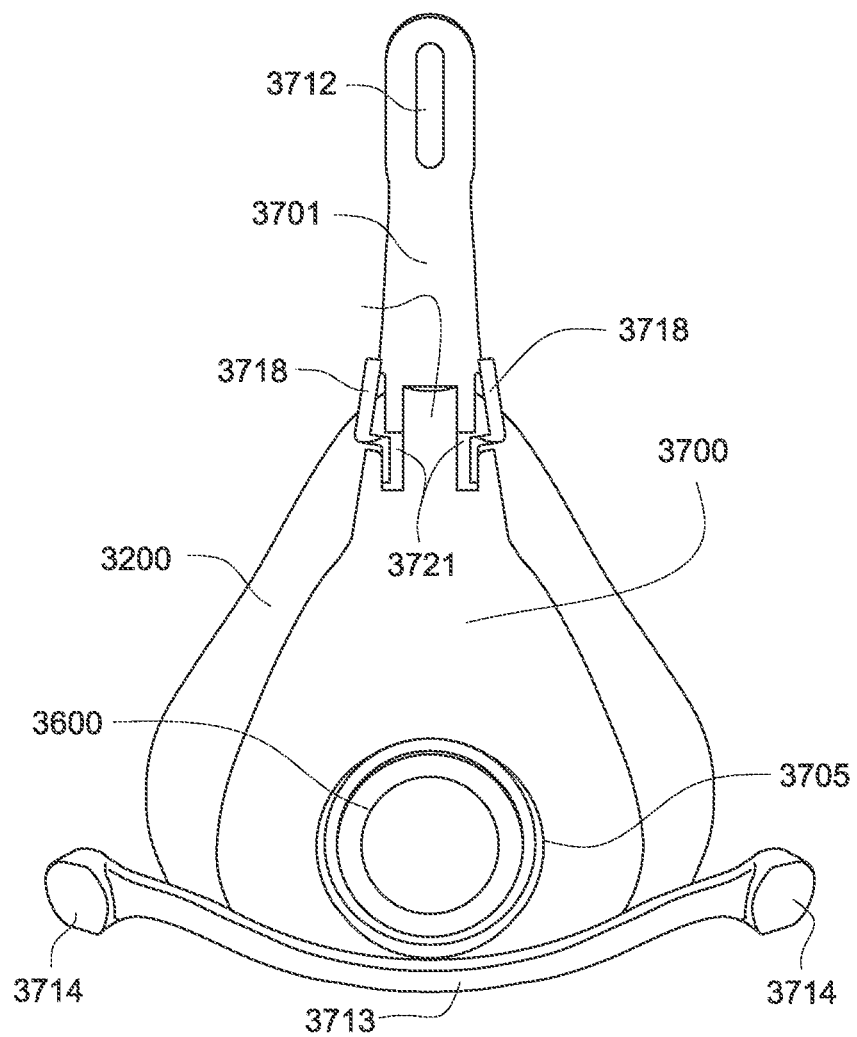

FIG. 25B depicts an anterior view of a patient interface according to an example of the present technology.

Figure 25C:
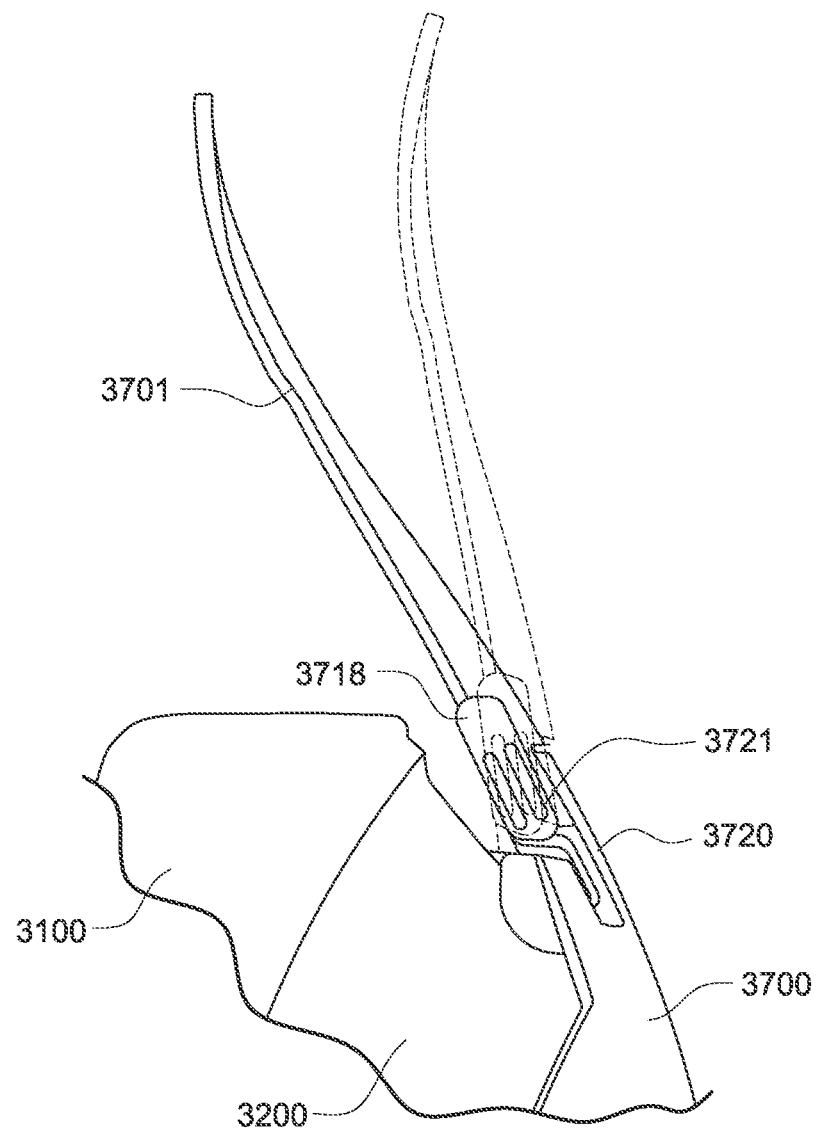

FIG. 25C depicts a detailed lateral view of a patient interface according to an example of the present technology.

Figure 26A:
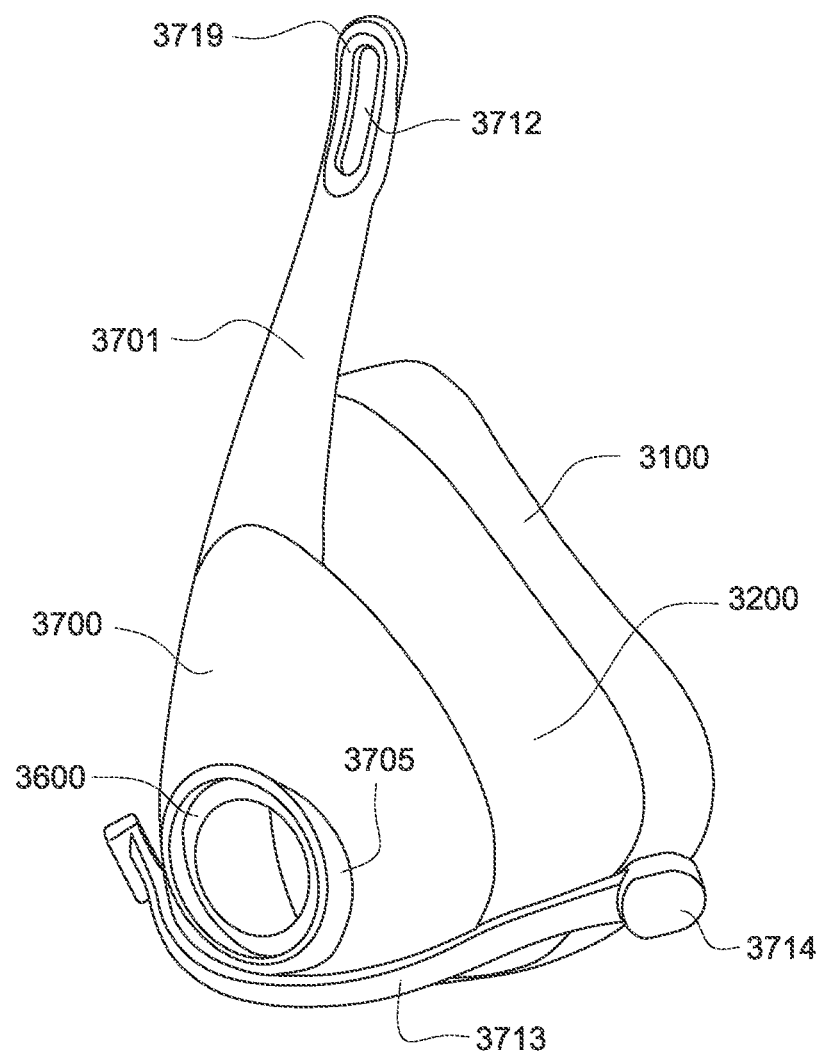

FIG. 26A depicts an anterior perspective view of a patient interface according to an example of the present technology.

Figure 26B:
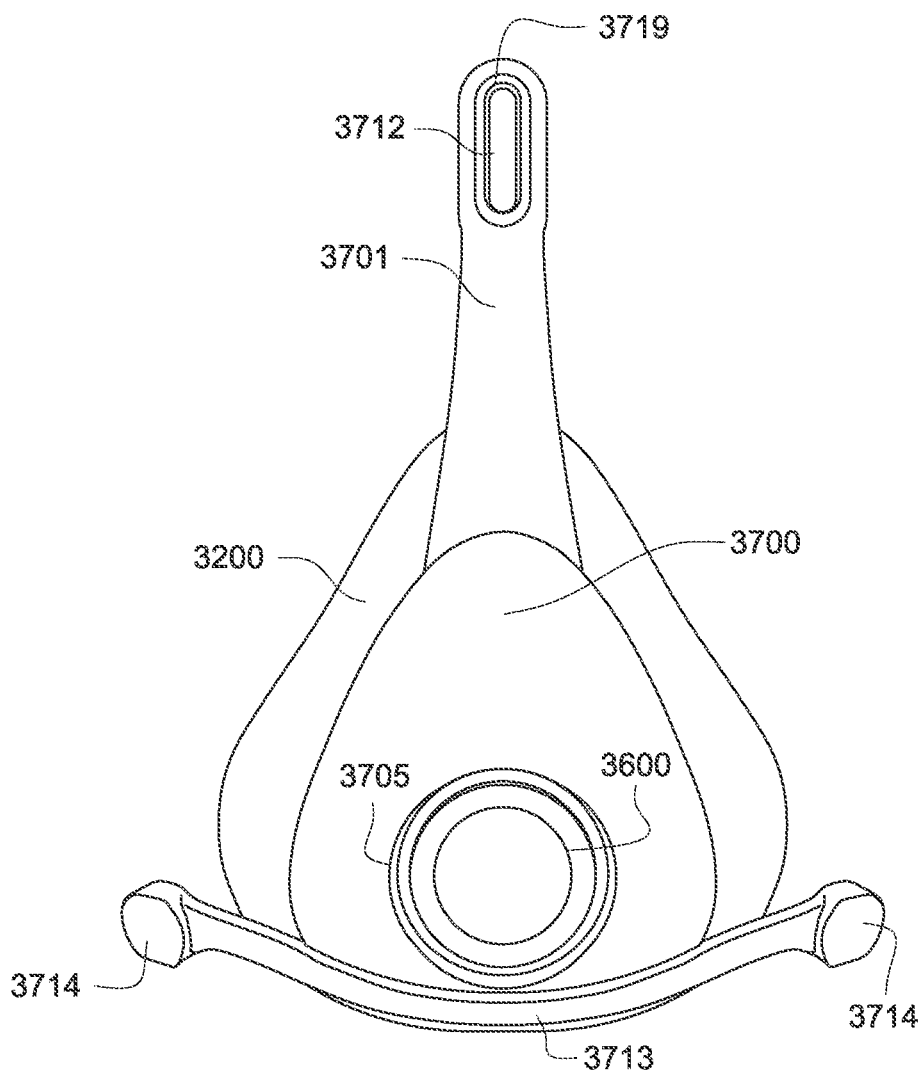

FIG. 26B depicts an anterior view of a patient interface according to an example of the present technology.

Figure 26C:
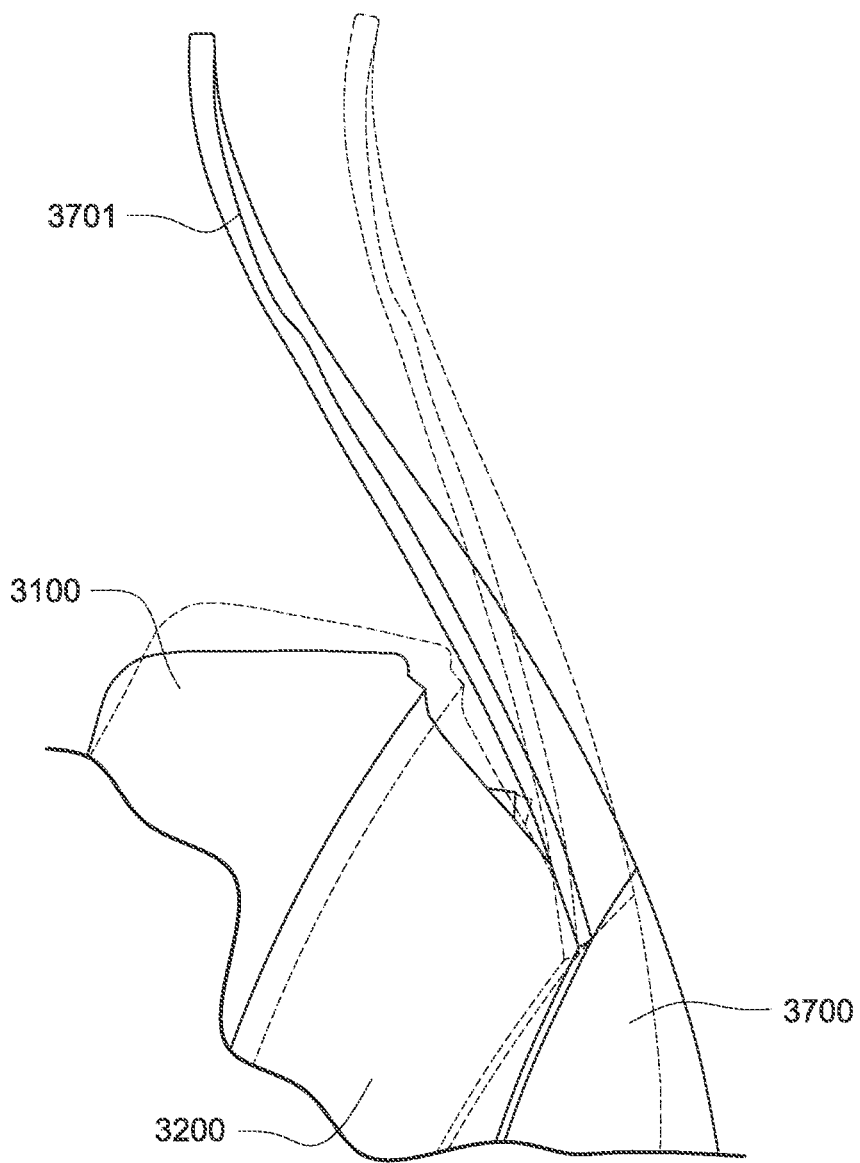

FIG. 26C depicts a detailed lateral view of a patient interface according to an example of the present technology.

Figure 27A:
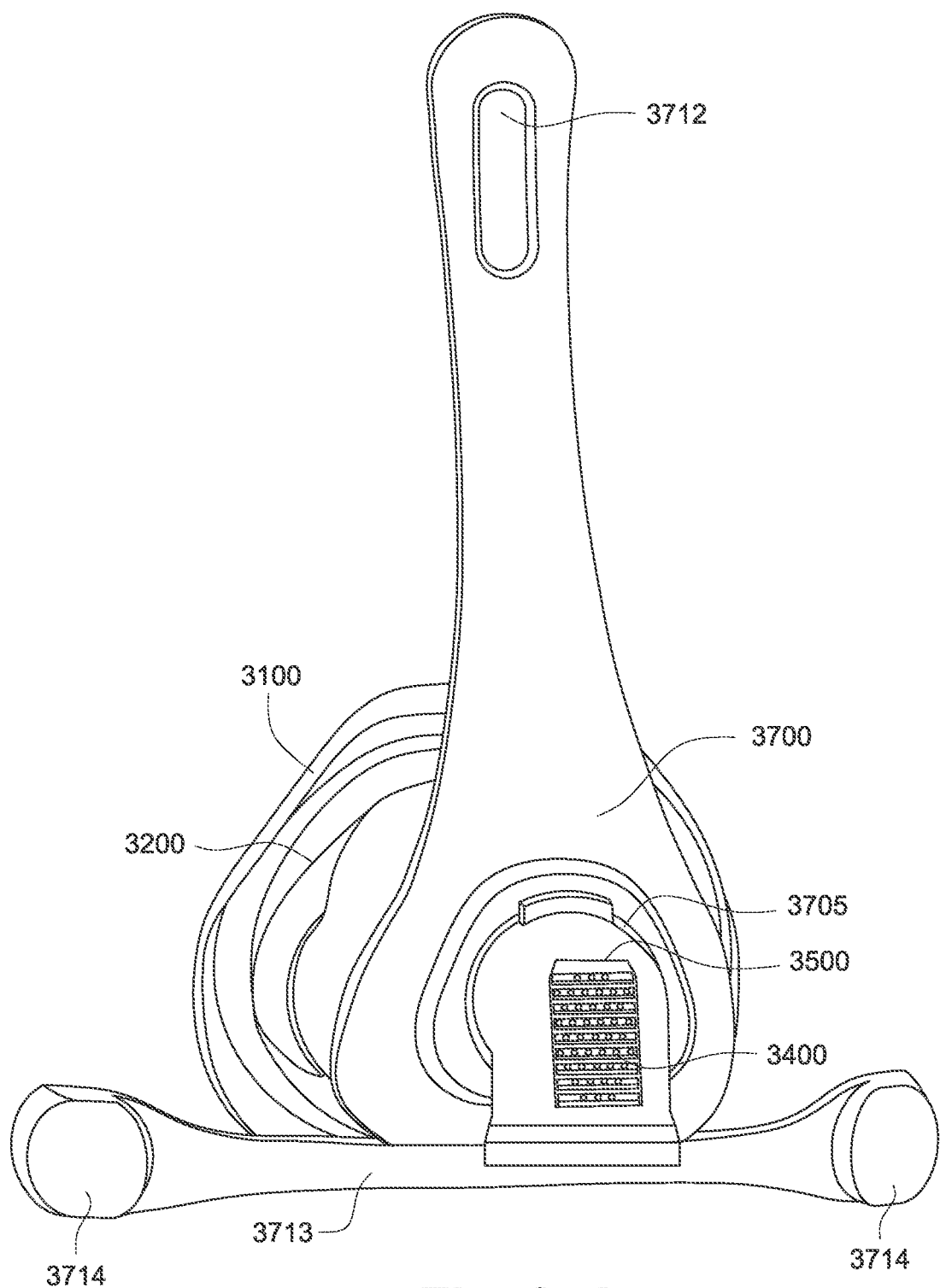

FIG. 27A depicts an anterior perspective view of a patient interface according to an example of the present technology.

Figure 27B:
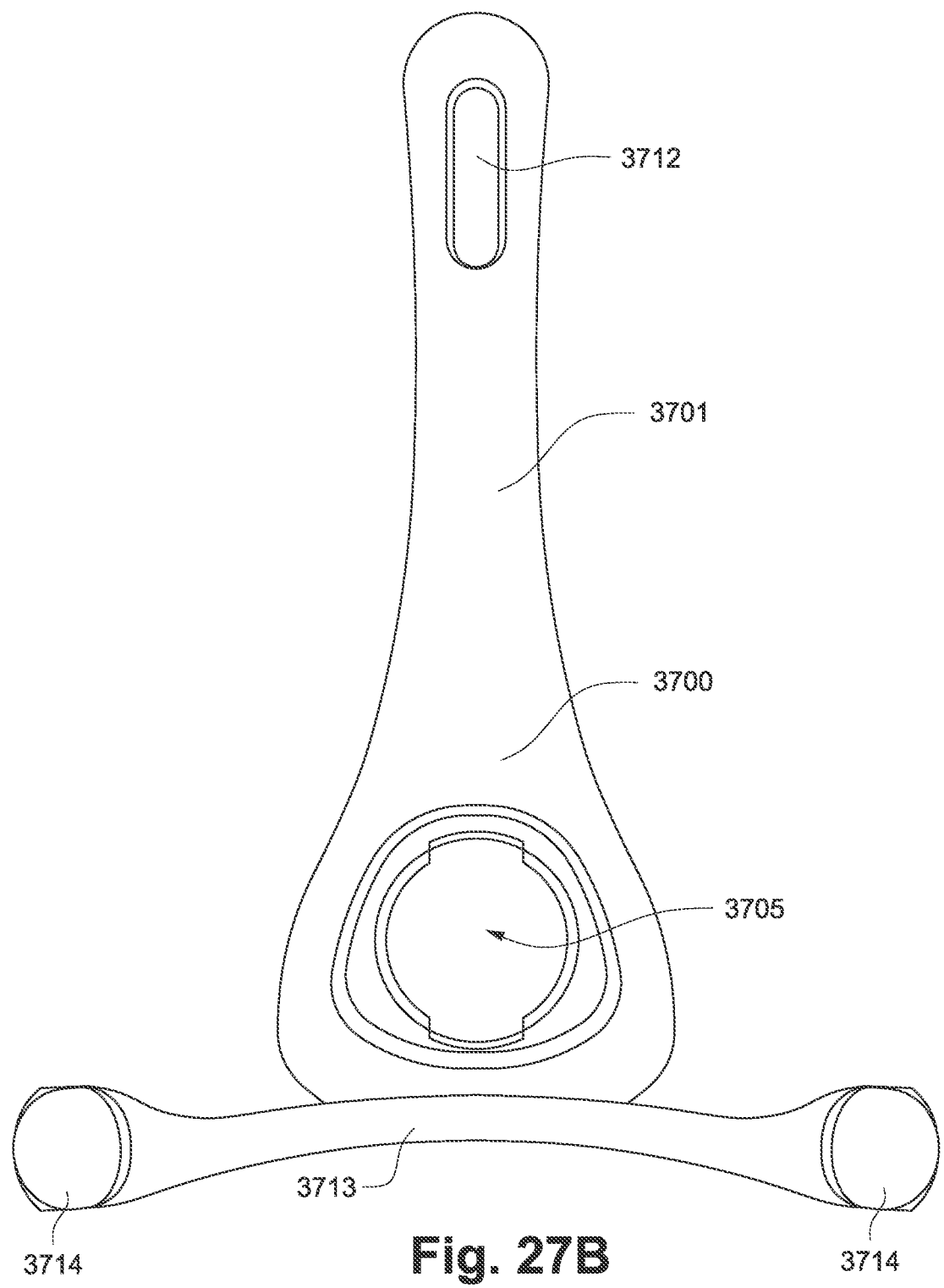

FIG. 27B depicts an anterior view of a patient interface according to an example of the present technology.

Figure 27C:
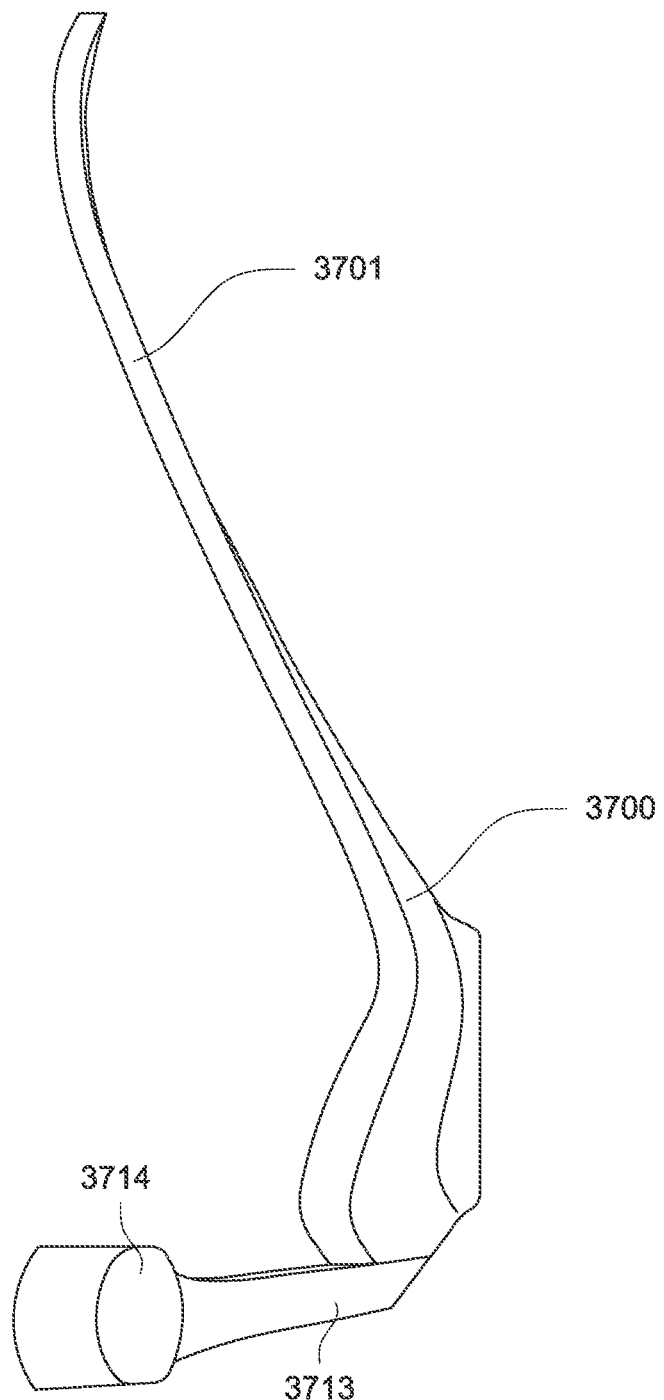

FIG. 27C depicts a lateral view of a patient interface according to an example of the present technology.

Figure 27D:
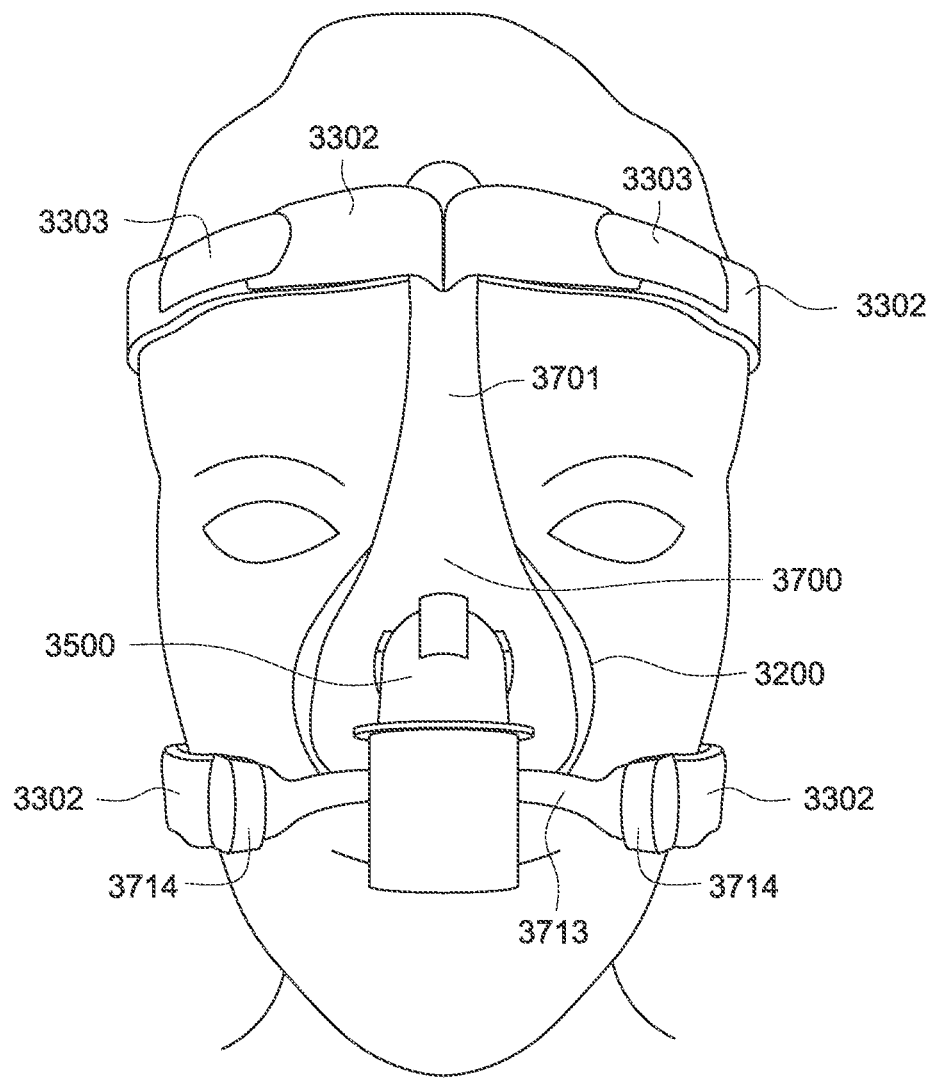

FIG. 27D depicts an anterior view of a patient interface on a patient according to an example of the present technology.

Figure 28A:
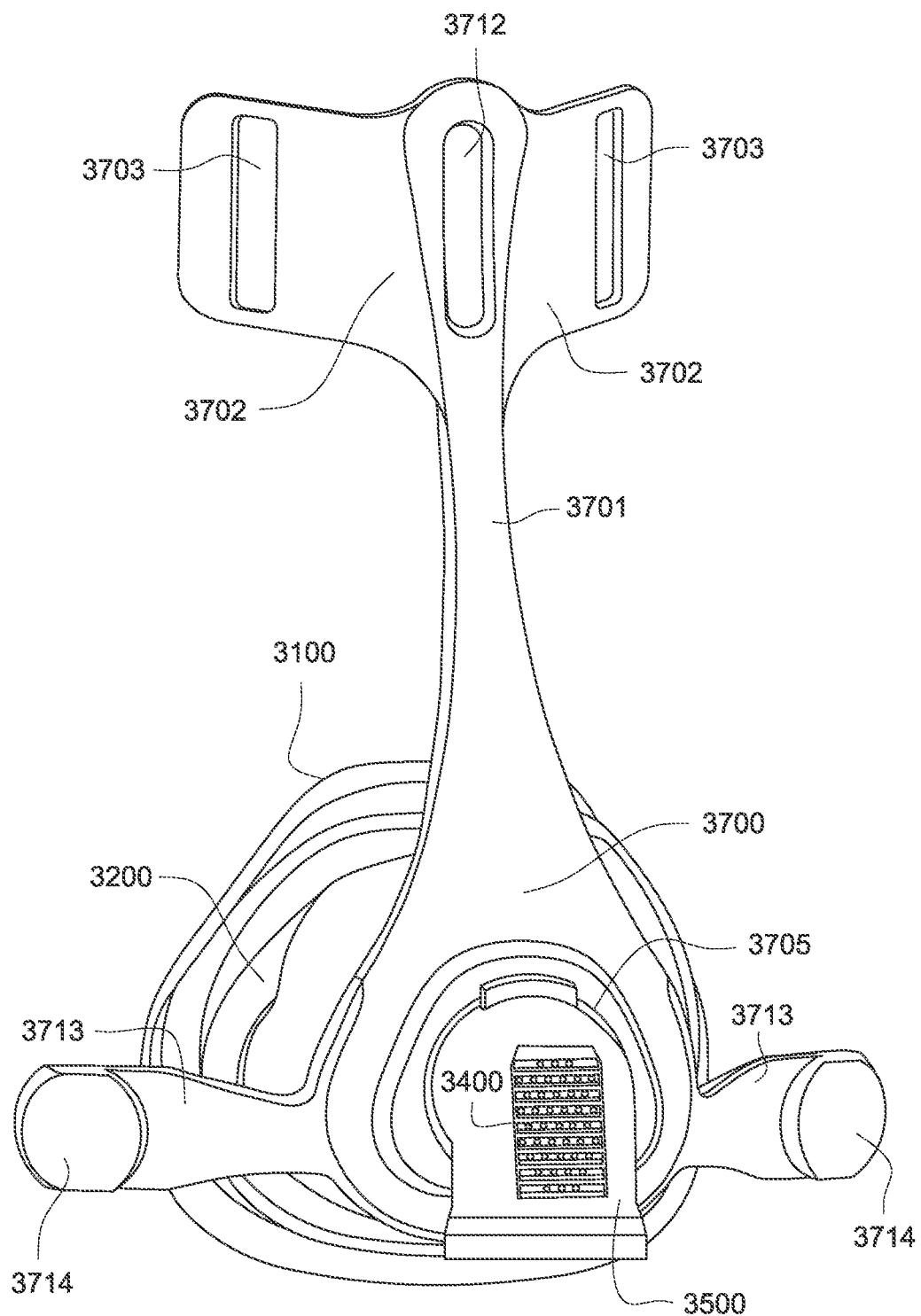

FIG. 28A depicts an anterior perspective view of a patient interface according to an example of the present technology.

Figure 28B:
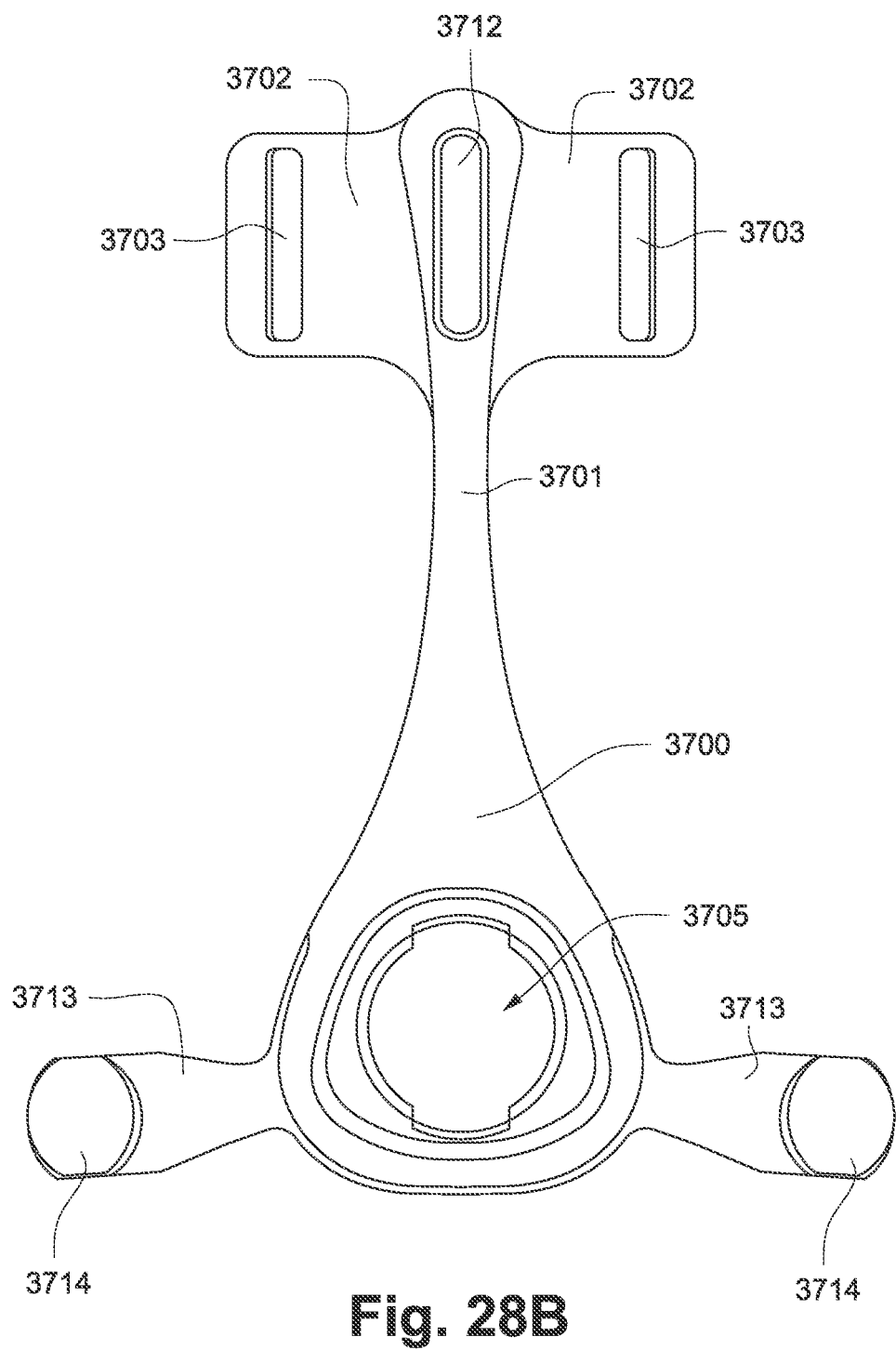

FIG. 28B depicts an anterior view of a patient interface according to an example of the present technology.

Figure 28C:
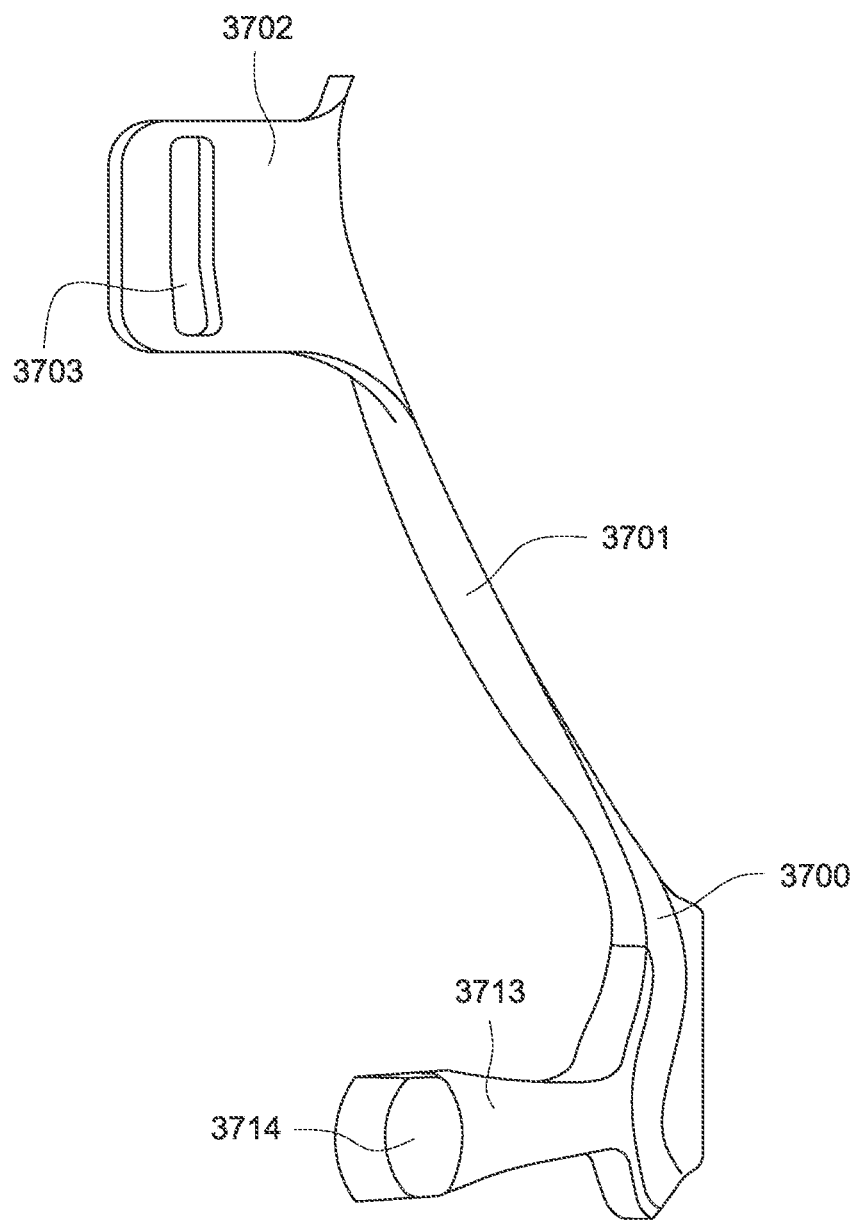

FIG. 28C depicts a lateral view of a patient interface according to an example of the present technology.

Figure 28D:
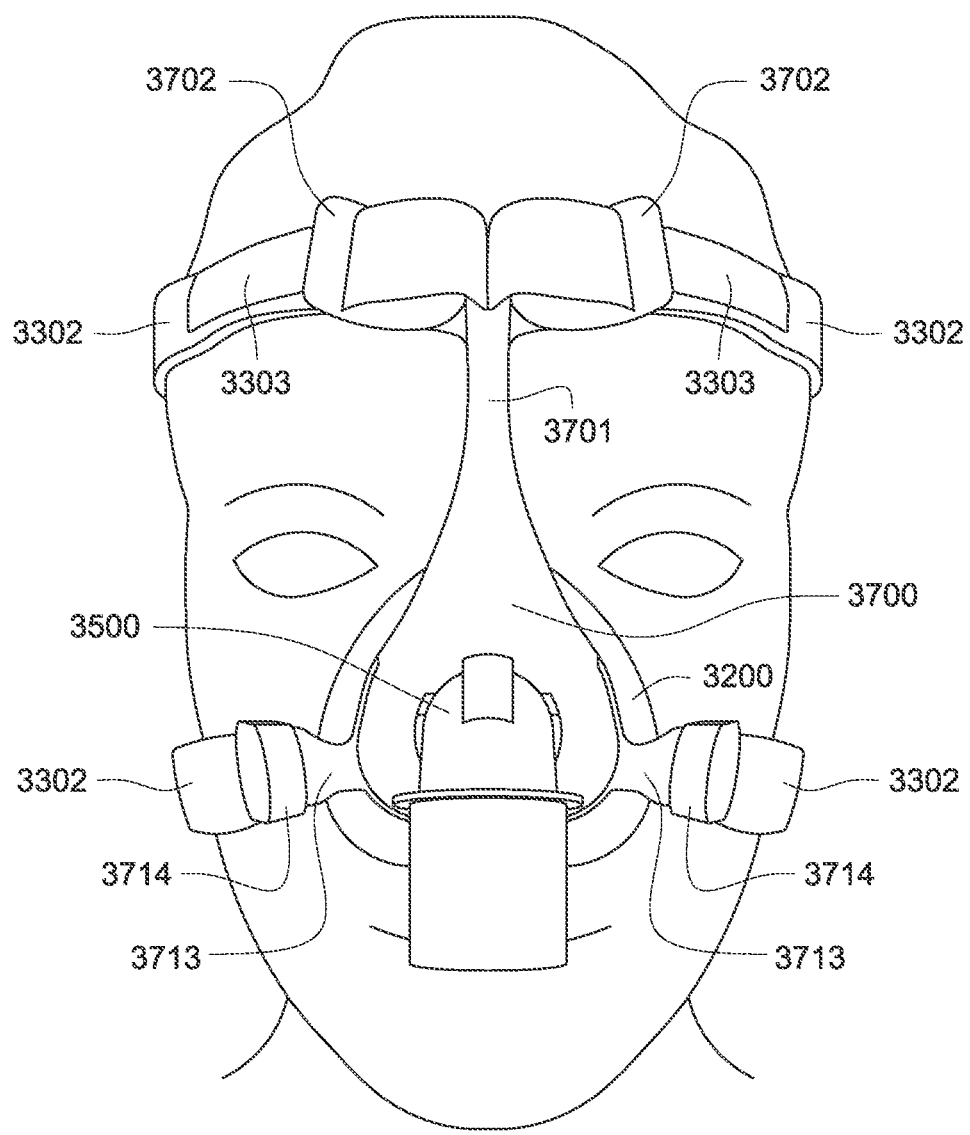

FIG. 28D depicts an anterior view of a patient interface on a patient according to an example of the present technology.

Figure 29A:
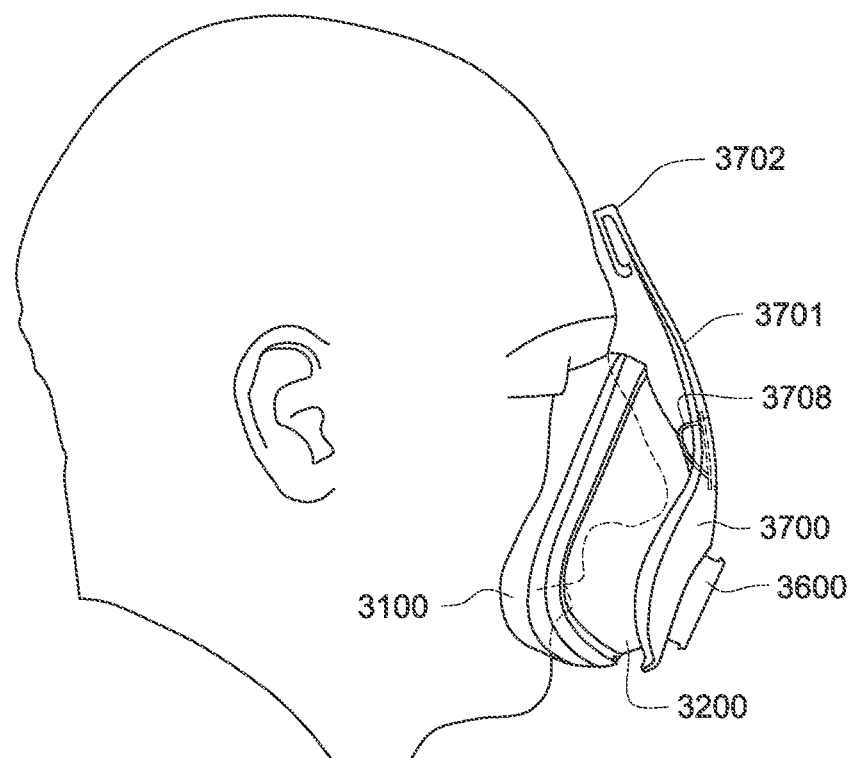

FIG. 29A depicts a lateral view of a patient interface on a patient according to an example of the present technology.

Figure 29B:
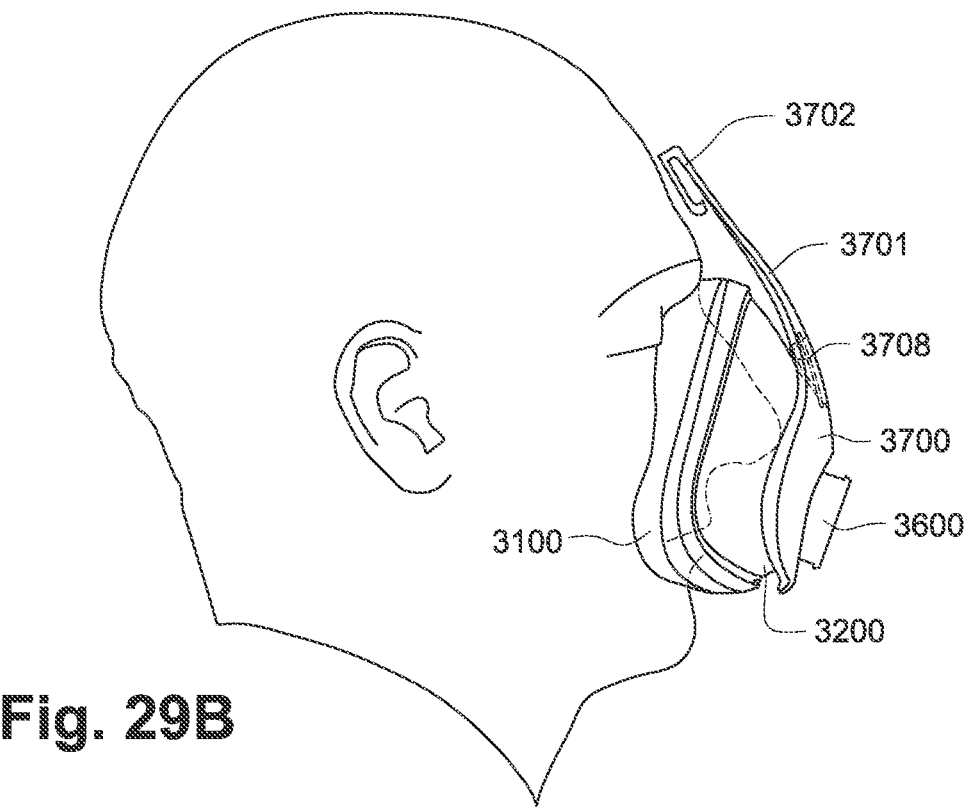

FIG. 29B depicts a lateral view of a patient interface on a patient according to an example of the present technology.

Figure 30A:
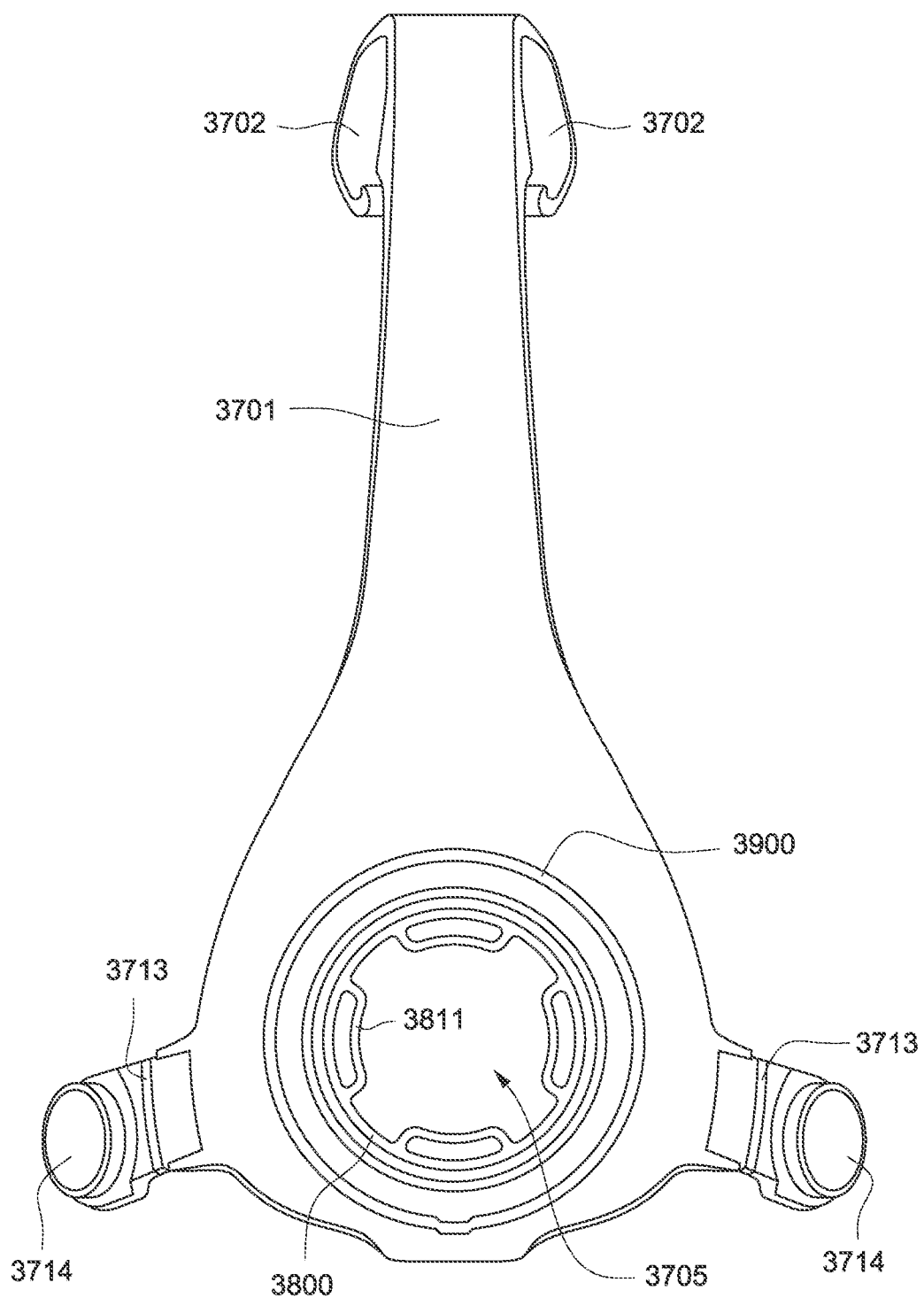

FIG. 30A depicts an anterior view of a frame of a patient interface according to an example of the present technology.

Figure 30B:
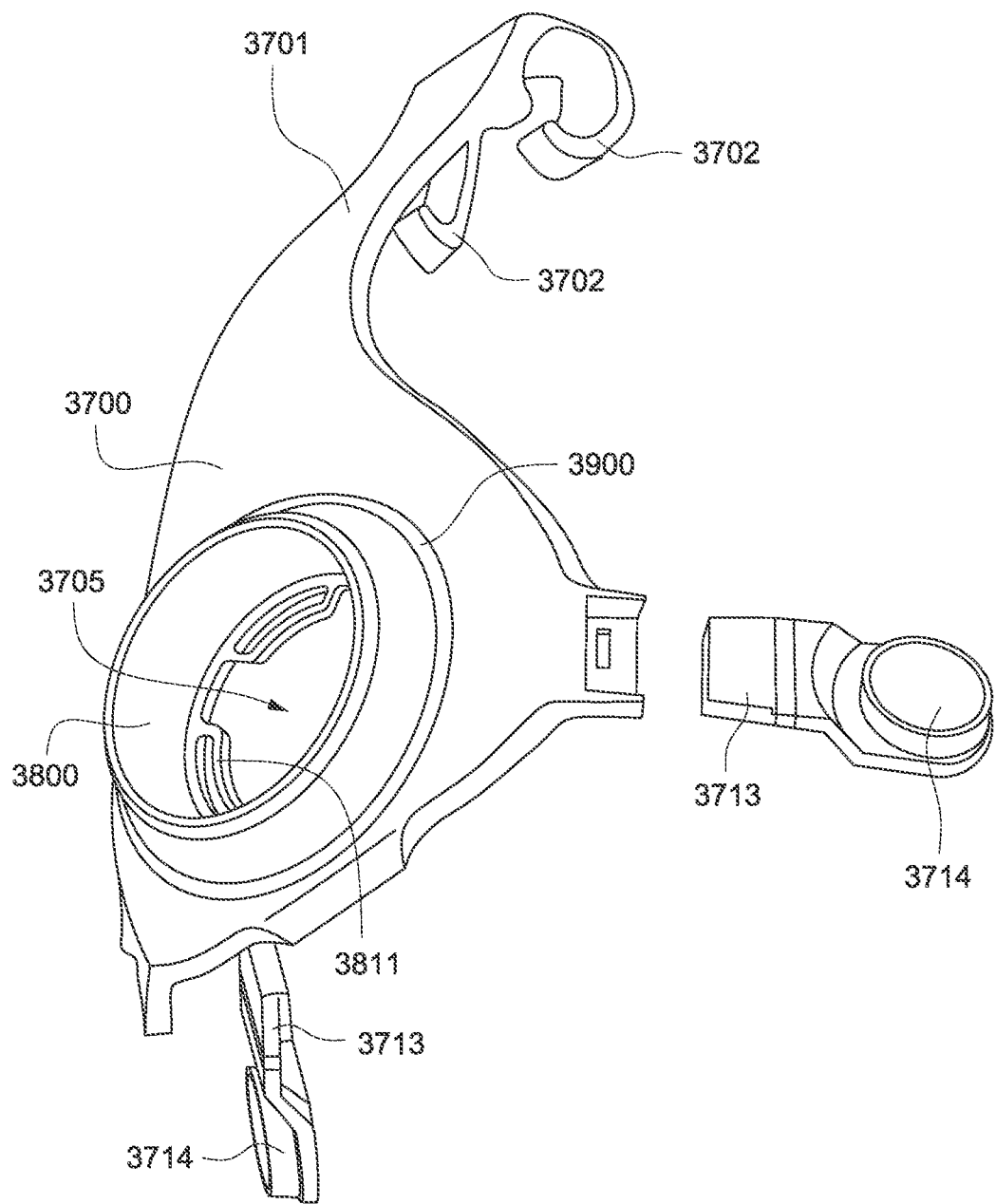

FIG. 30B depicts an anterior perspective view of a frame of a patient interface according to an example of the present technology.

Figure 30C:
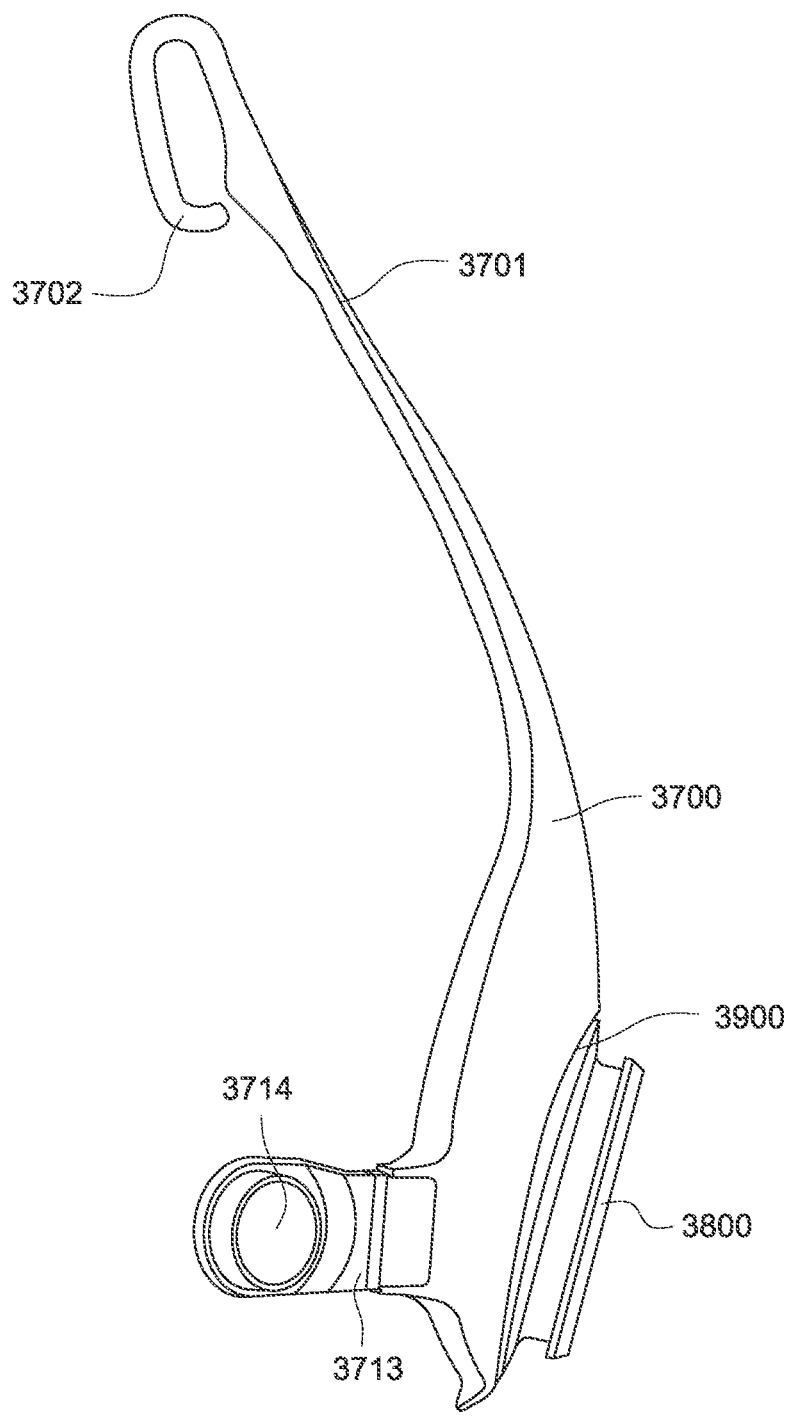

FIG. 30C depicts a lateral view of a frame of a patient interface according to an example of the present technology.

Figure 30D:
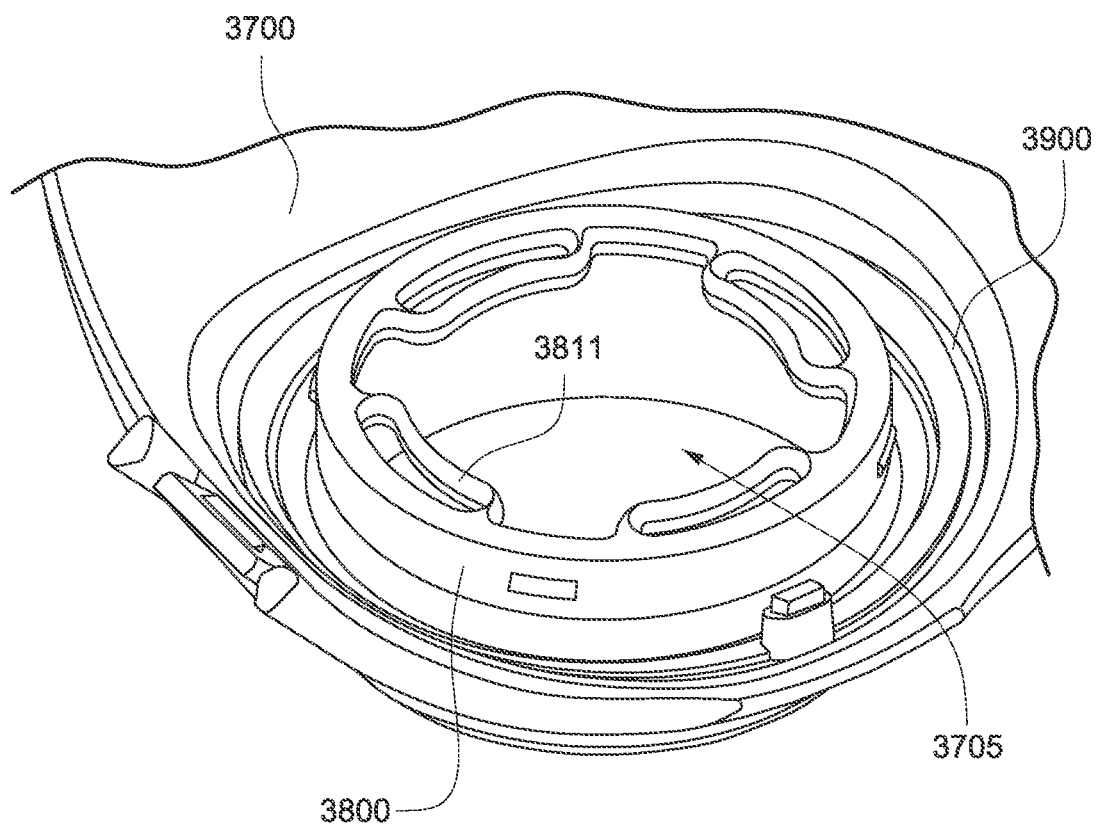

FIG. 30D depicts a detailed posterior perspective view of a frame of a patient interface according to an example of the present technology.

Figure 31A:
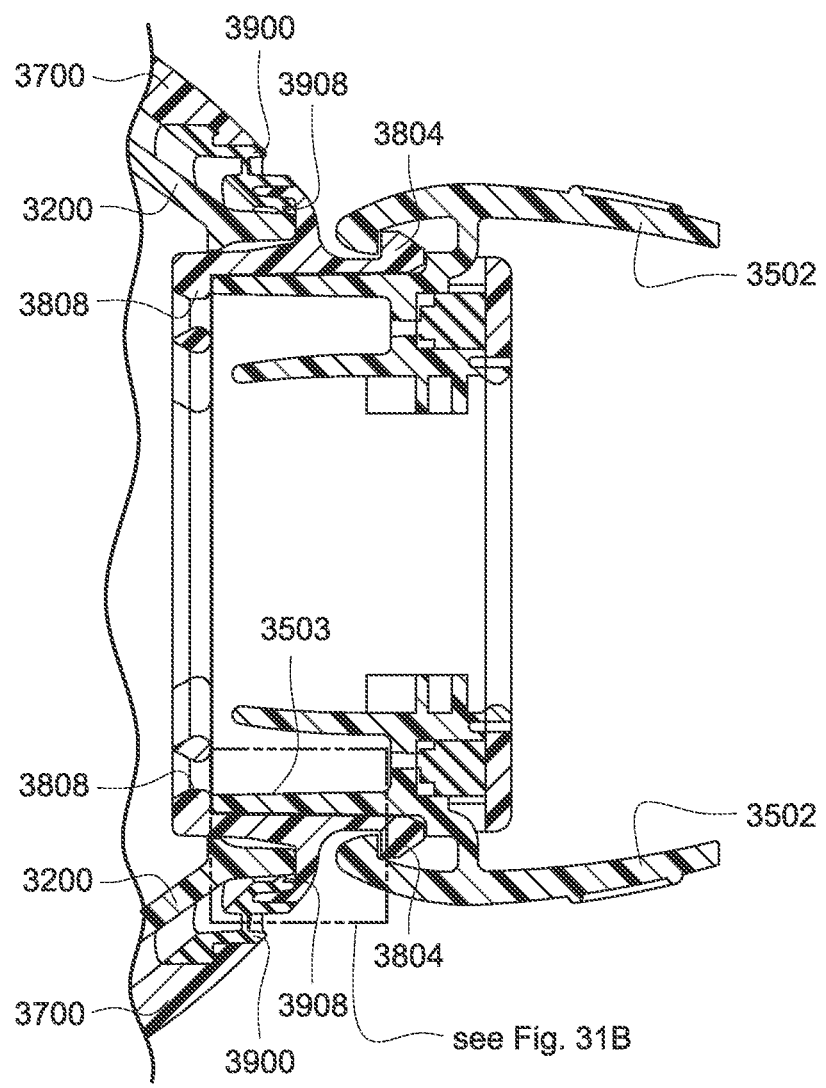

FIG. 31A depicts a cross-sectional view of a decoupling structure engaged with a plenum chamber and a frame according to an example of the present technology.

Figure 31B:
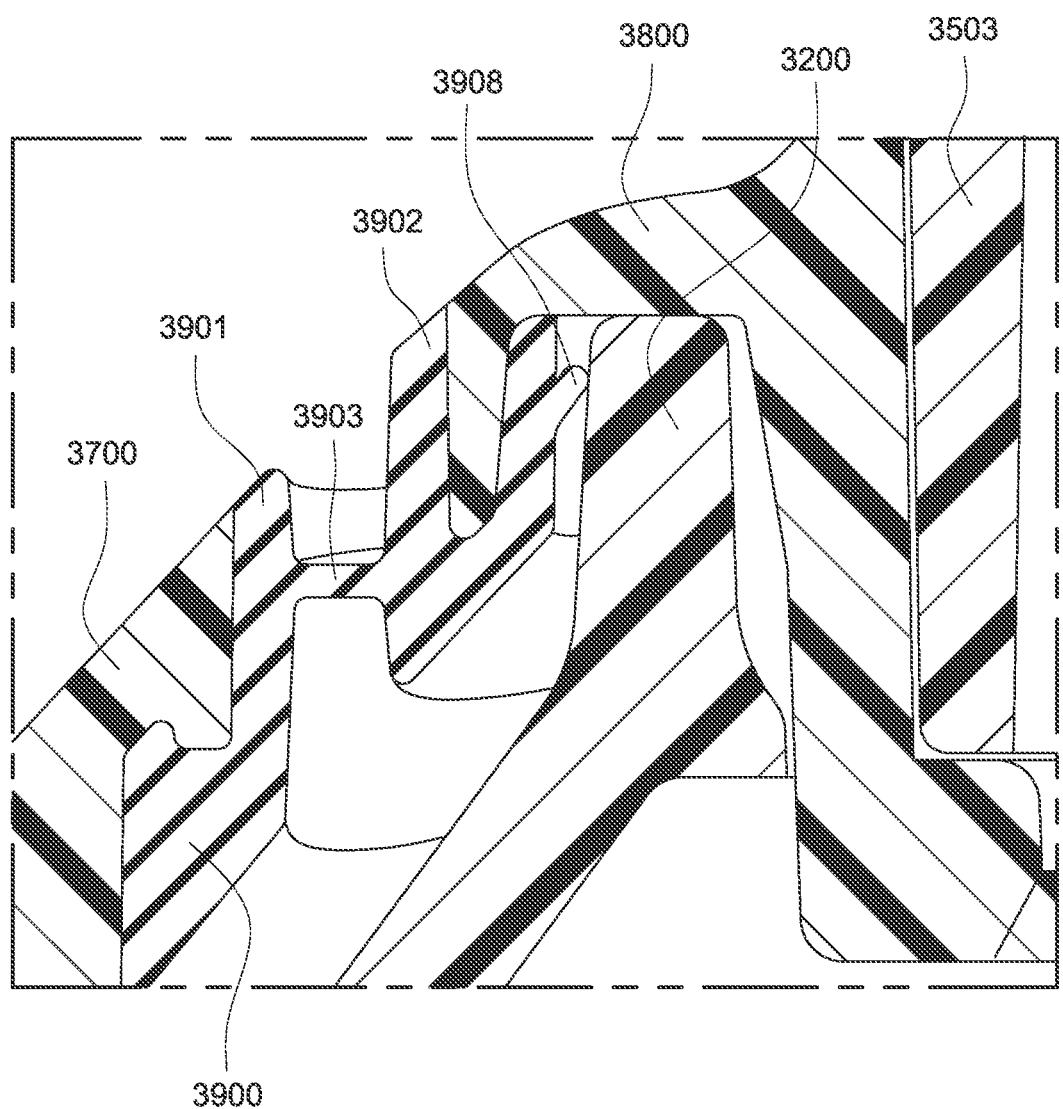

FIG. 31B depicts a detailed view of the cross-section shown in FIG. 31A of a decoupling structure engaged with a plenum chamber and a frame according to an example of the present technology.

Figure 32A:
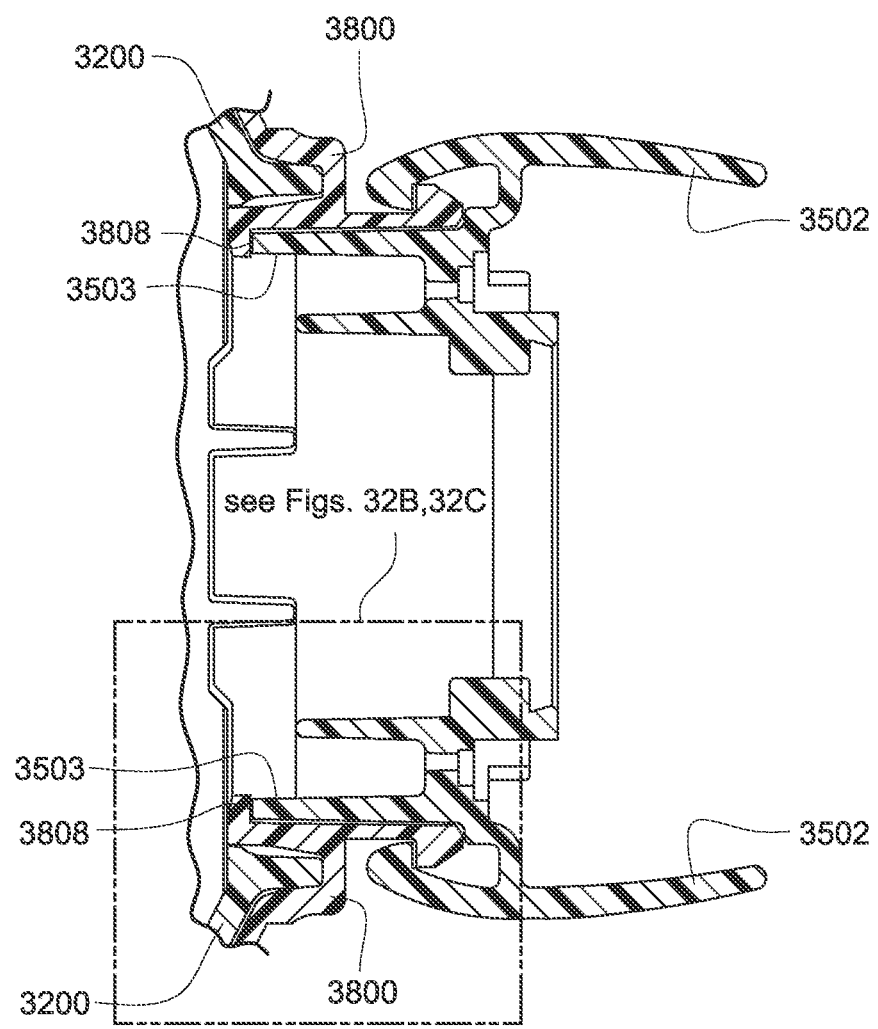

FIG. 32A depicts a cross-sectional view of a decoupling structure engaged with a plenum chamber and a frame according to an example of the present technology.

Figure 32B:
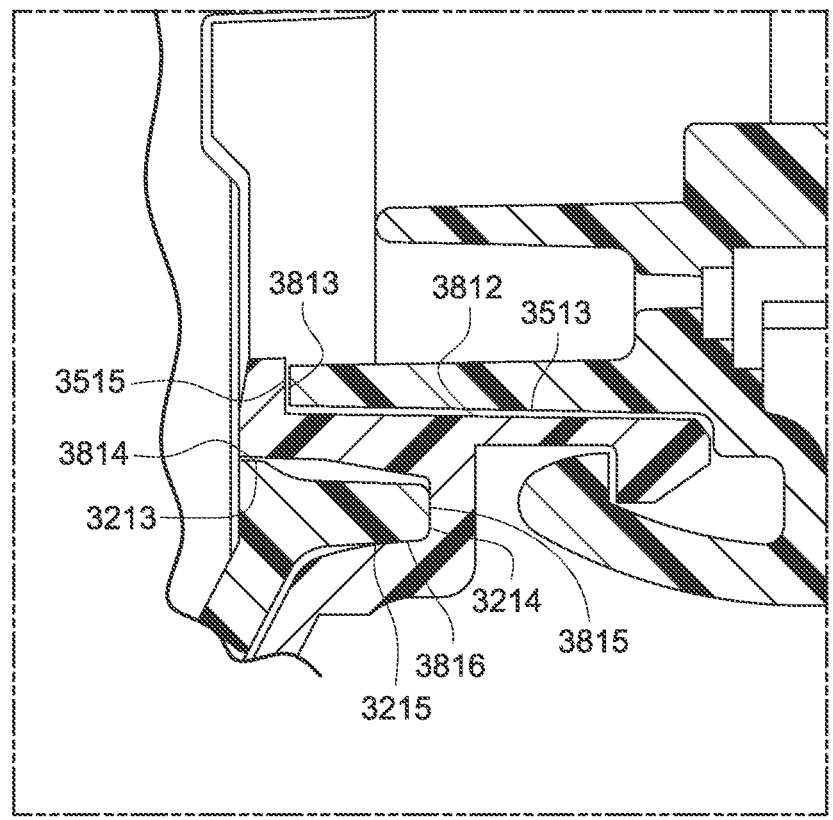

FIG. 32B depicts a detailed view of the cross-section shown in FIG. 31A of a decoupling structure engaged with a plenum chamber and a frame according to an example of the present technology.

Figure 32C:
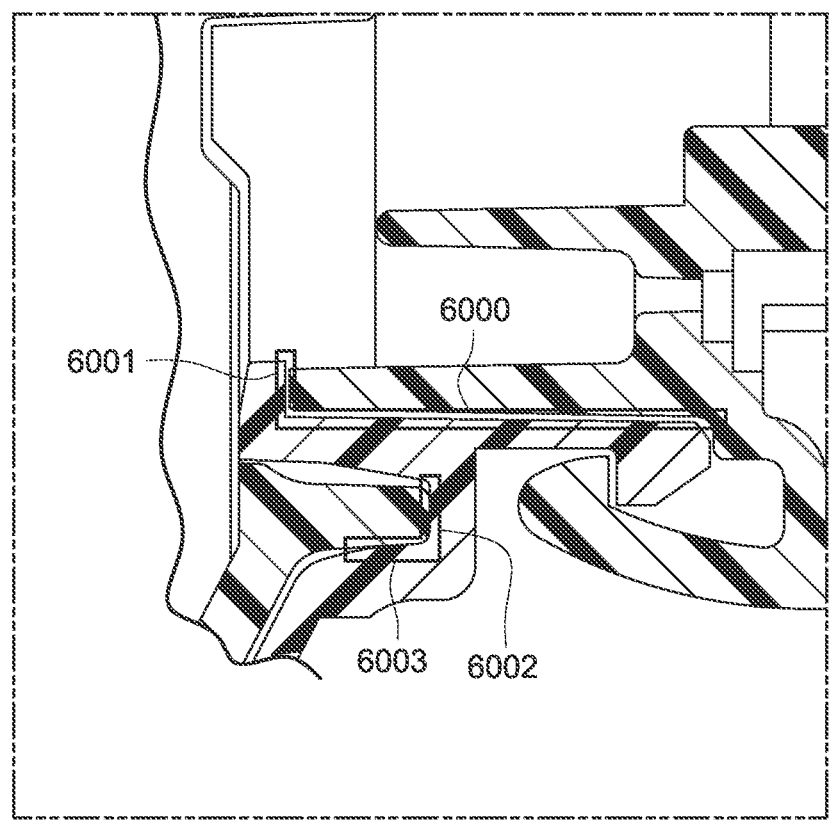

FIG. 32C depicts a detailed view of the cross-section shown in FIG. 31A of a decoupling structure engaged with a plenum chamber and a frame according to an example of the present technology.

Figure 33A:
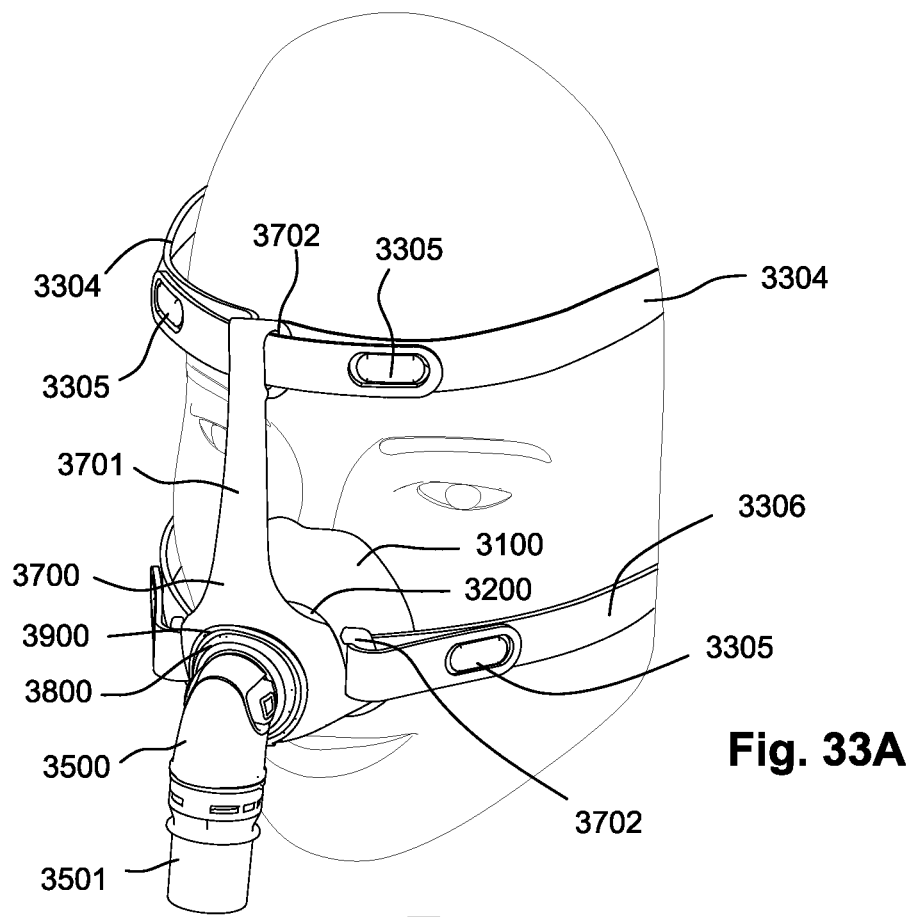

FIG. 33A shows a front perspective view of a patient interface according to an example of the present technology on a patient.

Figure 33B:
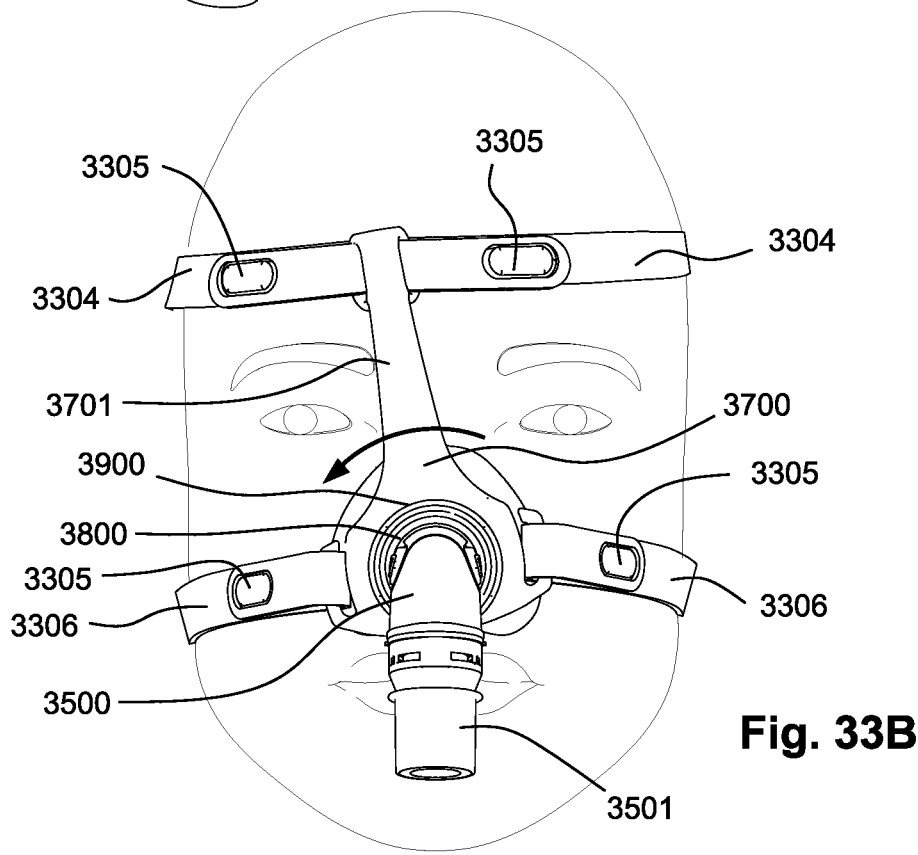

FIG. 33B shows a front view of a patient interface according to an example of the present technology on a patient.

Figure 33C:
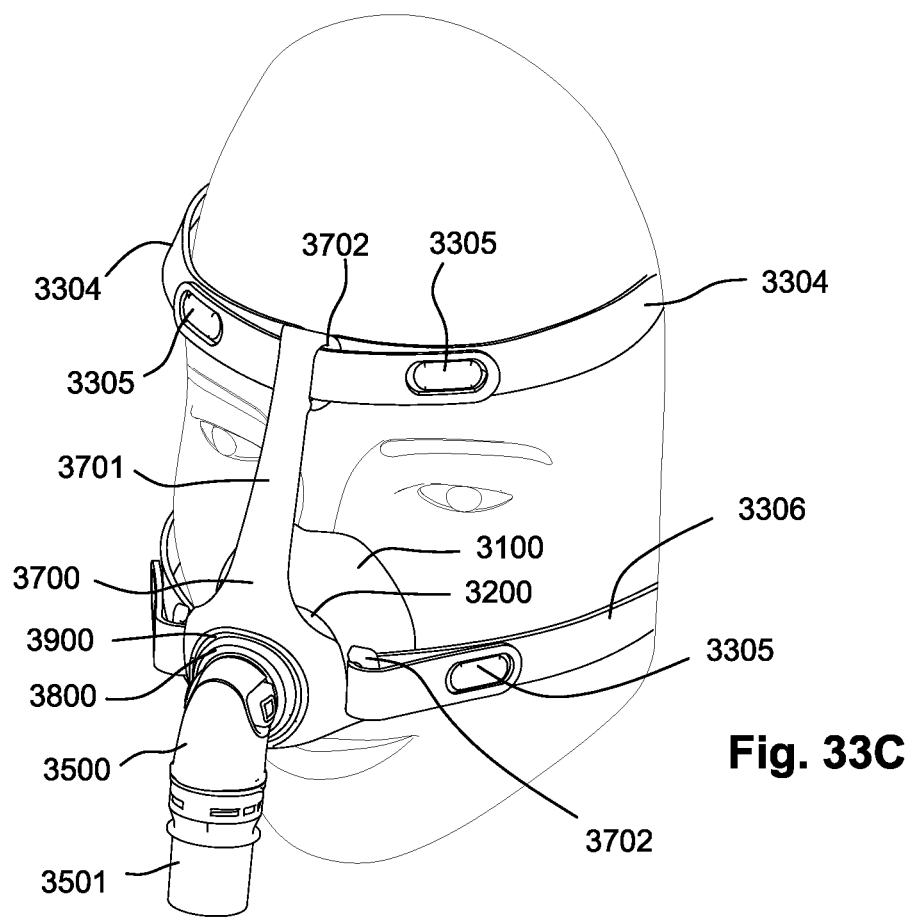

FIG. 33C shows a front perspective view of a patient interface according to an example of the present technology on a patient.

Figure 33D:
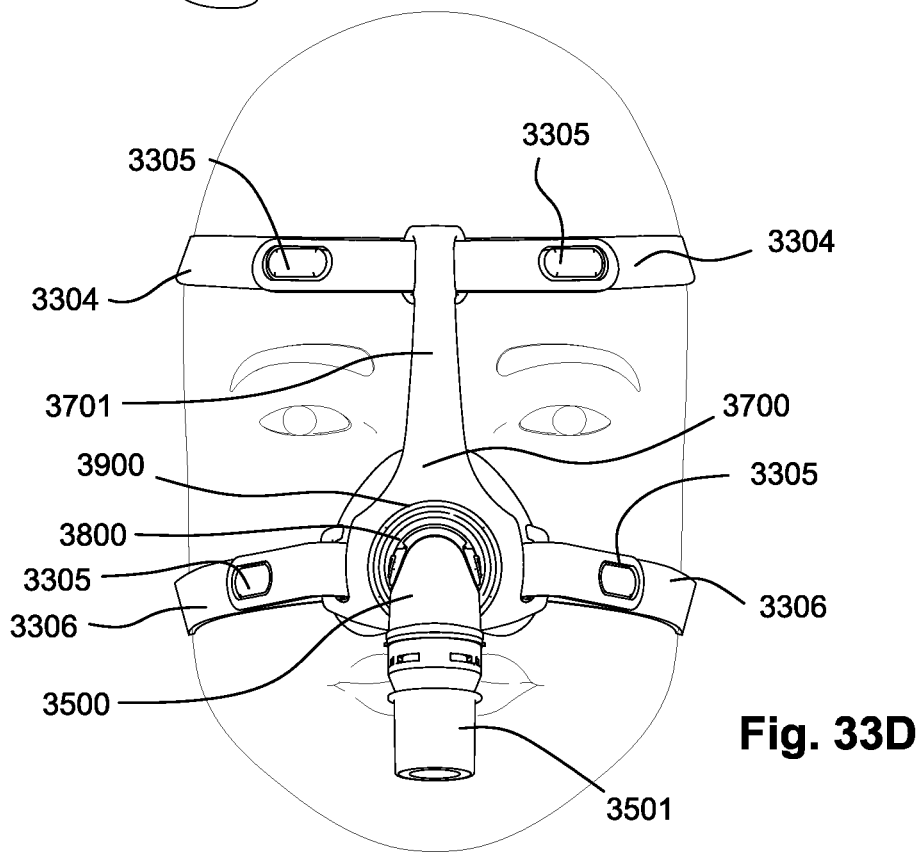

FIG. 33D shows a front view of a patient interface according to an example of the present technology on a patient.

Figure 33E:
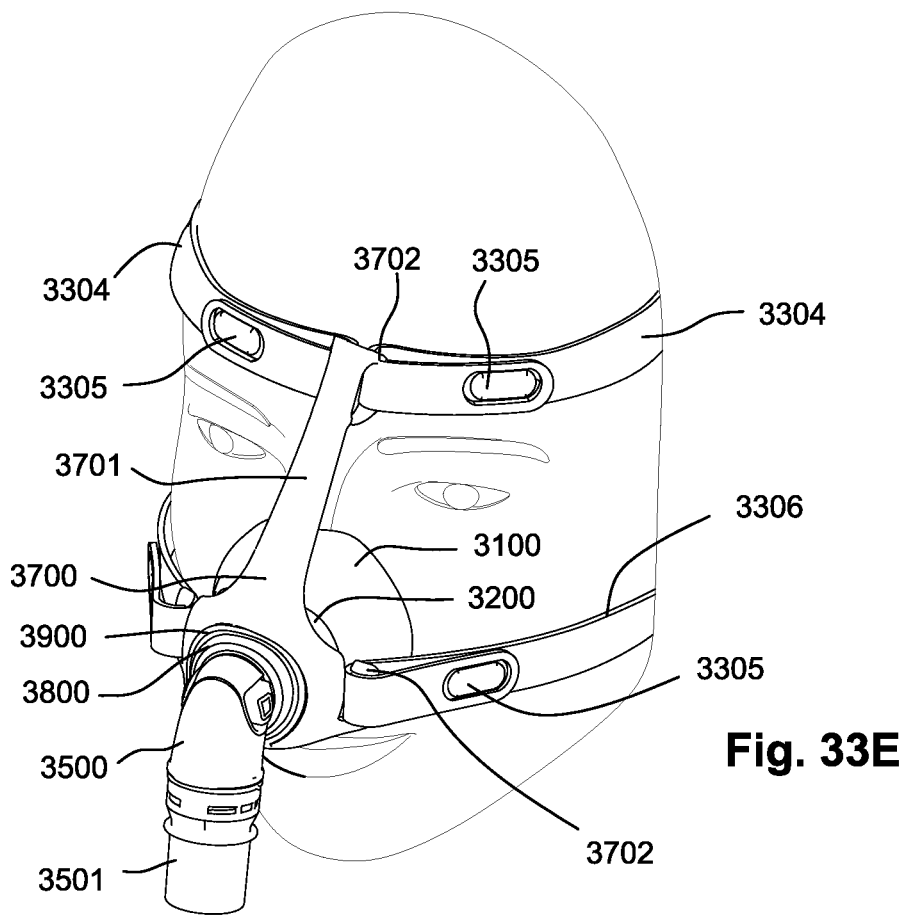

FIG. 33E shows a front perspective view of a patient interface according to an example of the present technology on a patient.

Figure 33F:
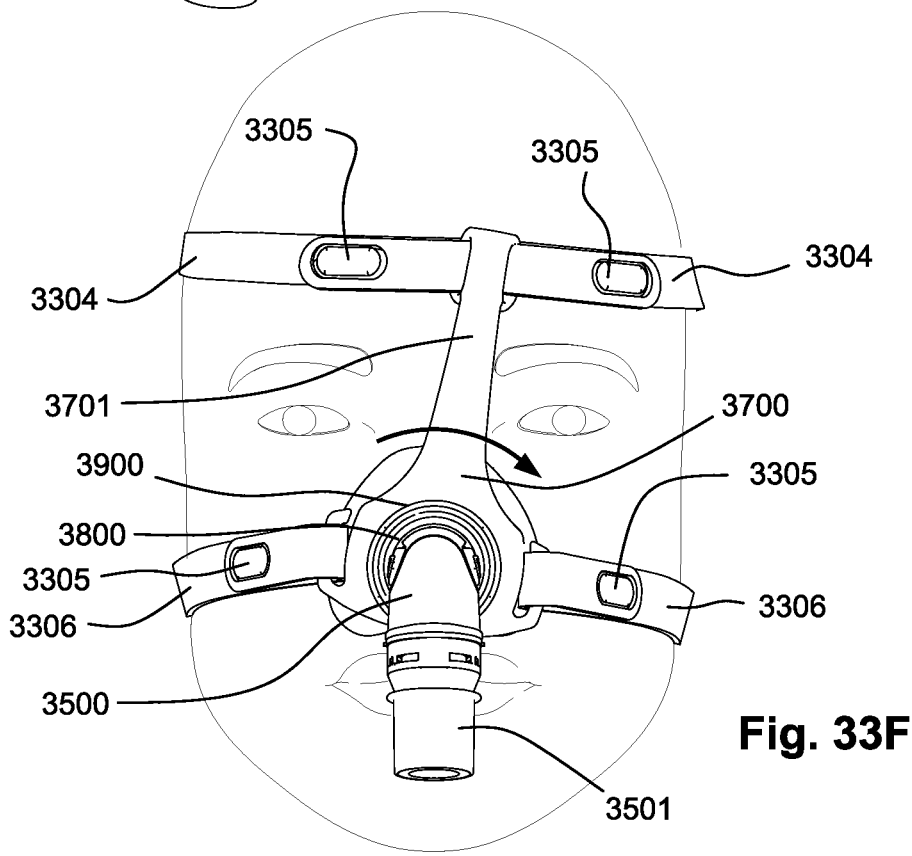

FIG. 33F shows a front view of a patient interface according to an example of the present technology on a patient.

Figure 33G:
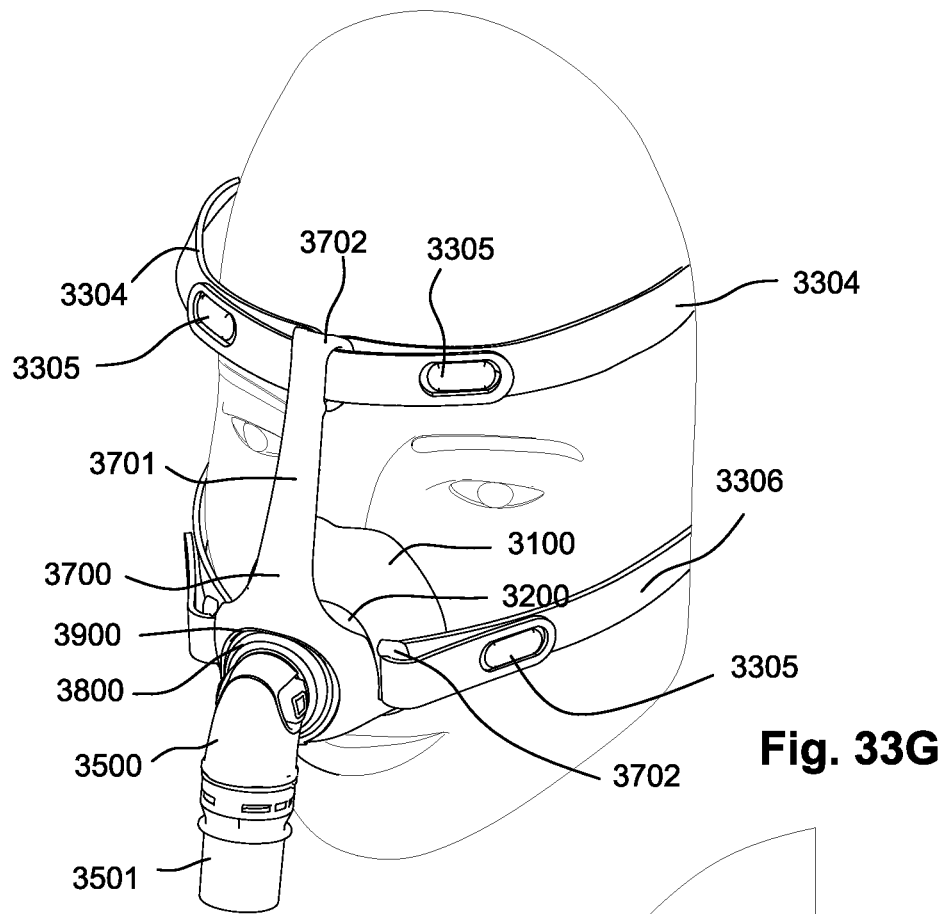

FIG. 33G shows a front perspective view of a patient interface according to an example of the present technology on a patient.

Figure 33H:
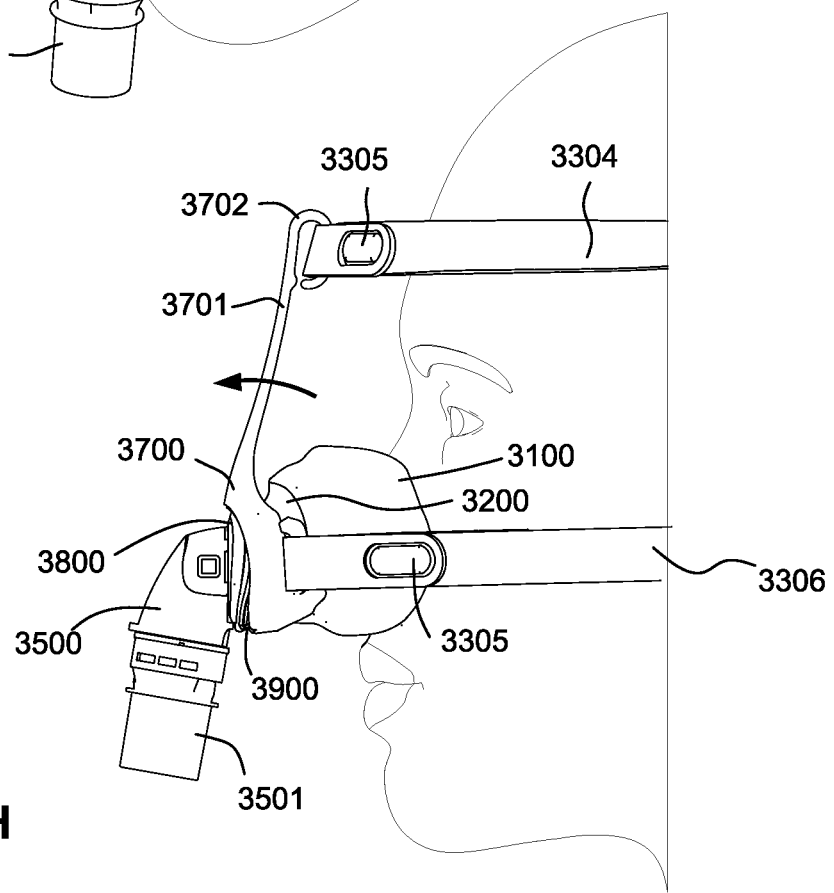

FIG. 33H shows a side view of a patient interface according to an example of the present technology on a patient.

Figure 33I:
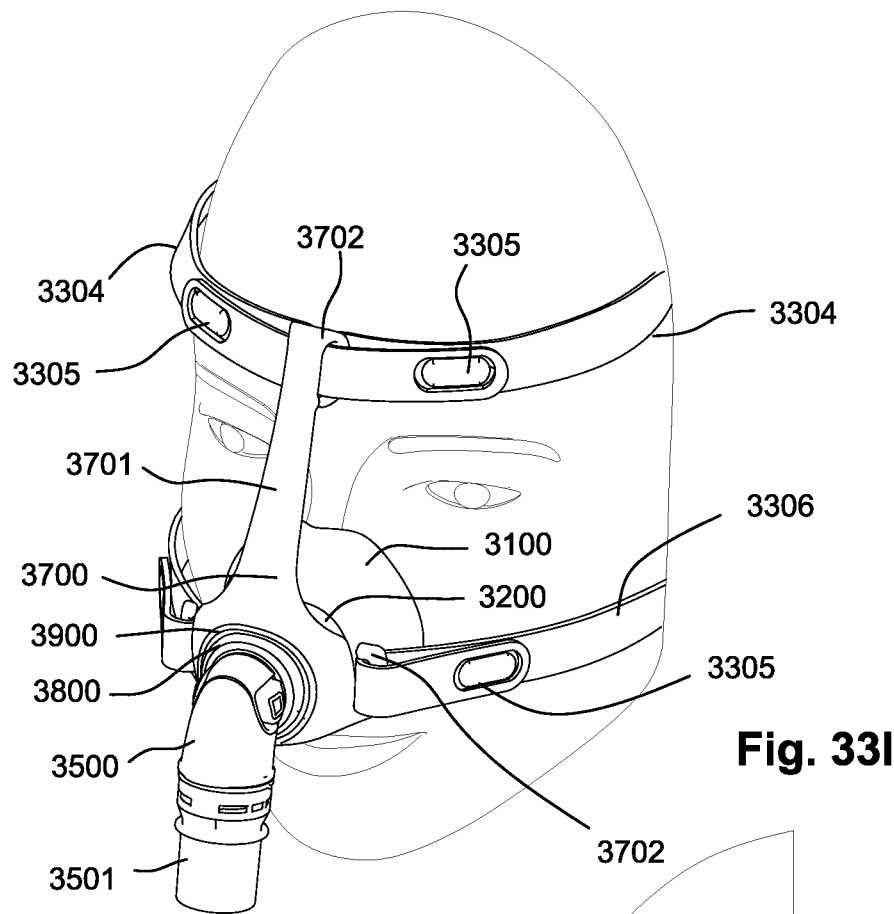

FIG. 33I shows a front perspective view of a patient interface according to an example of the present technology on a patient.

Figure 33J:
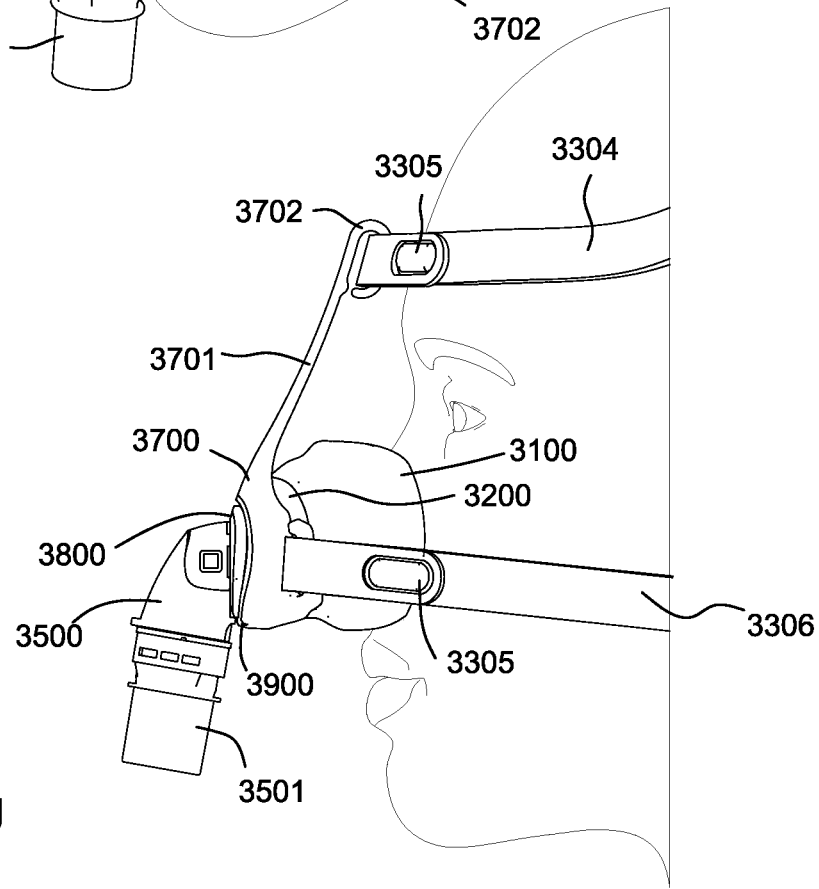

FIG. 33J shows a side view of a patient interface according to an example of the present technology on a patient.

Figure 33K:
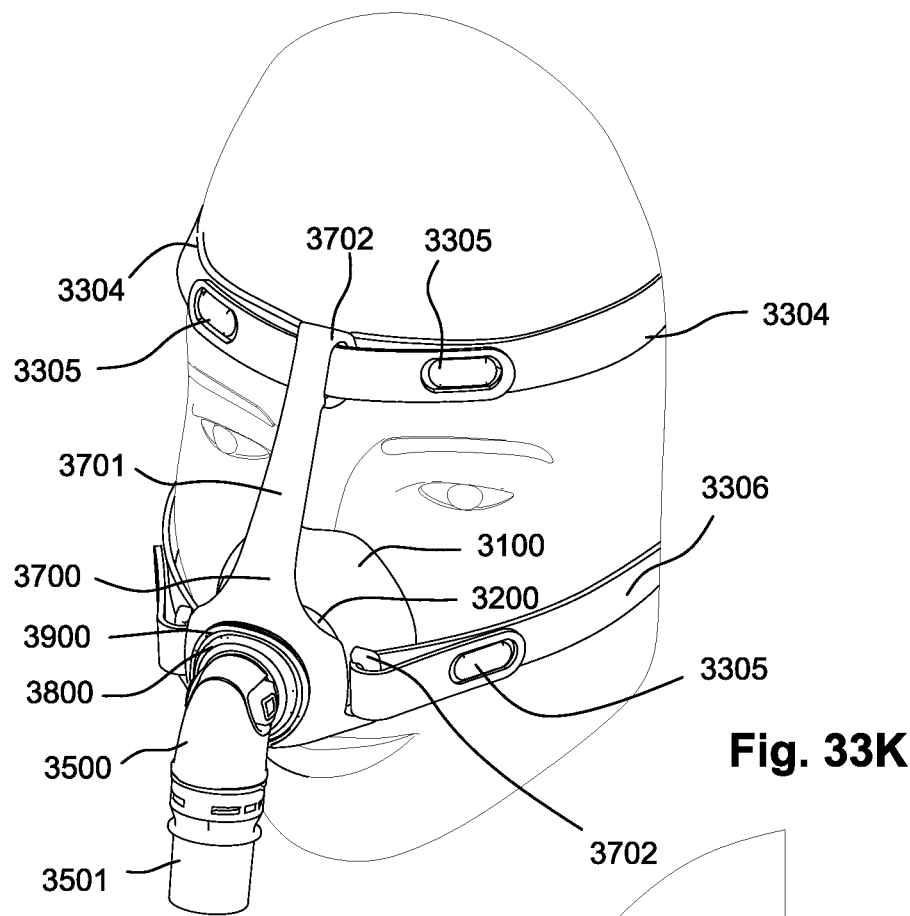

FIG. 33K shows a front perspective view of a patient interface according to an example of the present technology on a patient.

Figure 33L:
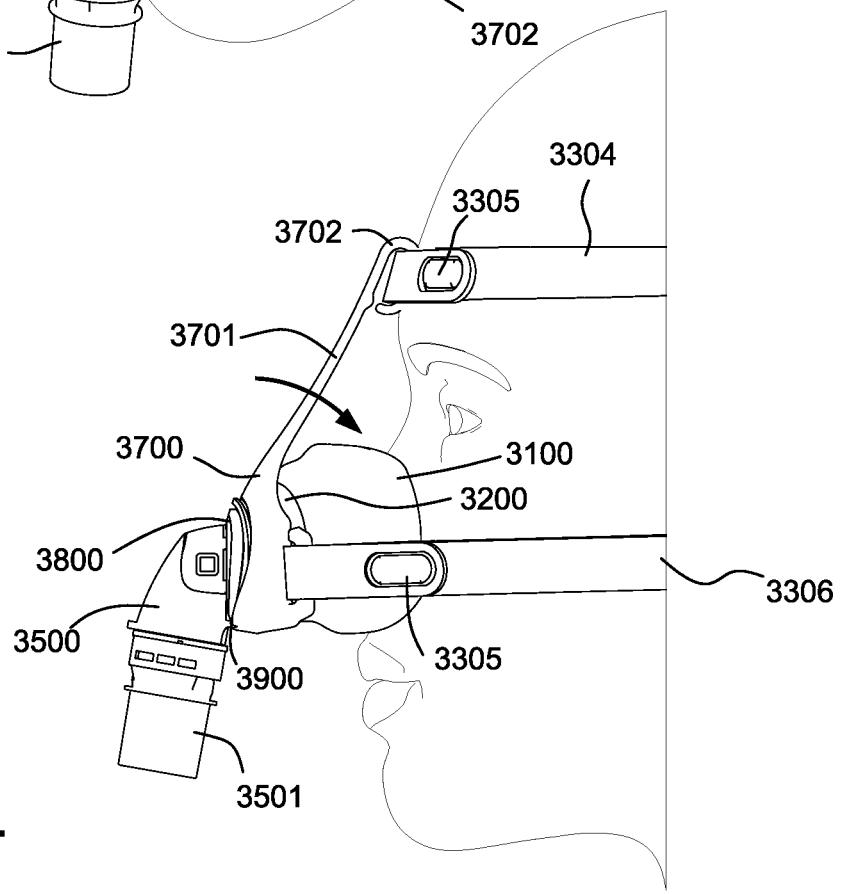

FIG. 33L shows a side view of a patient interface according to an example of the present technology on a patient.

Figure 33M:
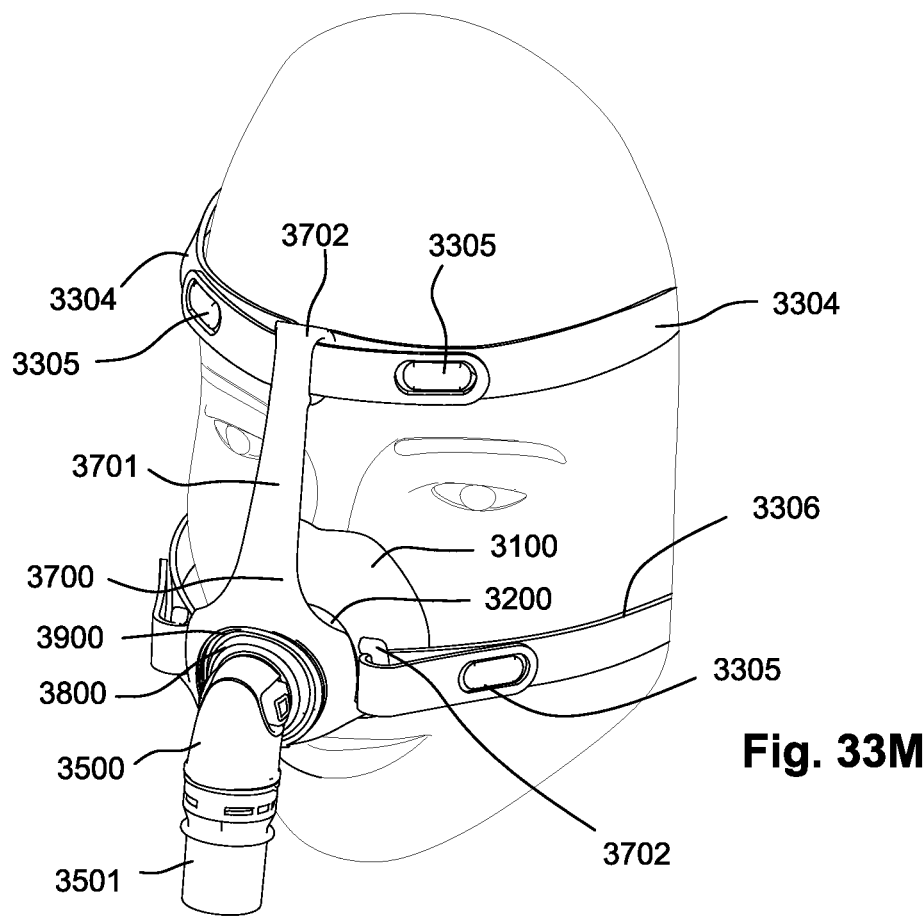

FIG. 33M shows a front perspective view of a patient interface according to an example of the present technology on a patient.

Figure 33N:
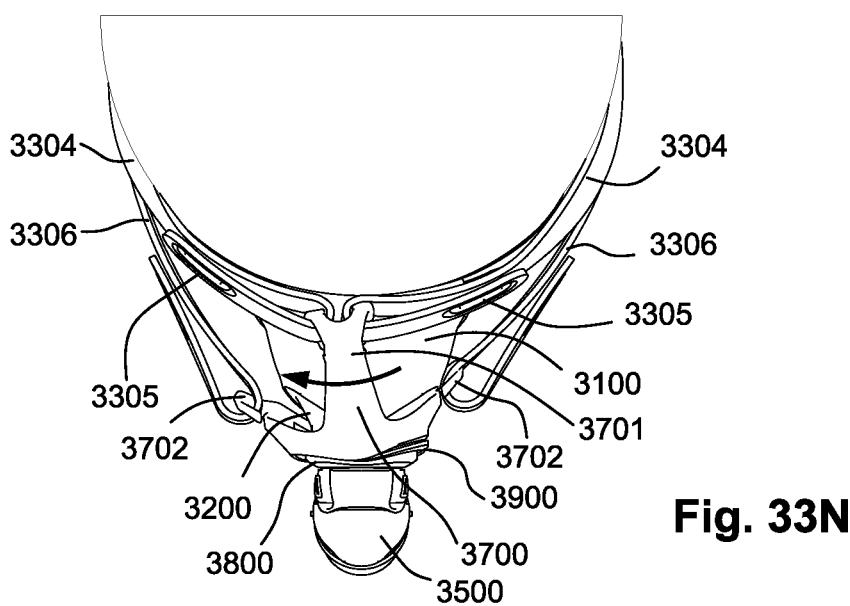

FIG. 33N shows a top view of a patient interface according to an example of the present technology on a patient.

Figure 33O:
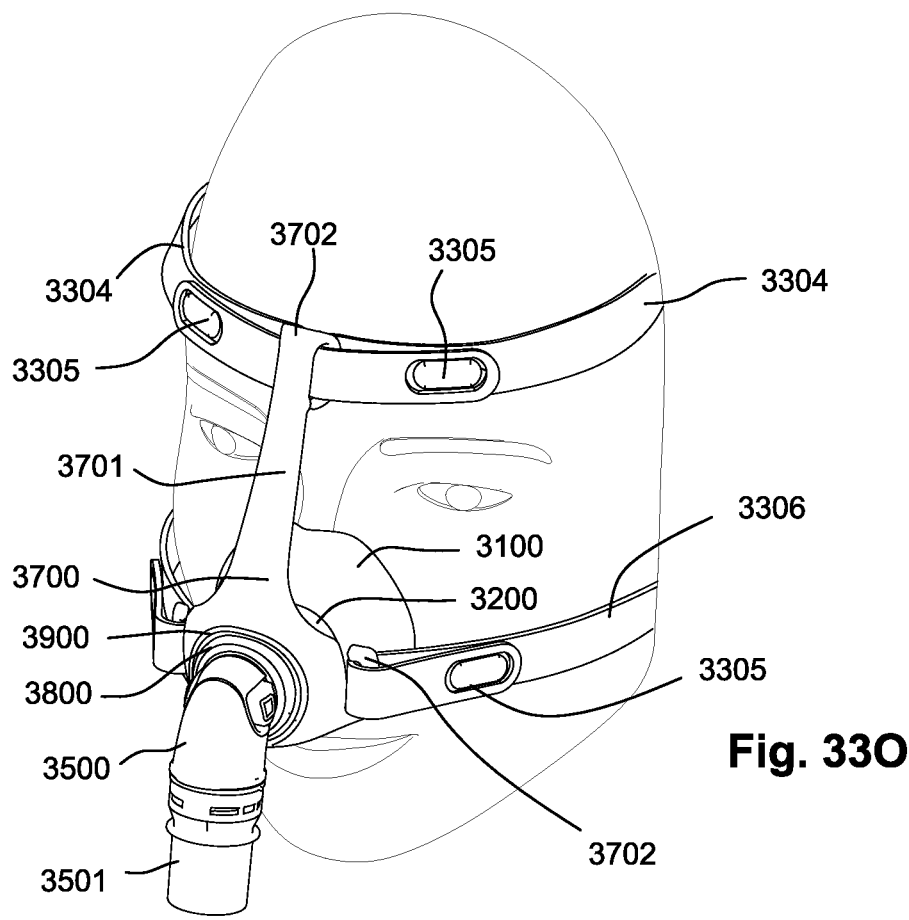

FIG. 33O shows a front perspective view of a patient interface according to an example of the present technology on a patient.

Figure 33P:
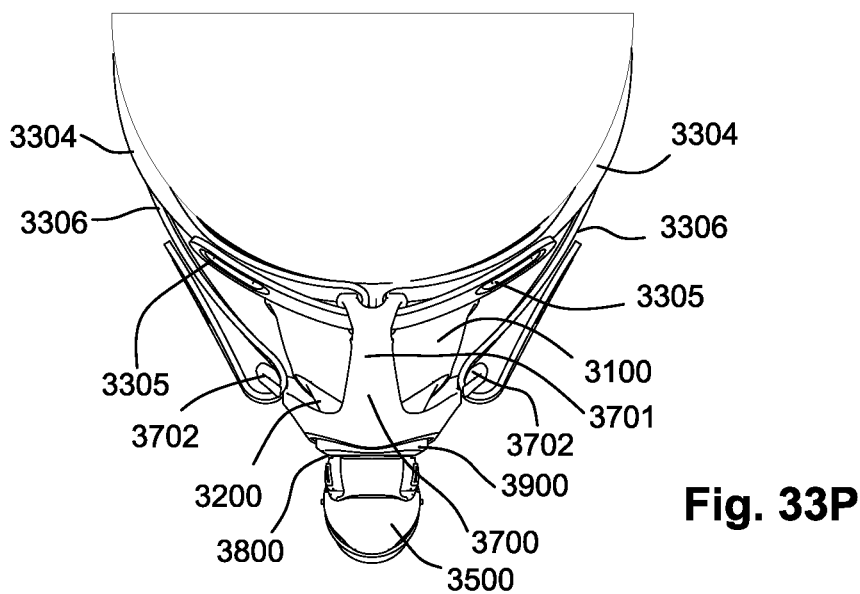

FIG. 33P shows a top view of a patient interface according to an example of the present technology on a patient.

Figure 33Q:
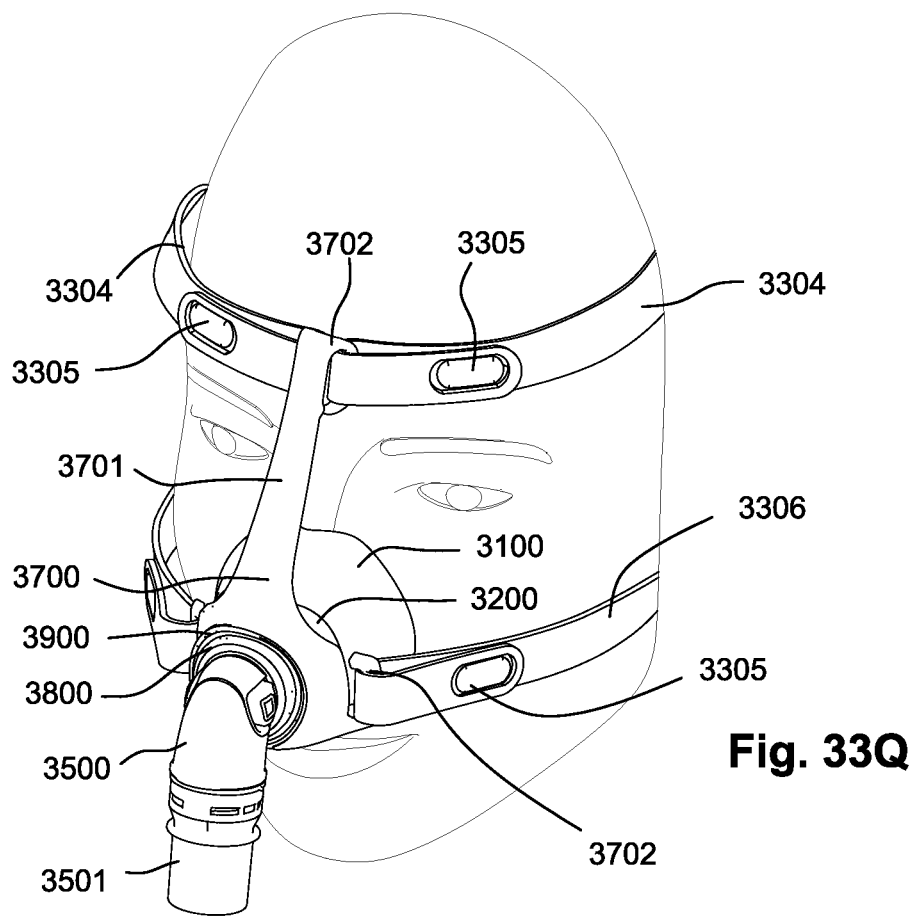

FIG. 33Q shows a front perspective view of a patient interface according to an example of the present technology on a patient.

Figure 33R:
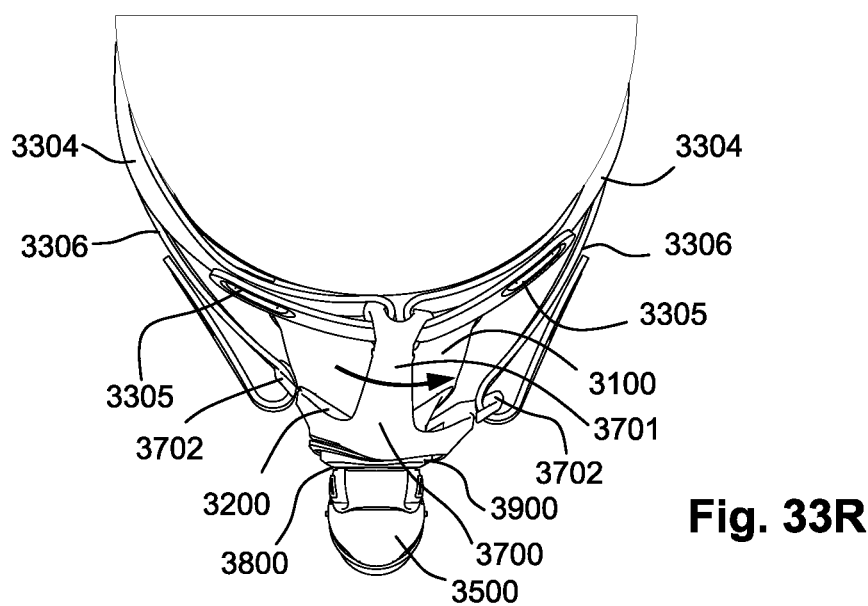

FIG. 33R shows a top view of a patient interface according to an example of the present technology on a patient.

Figure 34A:
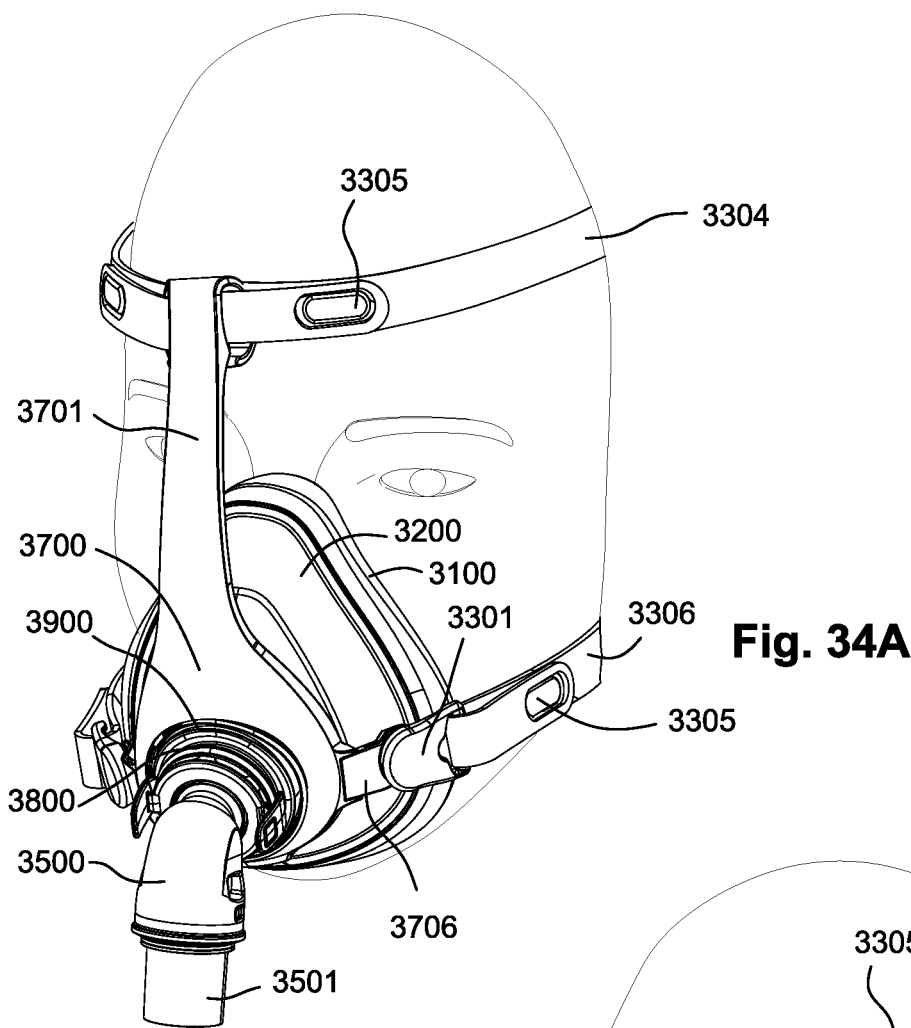

FIG. 34A shows a front perspective view of a patient interface according to an example of the present technology on a patient.

Figure 34B:
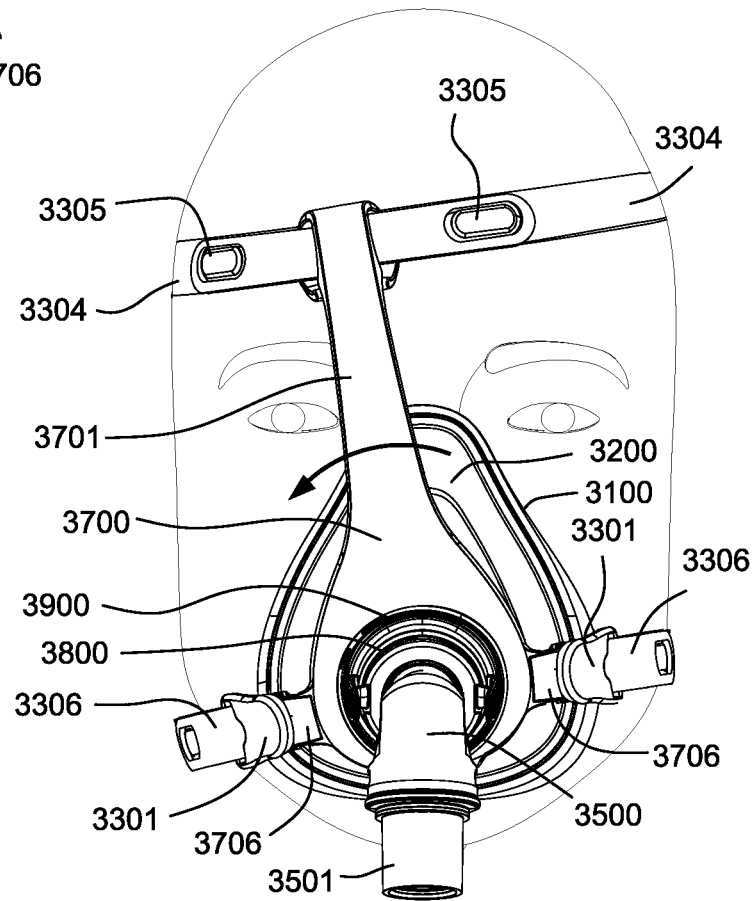

FIG. 34B shows a front view of a patient interface according to an example of the present technology on a patient.

Figure 34C:
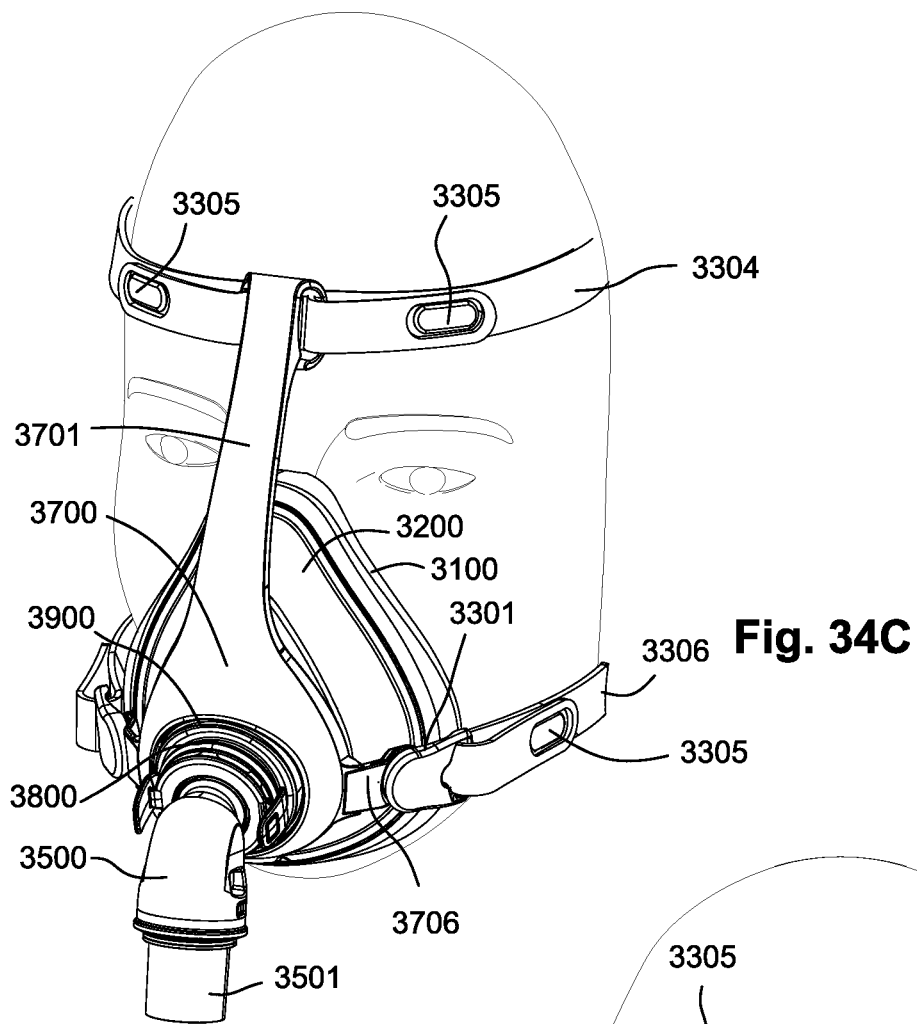

FIG. 34C shows a front perspective view of a patient interface according to an example of the present technology on a patient.

Figure 34D:
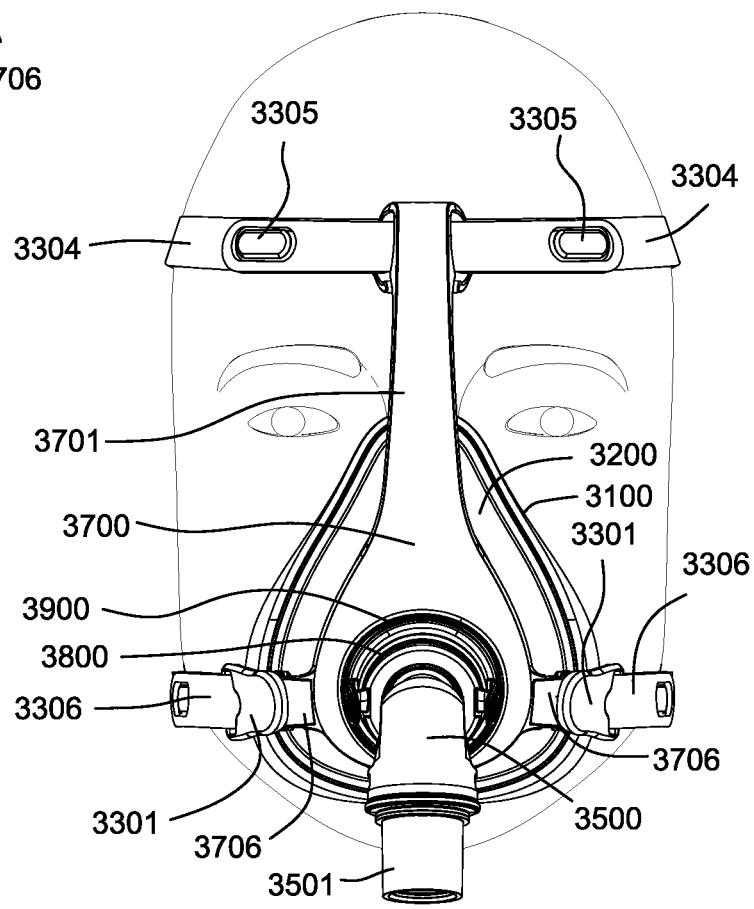

FIG. 34D shows a front view of a patient interface according to an example of the present technology on a patient.

Figure 34E:
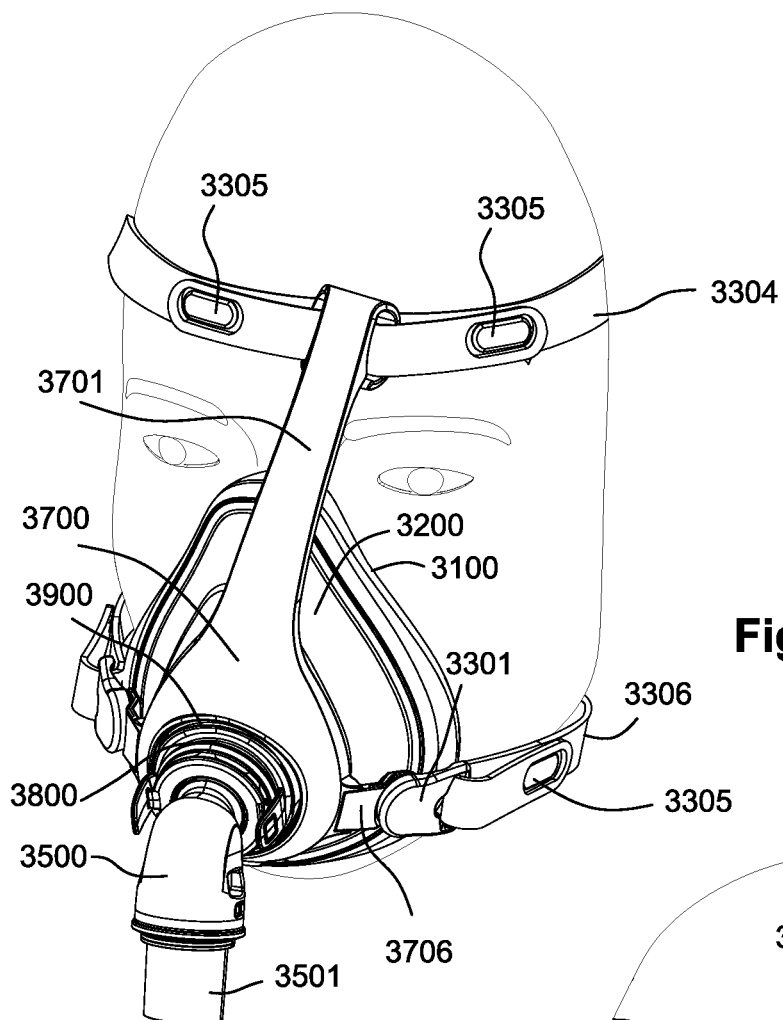

FIG. 34E shows a front perspective view of a patient interface according to an example of the present technology on a patient.

Figure 34F:
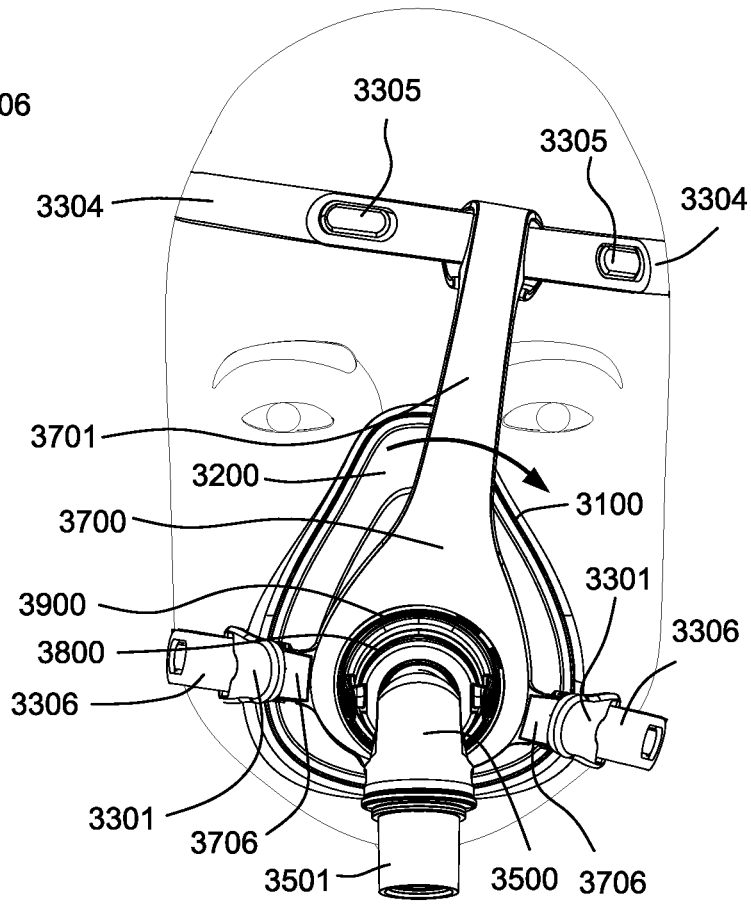

FIG. 34F shows a front view of a patient interface according to an example of the present technology on a patient.

Figures 34G, 34H:
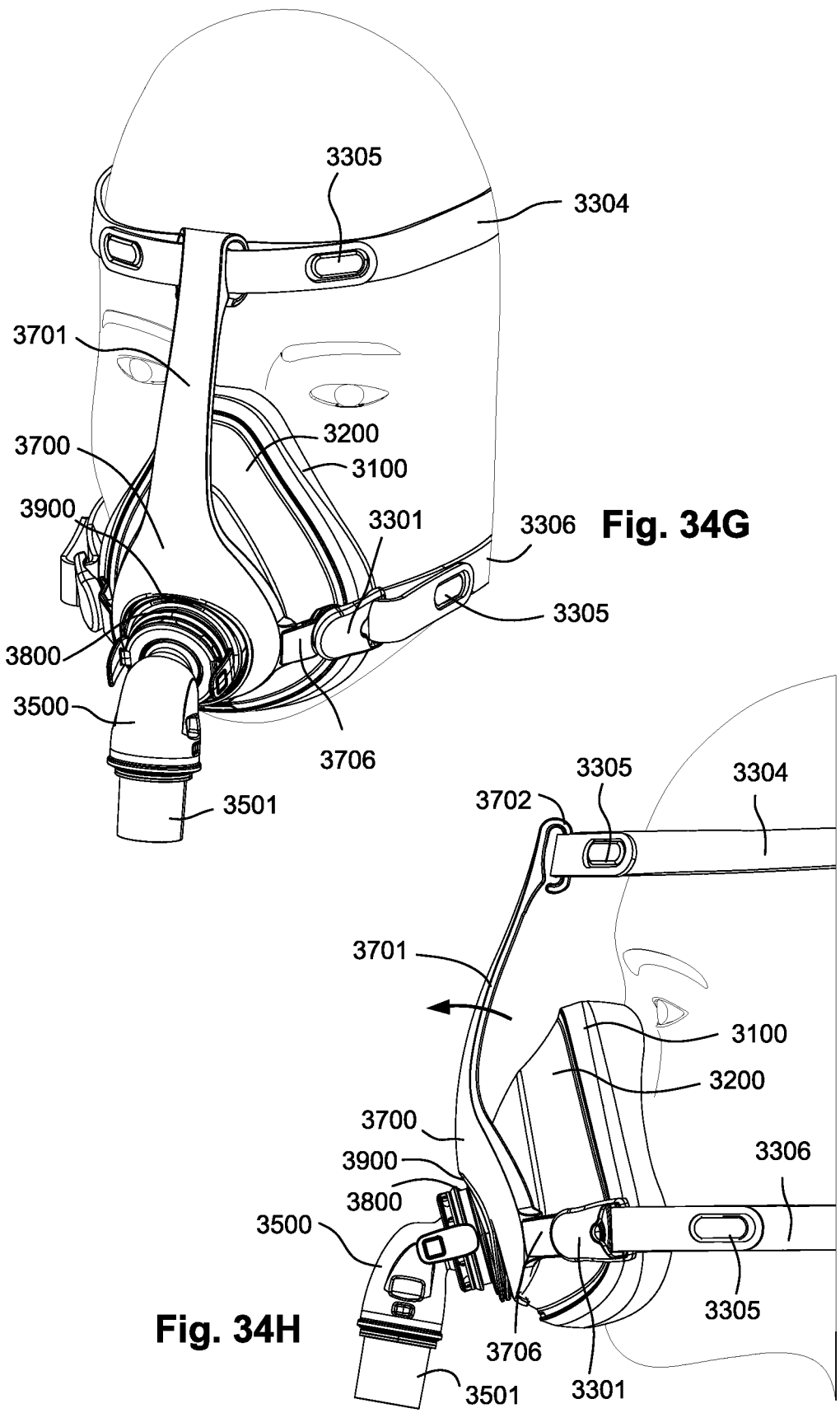
Figure 34I:
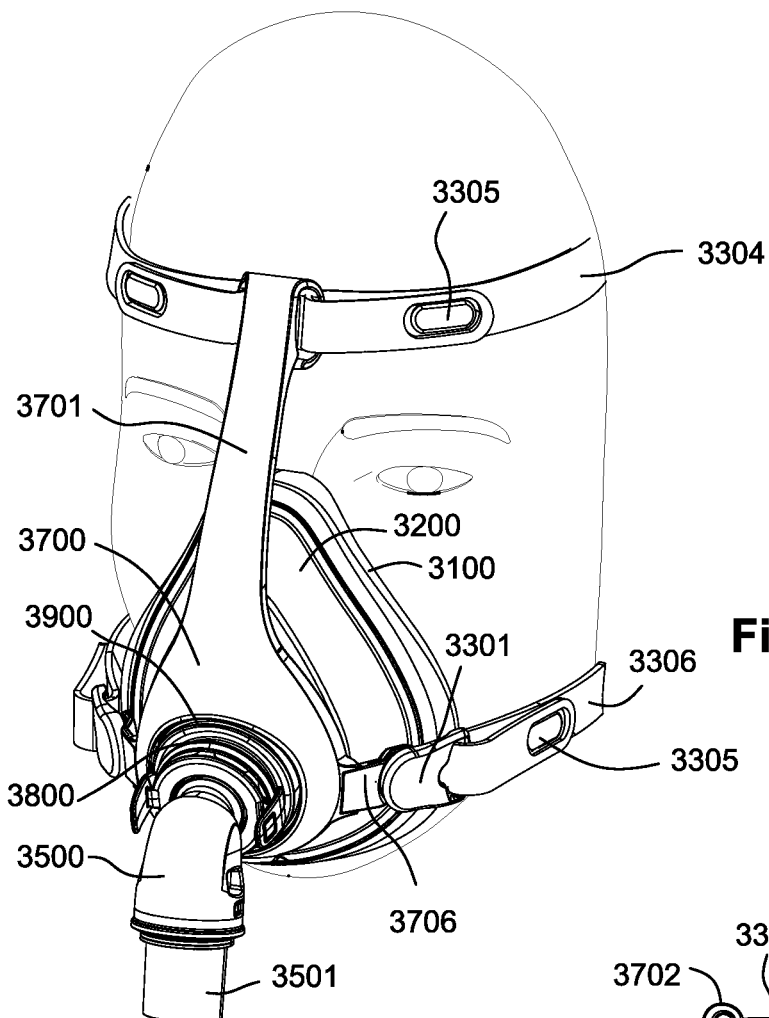

FIG. 34G shows a front perspective view of a patient interface according to an example of the present technology on a patient.

FIG. 34H shows a side view of a patient interface according to an example of the present technology on a patient.

FIG. 33I shows a front perspective view of a patient interface according to an example of the present technology on a patient.

Figure 34J:
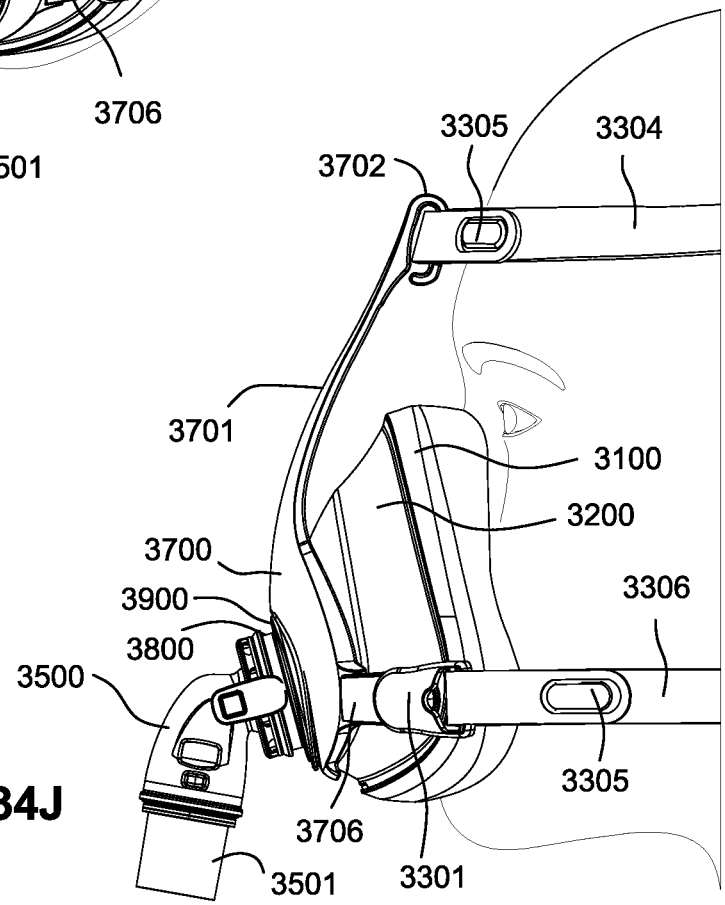

FIG. 34J shows a side view of a patient interface according to an example of the present technology on a patient.

FIG. 34K shows a front perspective view of a patient interface according to an example of the present technology on a patient.

FIG. 34L shows a side view of a patient interface according to an example of the present technology on a patient.

Figure 34M:
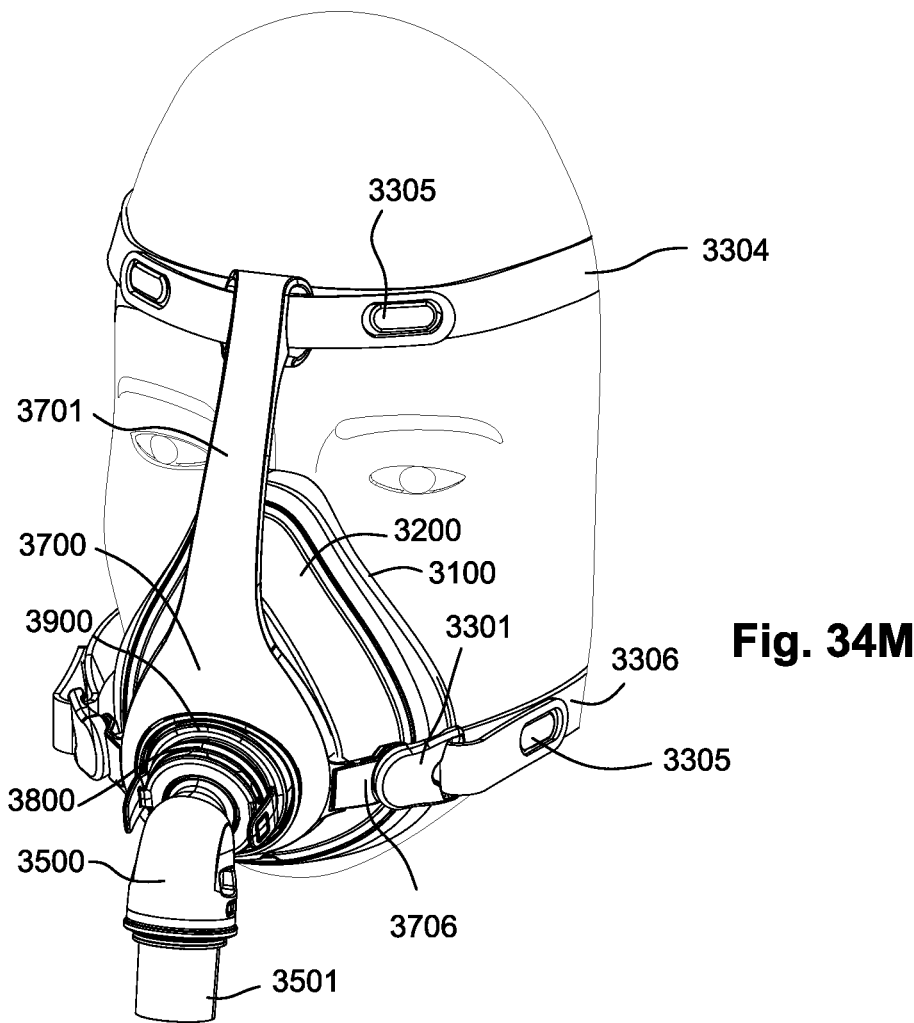

FIG. 34M shows a front perspective view of a patient interface according to an example of the present technology on a patient.

Figure 34N:
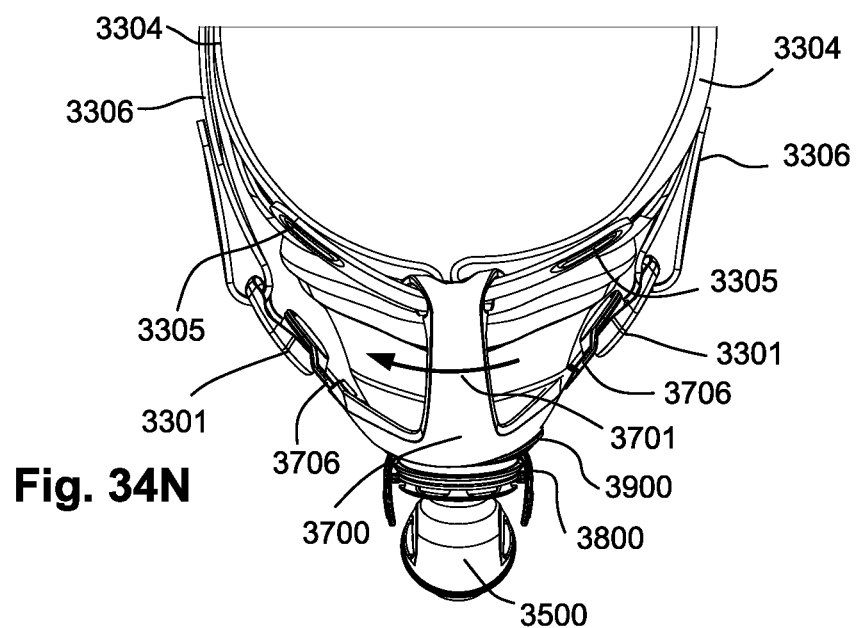

FIG. 34N shows a top view of a patient interface according to an example of the present technology on a patient.

Figure 34O:
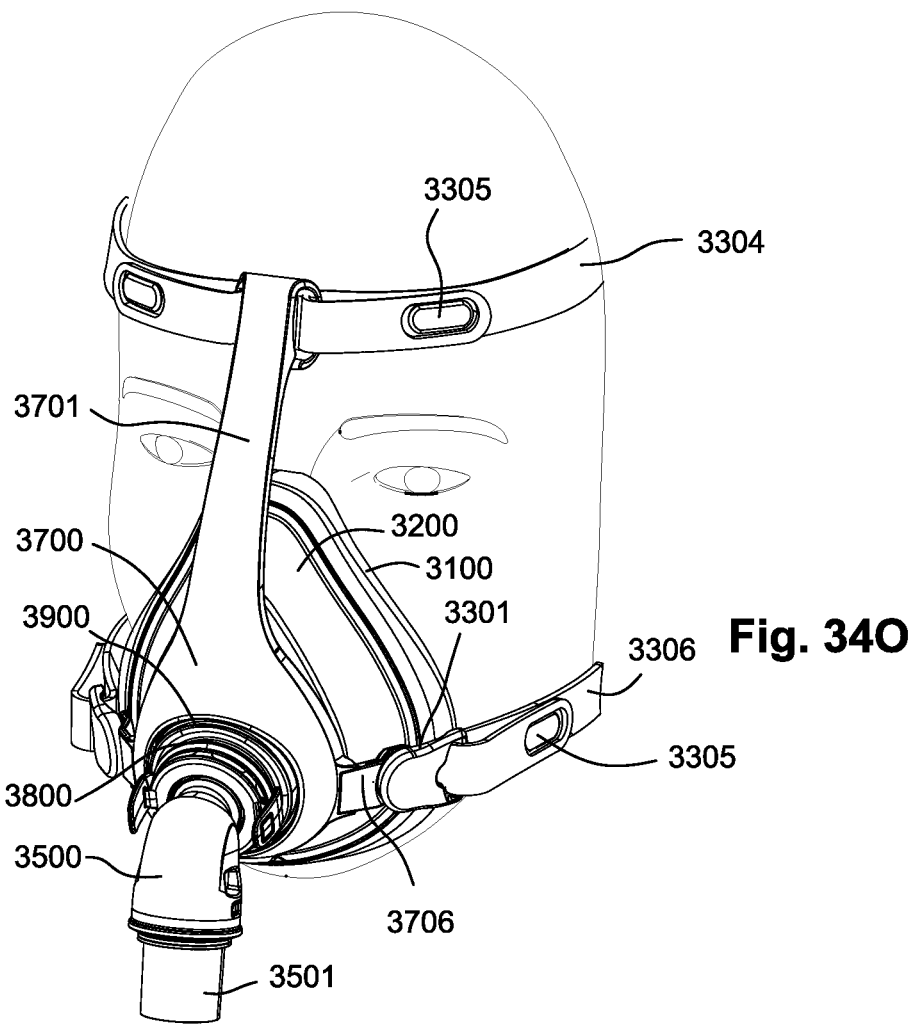

FIG. 34O shows a front perspective view of a patient interface according to an example of the present technology on a patient.

Figure 34P:
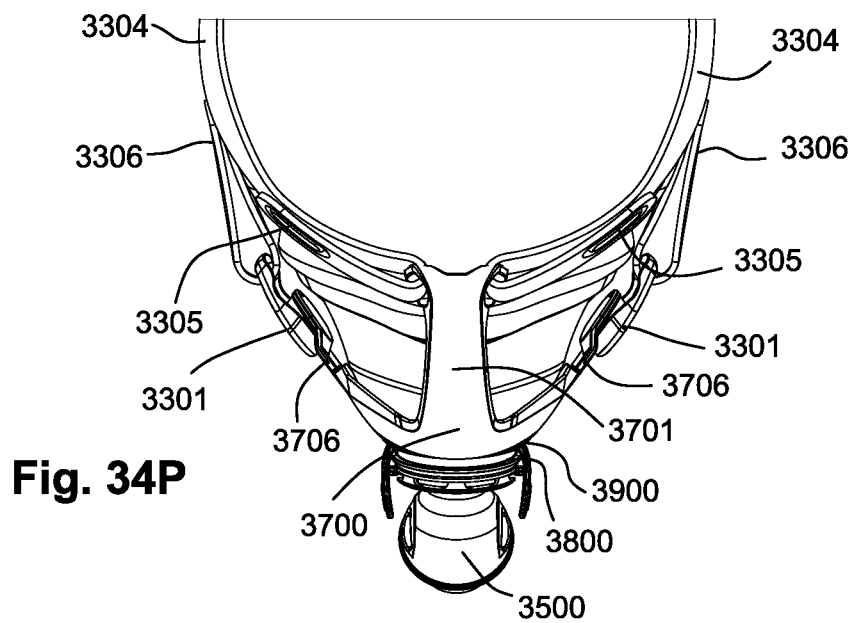

FIG. 34P shows a top view of a patient interface according to an example of the present technology on a patient.

Figure 34Q:
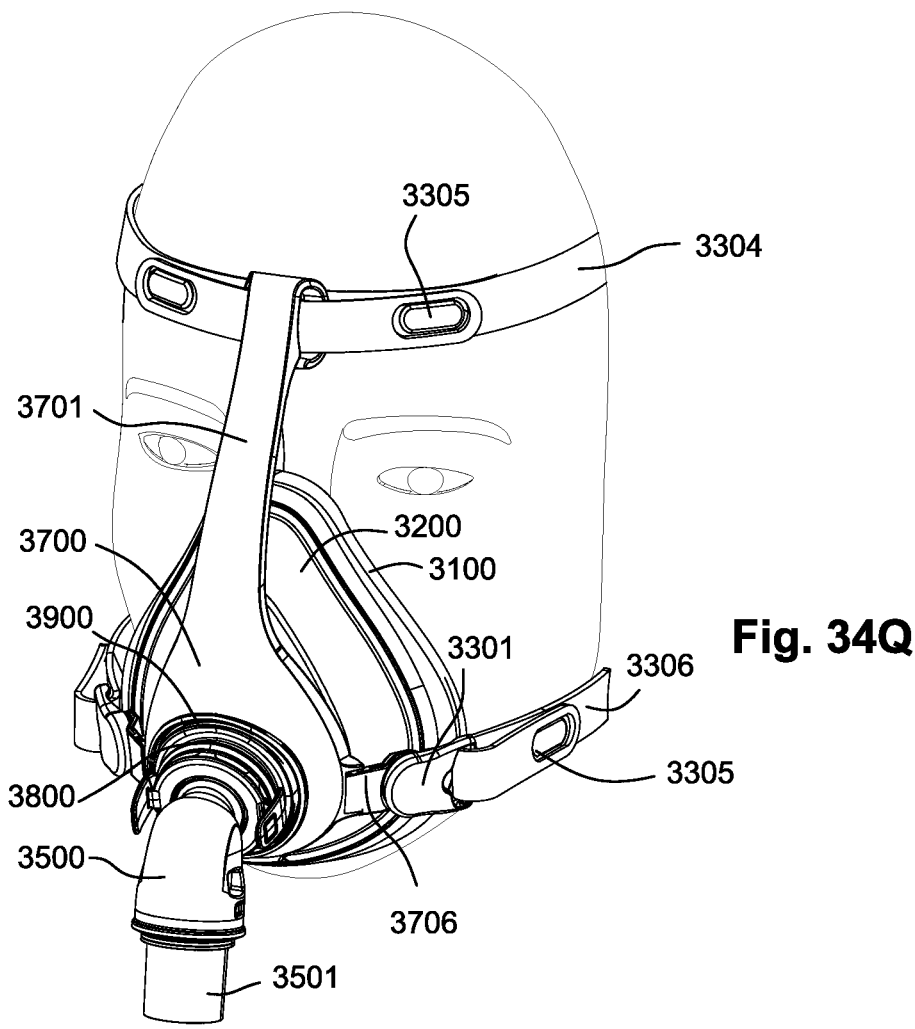

FIG. 34Q shows a front perspective view of a patient interface according to an example of the present technology on a patient.

Figure 34R:
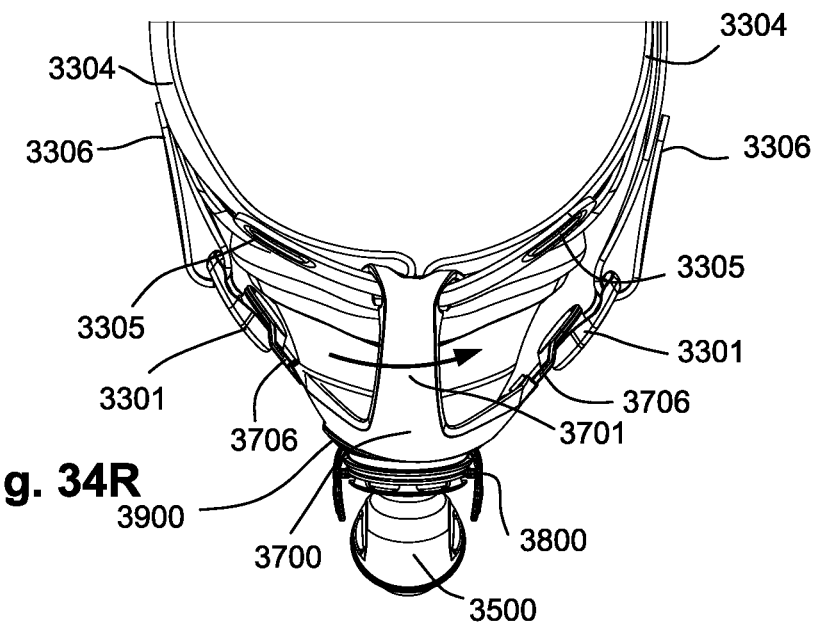

FIG. 34R shows a top view of a patient interface according to an example of the present technology on a patient.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3701. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including, for example, where the patient interface was placed on the face, tension in the positioning and stabilising structure and the shape of a patient's face.

In one form, the target seal-forming region is located on an outside surface of the seal-forming structure 3100.

In certain forms of the present technology, the seal-forming structure 3100 is constructed from a biocompatible material, e.g., silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. The support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g., as a result of elastic tension in the positioning and stabilising structure.

In one form, the seal-forming structure comprises a tension portion. In use, the tension portion is held in tension, e.g., by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper lip region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead region

In one form, the seal-forming structure that forms a seal in use on a forehead region of the patient's face. In such a form, the plenum chamber may cover the eyes in use.

5.3.1.6 Nasal pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Plenum Chamber

The plenum chamber 3200 has a perimeter that is shaped to be complementary to the surface contour of the face of an average person in the region where a seal will form in use. Actual contact with the face is provided by the seal-forming structure 3100. The seal-forming structure 3100 may extend in use about the entire perimeter of the plenum chamber 3200 and be joined to the plenum chamber 3200 at a joint 3205. In some forms, the plenum chamber 3200 and the seal-forming structure 3100 are formed from a single homogeneous piece of material. The joint 3205 may be permanent, e.g., via overmoulding or adhesive, or the joint 3205 may allow the patient to separate and reattach the seal-forming structure 3100 and the plenum chamber 3200, e.g., for cleaning.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g., a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

5.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example, the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example, the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g., a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g., resiliently extensible. For example the strap may be configured in use to be in tension, and to direct a force to draw a seal-forming structure into sealing contact with a portion of a patient's face. In an example, the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of the parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and, e.g., non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example, the system may comprise one form of positioning and stabilizing structure 3300 suitable for a large sized head, but not a small sized head, and another. suitable for a small sized head, but not a large sized head.

5.3.4 Frame

The patient interface 3000 may also include a frame or a shroud 3700 to connect the positioning and stabilising structure 3300 to the other components of the patient interface 3000, e.g., the seal-forming structure 3100, the plenum chamber 3200, and a decoupling structure 3500 (described below). The frame 3700 may include a forehead support 3701 to stabilize engagement of the patient interface 3000 with the patient. The frame 3700 may alternatively take the form of a shroud such that the shroud covers at least a portion or the entirety of the plenum chamber 3200 when viewed from an anterior position.

The frame 3700 may include at least one tie attachment structure 3702 and each tie attachment structure 3702 may receive a corresponding tie of the positioning and stabilising structure 3300. In the example depicted in FIGS. 6A to 6M and 9A to 9E, the frame 3700 has four tie attachment structures 3702 and each tie attachment structure 3702 has a tie attachment structure opening 3703. In this example, the forehead support 3701 includes two of the tie attachment structures 3702 at its superior end and there are two other tie attachment structures 3702, each at a lateral side of the frame 3700. The tie attachment structure openings 3703 allow the patient to adjust each tie to a desired length, e.g., with a hook and loop connection as depicted in FIG. 3A, and leave the ties at the adjusted length without needing to detach or reattach the hook and loop connection each time the patient interface 3000 is put on or taken off. Rather, the loop formed by the ties when the hook and loop connection is secured may be passed through each tie attachment structure opening 3703 to attach each tie to the respective tie attachment structure 3702.

The exemplary frames 3700 depicted in FIGS. 12A to 12M and 15A to 15E and FIGS. 18A to 18M and 20A to 20E also include a forehead support 3701. The forehead support 3701 in each of these examples also includes a pair of tie attachment structures 3702. Instead of also having a tie attachment structure 3702 on each lateral side of the frame 3700, the frame 3700 of these examples has a clip receptacle 3706 on each lateral side. The clip receptacle 3706 is structured to receive a correspondingly shaped clip 3301. The clip receptacles 3706 may be separate components that are joined to the frame 3700, e.g., via overmoulding, a hinge, or a snap fit. The clip 3301 may join the clip receptacle 3706 with a releasable connection, e.g., with magnets or a snap fit. The clip receptacle 3706/clip 3301 arrangement is similar to having tie attachment structures 3702 at each lateral side of the frame 3700 in that the patient does not need to adjust the length of at least one of the ties to put on and take off the patient interface 3000.

The frame 3700 may include a frame opening 3705 through which the plenum chamber 3200 and the decoupling structure 3500 are fluidly connected to allow the flow of pressurized gas to pass from the decoupling structure 3500 and into the plenum chamber 3200.

As will be described below, a spring 3708 or a flexible joint structure 3900 may be provided to allow the frame 3700 to move relative to the other components of the patient interface 3000 to accommodate differing patient facial geometries. Other forehead support technologies that are not self-adjusting may apply a varying load onto the patient's nasal bridge depending on the facial geometry. That is, in such non-adjustable forehead support technologies, the position of the upper headgear attachment points may be fixed in relation to where the frame connects to the superior part of the plenum chamber (e.g., the shell). As such, the position of the seal in the nasal bridge region cannot be adjusted by simply tightening or loosening the upper headgear straps. However, the present technology allows the frame 3700 to move such that the frame 3700 can be moved into a more optimal position by adjusting the positioning and stabilising structure 3300, while the seal-forming structure 3100 and the plenum chamber 3200 are able to maintain an optimal sealing position relative to the patient's airways.

5.3.4.1 Flexible Tie Attachment Structure

FIGS. 22A to 22G depict additional examples of a patient interface 3000 according to the present technology. These examples includes a tie attachment structure 3702 on the forehead support 3701 of the frame 3700. The tie attachment structure 3702 in these examples may be made from a material that is flexible and/or elastically deformable, while the frame 3700 (including the forehead support 3701) may be made from relatively rigid material. For example, the tie attachment structure 3702 in these examples may be made from silicone rubber and the frame 3700 (including the forehead support 3701) may be made from polycarbonate.

The examples of FIGS. 22A to 22G may also include a lower tie attachment structure 3713 with lower tie attachment points 3714. The lower tie attachment structure 3713 and the lower tie attachment points 3714 may receive lower ties 3302 of the positioning and stabilising structure 3300, e.g., the ties 3302 that extend below the patient's ears on each side of the head. The lower tie attachment structure 3713 may be made from an elastically deformable material. The lower tie attachment structure 3713 may be made from a material that is more rigid than the frame 3700 and less rigid than the tie attachment structure 3702. For example, the lower tie attachment structure 3713 may be made from a thermoplastic elastomer such as Hytrel® from DuPont™. The lower tie attachment structure 3713 may also include magnets at the lower tie attachment points 3714 to attach corresponding clips on the ties 3302 of the positioning and stabilising structure 3300. Alternatively, the lower tie attachment structure 3713 may include slots or openings at the lower tie attachment points 3714 to allow the ties 3302 of the positioning and stabilising structure 3300 to be looped through and secured on themselves with hook and loop material. The ends of the ties 3302 may include tabs 3303 that may be made from a hook material or a loop material to correspond with the material of the ties 3302.

The patient interface 3000 depicted in FIGS. 22A to 22D includes a tie attachment structure 3702 that may be made from an elastically deformable material, such as silicone rubber. The tie attachment structure 3702 may include a central tie opening 3712 and tie attachment structure openings 3703 at each lateral side to allow the ties of the positioning and stabilising structure 3300 to first pass through the central tie opening 3712 and then through respective tie attachment structure openings 3703 to be secured on themselves with hook and loop material. The ends of the ties 3302 may include tabs 3303 that may be made from a hook material or a loop material to correspond with the material of the ties 3302. As can be seen in FIGS. 22A and 22B, the tie attachment structure 3702 is in an undeformed state in which it points in a posterior direction relative to the patient interface 3000. However, in FIGS. 22C and 22D, the tie attachment structure 3702 can be seen deformed against the patient's forehead by the tension from the ties 3302. The flexible nature of the tie attachment structure 3702 may balance out potential over-tightening of the ties 3302 and/or account for variations in the anthropometry of the patient's head to allow the forehead support 3701 and the frame 3700 to assume an optimal position, thereby ensuring optimal contact of the seal-forming structure 3100 with the patient's face. Thus, as the ties 3302 are pulled increasingly tighter, the tie attachment structure 3702 and the forehead support 3701 are pulled increasingly closer to the patient's forehead, thereby deforming the tie attachment structure 3702 into a flatter shape. It should be understood that the plenum chamber 3200, which is secured to the seal-forming structure 3100, may be fixedly and/or immovably attached to the frame 3700 at the interface between the connection port 3600 and the frame opening 3705, such that the flexibility of the tie attachment structure 3702 is able to affect the position of the seal-forming structure 3100.

FIGS. 22E to 22G depict variations of the example depicted in FIGS. 22A to 22D. The principles of operation described immediately above are similarly applicable to the variations in FIGS. 22E to 22G. In FIG. 22E, there is no central tie opening 3712. Instead, there are just the two tie attachment structure openings 3703 on the tie attachment structure 3702, each of which is configured to receive a corresponding tie 3302. In FIG. 22F, there is again no central tie opening 3712. Rather, the two tie attachment structure openings 3703 are both located on the forehead support 3701. FIG. 22G, on the other hand, lacks the tie attachment structure openings 3703 and, instead, has just the central tie opening 3712 for receiving the ties 3302.

FIGS. 28A to 28D depict another example of a patient interface 3000 according to the present technology. The example of FIGS. 28A to 28D is similar to the example of FIGS. 22A to 22D. However, in this example the seal-forming structure 3100 and the plenum chamber 3200 are shaped and dimensioned to form seal around the patient's nose only, while the examples of FIGS. 28A to 28D have a seal-forming structure 3100 and a plenum chamber 3200 that are shaped and dimensioned to form seal around the patient's nose and mouth.

5.3.4.2 Hinged Frame with Spring

FIGS. 23A to 23G depicts another example of a patient interface 3000 according to the present technology. In this example, the frame 3700 can be seen attached to the plenum chamber 3200 with hinges 3715 to allow the frame 3700 to move relative to the plenum chamber 3200 and the seal-forming structure 3100. The frame 3700 and the plenum chamber 3200 in this example may be made from a relatively rigid material, such as polycarbonate. The hinges 3715 may be made from an elastically deformable material such silicone rubber.

A spring 3708 may also be positioned between the forehead support 3701 and the plenum chamber 3200. The spring 3708 may be made from an elastically deformable material such silicone rubber. The spring 3708 may limit movement of the frame 3700 relative to the plenum chamber 3200 as the ties 3302 are pulled tight so that the seal-forming structure 3100 can engage the patient's face in an optimal sealing position. In other words, the spring 3708 allows the seal-forming structure 3100 to assume an optimal sealing position by decoupling the plenum chamber 3200 from the frame 3700 such that variations in the patient's anthropometry and/or over-tightening of the ties 3302 does not have any significant effect on the seal with the patient's face. The spring 3708 may limit movement of the frame 3700 relative to the plenum chamber 3200 in a direction substantially parallel to the patient's sagittal plane. The spring 3708 in this example has an open, cylindrical shape.

FIGS. 23E to 23G depict the spring 3708 in different states of deformation and in which the frame 3700 is in different positions relative to the plenum chamber 3200. In FIG. 23E, the spring 3708 is not deformed between the frame 3700 and the plenum chamber 3200. In FIG. 23F, the spring 3708 is substantially deformed by the frame 3700 and the plenum chamber 3200 being moved close together. In FIG. 23G, the spring 3708 is deformed but less so in comparison with FIG. 23F and the frame 3700 and the plenum chamber 3200 are not as close together. As explained above, the amount of deformation in the spring 3708 and the distance between the frame 3700 and the plenum chamber 3200 may be effected by the tension in the ties 3302 and/or the patient's anthropometry.

The hinges 3715 may also provide a spring function to limit movement of the frame 3700 relative to the plenum chamber 3200 in a lateral direction that is orthogonal to the patient's sagittal plane.

The example depicted in FIGS. 23A to 23G may include a central tie opening 3712 at a superior end of the forehead support 3701 to receive the ties 3302.

The example depicted in FIGS. 23A to 23G may also include the lower tie attachment structure 3713 and the lower tie attachment points 3714 similar to the examples of FIGS. 22A to 22G.

5.3.4.3 Receptacle with Adjustable Positioning Structure

FIGS. 24A to 24G depict another exemplary patient interface 3000 according to the present technology. In this example, the frame 3700 may be movably attached to the plenum chamber 3200 with hinges 3715 similar to those of FIGS. 23A to 23G. The frame 3700 and the plenum chamber 3200 may be made from a relatively rigid material, such as polycarbonate. The frame 3700 may include a central tie opening 3712 at the superior end of the forehead support 3701 to receive ties 3302 of the positioning and stabilising structure 3300.

The frame 3700 may also include a receptacle 3717 with an adjustable positioning structure 3716 to adjust the distance between the forehead support 3701 and the plenum chamber 3200. The adjustable positioning structure 3716 may be rotatably hinged to the frame 3700 within the receptacle 3717. FIGS. 24C to 24E show the adjustable positioning structure 3716 in three different positions within the receptacle 3717. However, it should be understood that the adjustable positioning structure 3716 may be adjustable to an infinite number of positions within a given range. Alternatively, the adjustable positioning structure 3716 may be adjustable to a number of discrete positions within a given range and the number of discrete positions may be at least 2. The adjustable positioning structure 3716 may also be made from a relatively rigid material, such as polycarbonate.

FIG. 24C shows the adjustable positioning structure 3716 in a position where the forehead support 3701 is furthest from the plenum chamber 3200. FIG. 24E shows the adjustable positioning structure 3716 in a position where the forehead support 3701 is nearest to the plenum chamber 3200. FIG. 24D shows the adjustable positioning structure 3716 in a position where the forehead support 3701 is in an intermediate distance from the plenum chamber 3200. The adjustable positioning structure 3716 may allow the frame's 3700 position relative to the plenum chamber 3200 to be adjusted to account for a relatively wide range of patient anthropometries. It should be understood that the hinges 3715 may allow the frame 3700 to be freely movable relative to the plenum chamber 3200, but when the patient interface 3000 is donned by the patient the tension in the ties 3302 may pull the frame 3700 against the plenum chamber 3200 such that the distance therebetween is controlled by the adjustable positioning structure 3716.

FIGS. 24F and 24G show another variation of this example that includes a spring 3708, such as the spring 3708 described with respect to FIGS. 23A to 23G above. The spring 3708 may provide additional control of the movement of the frame 3700 relative to the plenum chamber 3200. FIG. 24F shows the frame 3700 in a first position relative to the plenum chamber 3200 and the adjustable positioning structure 3716 prevents the frame 3700 from compressing the spring 3708 against the plenum chamber 3200. FIG. 24G shows the adjustable positioning structure 3716 in a different position such that the frame 3700 is in a position closer to the plenum chamber 3200 and the spring 3708 being compressed therebetween.

The example depicted in FIGS. 24A to 24G may also include the lower tie attachment structure 3713 and the lower tie attachment points 3714 similar to the examples of FIGS. 22A to 22G.

5.3.4.4 Hinged Forehead Support

FIGS. 25A to 25C show another example of a patient interface 3000 according to the present technology. In this example, the forehead support 3701 is a separate structure with respect to the frame 3700. The frame 3700 may include a frame extension 3720 extending from a superior side of the frame 3700. The frame extension 3720 may be joined to the forehead support 3701 with hinges 3721 on each side of the frame extension 3720. Adjustment buttons 3718 may also be provided on each side of the forehead support 3701 to allow the forehead support 3701 to be adjusted about the hinges 3721 relative to the frame 3700. The frame 3700, the forehead support 3701, and the adjustment buttons 3718 may all be separate structures. The frame 3700, the forehead support 3701, and the adjustment buttons 3718 may also be made from a relatively rigid material such as polycarbonate. The forehead support 3701 may also include a central tie opening 3712 to receive ties 3302 of the positioning and stabilising structure 3300.

FIG. 25C shows that the forehead support 3701 may be adjusted between at least two positions relative to the frame 3700 to account for different patient anthropometries. The adjustment buttons 3718 allow the patient to adjust the forehead support 3701 between these positions.

The frame 3700 may also be fixed to the plenum chamber 3200 as the forehead support 3701 itself is movable.

The example depicted in FIGS. 25A to 25G may also include the lower tie attachment structure 3713 and the lower tie attachment points 3714 similar to the examples of FIGS. 22A to 22G.

5.3.4.5 Flexible Forehead Support

FIGS. 26A to 26C depict another patient interface 3000 according to an example of the present technology. In this example, the forehead support 3701 is made from an elastically deformable material such as silicone rubber. The forehead support 3701 may be joined to the frame 3700 at a superior end of the frame 3700. The frame 3700 may be made from a relatively rigid material such as polycarbonate. The frame 3700 and the forehead support 3701 may be separate structures made from distinct materials. The frame 3700 and the forehead support 3701 may be joined together with a permanent connection such as mechanical interlock or a chemical bond, e.g., via overmoulding.

The forehead support 3701 may also include a central tie opening 3712 to receive the ties 3302 of the positioning and stabilising structure 3300. The forehead support 3701 may also include an eyelet 3719 through which the central tie opening 3712 may be defined. The eyelet 3719 may be formed from a relatively rigid material such as polycarbonate.

The frame 3700 may also be fixed to the plenum chamber 3200 as the forehead support 3701 itself is movable.

FIG. 26C shows the forehead support 3701 in at least two different positions. The forehead support 3701 may be flexible relative to the frame 3700 due to being made from an elastically deformable material. The forehead support 3701 may be adjustable to an infinite number of positions within a given range. The forehead support 3701 may be flexible as a whole relative to the frame 3700 at the joint between the forehead support and the frame 3700. The forehead support 3701 may also be flexible along its length. The flexibility of the forehead support 3701 relative to the frame 3700 may allow the forehead support 3701 to accommodate a wide range of patient anthropometries.

The example depicted in FIGS. 26A to 26G may also include the lower tie attachment structure 3713 and the lower tie attachment points 3714 similar to the examples of FIGS. 22A to 22G.

5.3.4.6 Fixed Forehead Support

FIGS. 27A to 27D depict another example of patient interface 3000 according to an example of the present technology. In this example, the frame 3700 and the forehead support 3701 comprise a single piece of homogeneous material that may be relatively rigid, such as polycarbonate. Thus, the forehead support 3701 may not be movable relative to the plenum chamber 3200 other than by virtue of elastic deformation of the frame 3700 and the forehead support 3701 when the ties 3302 are pulled taught by the patient.

The example depicted in FIGS. 27A to 27D may also include the lower tie attachment structure 3713 and the lower tie attachment points 3714 similar to the examples of FIGS. 22A to 22G.

5.3.5 Connector Ring

A connector ring 3800 may be joined to the frame 3700 to allow the frame 3700 to be freely and/or resiliently movable relative to the other components of the patient interface 3000, such as the seal-forming structure 3100, the plenum chamber 3200, and the decoupling structure 3500. Connecting the frame 3700, which connects to the positioning and stabilising structure 3300, to the other components of the patient interface 3000 in a manner that allows the frame 3700 to move relative to the other components of the patient interface 3000, e.g., via the connector ring 3800, may allow for a more flexible fit on the patient by accounting for the possibility that the positioning and stabilising structure 3300 may not be adjusted to an optimal length and tension.

Examples of the connector ring 3800 are depicted in FIGS. 7A to 7F, FIGS. 13A to 13E, and FIGS. 19A to 19E.

The decoupling structure 3500 may be releasably connected to the connector ring 3800. The decoupling structure 3500 may include a button 3502 that is depressible, e.g., by the patient or a clinician, to release the decoupling structure 3500 from the connector ring 3800. The connector ring 3800 may have an attachment lip 3804 and the button 3502 may have a retainer 3508 to releasably connect to the attachment lip 3804. The button 3502 may engage the attachment lip 3804 with a snap fit whereby the attachment lip 3804 contacts the retainer 3508 to deflect the button 3502 during engagement and then the button 3502 may snap back into position once engaged.

The connector ring 3800 and the decoupling structure 3500 may also be rotatable relative to one another when connected to minimize the effects of tube drag due to the air circuit 4170 that may be joined to the decoupling structure 3500. The attachment lip 3804 may be shaped uniformly around at least a portion of the connector ring 3800 such that the decoupling structure 3500 is rotatable relative to the connector ring 3800 through the uniformly shaped portion while the retainer 3508 is connected to the attachment lip 3804. The attachment lip 3804 may also be shaped uniformly around the entire perimeter of the connector ring 3800 such that the decoupling structure 3500 is rotatable 360° relative to the connector ring 3800 while the retainer 3508 is connected to the attachment lip 3804.

The plenum chamber 3200 may also releasably connect to the connector ring 3800. The connector ring 3800 may have an attachment structure 3802 and the plenum chamber 3200 may have a neck 3202 with an outer rim 3212 and the attachment structure 3802 may releasably connect to the outer rim 3212 with a snap fit or a friction fit. The neck 3202 may surround a plenum chamber inlet port 3211 through the flow of pressurized gas enters the plenum chamber 3200. In the example shown in FIGS. 7A to 7E, the connector ring 3800 has three attachment structures 3802, but other examples may include greater or fewer than three attachment structures 3802. The connector ring 3800 may also have a notch 3805 and the plenum chamber 3200 may have a wing 3203 that extends from the neck 3202 such that the wing 3203 engages the notch 3805 to prevent rotation of the plenum chamber 3200 relative to the connector ring 3800. As can be seen in the example shown in FIGS. 7A to 7E and 10A to 10E, there are two corresponding pairs of wings 3203 and notches 3805. Other examples may include greater or fewer corresponding pairs of wings 3203 and notches 3805. The neck 3202 of the plenum chamber 3200 may also have a projection 3204 on each side that corresponds to one of the attachment structures 3802 to facilitate the releasable connection.

The connector ring may also include a spacer 3801 to contact the plenum chamber 3200 to limit movement of the connector ring 3800 toward the plenum chamber 3200. Since the connector ring 3800 may be connected to the frame 3700 such that the frame 3700 is movable relative to at least the connector ring 3800, as well as the seal-forming structure 3100, the plenum chamber 3200, and the decoupling structure 3500 in examples, the spacer 3801 may prevent the frame 3700 and the forehead support 3701 from being pivoted beyond a desirable point in the direction of the patient's head, i.e., in a posterior direction. In other words, an undesirable magnitude of movement of the frame 3700 toward the plenum chamber 3200 may be limited by the spacer 3801 on the connector ring 3800.

In the example depicted in FIGS. 18A to 21E, the frame 3700 and the connector ring 3800 are rotatable relative to one another. In this example, the frame 3700 has a pivot post 3710 and the connector ring 3800 has a pivot hole 3810. The pivot hole 3810 may receive the pivot post 3710 such that the connector ring 3800 is connected to the frame 3700 and pivotable about the pivot post 3710. The connector ring 3800 may also include a pivot hole support 3809 and the pivot hole 3810 may extend through the pivot hole support 3809. As can be seen, this example includes two pivot holes 3810 each supported by a pivot hole support 3809 and each of the pivot holes 3810 corresponds to a pivot post 3710 of the frame 3700. This arrangement may allow the frame 3700 to pivot or move freely relative to at least the connector ring 3800 in a direction parallel to the patient's sagittal plane. Accordingly, the plenum chamber 3200 and the decoupling structure 3500 may also be connected to the connector ring 3800 such that the frame 3700 is pivotable relative to the plenum chamber 3200, the decoupling structure 3500, and the connector ring 3800. The frame opening 3705 may also be shaped and dimensioned such that the connector ring 3800 is able to rotate therein.

FIGS. 16B and 21B also depict a protrusion 3206 extending from the plenum chamber 3200 below the neck 3202. The protrusion 3206 may engage the connector ring 3800 in these examples to prevent relative rotation between the connector ring 3800 and the plenum chamber 3200.

The connector ring 3800 may be made from a relatively rigid material such as polycarbonate. The connector ring 3800 may be made from the same material as the frame 3700 and/or the plenum chamber 3200. The connector ring 3800 and the flexible joint structure may be joined by overmoulding and the joint may be permanent.

Alternatively, the connector ring 3800 may be made from a relatively flexible material, such as silicone or another resiliently deformable material. The connector ring 3800 and the flexible joint structure 3900 may also be formed from one homogenous piece of material, such as those described in the immediately preceding sentence. Alternatively, while the connector ring 3800 and the flexible joint structure 3900 may each be formed from a relatively flexible material, such as silicone or another resiliently deformable material, they may be separate components that are joined together when the patient interface 3000 is assembled.

FIGS. 30A to 30D show another exemplary frame 3700 assembly according to the present technology. In this example, the frame 3700 includes a connector ring 3800 joined to the frame 3700 with a flexible joint structure 3900, e.g., as described above. The connector ring 3800 in this example also includes blocking structures 3811 around its inner periphery. These blocking structures 3811 may have an open construction to allow gas to pass therethrough while preventing the patient from attempting to connect an air circuit 4170 or a decoupling structure 3500 that does not fit the connector ring 3800. By preventing the connection with improperly sized components, the patient is not able to use the system and suboptimal therapy is prevented.

The blocking structures 3811 may also be shaped as solid structures so long as they are not so large as to substantially disrupt the airflow through the connector ring 3800. Also, there may be one or more blocking structures 3811 distributed around the inner periphery of the connector ring 3800 or the blocking structure 3811 may be a single continuous piece extending from the entire inner periphery of the connector ring 3800. The blocking structures 3811 and the connector ring 3800 may be formed from a single homogeneous piece of material.

5.3.6 Spring

In the example depicted in FIGS. 18A to 21E, the frame 3700 may also include a spring 3708 joined to the frame 3700 to limit movement of the frame 3700 toward the plenum chamber 3200. Otherwise, the frame 3700 may be freely movable relative to the connector ring 3800 such that the frame 3700 could come into undesired contact with the plenum chamber 3200. Since the frame 3700 and the plenum chamber 3200 may be made from relatively rigid materials, this contact may be undesirable, for example, due to wear issues, noise, and/or a poor fit on the patient. The spring 3708 may be made from a resiliently deformable material, such as silicone, to provide a cushioning function and/or a movement limiting function for the frame 3700 relative to the plenum chamber 3200.

The frame 3700 may include a spring opening 3709 and the spring 3708 may include a spring attachment structure 3707. The spring 3708 may be joined to the frame 3700 at the spring opening 3709 by the spring attachment structure 3707. The spring 3708 may be joined to the frame 3700 by overmoulding. The spring 3708 may be an arcuately shaped beam fixed at both ends to the spring attachment structure 3707 and that is configured to deform toward the frame 3700 due to contact with the plenum chamber 3200 in use.

The spring 3708 may be effective in limiting movement of the frame 3700 in the exemplary patient interface 3000 that uses the connector ring 3800 shown in FIGS. 19A to 19E, because in use the frame 3700 and the connector ring 3800 will only be rotatable relative to one another in a direction parallel to the patient's sagittal plane. Thus, this relative movement may allow for a more comfortable fit and a better seal that accounts for differing patient head shapes and/or suboptimal tension in the positioning and stabilising structure 3300, while the spring 3708 prevents undesired contact between the frame 3700 and the plenum chamber 3200 that may be caused, for example, by overtightening the positioning and stabilising structure 3300. Additionally, since the relative movement between the frame 3700 and the connector ring 3800 is through one plane in this example, the spring 3708 alone may be sufficient to prevent the undesired contact between the frame 3700, specifically the forehead support 3701, and the plenum chamber 3200.

The spring 3708 may have a generally constant force-displacement curve when the frame 3700 is moving towards the plenum chamber 3200, i.e., when the spring 3708 is being compressed. In other words, the spring 3708 may a constant spring and may be designed to always be under at least some degree of compression in use. Additionally, adjustment of the patient interface 3000 by tightening the ties of the positioning and stabilising structure 3300 may cause the frame 3700 to move closer to the patient's face. Accordingly, the spring 3708 may allow the connector ring 3800 to be decoupled from this movement and allow the plenum chamber 3200 to remain in a position relative to the patient that allows a relatively constant force on the face, e.g., around the patient's nasal bridge.

FIGS. 29A and 29B show further examples of the frame 3700 and the forehead support 3701 in different positions relative to the plenum chamber 3200. In FIG. 29A, the forehead support 3701 is further away from the plenum chamber 3200 such that the spring 3708 is deformed relatively little or not at all. In FIG. 29B, the forehead support 3701 is closer to the plenum chamber 3200 such that the spring 3708 is deformed and compressed. The position of the forehead support 3701 relative to the plenum chamber 3200 and, in turn the deformation of the spring 3708, is effected in these examples, at least partly, by the different anthropometry of the patient. In FIG. 29B the patient's chin protrudes further forward than in FIG. 29A such that the plenum chamber 3200 is in a different position due to the seal-forming structure's 3100 contact with the patient's face. Thus, when ties 3302 of the positioning and stabilising structure 3300 (not shown) are pulled taught, the frame 3700 takes a different position relative to the plenum chamber 3200 due to the different patient anthropometries. Accordingly, the spring 3708 is deformed differently in each scenario.

5.3.7 Flexible Joint Structure

In the examples depicted in FIGS. 6A to 6M and 12A to 12M, the connector ring 3800 may be joined to the frame 3700 with a flexible joint structure 3900. The flexible joint structure 3900 may allow the frame 3700 and the connector ring 3800 to be resiliently movable relative to one another. As can be seen in these examples, the flexible joint structure 3900 surrounds the connector ring 3800 and the frame 3700 surround the flexible joint structure 3900. Thus, the frame 3700 may be resiliently movable relative to the connector ring 3800 in any direction around the connector ring 3800. In other words, the flexible joint structure 3900 may allow the frame 3700 to be resiliently movable relative to the connector ring 3800 in any direction having at least one of a component parallel to the patient's sagittal plane, a component parallel to the patient's coronal plane, a component parallel to the patient's Frankfort horizontal plane. Examples of the flexible joint structure 3900 are shown in FIGS. 8A to 8E and FIGS. 14A to 14E.

In the examples depicted in FIGS. 6A to 6M and 12A to 12M, the frame 3700 may be made from a first material, the connector ring 3800 may be made from a second material, and the flexible joint structure 3900 may be made from a third material. The first material and the second material may be more rigid than the third material and the third material may be a resiliently deformable material. Each of the first material, the second material, and the third material may have at least one different property. For example, the frame 3700 and the connector ring 3800 may be made from polycarbonate, while the flexible joint structure may be made from silicone.

The flexible joint structure 3900 may be attached to the frame 3700 within the frame opening 3705. The flexible joint structure 3900 may have a frame joining portion 3901 that is joined to the frame 3700 around at least a portion of or the entirety of the perimeter of the frame opening 3705. For example, in FIGS. 6H, 6J, 6L, 12H, 12J, and 12L the frame 3700 has a frame opening extension 3704 around the frame opening 3705 and the frame joining portion 3901 of the flexible joint structure 3900 is joined to the frame opening extension 3704. The frame joining portion 3901 may have a frame joining channel 3905 that receives the frame opening extension 3704. The flexible joint structure 3900 may be joined to the frame 3700 by at least one of overmoulding, an adhesive, and a friction fit. The frame 3700 may have one or more frame opening projections 3711 around the frame opening 3705 that provide structures to support the connection with the flexible joint structure 3900. The flexible joint structure 3900 may also have outer peripheral recesses 3907 that correspond to the frame opening projections 3711.

The flexible joint structure 3900 may also include a connector ring joining portion 3902 that is joined to the connector ring 3800 such that the connector ring 3800 is suspended within the frame opening 3705 by the flexible joint structure 3900. The connector ring joining portion 3902 may include a connector ring joining channel 3906 that receives a peripheral extension lip 3807 of the connector ring 3800. The peripheral extension lip 3807 may extend from a peripheral extension 3803 that extends around the outer periphery of the connector ring 3800. The flexible joint structure 3900 may be joined to the connector ring 3800 by at least one of overmoulding, an adhesive, and a friction fit. The connector ring 3800 may have one or more protrusions 3806 around its outer perimeter that provide structures to support the connection with the flexible joint structure 3900. The flexible joint structure 3900 may also have inner peripheral recesses 3904 that correspond to the protrusions 3806.

The flexible joint structure 3900 may also include a web 3903 that connects the frame joining portion 3901 and the connector ring joining portion 3902. The web 3903 may be relatively thinner than the frame joining portion 3901 and the connector ring joining portion 3902 such that the frame 3700 is resiliently movable relative to the connector ring 3800. The flexible joint structure 3900 may also include more than one web 3903 that connects the frame joining portion 3901 and the connector ring joining portion 3902. In this example, there may be a space between each web 3903. The web 3903 may alternatively be approximately the same thickness as the frame joining portion 3901 and the connector ring joining portion 3902.

The flexible joint structure 3900 may be comprised of a single piece of homogeneous material. Alternatively, the flexible joint structure 3900 may be made of multiple separate pieces of material.

In an alternative example, the flexible joint structure 3900 may be joined to the plenum chamber 3200, e.g., around the plenum chamber inlet port 3211. Accordingly, the frame 3700 may be attached to the plenum chamber 3200 via the flexible joint structure 3900. In such an example, the connector ring 3800 may be included to facilitate connection of the flexible joint structure 3900 to the plenum chamber 3200 or the connector ring 3800 may be excluded such that the flexible joint structure 3900 is joined directly to the plenum chamber 3200 or structures thereof.

In another alternative example, the frame 3700, the connector ring 3800, and the plenum chamber 3200 may all be permanently joined to one another by an overmoulded connection via the flexible joint structure 3900. In a further alternative, the connector ring 3800 may be excluded from this arrangement.

FIG. 31A shows a cross-sectional view through the assembly of the frame 3700, the decoupling structure 3500, the flexible joint structure 3900, the connector ring 3800, and the plenum chamber 3200 similar to FIG. 12J. FIG. 31B is a detailed view of FIG. 31A. These components are similar to those depicted in FIG. 12J, however, the flexible joint structure 3900 depicted in FIGS. 31A and 31B is shown with an annular lip seal 3908 that extends around the inner periphery of the flexible joint structure 3900 to engage with the outer periphery of the neck 3202 of the plenum chamber 3200 to form a seal therebetween and prevent gas from leaking from the plenum chamber 3200. The annular lip seal 3908 may be elastically deformable and may be deformed by contact with the neck 3202 so that the tendency of the annular lip seal 3908 to return to the undeformed position keeps the annular lip seal 3908 in sealing engagement with the neck 3202 of the plenum chamber 3200.

FIGS. 32A to 32C depict an alternative sealing arrangement that may also be applied to the example depicted in FIG. 12J, for example. In the example of FIGS. 32A to 32C the flexible joint structure 3900 does not have an annular lip seal 3908. Rather, in this example the junction between the decoupling structure 3500, the connector ring 3800, and the plenum chamber 3200 may form tortuous paths that limit the amount of pressurized gas that can be leaked through the interfaces between these components.

FIGS. 32B and 32C show detailed views of the cross-section shown in FIG. 32A. The interfaces forming the tortuous paths that prevent or limit leak can be seen in FIG. 32B. For example, the decoupling structure 3500 has an outer annular connector surface 3513 that may face a connector ring inner surface 3812 of the connector ring 3800 to form a dynamic diametric seal 6000. The decoupling structure 3500 may also have an annular connector end surface 3515 that may face an annular stop anterior surface 3813 of the connector ring's 3800 annular stop 3808 to form a dynamic face seal 6001. The dynamic diametric seal 6000 and the dynamic face seal 6001 may be considered dynamic because the decoupling structure 3500 may be freely rotatable relative to the connector ring 3800. Thus, these interfaces may be dimensioned such that the tolerances therebetween are small enough to limit the flow of gas therethrough while allowing the decoupling structure 3500 to rotate relative to the connector ring 3800 with minimal resistance.

The connector ring 3800 may also have a peripheral extension posterior surface 3815 on the peripheral extension 3803 that may form a static face seal 6002 with an anterior neck surface 3214 of the neck 3202 of the plenum chamber 3200. Also, the connector ring 3800 may also include a peripheral extension inner surface 3816 on the peripheral extension 3803 that may form a static diametric seal 6003 with an outer neck surface 3215 of the neck 3202 of the plenum chamber 3200. The static diametric seal 6003 and the static face seal 6002 may be considered static because the plenum chamber 3200 may not move relative to the connector ring 3800. Thus, these interfaces may be dimensioned such that these components engage directly—since there is no relative movement between these components it may not be necessary to provide a tolerance therebetween to reduce friction and allow movement.

The connector ring 3800 may also include a connector ring outer surface 3814 that may face a neck inner lip 3213 of the neck 3202 of the plenum chamber 3200. It may not be necessary to tolerance the gap between these surfaces to provide a seal because the static diametric seal 6003 and the static face seal 6002 may provide a sufficient sealing effect on their own.

5.3.8 Relative Movement of Frame

FIGS. 33A-33R and 34A-34R show examples of the present technology in which the frame 3700 is moved relative to the seal-forming structure 3100 and the plenum chamber 3200, while the seal-forming structure 3100 is maintained in a generally stable position on the patient's face so that disruption of the seal is minimized. As explained above, the flexible join structure 3900 permits the frame 3700 to move relative to the seal-forming structure 3100 and the plenum chamber 3200 so that the transmission of forces due to strap tension, movement of the patient's head, and/or other displacing effects (e.g., the patient's head rolling on a pillow such that the frame 3700 is pushed on one side by the pillow) to the seal-forming structure 3100 and the plenum chamber 3200 is minimized, thereby reducing seal disruption. FIGS. 33A-33R show relative motion of the frame 3700 of the patient interface 3000 of FIGS. 6A-6M. FIGS. 34A-34R show relative motion of the frame 3700 of the patient interface 3000 of FIGS. 12A-12M.

FIGS. 33A-33F and 34A-34F show rotational movement of the frame 3700 relative to the seal-forming structure 3100 and the plenum chamber 3200. The frame 3700 is shown in these views to be rotated about an axis of rotation that is coextensive with the central axis of the frame opening 3705. FIGS. 33A, 33B, 34A, and 34B show the frame 3700 rotated in a counter-clockwise direction about the axis of rotation, which may be understood to show the forehead support 3701 being moved laterally to the patient's right. The arrow in FIGS. 33B and 34B shows the direction of motion. FIGS. 33C, 33D, 34C, and 34D show the frame 3700 in a neutral position. FIGS. 33E, 33F, 34E, and 34F show the frame 3700 rotated in a clockwise direction about the axis of rotation, which may also be understood to show the forehead support 3701 being moved laterally to the patient's left. The arrow in FIGS. 33F and 34F shows the direction of motion.

When the frame 3700 and the forehead support 3701 are moved as shown in FIGS. 33A, 33B, 33E, 33F, 34A, 34B, 34E, and 34F, the flexible joint structure 3900 may be understood to experience torsion. Since the connector ring joining portion 3902 is fixed to the connector ring 3800, which is in turn connected to the seal-forming structure 3100 and the plenum chamber 3200 that are intended to be stationary relative to the patient's head, and the frame joining portion 3901 is fixed to the frame 3700 around the frame opening 3705, movement of the frame 3700 relative to the connector ring, 3800, the plenum chamber 3200, and the seal-forming structure 3100 will cause twisting or torsion of the flexible joint structure 3900. In the neutral position of FIGS. 33C, 33D, 34C, and 34D, the flexible joint structure 3900 does not experience torsion.

FIGS. 33G-33L and 34G-34L also show rotational movement of the frame 3700 relative to the seal-forming structure 3100 and the plenum chamber 3200. The frame 3700 is shown in these views to be rotated about an axis or rotation that is normal to the central axis of the frame opening 3705 and that extends in the lateral directions relative to the patient. FIGS. 33G, 33H, 34G, and 34H show the frame 3700 rotated in a counter-clockwise direction about the axis of rotation, which may also be understood to show the forehead support 3701 being moved in an anterior direction away from the patient's forehead. The arrow in FIGS. 33H and 34H shows the direction of motion. FIGS. 33I, 33J, 34I, and 34J show the frame 3700 in a neutral position. FIGS. 33K, 33L, 34K, and 34L show the frame 3700 rotated in a clockwise direction about the axis of rotation, which may also be understood to show the forehead support 3701 being moved in a posterior direction away from the patient's forehead. The arrow in FIGS. 33L and 34L shows the direction of motion.

When the frame 3700 and the forehead support 3701 are moved as shown in FIGS. 33G, 33H, 33K, 33L, 34G, 34H, 34K, and 34L, a superior portion and an inferior portion of the flexible joint structure 3900 may be deformed. Since the connector ring joining portion 3902 is fixed to the connector ring 3800, which is in turn connected to the seal-forming structure 3100 and the plenum chamber 3200 that are intended to be stationary relative to the patient's head, and the frame joining portion 3901 is fixed to the frame 3700 around the frame opening 3705, movement of the frame 3700 relative to the connector ring, 3800, the plenum chamber 3200, and the seal-forming structure 3100 may cause a superior portion of the flexible joint structure 3900 to be deformed by stretching away from the patient and an inferior portion of the flexible joint structure 3900 to be deformed by stretching towards the patient, or vice versa. In the neutral position of FIGS. 33I, 33J, 34I, and 34J, the flexible joint structure 3900 does not experience deformation.

FIGS. 33M-33R and 34M-34R also show rotational movement of the frame 3700 relative to the seal-forming structure 3100 and the plenum chamber 3200. The frame 3700 is shown in these views to be rotated about an axis or rotation that is normal to the central axis of the frame opening 3705 and that extends in the superior-inferior direction relative to the patient. FIGS. 33M, 33N, 34M, and 34N show the frame 3700 rotated in a counter-clockwise direction about the axis of rotation, which may also be understood to show a left side portion of the forehead support 3701 being moved towards the patient's head and a right side portion of the forehead support 3701 being moved away from the patient's head. The arrow in FIGS. 33N and 34N shows the direction of motion. FIGS. 33O, 33P, 34O, and 34P show the frame 3700 in a neutral position. FIGS. 33Q, 33R, 34Q, and 34R show the frame 3700 rotated in a clockwise direction about the axis of rotation, which may also be understood to show a right side portion of the forehead support 3701 being moved towards the patient's head and a left side portion of the forehead support 3701 being moved away from the patient's head. The arrow in FIGS. 33R and 34R shows the direction of motion.

When the frame 3700 and the forehead support 3701 are moved as shown in FIGS. 33M, 33N, 33Q, 33R, 34M, 34N, 34Q, and 34R, right and left lateral portions of the flexible joint structure 3900 may be deformed. Since the connector ring joining portion 3902 is fixed to the connector ring 3800, which is in turn connected to the seal-forming structure 3100 and the plenum chamber 3200 that are intended to be stationary relative to the patient's head, and the frame joining portion 3901 is fixed to the frame 3700 around the frame opening 3705, movement of the frame 3700 relative to the connector ring, 3800, the plenum chamber 3200, and the seal-forming structure 3100 may cause a left portion of the flexible joint structure 3900 to be deformed by stretching away from the patient and a right portion of the flexible joint structure 3900 to be deformed by stretching towards the patient, or vice versa. In the neutral position of FIGS. 33I, 33J, 34I, and 34J, the flexible joint structure 3900 does not experience deformation.

As depicted in each of the examples described above, the flexible joint structure 3900 may be deformed by movement of the frame 3700 relative to the connector ring, 3800, the plenum chamber 3200, and the seal-forming structure 3100. Since the flexible joint structure 3900 may be constructed of an elastic material, the flexible joint structure 3900 will also urge the frame 3700 to return to its neutral position when the displacing force is removing. The flexible joint structure 3900 may cause the frame 3700 to spring back into its neutral position due to the elastic characteristics of the flexible joint structure 3900.

Furthermore, the flexible joint structure 3900 may provide a relatively flat force-displacement curve to ensure that the seal-forming structure 3100 is maintained in sealing engagement with the patient. Thus, as the force applied against the flexible joint structure 3900 increases, e.g., by relative movement of the frame 3700, the deformation of the flexible joint structure 3900 increases proportionately. Likewise, as the force applied against the flexible joint structure 3900 decreases, e.g., by relative movement of the frame 3700, the deformation of the flexible joint structure 3900 decreases proportionately.

The flexible joint structure 3900 is also capable of decoupling or absorbing forces caused by excessive tension in the upper straps 3304 and the lower straps 3306 to compensate for over-tightening the straps by deformation of the flexible joint structure 3900. When the flexible joint structure 3900 absorbs force due to over-tightened straps, the seal-forming structure 3100 is less likely to deform because the excessive force is used to deform the flexible joint structure 3900 and not the seal-forming structure 3100. This can be beneficial because excessive deformation of the seal-forming structure 3100 can prevent the seal-forming structure 3100 from forming an optimal seal with the patient's face. Deformation of the flexible joint structure 3900 before deformation of the seal-forming structure 3100 can ensure that excessive force is not provided onto the plenum chamber 3200 and the seal-forming structure 3100 to avoid patient discomfort as a result of the over-tightening of the straps.

FIGS. 33A-33R and 34A-34R also show how upper straps 3304 and lower straps 3306 may be pulled and/or stretched by moving of the head, which in turn may be the cause of movement of the frame 3700 relative to the connector ring, 3800, the plenum chamber 3200, and the seal-forming structure 3100. Additionally, these examples depict that the upper straps 3304 and lower straps 3306 may each include a connector 3305. The connector 3305 may include a hook material or a loop material and each of the upper straps 3304 and lower straps 3306 may include the other of a hook material or a loop material so that the upper straps 3304 and lower straps 3306 can be passed through the tie attachment structures 3702 and attached back on themselves. This arrangement may also provide length adjustment.

5.3.9 Decoupling Structure(s)

In one form, the patient interface 3000 includes at least one decoupling structure 3500, for example, a swivel or a ball and socket. In the depicted examples, the decoupling structure 3500 has an elbow shape and includes a swivel 3501. The swivel 3501 may be shaped and dimensioned to be connected to an air circuit 4170.

The decoupling structure 3500 may have an annular connector 3503 and the plenum chamber 3200 may have a sealing lip 3201, which may contact the annular connector 3503 to form a sealed flow path for the flow of air at the therapeutic pressure from the decoupling structure 3500 to the plenum chamber 3200 for breathing by the patient. The annular connector 3503 of the decoupling structure 3500 may also be limited in the distance in which it can be inserted into the connector ring 3800 by an annular stop 3808. The annular stop 3808 can prevent the annular connector 3503 of the decoupling structure 3500 from being inserted into the plenum chamber 3200.

The swivel 3501 of the decoupling structure 3500 may include an inner sleeve 3504 and an outer sleeve 3505. The inner sleeve 3504 may be fixed relative to the other components of the decoupling structure 3500 while the outer sleeve 3505 is relatively rotatable to minimize the effects of tube drag when the air circuit 4170 is joined to the decoupling structure 3500 at the outer sleeve 3505.

The swivel 3501 may be joined to the decoupling structure 3500 with a swivel connector 3506. For example, the inner sleeve 3504 may be fixed to the swivel connector 3506 so that the outer sleeve 3505 can rotate relative to the rest of the decoupling structure 3500.

The decoupling structure 3500 may also include a cover 3507 that is overmoulded to the decoupling structure 3500 to provide a pneumatic seal and a grip for the buttons 3502.

In the examples depicted in FIGS. 12A to 17E and FIGS. 18A to 21E, the decoupling structure 3500 may also include a ball and socket joint to increase freedom of motion. The ball and socket joint may be formed by a ball portion 3510 and a socket portion 3511. The ball portion 3510 may engage with pivot pegs 3512 of the socket portion 3511 to constrain movement of the ball and socket joint to desired degree.

5.3.9.1 Vent

In one form, the patient interface 3000 includes a vent 3400 constructed and arranged to allow for the washout of exhaled gases, e.g., carbon dioxide.

In certain forms, the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled CO2 by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 may be included on the decoupling structure 3500, as in the depicted examples.

5.3.9.2 Anti-Asphyxia Valve

In one form, the patient interface 3000 includes an anti-asphyxia valve 3509. In the examples depicted in FIGS. 12A to 12M, 17A to 17E, and 18A to 18M, the anti-asphyxia valve 3509 is provided as part of the decoupling structure 3500. The examples depicted in FIGS. 6A to 6M and 11A to 11E, the patient interface 3000 is not intended to form a seal over the patient's mouth, so an anti-asphyxia valve 3509 is not included.

5.3.10 Ports

In one form of the present technology, a patient interface 3000 includes one or more ports that allow access to the volume within the plenum chamber 3200. In one form, this allows a clinician to supply supplemental oxygen. In one form, this allows for the direct measurement of a property of gases within the plenum chamber 3200, such as the pressure.

5.4 RPT Device

An RPT device 4000 in accordance with one aspect of the present technology comprises mechanical, pneumatic, and/or electrical components and is configured to execute one or more algorithms 4300. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10 $cmH_2O$, or at least 20 $cmH_2O$.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors and flow rate sensors.

One or more of the air path items may be located within a removable unitary structure which will be referred to as a pneumatic block 4020. The pneumatic block 4020 may be located within the external housing 4010. In one form, a pneumatic block 4020 is supported by, or formed as part of the chassis 4016.

The RPT device 4000 may have an electrical power supply 4210, one or more input devices 4220, a central controller, a therapy device controller, a pressure generator 4140, one or more protection circuits, memory, transducers 4270, data communication interface and one or more output devices. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example, the blower 4142 may include a brushless DC motor 4144 with one or more impellers housed in a volute. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller.

In other forms, a pressure generator 4140 may be a piston-driven pump, a pressure regulator connected to a high pressure source (e.g., compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors, such as a Doppler radar movement sensor, that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure, or a temperature at that point in the pneumatic path.

In one form of the present technology, one or more transducers 4270 may be located proximate to the patient interface 3000.

In one form, a signal from a transducer 4270 may be filtered, such as by low-pass, high-pass, or band-pass filtering.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

5.5.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.6 Humidifier

5.6.1 Humidifier Overview

In one form of the present technology there is provided a humidifier 5000 (e.g., as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element.

5.6.2 Humidifier Components
5.6.2.1 Water Reservoir

According to one arrangement, the humidifier 5000 may comprise a water reservoir 5110 configured to hold, or retain, a volume of liquid (e.g., water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g., 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.6.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g., approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.6.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.7 Glossary

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g., atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g., the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g., from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g$-$f/cm^2$ and hectopascal. 1 $cmH_2O$ is equal to 1 $g$-$f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.7.1.2 Mechanical Properties

Resilience: Ability of a material to absorb energy when deformed elastically and to release the energy upon unloading.

Resilient: Will release substantially all of the energy when unloaded. Includes, e.g., certain silicones, and thermoplastic elastomers.

Hardness: The ability of a material per se to resist deformation (e.g., described by a Young's Modulus, or an indentation hardness scale measured on a standardised sample size).

'Soft' materials may include silicone or thermo-plastic elastomer (TPE), and may, e.g., readily deform under finger pressure.

'Hard' materials may include polycarbonate, polypropylene, steel or aluminium, and may not e.g., readily deform under finger pressure.

Stiffness (or rigidity) of a structure or component: The ability of the structure or component to resist deformation in response to an applied load. The load may be a force or a moment, e.g., compression, tension, bending or torsion. The structure or component may offer different resistances in different directions.

Floppy structure or component: A structure or component that will change shape, e.g., bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g., at a load of approximately 20 to 30 cmH$_2$O pressure.

As an example, an I-beam may comprise a different bending stiffness (resistance to a bending load) in a first direction in comparison to a second, orthogonal direction. In another example, a structure or component may be floppy in a first direction and rigid in a second direction.

5.7.2 Anatomy
5.7.2.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

Bony framework (nose): The bony framework of the nose comprises the nasal bones, the frontal process of the maxillae and the nasal part of the frontal bone.

Cartilaginous framework (nose): The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labialfold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittalplane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 5.7.2.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.7.2.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.7.3 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g., about 360 degrees. In certain forms an elbow may be removable from a mating component, e.g., via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.7.4 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example, a structure may comprise one or more of an anterior surface, a posterior surface, an interior surface and an exterior surface. In another example, a seal-forming structure may comprise a face-contacting (e.g., outer) surface, and a separate non-face-contacting (e.g., underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.7.4.1 Curvature in One Dimension

The curvature of a plane curve at p may be described as having a sign (e.g., positive, negative) and a magnitude (e.g., 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.7.4.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g., relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g., curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g., both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g., a continuous space curve from f(0) to f(1) on a surface. In certain forms of the present technology, a 'path' may be described as a route or course, including e.g., a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.7.4.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g., the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g., FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g., a gently sloping helical path). A space curve which deviates a relatively large amount from the osculating plane will have a relatively large magnitude of torsion (e.g., a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g., a right-hand helix as shown in FIG. 3S). A space curve turning away from the direction of the right-hand binormal may be considered as having a right-hand negative torsion (e.g., a left-hand helix).

Equivalently, and with reference to a left-hand rule (see FIG. 3O), a space curve turning towards the direction of the left-hand binormal may be considered as having a left-hand positive torsion (e.g., a left-hand helix). Hence left-hand positive is equivalent to right-hand negative. See FIG. 3T.

5.7.4.4 Holes

A surface may have a one-dimensional hole, e.g., a hole bounded by a plane curve or by a space curve. Thin structures (e.g., a membrane) with a hole, may be described as having a one-dimensional hole. See, for example, the one dimensional hole in the surface of structure shown in FIG. 3I, bounded by a plane curve.

A structure may have a two-dimensional hole, e.g., a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g., at its entrance or at its exit), and a two-dimension hole bounded by the inside surface of the conduit. See also the two dimensional hole through the structure shown in FIG. 3K, bounded by a surface as shown.

5.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

Also, it should be appreciated that one or more aspects of the present technology may be combinable with one or more aspects of: PCT Application No. PCT/AU2016/050891, filed Sep. 23, 2016 and entitled "Patient Interface", which claims the benefit of U.S. Provisional Application No. 62/222,593, filed Sep. 23, 2015 and U.S. Provisional Application No. 62/376,961, filed Aug. 19, 2016; U.S. Provisional Application No. 62/377,217, filed Aug. 19, 2016 and entitled "Patient Interface with a Seal-Forming Structure having Varying Thickness"; U.S. Provisional Application No. 62/377,158, filed Aug. 19, 2016 and entitled "Patient Interface with a Seal-Forming Structure having Varying Thickness"; PCT Application No. PCT/AU2016/050892, filed Sep. 23, 2016 and entitled "Elbow Assembly", which claims the benefit of U.S. Provisional Application No. 62/222,435, filed Sep. 23, 2015 and U.S. Provisional Application No. 62/376,718, filed Aug. 18, 2016; U.S. Provisional Application No. 62/377,217, filed Aug. 19, 2016 and entitled "Patient Interface with a Seal-Forming Structure having Varying Thickness"; U.S. Provisional Application No. 62/377,158, filed Aug. 19, 2016 and entitled "Patient Interface with a Seal-Forming Structure having Varying Thickness"; PCT Application No. PCT/AU2016/050893, filed Sep. 23, 2016 and entitled "Vent Adaptor for a Respiratory Therapy System", which claims the benefit of U.S. Provisional Application No. 62/222,604, filed Sep. 23, 2015; and/or PCT Application No. PCT/AU2016/050228 filed Mar. 24, 2016 and entitled "Patient Interface with Blowout Prevention for Seal-Forming Portion", which claims the benefit of U.S. Provisional Application No. 62/138,009, filed Mar. 25, 2015 and U.S. Provisional Application No. 62/222,503, filed Sep. 23, 2015; each of the above-noted applications of which is incorporated herein by reference in its entirety.

It is therefore to be understood that numerous modifications may be made to the illustrative examples and that other arrangements may be devised without departing from the spirit and scope of the technology.

5.9 REFERENCE SIGNS LIST

| | |
|---|---|
| plane curve | 301D |
| surface | 302D |
| patient | 1000 |
| sleeping patient | 1000 |
| bed partner | 1100 |
| patient interface | 3000 |
| seal - forming structure | 3100 |
| plenum chamber | 3200 |
| sealing lip | 3201 |
| neck | 3202 |
| wing | 3203 |
| projection | 3204 |
| joint | 3205 |
| protrusion | 3206 |
| perimeter | 3210 |
| plenum chamber inlet port | 3211 |
| outer rim | 3212 |
| neck inner lip | 3213 |
| anterior neck surface | 3214 |
| outer neck surface | 3215 |
| marginal edge | 3220 |
| positioning and stabilising structure | 3300 |
| clip | 3301 |
| tie | 3302 |
| tab | 3303 |
| upper strap | 3304 |
| connector | 3305 |
| lower strap | 3306 |
| vent | 3400 |
| decoupling structure | 3500 |
| swivel | 3501 |
| button | 3502 |
| annular connector | 3503 |
| swivel inner sleeve | 3504 |
| swivel outer sleeve | 3505 |
| swivel connector | 3506 |
| cover | 3507 |
| retainer | 3508 |
| anti-asphyixia valve | 3509 |
| ball portion | 3510 |
| socket portion | 3511 |
| pivot peg | 3512 |
| outer annular connector surface | 3513 |
| inner annular connector surface | 3514 |
| annular connector end surface | 3515 |
| connection port | 3600 |
| frame | 3700 |
| forehead support | 3701 |
| tie attachment structure | 3702 |
| tie attachment structure opening | 3703 |
| frame opening extension | 3704 |
| frame opening | 3705 |
| clip receptacle | 3706 |
| spring attachment structure | 3707 |
| spring | 3708 |
| spring opening | 3709 |
| pivot post | 3710 |
| frame opening projection | 3711 |
| central tie opening | 3712 |
| lower tie attachment structure | 3713 |
| lower tie attachment point | 3714 |
| hinge | 3715 |
| adjustable positioning structure | 3716 |
| receptacle | 3717 |
| adjustment button | 3718 |
| eyelet | 3719 |
| frame extension | 3720 |
| hinge | 3721 |
| connector ring | 3800 |
| spacer | 3801 |
| attachment structure | 3802 |
| peripheral extension | 3803 |
| attachment lip | 3804 |
| notch | 3805 |
| protrusion | 3806 |
| peripheral extension lip | 3807 |
| annular stop | 3808 |
| pivot hole support | 3809 |
| pivot hole | 3810 |
| blocking structure | 3811 |
| connector ring inner surface | 3812 |
| annular stop anterior surface | 3813 |
| connector ring outer surface | 3814 |
| peripheral extension posterior surface | 3815 |
| peripheral extension inner surface | 3816 |
| flexible joint structure | 3900 |
| frame joining portion | 3901 |
| connector ring joining portion | 3902 |
| web | 3903 |
| inner peripheral recess | 3904 |
| frame joining channel | 3905 |
| connector ring joining channel | 3906 |
| outer peripheral recess | 3907 |
| annular lip seal | 3908 |
| dynamic diametric seal | 6000 |
| dynamic face seal | 6001 |
| static face seal | 6002 |
| static diametric seal | 6003 |

The invention claimed is:

1. A patient interface comprising:
a plenum chamber pressurisable to a therapeutic pressure of at least 6 cmH$_2$O above ambient air pressure by a flow of air;
a seal-forming structure connected to the plenum chamber and constructed and arranged to contact and seal against a region of a patient's face surrounding an entrance to the patient's airways such that the flow of air is delivered to at least the entrance to the patient's nares, the seal-forming structure being constructed and arranged to maintain said therapeutic pressure in the plenum chamber throughout the patient's respiratory cycle in use, and the seal-forming structure being configured to leave the patient's mouth uncovered during use;
a positioning and stabilising structure configured to hold the seal-forming structure in a therapeutically effective position on the patient's head, the positioning and stabilising structure comprising a tie, the tie being constructed and arranged so that at least a portion of the tie overlies a region of the patient's head superior to an otobasion superior on a corresponding side of the patient's head in use;

a frame pivotable relative to the plenum chamber in a direction parallel to the patient's sagittal plane, the tie of the positioning and stabilising structure being removably connected to the frame;

an elbow assembly rotatable relative to the frame and having a swivel configured to be connected to an air circuit to provide a fluid connection between the plenum chamber and the air circuit for the flow of air, and the elbow assembly having a plurality of vent holes configured to allow a continuous flow of gases exhaled by the patient to pass from an interior of the plenum chamber to ambient during use, the vent holes being sized and shaped to maintain the therapeutic pressure in the plenum chamber during use; and a spring joined to the frame, the spring being in contact with the plenum chamber to resiliently limit pivoting of the frame toward the plenum chamber, wherein the frame further comprises a pair of pivot posts that define a pivot axis for the frame relative to the plenum chamber.

2. The patient interface of claim 1, wherein the spring is constructed from a resiliently deformable material.

3. The patient interface of claim 2, wherein the resiliently deformable material is silicone.

4. The patient interface of claim 1, wherein the seal-forming structure and the plenum chamber are separable.

5. The patient interface of claim 1, wherein the seal-forming structure is constructed from a soft, flexible, resilient material, and
wherein the plenum chamber and the frame are each constructed from a rigid material.

6. The patient interface of claim 5, wherein the soft, flexible, resilient material is silicone.

7. The patient interface of claim 5, wherein the rigid material is polycarbonate.

8. The patient interface of claim 1, wherein the spring has an arcuate shape.

9. The patient interface of claim 1, wherein the frame comprises a spring opening and the spring extends from a spring attachment structure, and
wherein the spring is joined to the frame at the spring opening by the spring attachment structure.

10. The patient interface of claim 1, wherein the spring is joined to the frame with an overmoulded joint.

11. The patient interface of claim 1, wherein the spring is configured to always be under compression during use.

12. The patient interface of claim 1, wherein the frame further comprises a forehead support.

13. The patient interface of claim 12, wherein a superior end of the forehead support comprises a post, and
wherein the tie is constructed from a layer of loop material and includes a tab of hook material configured to be releasably connected to the layer of loop material to form a loop that is removably connected to the post.

14. The patient interface of claim 1, wherein:
the spring is constructed from a resiliently deformable material,
the resiliently deformable material is silicone,
the seal-forming structure and the plenum chamber are separable,
the seal-forming structure is constructed from a soft, flexible, resilient material,
the plenum chamber and the frame are each constructed from a rigid material,
the spring has an arcuate shape,
the frame comprises a spring opening and the spring extends from a spring attachment structure,
the spring is joined to the frame at the spring opening by the spring attachment structure,
the spring is joined to the frame with an overmoulded joint,
the spring is configured to always be under compression during use,
the frame further comprises a forehead support,
a superior end of the forehead support comprises a post, and
the tie is constructed from a layer of loop material and includes a tab of hook material configured to be releasably connected to the layer of loop material to form a loop that is removably connected to the post.

15. A patient interface comprising:
a plenum chamber pressurisable to a therapeutic pressure of at least 6 cmH$_2$O above ambient air pressure by a flow of air;

a seal-forming structure connected to the plenum chamber and constructed and arranged to contact and seal against a region of a patient's face surrounding an entrance to the patient's airways such that the flow of air is delivered to at least the entrance to the patient's nares, the seal-forming structure being constructed and arranged to maintain said therapeutic pressure in the plenum chamber throughout the patient's respiratory cycle in use, and the seal-forming structure being configured to leave the patient's mouth uncovered during use;

a positioning and stabilising structure configured to hold the seal-forming structure in a therapeutically effective position on the patient's head, the positioning and stabilising structure comprising a tie, the tie being constructed and arranged so that at least a portion of the tie overlies a region of the patient's head superior to an otobasion superior on a corresponding side of the patient's head in use;

a frame assembly connected to the plenum chamber and including a frame, the frame being movable towards or away from the patient, the tie of the positioning and stabilising structure being removably connected to the frame;

an elbow assembly rotatably connected at a first end to the frame assembly and having a swivel at a second end that is configured to be connected to an air circuit to provide a fluid connection between the plenum chamber and the air circuit for the flow of air, and the elbow assembly having a plurality of vent holes configured to allow a continuous flow of gases exhaled by the patient to pass from an interior of the plenum chamber to ambient during use, the vent holes being sized and shaped to maintain the therapeutic pressure in the plenum chamber during use; and an elastic member that extends from the frame to the plenum chamber to resiliently limit movement of the frame relative to the plenum chamber, wherein the frame assembly further comprises a pair of pivot posts that define a pivot axis for the frame relative to the plenum chamber.

16. The patient interface of claim 15, wherein the elastic member is constructed from a resiliently deformable material.

17. The patient interface of claim 16, wherein the resiliently deformable material is silicone.

18. The patient interface of claim 15, wherein the seal-forming structure and the plenum chamber are separable.

19. The patient interface of claim 15, wherein the seal-forming structure is constructed from a soft, flexible, resilient material, and wherein the plenum chamber and the frame are each constructed from a rigid material.

20. The patient interface of claim 19, wherein the soft, flexible, resilient material is silicone.

21. The patient interface of claim 19, wherein the rigid material is polycarbonate.

22. The patient interface of claim 15, wherein the elastic member has an arcuate shape.

23. The patient interface of claim 15, wherein the frame comprises an elastic member hole and the elastic member extends from an elastic member attachment structure, and wherein the elastic member is joined to the frame at the elastic member hole by the elastic member attachment structure.

24. The patient interface of claim 15, wherein the elastic member is joined to the frame with an overmoulded joint.

25. The patient interface of claim 15, wherein the elastic member is configured to always be under compression during use.

26. The patient interface of claim 15, wherein the frame further comprises a forehead support.

27. The patient interface of claim 26, wherein a superior end of the forehead support comprises a post, and wherein the tie is constructed from a layer of loop material and includes a tab of hook material configured to be releasably connected to the layer of loop material to form a loop that is removably connected to the post.

28. The patient interface of claim 15, wherein:

the elastic member is constructed from a resiliently deformable material, the resiliently deformable material is silicone, the seal-forming structure and the plenum chamber are separable, the seal-forming structure is constructed from a soft, flexible, resilient material, the plenum chamber and the frame are each constructed from a rigid material, the elastic member has an arcuate shape, the frame comprises an elastic member hole and the elastic member extends from an elastic member attachment structure, the elastic member is joined to the frame at the elastic member hole by the elastic member attachment structure, the elastic member is joined to the frame with an overmoulded joint, the elastic member is configured to always be under compression during use, the frame further comprises a forehead support, a superior end of the forehead support comprises a post, and the tie is constructed from a layer of loop material and includes a tab of hook material configured to be releasably connected to the layer of loop material to form a loop that is removably connected to the post.

* * * * *